US012065655B2

(12) United States Patent
Kock et al.

(10) Patent No.: US 12,065,655 B2
(45) Date of Patent: Aug. 20, 2024

(54) CMV RESISTANCE ALLELE

(71) Applicant: RIJK ZWAAN ZAADTEELT EN ZAADHANDEL B.V., De Lier (NL)

(72) Inventors: Vincent Laurens Adrianus Kock, De Lier (NL); Johannes Geert Jan Feitsma, De Lier (NL); Raoul Jacobus Johannes Maria Frijters, De Lier (NL)

(73) Assignee: RIJK ZWAAN ZAADTEELT EN ZAADHANDEL B.V., De Lier (NL)

( * ) Notice: Subject to any disclaimer, the term of this patent is extended or adjusted under 35 U.S.C. 154(b) by 0 days.

(21) Appl. No.: 17/474,160

(22) Filed: Sep. 14, 2021

(65) Prior Publication Data

US 2021/0403937 A1 Dec. 30, 2021

Related U.S. Application Data

(60) Division of application No. 16/279,011, filed on Feb. 19, 2019, now Pat. No. 11,136,592, which is a continuation-in-part of application No. PCT/EP2018/076640, filed on Oct. 1, 2018, which is a continuation-in-part of application No. PCT/EP2017/074862, filed on Sep. 27, 2017, which is a continuation-in-part of application No. 15/720,757, filed on Sep. 27, 2017, now abandoned.

(51) Int. Cl.

| | |
|---|---|
| ***C12N 15/82*** | (2006.01) |
| ***A01H 5/12*** | (2018.01) |
| ***A01H 6/02*** | (2018.01) |
| ***C07K 14/415*** | (2006.01) |
| ***C12Q 1/6895*** | (2018.01) |

(52) U.S. Cl.

CPC ........... *C12N 15/8283* (2013.01); *A01H 5/12* (2013.01); *A01H 6/028* (2018.05); *C07K 14/415* (2013.01); *C12Q 1/6895* (2013.01); *C12Q 2600/13* (2013.01)

(58) Field of Classification Search

None

See application file for complete search history.

(56) References Cited

U.S. PATENT DOCUMENTS 9,402,363 B1 8/2016 Feitsma

FOREIGN PATENT DOCUMENTS

WO 2018/060474 A1 4/2018

OTHER PUBLICATIONS

Verma, Ravi, Vineet Ahuja, and Jaishree Paul. "Detection of single-nucleotide polymorphisms in the intron 9 region of the nucleotide oligomerization domain-1 gene in ulcerative colitis patients of North India." Journal of Gastroenterology and Hepatology 27.1 (2012): 96-103. (Year: 2012).*

Yang, Yanmign, Jameel M. Al-Khayri, and Edwin J. Anderson. "Transgenic spinach plants expressing the coat protein of cucumber mosaic virus." In Vitro Cellular & Developmental Biology-Plant 33 (1997): 200-204. (Year: 1997).*

Chunda Feng et al., Construction of a Spinach Bacterial Artificial Chromosome (BAC) Library as a Resource for Gene Identification and Marker Development, Plant Mol. Biol. Rep. (2015) 33:1996-2005.

B. M. Irish, et al., Characterization of a Resistance Locus (Pfs-1) to the Spinach Downy Mildew Pathogen (*Peronospora farinosa*f. sp. *spinaciae*) and Development of a Molecular Marker Linked to Pfs-1, Phytopathology (2008) vol. 98, No. 8, p. 894-900.

H.E. Schmidt, et al., Multiple Resistance of Spinach (*Spinacia oleracea* L.) to Cucumber Mosaic and Beet Mild Yellowing Viruses, Zentralbl. Mikrobiol. (1989) 144:13-18.

Hideki Takahashi, et al., RCY1, an Arabidopsis Thaliana RPP8/HRT Family Resistance Gene, Conferring Resistance to Cucumber Mosaic Virus Requires Salicylic Acid, Ethylene and a Novel Signal Transduction Mechanism, The Plant Journal (2002) vol. 32, p. 655-667.

International Search Report and Written Opinion issued Jan. 2, 2019 in PCT/EP2018/076640.

* cited by examiner

*Primary Examiner* — Weihua Fan
*Assistant Examiner* — Brian James Sullivan
(74) *Attorney, Agent, or Firm* — Duane Morris LLP; Thomas J. Kowalski

(57) ABSTRACT

The present invention relates to an allele designated alpha-CMV which confers resistance to CMV when present in a spinach plant, wherein the protein encoded by said allele is a CC-NBS-LRR protein that comprises in its amino acid sequence: a) the motif "MAEIGYSVC" (SEQ ID NO: 22) at its N-terminus; and b) the motif "KWMCLR" (SEQ ID NO: 23); and c) an LRR domain that has in order of increased preference at least 95%, 96%, 97%, 98%, 99%, 100% sequence similarity to SEQ ID NO: 10. The allele has a genomic nucleotide sequence which in order of increased preference has at least 80%, 81%, 82%, 83%, 84%, 85%, 86%, 87%, 88%, 89%, 90%, 91%, 92%, 93%, 94%, 95%, 96%, 97%, 98%, 99%, 100% sequence similarity to SEQ ID NO: 1. The invention further relates to plants comprising the allele and to various methods involving the allele.

17 Claims, No Drawings

Specification includes a Sequence Listing.

CMV RESISTANCE ALLELE

RELATED APPLICATIONS AND INCORPORATION BY REFERENCE

This application is a divisional of application Ser. No. 16/279,011 filed Feb. 19, 2019, which is a continuation-in-part application of international patent application Serial No. PCT/EP2018/076640 filed 1 Oct. 2018, which application is a continuation-in-part of international patent application Serial No. PCT/EP2017/074862 filed 29 Sep. 2017, and which is a continuation-in-part of U.S. patent application Ser. No. 15/720,757 filed 29 Sep. 2017, now abandoned.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

SEQUENCE STATEMENT

The instant application contains a Sequence Listing which has been submitted electronically and is hereby incorporated by reference in its entirety. Said ASCII copy, is named Y795400417.txt and is 166 bytes in size.

FIELD OF THE INVENTION

The invention relates to an allele capable of conferring resistance in a spinach plant against Cucumber Mosaic Virus (CMV). The invention also relates to a spinach plant, to propagation material of said spinach plant, to a cell of said spinach plant, and to seed of said spinach plant carrying the allele. The invention further relates to a method of producing a spinach plant carrying the allele and to the use of the allele in breeding to confer CMV resistance.

BACKGROUND OF THE INVENTION

Spinach (*Spinacia oleracea* L.) is a flowering plant from the Amaranthaceae family that is grown as a vegetable. The consumable parts of spinach are the leaves and petioles from the vegetative stage. Spinach is sold loose, bunched, in pre-packed bags, canned, or frozen. There are three basic types of spinach: industry-, fresh and Asiatic spinach. Within these types three different leaf types can be recognised: savoy, semi-savoy and smooth types. Savoy has crinkly and curly leaves. Flat or smooth leaf spinach has broad, smooth leaves. Semi-savoy is a variety with slightly crinkled leaves. The main market for spinach is baby-leaf. Baby spinach leaves are often of the flat-leaf variety and usually the harvested leaves are not longer than about eight centimeter. These tender, sweet leaves are sold loose rather than in bunches. They are often used in salads, but can also be lightly cooked.

One of the diseases threatening the production of spinach is Cucumber Mosaic Virus (CMV). Cucumber Mosaic Virus is a positive-sense single stranded RNA virus belonging to the Bromoviridae family and the Cucumovirus genus. The virus has a worldwide distribution and it is believed to have the broadest host range of any known plant virus. It has been reported to be able to infect over 1200 plant species in over 100 plant families.

The virus can be transmitted in many different ways e.g. mechanically, by insect vectors such as aphids, on seeds and even by parasitic weeds. The symptoms and severity of CMV infection depend on the species and the age of the plant. Typical symptoms for CMV are mottling, yellowing, the formation of ringspots, stunting and distortion of leaf, fruit and flowers.

CMV is in spinach also known as spinach blight. Symptoms observed on infected spinach plants commonly are leaf chlorotic mottle, narrowing, wrinkling and inward rolling of the leaves, and distortion of the veins.

Although CMV resistance is observed in some spinach cultivars, the genetic basis for the resistance in those cultivars has never been characterized at the molecular level, i.e. the responsible gene and its sequence until now were unknown. Furthermore, there are no closely linked molecular markers known in the art that may identify CMV resistance in spinach, nor are the molecular characteristics of the genes themselves known in the art. Therefore, the identification of CMV resistance in spinach plants is currently based on phenotypic assays in which many accessions are screened for resistance based on the absence of disease symptoms in a disease test.

Citation or identification of any document in this application is not an admission that such document is available as prior art to the present invention.

SUMMARY OF THE INVENTION

Therefore, it is the object of the invention to provide a new resistance allele conferring resistance to CMV in spinach and to provide molecular tools for identifying this resistance allele.

In the research leading to the present invention, it was surprisingly found that at the same locus on which several *Peronospora farinosa* f. sp. *spinaciae* resistance conferring alleles have been observed also a CMV resistance conferring allele is located.

At this locus one or two so-called WOLF-genes are located. These one or two genes, which are either "alpha-WOLF" type or "beta-WOLF" type genes (together referred to as "the WOLF genes or alpha/beta-WOLF genes") each encode a protein that belongs to the CC-NBS-LRR (Coiled Coil-Nucleotide Binding Site-Leucine-Rich Repeat) family. Depending on the allelic variant (or the allelic variants) that is (are) present in a spinach plant, said plant will produce a variant of the WOLF protein that confers a certain resistance profile to pathogenic races of downy mildew. The research leading to the present invention has now elucidated that one allelic variant of the alpha-WOLF type does not provide resistance to downy mildew, but instead confers resistance to CMV.

In the context of this invention the term "allele" or "allelic variant" is used to designate a version of a gene that is linked to a specific phenotype, i.e. resistance, more in particular CMV resistance. It was found that a spinach plant may carry one or two WOLF genes. For each of these two WOLF genes multiple alleles exist. The WOLF gene allele of the invention confers resistance to CMV. In the context of this invention an allele or allelic variant is a nucleic acid.

The beta-WOLF gene of spinach variety Viroflay is located on scaffold12735 (sequence: GenBank: KQ143339.1), at position 213573-221884. In case the spinach plant also carries or only carries an alpha-WOLF gene, the alpha-WOLF gene is located at approximately the same location as where the beta-WOLF gene is located on scaffold12735 in the Viroflay genome assembly.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. All rights to explicitly disclaim any embodiments that are the subject of any granted patent(s) of applicant in the lineage of this application or in any other lineage or in any prior filed application of any third party is explicitly reserved. Nothing herein is to be construed as a promise.

It is noted that in this disclosure and particularly in the claims and/or paragraphs, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

DEPOSIT

Seeds of a plant comprising the alpha-CMV allele of the invention heterozygously in its genome were deposited with NCIMB Ltd, Ferguson Building, Craibstone Estate, Bucksburn, Aberdeen AB21 9YA, UK, on Sep. 9, 2016, under deposit accession number 42651. The Deposits with NCIMB Ltd., under deposit accession number 42651 were made pursuant to the terms of the Budapest Treaty. Upon issuance of a patent, all restrictions upon the deposit will be removed, and the deposit is intended to meet the requirements of 37 CFR §§ 1.801-1.809. The deposit will be irrevocably and without restriction or condition released to the public upon the issuance of a patent and for the enforceable life of the patent. The deposit will be maintained in the depository for a period of 30 years, or 5 years after the last request, or for the effective life of the patent, whichever is longer, and will be replaced if necessary during that period.

DETAILED DESCRIPTION OF THE INVENTION

A genome assembly for spinach variety Viroflay—which is susceptible to CMV—is publicly available (*Spinacia oleracea* cultivar SynViroflay, whole genome shotgun sequencing project; Bioproject: PRJNA41497; GenBank: AYZV00000000.2; BioSample: SAMN02182572, see also Dohm et al, 2014, *Nature* 505: 546-549). In this genome assembly for Viroflay, the beta-WOLF gene is located on scaffold12735 (sequence: GenBank: KQ143339.1), at position 213573-221884. The sequence covered by this interval may comprise the entire genomic sequence of the beta-WOLF gene of Viroflay, plus 2000 basepairs sequence upstream of the gene, plus the sequence downstream of the gene, up to the locus of the neighbouring gene that is situated downstream of the WOLF gene. Spinach variety Viroflay only possesses a single WOLF gene, namely a beta-WOLF gene, but many other spinach lines harbor a single alpha-type WOLF gene at the same location in the genome. Other spinach lines harbor two WOLF genes at approximately the same location in the genome. In such cases, the two WOLF genes are positioned adjacent to each other. In most spinach lines that harbor two WOLF genes, one of said WOLF genes belongs to the alpha-type, and the other WOLF gene belongs to the beta-type. In the research leading to the present invention, it was observed that this allelic variation in the WOLF locus is responsible for differences in resistance to pathogenic races of *Peronospora farinosa* f. sp. *spinaciae*, but surprisingly enough one of the allelic variants confers resistance to CMV instead of downy mildew.

The difference between an allele of an alpha-WOLF gene and an allele of a beta-WOLF gene lies in the presence of specific conserved amino acid motifs in the encoded protein sequence. As mentioned above, all WOLF proteins possess—from N- to C-terminus—the following domains that are generally known in the art: a coiled coil domain (RX-CC-like, cd14798), an NBS domain (also referred to as "NB-ARC domain", pfam00931; van der Biezen & Jones, 1998, *Curr. Biol.* 8: R226-R228), and leucine-rich repeats (IPR032675) which make up the LRR domain. In addition, all WOLF proteins comprise in their amino acid sequence the motif "MAEIGYSVC" (SEQ ID NO: 22) at the N-terminus. In addition to this, all alpha-WOLF proteins comprise the motif "KWMCLR" (SEQ ID NO: 23) in their amino acid sequence, whereas all beta-WOLF proteins comprise the motif "HVGCVVDR" (SEQ ID NO: 12) in their amino acid sequence.

The present invention relates to a new CMV resistance conferring allele of the alpha-WOLF gene designated alpha-CMV.

In particular, the invention relates to a CMV resistance conferring allele designated alpha-CMV wherein the protein encoded by said allele is a CC-NBS-LRR protein that may comprise in its amino acid sequence: a) the motif "MAEIGYSVC" (SEQ ID NO: 22) at its N-terminus; b) the motif "KWMCLR" (SEQ ID NO: 23); and c) an LRR domain that has in order of increased preference at least 95%, 96%, 97%, 98%, 99%, 100% sequence similarity to SEQ ID NO: 10. Optionally, the alpha-CMV allele further may comprise an additional motif in its amino acid sequence, namely "DQEDEGEDN" (SEQ ID NO: 25).

For the purpose of this invention, the LRR domain of the protein encoded by the alpha-CMV allele is defined as the amino acid sequence that in order of increased preference has at least 95%, 96%, 97%, 98%, 99%, 100% sequence similarity to SEQ ID NO:10. The LRR domain of the invention starts with the motif "KWMCLR" (SEQ ID NO: 23).

The skilled person is familiar with methods for the calculation of sequence similarity. Suitably, sequence similarity is calculated using EMBOSS stretcher 6.6.0, using the EBLOSUM62 matrix and the resulting "similarity score".

In one embodiment, the LRR domain of the protein encoded by the alpha-CMV allele is defined as the amino acid sequence that in order of increased preference has at least 95%, 96%, 97%, 98%, 99%, 100% sequence similarity to SEQ ID NO:10.

In one embodiment, the invention relates to a nucleic acid encoding a CC-NBS-LRR protein that may comprise in its amino acid sequence: a) the motif "MAEIGYSVC" (SEQ ID NO: 22) at its N-terminus; b) the motif "KWMCLR" (SEQ ID NO: 23); and c) an LRR domain that has in order of increased preference at least 95%, 96%, 97%, 98%, 99%, 100% sequence similarity to SEQ ID NO:10.

In a further embodiment, the invention relates to a nucleic acid having a genomic nucleotide sequence which in order of increased preference has at least 80%, 81%, 82%, 83%, 84%, 85%, 86%, 87%, 88%, 89%, 90%, 91%, 92%, 93%, 94%, 95%, 96%, 97%, 98%, 99%, 100% sequence similarity to SEQ ID NO:1.

In one embodiment, the invention relates to a nucleic acid having a coding sequence which in order of increased preference has at least 80%, 81%, 82%, 83%, 84%, 85%, 86%, 87%, 88%, 89%, 90%, 91%, 92%, 93%, 94%, 95%, 96%, 97%, 98%, 99%, 100% sequence similarity to SEQ ID NO:2 or SEQ ID NO:3.

The LRR domain of the alpha-CMV allele as defined herein may be determined by amplifying and sequencing the genomic DNA encoding for the amino acid sequence of LRR domain using specific primers, and subsequently translating the DNA sequence into an amino acid sequence, thereby applying common sense in choosing the correct reading frame. The skilled person is capable of doing this, using freely available online bioinformatics tools such as can be found here: web.expasy.org/translate/

The genomic sequence of an LRR domain of an alpha-WOLF gene such as alpha-CMV may be amplified using a primer pair having a forward primer which is a nucleic acid molecule having the sequence of SEQ ID No:6 and a reverse primer which is a nucleic acid molecule having the sequence of SEQ ID No:7.

PCR conditions for amplifying the LRR domain-encoding region of an alpha-WOLF gene such as the alpha-CMV allele using primers having SEQ ID No:6 and SEQ ID No:7 are, using Platinum Taq enzyme (Thermo Fisher Scientific): 3 minutes at 95° C. (initial denaturing step); 40 amplification cycles, each cycle consisting of: 30 seconds denaturation at 95° C., 30 seconds annealing at 60° C., and 30 seconds extension at 72° C.; 2 minutes at 72° C. (final extension step).

The LRR domain of a beta-WOLF gene, e.g. the null allele as present in variety Viroflay, may be amplified using a forward primer which is a nucleic acid molecule having the sequence of SEQ ID No:8 and a reverse primer which is a nucleic acid molecule having the sequence of SEQ ID No:7.

PCR conditions for amplifying the LRR domain-encoding region of a beta-WOLF gene using primers having SEQ ID No:8 and SEQ ID No:7 are as follows, using Platinum Taq enzyme (Thermo Fisher Scientific): 3 minutes at 95° C. (initial denaturing step); 40 amplification cycles, each cycle consisting of: 30 seconds denaturation at 95° C., 50 seconds annealing at 58° C. and 50 seconds extension at 72° C.; 2 minutes at 72° C. (final extension step).

Therefore, the invention also relates to a primer pair for amplifying the LRR domain of an alpha-WOLF gene, more in particular for amplifying the LRR domain of an alpha-CMV allele wherein the forward primer is a nucleic acid molecule which may comprise the sequence of SEQ ID No:6 and the reverse primer which is a nucleic acid molecule which may comprise the sequence of SEQ ID No:7. The primers disclosed herein have been specifically designed for selectively amplifying part of a WOLF gene, and not of any other CC-NBS-LRR protein-encoding genes using the conditions as set forth above.

The invention relates to an alpha-CMV which confers resistance to CMV when present in a spinach plant, wherein the protein encoded by said allele is a CC-NBS-LRR protein that may comprise in its amino acid sequence: a) the motif "MAEIGYSVC" (SEQ ID NO: 22) at its N-terminus; and b) the motif "KWMCLR" (SEQ ID NO: 23); and wherein the allele has a genomic nucleotide sequence which in order of increased preference has at least 80%, 81%, 82%, 83%, 84%, 85%, 86%, 87%, 88%, 89%, 90%, 91%, 92%, 93%, 94%, 95%, 96%, 97%, 98%, 99%, 100% sequence similarity to SEQ ID NO:1.

The invention relates to an alpha-CMV allele which has a genomic sequence that in order of increased preference has at least 80%, 81%, 82%, 83%, 84%, 85%, 86%, 87%, 88%, 89%, 90%, 91%, 92%, 93%, 94%, 95%, 96%, 97%, 98%, 99%, 100% sequence similarity to SEQ ID No:1.

SEQ ID No:21 provided in Table 1 represents the genomic sequence of the alpha-CMV allele and the genomic sequence of the beta-CMV allele. SEQ ID No:21 further may comprise a 2 kilobase region upstream of the start codon (ATG) of the alpha-CMV allele. By using the coding sequence of the alpha-CMV allele represented by SEQ ID No: 2 the skilled person is able to identify the genomic sequence of the alpha-CMV allele with a 2 kilobase region upstream of the start codon (ATG) represented by SEQ ID No: 1.

The invention relates to two different splice variants. In one embodiment, the invention relates to an alpha-CMV allele which has a coding sequence which in order of increased preference has at least 80%, 81%, 82%, 83%, 84%, 85%, 86%, 87%, 88%, 89%, 90%, 91%, 92%, 93%, 94%, 95%, 96%, 97%, 98%, 99%, 100% sequence similarity to SEQ ID No:2. This is the first splice variant of the alpha-CMV allele. In another embodiment, the invention relates to an alpha-CMV allele which has a coding sequence which in order of increased preference has at least 80%, 81%, 82%, 83%, 84%, 85%, 86%, 87%, 88%, 89%, 90%, 91%, 92%, 93%, 94%, 95%, 96%, 97%, 98%, 99%, 100% sequence similarity to SEQ ID No:3. This is the second splice variant of the alpha-CMV allele.

In a further aspect of the invention the alpha-CMV allele encodes for a protein having an amino acid sequence which in order of increased preference has at least 95%, 96%, 97%, 98%, 99%, 100% sequence similarity to SEQ ID No:4.

In another embodiment the alpha-CMV allele encodes for a protein having an amino acid sequence which in order of increased preference has at least 95%, 96%, 97%, 98%, 99%, 100% sequence similarity to SEQ ID No:5.

The alpha-CMV allele when present in a spinach plant confers resistance to CMV, preferably complete resistance to CMV. Resistance against CMV in spinach plants may be tested by mechanically inoculating plants with the CMV virus which is a mixture of two isolates (NL 16 and SP 43) when the plant has two or three true leaves. Plants to be tested are grown under a regime with a day temperature of 20° C. and a night temperature of 18° C. and receive at least 16 hours of light. Inoculation is done by dusting all true leaves of the plants with carborundrum powder and subsequently rubbing them with a sponge soaked with inoculum. The inoculum is a mixture of equal amounts of both isolates diluted in water, preferably a 1:10 dilution. After inoculation, plants may be slightly rinsed with water. Symptoms may be observed 7 to 9 days after inoculation. A resistant plant, i.e. a plant which may comprise the allele of the invention, shows no symptoms, while a susceptible plant typically shows dwarf growth and mosaic symptoms in the heart of the plant.

A detailed example of the test described herein can be found in the CPVO protocol for tests on distinctness, uniformity, and stability for spinach is available online.

Another aspect of the invention relates to a spinach plant, which may comprise the alpha-CMV allele of the invention, of which a representative sample of seed was deposited with the NCIMB under NCIMB accession number 42651.

In a further embodiment the plant of the invention which may comprise the alpha-CMV allele is an agronomically elite spinach plant.

In the context of this invention an agronomically elite spinach plant is a non-naturally occurring plant having a genotype that results into an accumulation of distinguishable and desirable agronomic traits which is the result of human intervention, and is e.g. achieved by crossing and selection, mutagenizing, transforming or otherwise introducing such traits. An agronomically elite spinach plant includes any cultivated *Spinacia oleracea* plant regardless of type, such as breeding lines (e.g. backcross lines, inbred lines), cultivars and varieties (open pollinated or hybrids). Plants of *Spinacia oleracea* occurring in the wild (i.e. not cultivated spinach) or wild relatives of *Spinacia oleracea*, such as *Spinacia tetrandra* and *Spinacia turkestanica*, are not encompassed by this definition.

Preferably, the agronomically elite spinach plant which may comprise the alpha-CMV allele is a plant of an inbred line or a hybrid.

As used herein, a plant of an inbred line is a plant of a population of plants that is the result of three or more rounds of selfing, or backcrossing; or which plant is a double haploid. An inbred line may e.g. be a parent line used for the production of a commercial hybrid.

As used herein, a hybrid plant is a plant which is the result of a cross between two different plants having different genotypes. More in particular, a hybrid plant is the result of a cross between plants of two different inbred lines, such a hybrid plant may e.g. be a plant of an $F_1$ hybrid variety.

A plant carrying the alpha-CMV allele in heterozygous form may further comprise a beta-WOLF 0 allele as e.g. present in variety Viroflay wherein the beta-WOLF 0 allele does not confer any resistance to CMV or downy mildew. Alternatively, a plant heterozygous for the alpha-CMV allele may further comprise an allele of the alpha/beta-WOLF gene that does provide resistance to downy mildew. Preferably, such an allele would provide at least an intermediate resistance to one or more races of downy mildew. More preferably, such an allele would provide at least an intermediate resistance to at least 10 races of downy mildew. Most preferably the allele of the alpha/beta-WOLF gene confers resistance against downy mildew such that the plant is completely resistant to *Peronospora farinosa* f. sp. *spinaciae* races Pfs:1 to Pfs:16.

In one embodiment, the invention relates to a plant which may comprise the alpha-CMV allele and a downy mildew resistance conferring allele of the alpha/beta-WOLF gene, wherein the downy mildew resistance conferring allele is beta-WOLF 3 having a genomic sequence which in order of increased preference has at least 90%, 91%, 92%, 93%, 94%, 95%, 96%, 97%, 98%, 99%, 100% sequence similarity to SEQ ID NO:13, and wherein the plant is at least resistant to CMV and *Peronospora farinosa* f sp. *spinaciae* races Pfs:1, Pfs:3, Pfs:5, Pfs:9, Pfs: 11, Pfs: 12, Pfs: 14, and Pfs: 16.

In another embodiment, the invention relates to a plant which may comprise the alpha-CMV allele and a downy mildew resistance conferring allele of the alpha/beta-WOLF gene, wherein the downy mildew resistance conferring allele is alpha-WOLF 6 having a genomic sequence which in order of increased preference has at least 90%, 91%, 92%, 93%, 94%, 95%, 96%, 97%, 98%, 99%, 100% sequence similarity to SEQ ID NO:14, and wherein the plant is at least resistant to CMV and *Peronospora farinosa* f sp. *spinaciae* races Pfs:1, Pfs:2, Pfs:3, Pfs:4, Pfs:5, Pfs:6, Pfs:9, Pfs:11, Pfs:12, Pfs:14, Pfs:15, and Pfs:16.

In another embodiment, the invention relates to a plant which may comprise the alpha-CMV allele and a downy mildew resistance conferring allele of the alpha/beta-WOLF gene, wherein the downy mildew resistance conferring allele is alpha-WOLF 6b having a genomic sequence which in order of increased preference has at least 90%, 91%, 92%, 93%, 94%, 95%, 96%, 97%, 98%, 99%, 100% sequence similarity to SEQ ID NO:15, and wherein the plant is at least resistant to CMV and *Peronospora farinosa* f sp. *spinaciae* races Pfs:1, Pfs:2, Pfs:3, Pfs:4, Pfs:5, Pfs:6, Pfs:9, Pfs:11, Pfs:12, Pfs:14, Pfs:15, Pfs:16 and isolate US1508.

In another embodiment, the invention relates to a plant which may comprise the alpha-CMV allele and a downy mildew resistance conferring allele of the alpha/beta-WOLF gene, wherein the downy mildew resistance conferring allele is alpha-WOLF 8 having a genomic sequence which in order of increased preference has at least 90%, 91%, 92%, 93%, 94%, 95%, 96%, 97%, 98%, 99%, 100% sequence similarity to SEQ ID NO:16, and wherein the plant shows at least resistance to CMV and *Peronospora farinosa* f. sp. *spinaciae* races Pfs:1, Pfs:2, Pfs:6, Pfs:8, Pfs:15, and intermediate resistance to Pfs:16.

In another embodiment, the invention relates to a plant which may comprise the alpha-CMV allele and a downy mildew resistance conferring allele of the alpha/beta-WOLF gene, wherein the downy mildew resistance conferring allele is alpha-WOLF 9 having a genomic sequence which in order of increased preference has at least 90%, 91%, 92%, 93%, 94%, 95%, 96%, 97%, 98%, 99%, 100% sequence similarity to SEQ ID NO:17, and wherein the plant is at least resistant to CMV and *Peronospora farinosa* f sp. *spinaciae* races Pfs:1, Pfs:2, Pfs:3, Pfs:4, Pfs:5, Pfs:6, Pfs:7, Pfs:8, Pfs:9, Pfs:10, Pfs:11, Pfs:12, and Pfs:13.

In another embodiment, the invention relates to a plant which may comprise the alpha-CMV allele and a downy mildew resistance conferring allele of the alpha/beta-WOLF gene, wherein the downy mildew resistance conferring allele is alpha-WOLF 11 having a genomic sequence which in order of increased preference has at least 90%, 91%, 92%, 93%, 94%, 95%, 96%, 97%, 98%, 99%, 100% sequence similarity to SEQ ID NO:18, and wherein the plant is at least resistant to CMV and *Peronospora farinosa* f sp. *spinaciae* races Pfs:1, Pfs:3, Pfs:4, Pfs:5, Pfs:7, Pfs:11, Pfs:13, Pfs:15, Pfs:16 and isolate US1508.

In another embodiment, the invention relates to a plant which may comprise the alpha-CMV allele and a downy mildew resistance conferring allele of the alpha/beta-WOLF gene, wherein the downy mildew resistance conferring allele is alpha-WOLF 12 having a genomic sequence which in order of increased preference has at least 90%, 91%, 92%, 93%, 94%, 95%, 96%, 97%, 98%, 99%, 100% sequence similarity to SEQ ID NO:19, and wherein the plant is at least resistant to CMV and *Peronospora farinosa* f sp. *spinaciae* races Pfs:1, Pfs:2, Pfs:3, Pfs:4, Pfs:6, Pfs:7, Pfs:8, Pfs:9, Pfs:10, Pfs:11, Pfs:12 and isolate Pfs:13.

In another embodiment, the invention relates to a plant which may comprise the alpha-CMV allele and a downy mildew resistance conferring allele of the alpha/beta-WOLF gene, wherein the downy mildew resistance conferring allele is alpha-WOLF 15 having a genomic sequence which in order of increased preference has at least 90%, 91%, 92%, 93%, 94%, 95%, 96%, 97%, 98%, 99%, 100% sequence similarity to SEQ ID NO:20, and wherein the plant is at least resistant to CMV and *Peronospora farinosa* f sp. *spinaciae* races Pfs:1, Pfs:2, Pfs:3, Pfs:4, Pfs:5, Pfs:6, Pfs:9, Pfs:11, Pfs:12, Pfs:13, Pfs:14, and Pfs:15.

In one embodiment a plant which may comprise the alpha-CMV allele and an allele of an alpha/beta-WOLF gene conferring resistance to one or more *Peronospora farinosa* f. sp. *spinaciae* races is an agronomically elite plant, preferably a hybrid plant.

The invention further relates to propagation material which may comprise the alpha-CMV allele. In one embodiment, the propagation material is suitable for sexual reproduction. Such propagation material may comprise for example a microspore, pollen, ovary, ovule, embryo sac and egg cell. In another embodiment, the propagation material is suitable for vegetative reproduction. Such propagation material may comprise for example a cutting, root, stem, cell, protoplast, and a tissue culture of regenerable cells. A part of the plant that is suitable for preparing tissue cultures is in particular a leaf, pollen, an embryo, a cotyledon, a hypocotyl, a meristematic cell, a root tip, an anther, a flower, a seed and a stem.

The invention further relates to the use of a tissue culture which may comprise the alpha-CMV allele for the production of a spinach plant showing resistance to CMV.

The invention also relates to the use of a spinach plant which may comprise the alpha-CMV allele, as a source of propagating material.

The invention also relates to the use of a spinach plant which may comprise the alpha-CMV allele, as a source of seed.

The invention furthermore relates to a cell of a spinach plant which may comprise the alpha-CMV allele. Such a cell may be either in isolated form or may be part of the complete plant or parts thereof and then still constitutes a cell of the invention because such a cell harbors the alpha-CMV allele that confers resistance to CMV. Each cell of the plant of the invention carries the genetic information that confers resistance to CMV. Such a cell of the invention may also be a regenerable cell that may be used to regenerate a new plant which may comprise the allele of the invention.

In one aspect the invention relates to the use of a cell which may comprise the alpha-CMV allele for the production of a spinach plant showing resistance to CMV.

Yet another aspect of the invention relates to a method for making a hybrid spinach seed which may comprise crossing a first parent spinach plant with a second parent spinach plant and harvesting the resultant hybrid spinach seed, wherein said first and/or second parent spinach plant may comprise the CMV allele. In a particular embodiment, the first and/or second parent plant is a plant of an inbred line as defined herein.

The invention further relates to a hybrid spinach plant grown from seed produced by crossing a first parent spinach plant with a second parent spinach plant and harvesting the resultant hybrid spinach seed, wherein said first and/or second parent spinach plant may comprise the alpha-CMV allele.

Another aspect of the invention relates to a method for identifying or detecting or genotyping or selecting a spinach plant carrying the alpha-CMV allele, which may comprise determining or detecting or measuring or quantitatively or qualitatively ascertaining or assaying a plant for the presence (or absence) of a genomic nucleotide sequence or a part thereof, wherein said sequence has in order of increased preference 80%, 81%, 82%, 83%, 84%, 85%, 86%, 87%, 88%, 89%, 90%, 91%, 92%, 93%, 94%, 95%, 96%, 97%, 98%, 99%, 100% sequence similarity to SEQ ID NO:1. Accordingly, the invention comprehends and includes characterizing a spinach plant as carrying or not carrying the alpha-CMV allele comprising determining or detecting or measuring or quantitatively or qualitatively ascertaining or assaying a plant for the presence (or absence) of a genomic nucleotide sequence or a part thereof, wherein said sequence has in order of increased preference 80%, 81%, 82%, 83%, 84%, 85%, 86%, 87%, 88%, 89%, 90%, 91%, 92%, 93%, 94%, 95%, 96%, 97%, 98%, 99%, 100% sequence similarity to SEQ ID NO:1; said method may include extracting or obtaining DNA or RNA of the plant and analysis thereof as to the presence or absence therein of a nucleotide sequence or a part thereof, wherein said sequence has in order of increased preference 80%, 81%, 82%, 83%, 84%, 85%, 86%, 87%, 88%, 89%, 90%, 91%, 92%, 93%, 94%, 95%, 96%, 97%, 98%, 99%, 100% sequence similarity to SEQ ID NO:1. By using the sequence information and the methods described herein, the skilled person is able to identify or detect or genotype or select a spinach plant carrying the alpha-CMV allele, by using SEQ ID NO:21, wherein said sequence has in order of increased preference 80%, 81%, 82%, 83%, 84%, 85%, 86%, 87%, 88%, 89%, 90%, 91%, 92%, 93%, 94%, 95%, 96%, 97%, 98%, 99%, 100% sequence similarity to SEQ ID NO:21. It is further understood that within the ambit of the invention one can also analyze expression product(s) such as a coding sequence or protein or parts thereof, of a spinach plant to ascertain that from which the product(s) was/were expressed, from which it can be determined whether the plant has (or does not have) a genomic nucleotide sequence or a part thereof, wherein said sequence has in order of increased preference 80%, 81%, 82%, 83%, 84%, 85%, 86%, 87%, 88%, 89%, 90%, 91%, 92%, 93%, 94%, 95%, 96%, 97%, 98%, 99%, 100% sequence similarity to SEQ ID NO: 1. Such a coding sequence would have in order of increased preference 80%, 81%, 82%, 83%, 84%, 85%, 86%, 87%, 88%, 89%, 90%, 91%, 92%, 93%, 94%, 95%, 96%, 97%, 98%, 99%, 100% sequence similarity to SEQ ID NO:2 and/or SEQ ID NO:3, whereas a protein has an amino acid sequence which has in order of increased preference 95%, 96%, 97%, 98%, 99%, 100% sequence similarity to SEQ ID NO:4 and/or to SEQ ID NO:5.

In one embodiment, a method for identifying or selecting a spinach plant carrying the alpha-CMV allele may comprise determining the presence of a genomic nucleotide sequence or a part thereof in the genome of a plant, wherein said sequence has in order of increased preference 80%, 81%, 82%, 83%, 84%, 85%, 86%, 87%, 88%, 89%, 90%, 91%, 92%, 93%, 94%, 95%, 96%, 97%, 98%, 99%, 100% sequence similarity to SEQ ID NO:1.

In one embodiment, a method for identifying or selecting a spinach plant carrying the alpha-CMV allele may comprise determining the presence of a genomic nucleotide sequence or a part thereof in the genome of a plant, wherein said sequence has in order of increased preference 80%, 81%, 82%, 83%, 84%, 85%, 86%, 87%, 88%, 89%, 90%, 91%, 92%, 93%, 94%, 95%, 96%, 97%, 98%, 99%, 100% sequence similarity to SEQ ID NO:21.

The invention further relates to a method for identifying or selecting a spinach plant carrying the alpha-CMV allele which may comprise determining the presence of a coding sequence or a part thereof in the genome of a plant, wherein said sequence has in order of increased preference 80%, 81%, 82%, 83%, 84%, 85%, 86%, 87%, 88%, 89%, 90%, 91%, 92%, 93%, 94%, 95%, 96%, 97%, 98%, 99%, 100% sequence similarity to SEQ ID NO:2.

The invention further relates a method for identifying or selecting a spinach plant carrying the alpha-CMV allele which may comprise determining the presence of a coding sequence or a part thereof in the genome of a plant, wherein said sequence has in order of increased preference 80%, 81%, 82%, 83%, 84%, 85%, 86%, 87%, 88%, 89%, 90%, 91%, 92%, 93%, 94%, 95%, 96%, 97%, 98%, 99%, 100% sequence similarity to SEQ ID NO:3.

Determining the genomic DNA or coding DNA sequence of at least part of a WOLF gene, to which the alpha-CMV allele belongs, in the genome of a spinach plant may be performed using any suitable molecular biological method known in the art, including but not limited to (genomic) PCR amplification followed by Sanger sequencing, whole-genome-sequencing, transcriptome sequencing, sequence-specific target capture followed by next-generation sequencing (using, for example, the xGen® target capture system of Integrated DNA Technologies), specific amplification of LRR-domain-which may comprise gene sequences (using, for example, the Resistance Gene Enrichment Sequencing (RenSeq) methodology, as described in Jupe et al., 2013, *Plant J.* 76: 530-544) followed by sequencing, etcetera.

In another embodiment, the invention relates to a method for identifying or selecting a plant carrying the alpha-CMV allele may comprise determining the DNA sequence coding for the LRR domain as defined herein.

In a further embodiment of the method, the LRR domain of the alpha-CMV allele is determined by using a primer pair to amplify the genomic DNA region of the LRR domain. The forward primer is preferably a nucleic acid molecule which may comprise the sequence of SEQ ID NO:6 and the reverse primer is preferably a nucleic acid molecule which may comprise the sequence of SEQ ID NO:7.

Another aspect of the invention relates to a method for producing a spinach plant which may comprise resistance to CMV which may comprise: (a) crossing a plant which may comprise the alpha-CMV allele, with another plant; (b) optionally performing one or more rounds of selfing and/or crossing; (c) optionally selecting after each round of selfing or crossing for a plant that may comprise the alpha-CMV allele.

Selecting a plant which may comprise the alpha-CMV allele may be done genotypically by determining the presence of the genomic DNA sequence of the allele having in order of increased preference 80%, 81%, 82%, 83%, 84%, 85%, 86%, 87%, 88%, 89%, 90%, 91%, 92%, 93%, 94%, 95%, 96%, 97%, 98%, 99%, 100% sequence similarity to SEQ ID NO:1.

Selecting a plant which may comprise the alpha-CMV allele may be done genotypically by determining the presence of the genomic DNA sequence of the allele having in order of increased preference 80%, 81%, 82%, 83%, 84%, 85%, 86%, 87%, 88%, 89%, 90%, 91%, 92%, 93%, 94%, 95%, 96%, 97%, 98%, 99%, 100% sequence similarity to SEQ ID NO:21.

In another embodiment, selecting a plant which may comprise the alpha-CMV allele may be done genotypically by determining the presence the coding sequence of an allele having in order of increased preference 80%, 81%, 82%, 83%, 84%, 85%, 86%, 87%, 88%, 89%, 90%, 91%, 92%, 93%, 94%, 95%, 96%, 97%, 98%, 99%, 100% sequence similarity to SEQ ID NO:2.

In another embodiment, selecting a plant which may comprise the alpha-CMV allele may be done genotypically by determining the presence the coding sequence of the allele having in order of increased preference 80%, 81%, 82%, 83%, 84%, 85%, 86%, 87%, 88%, 89%, 90%, 91%, 92%, 93%, 94%, 95%, 96%, 97%, 98%, 99%, 100% sequence similarity to SEQ ID NO:3.

Alternatively, the presence of the alpha-CMV allele may be determined phenotypically by assaying a plant in a disease test, for example the test as described herein, and identifying or selecting a plant carrying the alpha-CMV allele based on the absence of symptoms as described herein.

The invention further relates to the use of a spinach plant carrying the alpha-CMV allele in breeding to confer resistance against CMV.

The invention also relates to a breeding method for the development of spinach plants carrying the alpha-CMV allele of the invention wherein germplasm which may comprise said allele is used. Seed capable of growing into a plant which may comprise the allele of the invention and being representative for the germplasm was deposited with the NCIMB under deposit number NCIMB 42651.

In another aspect, the invention relates to a method for the production of a spinach plant which may comprise the alpha-CMV allele, which method may comprise: (a) crossing a plant which may comprise the allele with another plant; (b) optionally selecting for plants which may comprise said allele in the F1; (c) optionally backcrossing the resulting F1 with the preferred parent and selecting for plants that have the said allele in the BC1F1; (d) optionally performing one or more additional rounds of selfing, crossing, and/or backcrossing, and subsequently selecting for a plant which may comprise the said allele or shows resistance to CMV as conferred by said allele. The invention also encompasses a spinach plant produced by this method.

The invention also relates to the use of a spinach plant, of which representative seed was deposited with the NCIMB under accession number NCIMB 42651, in the production of a spinach plant which may comprise the alpha-CMV allele.

The invention also relates to a harvested leaf of a spinach plant of the invention and to a food product which may comprise a harvested leaf of a spinach plant of the invention, either in natural or in processed form.

The invention further relates to the use of a spinach plant which may comprise the alpha-CMV allele, for consumption.

Spinach leaves are usually sold in packaged form, including without limitation as pre-packaged spinach leaves or as processed in a salad which may comprise said leaves. Mention of such a package is e.g. made in U.S. Pat. No. 5,523,136, which provides packaging film, and packages from such packaging film, including such packaging containing leafy produce, and methods for making and using such packaging film and packages, which are suitable for use with the spinach leaves of the invention. Thus, the invention comprehends the use of and methods for making and using the leaves of the spinach plant of the invention, as well as leaves derived of spinach plants from the invention.

The invention further relates to a container which may comprise one or more plants of the invention, or one or more spinach plants derived from a plant of the invention, in a growth substrate for harvest of leaves from the plant, in a domestic environment. This way the consumer may pick very fresh leaves for use in salads, when the plant is in a ready-to-harvest condition.

Sequence Information

TABLE 1

| Sequence information. | |
|---|---|
| SEQ ID NO: 1: Genomic sequence of alpha-CMV (with a 2 kb region upstream of the start codon) | TTTGAAGTTAGGCTTAACTTGCTCACCAATTCTTAAATAGAC<br>TCGACTTACACTGAATTTATTGTGTACTATGTCTAGAAAGTA<br>AGGTCAACAACTTTCTTCTAAATTATTTTGGCATGTTTATTAG<br>GGTTATTATGAAAAACATATCAAATTGGTGTTGTTAGTTAGG<br>CTTGAATAATATGATTTTAAGTCACGAGACTTTTATAAATTA<br>GGTAATTTGATTTAAAAAATTGTTACATATCTAAGAAAATGG<br>ATGTTAAATTTATCAGTCAATGTATAAACAATAAAAGTCAAT<br>ATGTATGTAAAAGGGTTGCTAGATAAAATCTTTGGTTTTTTG<br>GTCCACAACTCCACACTAAGAGGAACTCCAATGCTTAGTTAC<br>AAGGTGGTGTAGTTAAAAAGTAACTCCAATAGTTAACTACA<br>CGGTATTATAGTTAAATTTGCCAACTCAAATTTCTAACTACA<br>ATATATTTAAGCTACAAAGTTTCTCATTGGCTGACTACAATA<br>CGTTGTAGCGCCTTATAATATTTTATTCAATATACAATTTTAT<br>TTATTTTACCTTTTTAACAATTTTTTTTTGATCTACCTGCTGTC<br>CTGTTCATATGAGCTACACTAATTTGATAGCTGCTTACGCAA<br>TTCTTATATCAACGGTTGGCTACTTGTTCAAATATTTTTATTT<br>TTTTACGAGTAAGTCATTTTATGATCATTGAAGTGGCTCTAT<br>TATTATTATCATGCACCGATTAACGCAAGAATAATTAACTCG<br>GTACGAATTAGTTTCAAAATAAAATCCCTCAAAAAAAAAAG<br>TTTCAAAATAAAATTAACAGAAAACCAACCTTCTCCGGTTTA<br>CTGTTGTTAGAGCATGGAATTTTCCAGTAATCGCAGACCCCA<br>AATTATCTTCCAGTTGAATCAATCCTTGATTTTTGGATTTGCC<br>AGAAAACTCCTTGAATTTTAGGGTTCATATTTGATCCGTAAT<br>TGGGAAAATTTTCAGCAATTGATCTTCCAAATCAGCCCTACT<br>TGTTTCCAGACTGCAAATGAAAGGTGCGAACTTTATACTGCA<br>TTTTGGTTTTCCATTAGTGTAATTTATTAAGATGAACTGCATT<br>TTGCAATTGTTTTATTCGACTACTCATTTTTAAATCAAATTGC<br>TTAATTGCTAGTTAGTTTTCTTATCATATTGCCAAAAAAAAT<br>TATTTTTGTTTAATTGGTGAAAAAGGGTAAATTATACCTAGT<br>GTACAAGATTTTCTTGCACACCACCGTTAATTTGTTGACACA<br>TCATCAAACGTACTGAAAAATGAGAATGAAAGACAATAAAT<br>ATGTCATTTTAACCAATAGAAAAACATGATGTAGTAAGATC<br>CTTAATTGATAGATAAATAATTAAATATCAGTCCATTAGTTG<br>AATATTCAATGAAAATGTATGGTCCAAAAATGGCGTTTAAT<br>AGTCAATGTCATGCTTTATGGGGTGGTGGAGTACTATGTGAC<br>TGTGTGTGGACTTGGAGAAGACTAGAGAGTATGATTATCAA<br>CCTATGGACCCTCAAAATGAAAATGAAAATGATGTTTACAC<br>GTGCTATTTGCACGGACTTCAATGCAAATAGTATAAATTTAC<br>GGTCAAAGTTTTCATTCTAAAGCGTAAATAACTTTCATGAAT<br>GGAGGACGGTAGTATAAGTATAACGTTATAGCCTACCATTTT<br>CTTATCATATTCACATAAATTTGTTGCTGAAATTTGTTTTACT<br>TGGCTAAAATACTTTTGTTCTTATTGGCAGATAAACATCAGT<br>ACGTCCATTATTGGCCAACTTGCTGAGTCCATTATTGGCCAA<br>CTTGAACATATACCTCCAAACAATAATCAATAATGTCGATTA<br>TGAAGTTTGTGAATGCAATTTATTATCACTTTCATTTATAAA<br>ATGACTACTTGATTAACACATACAATATTACCTTTCTCCAAA<br>CACCCTTTCAATTCTGCTTAATCTTGTTTTCTCATCATCTCTT<br>CATCTTTCTGAAAACACAACCCA**ATG**GCCGAAATCGGATAC<br>TCGGTTTGTGCGAAACTCATCGAAGTGATTGGCAGTGAGCTG<br>ATCAAAGAGATTTGTGACACATGGGGTTACAAATCTCTTCTT<br>GAGGACCTCAACAAAACTGTATTGACGGTCAGGAACGTTCT<br>CATTCAAGCCGGGGTGATGCGGGAGCTTACTAGTGAACAAC<br>AAGGTTTCATTGCAGACCTTAAAGATGTTGTTTATGATGCTG<br>ATGACTTGTTCGACAAGTTACTCACTCGTGCTGAGCGAAAAC<br>AGATTGATGGAAACGAAATCTCTGAAAAGGTACGTCGTTTC<br>TTTTCCTCTAGTAACAAGATCGGTCAAGCTTACTACATGTCT<br>CGTAAGGTTAAGGAAATTAAGAAGCAGTTGGATGAAATTGT<br>TGATAGGCATACAAAATTTGGGTTTAGTGCTGAGTTTATACC<br>TGTTTGTAGGGGAAGGGGAAACGAGAGGGAAACACGTTCAT<br>ATATAGATGTCAAGAATATTCTTGGGAGGGATAAAGATAAG<br>AATGATATCATAGATAGGTTGCTTAATCGTAATGGTAATGAA<br>GCTTGTAGTTTCCTGACCATAGTGGGAGCGGGAGGATTGGG<br>AAAAACTGCTCTTGCACAACTTGTGTTCAATGATGAAAGGGT<br>CAAAATTGAGTTCCATGATTTGAGGTATTGGGTTTGTGTCTC<br>TGATCAAGATGGGGGCCAATTTGATGTGAAAGAAATCCTTT<br>GTAAGATTTTAGAGGTGGTTACTAAGGAGAAAGTTGATAAT<br>AGTTCCACATTGGAATTGGTACAAAGCCAATTTCAAGAGAA<br>GTTAAGAGGAAAGAAGTACTTCCTTGTTCTTGATGATGTATG<br>GAACGAAGATCGTGAGAAGTGGCTTCCTTTGGAAGAGTTGT<br>TAATGTTGGGTCAAGGGGGAAGCAAGGTTGTAGTGACCACA<br>CGTTCAGAGAAGACAGCAAATGTCATAGGGAAAAGACATTT<br>TTATACACTGGAATGTTTGTCACCAGATTATTCATGGAGCTT |

TABLE 1-continued

| Sequence information. |
|---|
| ATTTGAAATGTCGGCTTTTCAGAAAGGGCATGAGCAGGAAA<br>ACCATCACGAACTAGTTGATATTGGGAAAAAGATTGTTGAA<br>AAATGTTATAACAATCCACTTGCTATAACGGTGGTAGGAAG<br>TCTTCTTTATGGAGAGGAGATAAGTAAGTGGCGGTCATTTGA<br>AATGAGTGAGTTGGCCAAAATTGGCAATGGGGATAATAAGA<br>TTTTGCCGATATTAAAGCTCAGTTACCATAATCTTATACCCT<br>CGTTGAAGAGTTGTTTTAGTTATTGTGCAGTGTTTCCCAAGG<br>ATCATGAAATAAAGAAGGAGATGTTGATTGAACTTTGGATG<br>GCACAAGGATATGTTGTGCCGTTGGATGGAGGTCAAAGTAT<br>AGAAGATGCTGCCGAGGAACATTTTGTAATTTTGTTACGAAG<br>GTGTTTCTTTCAAGATGTAAAGAAGGATAAATATGGTGATGT<br>TGATTCTGTTAAAATCCACGACTTGATGCACGATGTCGCCCA<br>AGAAGTGGGGAGGGAGGAATTATGTGTAGTGAATGATAATA<br>CAAAGAACTTGGGTGATAAAATCCGTCATGTACATCGTGAT<br>GTCATTAGATATGCACAAAGAGTCTCTCTGTGTAGCCATAGC<br>CATAAGATTCGTTCGTATATTGGTGGTAATTGTGAAAAACGT<br>TGTGTGGATACACTAATAGACAAGTGGATGTGTCTTAGGAT<br>GTTGGACTTGTCATGGTCGGATGTTAAAAATTTGCCTAATTC<br>AATAGGTAAATTGTTGCACTTGAGGTGTCTTAACCTGTCTTA<br>TAATAAAGATCTGTTGATACTCCCTGATGCAATTACAAGACT<br>GCATAATTTGCAGACACTGCTTTTAAAAGAGTGCAGAAGTTT<br>AAAGGAGTTGCCAAAAGATTTTTGCAAATTGGTCAAACTGA<br>GGCACTTGGATTTAAGGTGTTCTGATTTGAAGGAGTTGCCAA<br>AAGATTTTTGCAAATTGGTCAAACTGAGGCACTTGGATTTAT<br>GGGGTTGTGATGATTTGATTGGTGTGCCATTGGGAATGGATA<br>GGCTAATTAGTCTTAGAGTACTGCCATTCTTTGTGGTGGGTA<br>GGAAGGAACAAAGTGATGATGATGAGCTGAAAGCCCTAAA<br>AGGCCTCACCGAGATAAAAGGCTCCATTCGTATTAGAATCT<br>ATTCAAAGTATAGAATAGTTGAAGGCATGAATGACACAGGA<br>GGAGCTGGGTATTTAAAGAGCATGAAACATCTCACGGGGGT<br>TGATATTACATTTGATGGTGGATGTGTTAACCCTGAAGCTGT<br>GTTGGCAACCCTAGAGCCACCTTCAAATATCAAGAGGTTAG<br>AGATGTGGCATTACAGTGGTACAACAATTCCAGTATGGGGA<br>AGAGCAGAGATTAATTGGGCAATCTCCCTCTCACATCTTGTC<br>GACATCCAGCTTTGGCATTGTCGTAATTTGCAGGAGATGCCA<br>GTGCTGAGTAAACTGCCTCATTTGAAATCACTGGAACTTTAT<br>AATTTGATTAGTTTAGAGTACATGGAGAGCACAAGCAGAAG<br>CAGTAGCAGTGACACAGAAGCAGCAACACCAGAATTACCAA<br>CATTCTTCCCTTCCCTTGAAAAACTTACACTTTGGCGTCTGG<br>ACAAGTTGAAGGGTTTTGGGAACAGGAGATCGAGTAGTTTT<br>CCCCGCCTCTCTAAATTGGAAATCTGGAAATGCCCAGATCTA<br>ACGTCATTTCCTTCTTGTCCAAGCCTTGAAGAGTTGGAATTG<br>AAAGAAAACAATGAAGCATTGCAAATAATAGTAAAAATAAC<br>AACAACAAGAGGTAAAGAAGAAAAAGAAGAAGACAAGAAT<br>GCTGGTGTTGGAAATTCACAAGATGATGACAATGTCAAATT<br>ATGGACGGTGGAAATAGACAATCTGGGTTATCTCAAATCAC<br>TGCCCACAAATTGTCTTACTCTGTTGGACTCACTCGAACTTT<br>CAAATATAGAAGACCAGGAAGATGAGGGCGAAGACAACAT<br>CATATTCTGGAAATCCTTTCCTCAAAACCTCCGCAGTTTGGA<br>AATTGAAAACTCTTACAAAATGACAAGTTTGCCCATGGGGA<br>TGCAGTACTTAACCTCCCTCCAAACCCTCTATCTACACCATT<br>GTTATGAATTGAATTCCCTTCCAGAATGGATAAGCAGCTTAT<br>CATCTCTTCAATCCCTGCACATAGGAAAATGTCCAGCCCTAA<br>AATCACTACCAGAAGCAATGCGGAACCTCACCTCCCTTCAG<br>ACACTTGGGATATCGCGGTGTCCAGACCTAATTGAAAGATG<br>CGAAGAACCCAACGGCGAGGACTATCCCAAAATTCAACACA<br>TCCCCAAAATTGTAAGTCATTGCAGAAAGTAATTTATTCATT<br>TATATTTATTTTATGCTTAGAATGATATACACCGTCGTCCTTT<br>GGTTTCAAATCTTGAATTTGGTTTTTGTTTTCTTTCTTTGTTTC<br>TTTATTCAACACCAGCCCATTTATGATTGATTCATTAAAAAA<br>AGGATGGAGTTTTGTGGATTTGAAGAAGACAACGAATTGAG<br>ATTCCTGGGGTTTTCTTTTTGTTGGGGTTGGATTTCATGTATA<br>TGTTGCTGATTAAATACGAGACTGATGATGATGATGATGTGT<br>TTATGGGTTTTAAATCAGATTAAATATATGGGAAATGTAAGT<br>TAATTTGGGATGCACATAAGGTGTTTGCTGAAATGTCTATGA<br>GAAATGTTGTTTCTTGGACTTAGAATGATATACACTGTCGTC<br>CATTGGTTTCCAATCTTACATTTGGTTTGTGTTTTCTTAGTTT<br>GTTTCTTTAATCAACACCAACCCATTTTTTTAAAACTACCTGC<br>AACTACTAATTTACGTTGACCCTGTATCTCAGGTACTAAATG<br>AATATTGGTGATTTTCAGTTACTCAACACTAGCTTGATCCTG<br>AACGCACCCAACCTTCAGGTTAGAATCCGGCTTACTCATCCT<br>TTTGTCCAGTTTTCAAGTAATTGTTTTGGCAGGATCAATTCTC<br>TAATTGTTGTACACCGTATATTGCAATTTATAGTGACTACAG<br>TTAATGAATGTTTACAAAAAATTAGTCATGTAAAAACTTCTT<br>CTCTGTCCATTACATAAACTCTTTTTCTCTTTCTAACTTATCA<br>TGTTCATGTCTAAAAAATTAAACATGCTCACATCAATGTTCA<br>TTTAAGCTAACTTACTTCTGTAAGAGAGCGAGCTAGTTAAAA<br>ACTCCTTTAACTTTCTGTTTTATACTCAGGACATGGATTGATG |

TABLE 1-continued

| Sequence information. |
|---|
| CAAGCATGAAGAACTTCGGGAATTTGCTAAAACTCTACCAA |
| AGCGATGAGAGTTTGGACTTTGTTTCACTTGAAGTCAGGGAC |
| TGTCAACAAAGCCACAGTGTGCATGTTGGCTGTTTCACTTGG |
| ACGATAAAAAGGTTTATTTAATTGTTTTCCTAAGTGTATTTG |
| GCTTACAAGCTTTTACTTTTCGCTTGAAAGGGTTTTTCTTGTT |
| TTAAGCTTTTTGAATTAGAGTTTCGGTTGAAGTAAGAGTAGT |
| CGTATTAGTCTTTTACTTTGCAGGAGTCTATGCCTATATAAG |
| GTAAGACTCGTATTTGTAATTTTCAGATTATGCAATTCAAGT |
| TTTCGAGTGTTTTCTTAAAAAAACATATCATACCTGTGTGTA |
| GCATAAAGATAAATTCTGATGCTGTGCTTCTTGTTATGGCTC |
| ACATTGGTTTTCATTGTTTGGATTGTTTCACAGGGAAGCAGA |
| GAATACCTGGAACCTGTAAAGGACGCTATATCTATAGCAGC |
| TTTCACAGGCCAAGTAATATAATGTTCTTTATCAATCACTCA |
| ATACCTGGAGATTGTTTGAACACATAATTCACCTCTTTTTTTC |
| CATCTCAAATTGCAGACTTTTACTGGGATTTGAATGACAGCA |
| AACATTTGATTGTCACGAGGATTGATCTAACTGGTGAATGTT |
| GTGATCACCATATTGGTCTTTCTCATTCAAACAAACTTGCAT |
| ACCGTTCTTTTGAAGTTTGAAGACAAGCAGGCGATAATCAA |
| CTCAGGTCGAAGCTCATGTGCAGGAGAGAATAGAATATAGA |
| GGAGATTATTTTTAAAAGAAACGCTCAAAGGTATTGTAGCA |
| CCTTTCCTATTTGCTACTGCAGTGATGTTTTTATTTCTTGTTT |
| GCAGCGCTTGTTTCTCATATTTCAACCTACTTTTAGAAAAAA |
| AAACATCTCCGAACATAACCAAAAATAAAGTTCCCTTATCA |
| GTGCTTTCCCTGCTTTCTTCTAAACAACATATACAATTATAA |
| ACCCTTTTTCTCTCTTACCTTTGTTATTCTTCCTTGCTTCATTG |
| AGATAACACTCTCCTGTTTTTGTTTTGTTGTTAGTCATTACAT |
| GGATATATCAAGGACAACAGTTCTGTAGTCCGTCAACTGTG |
| GTTAGGAAGGCTAAACTGGAGCACAATAACCCCATGTCAAT |
| TGAATAGTAAAGGTGTGCTATATCAGTTTCGTTTGGCTTGGC |
| TTACCTGAAAAATGGCTGGTTATTTATCCTTGTCTCTTTCTAT |
| GACGTGCAGTGGCTTGTTAATGTGTCTCGGACAACAATTCCT |
| CACTTTCCAAGTTCCATACACGCTGATGTAACTATCTTCTGC |
| AGTCTGTTCTTTCATTTTTGCCACGTGCTCTAATTATAACTTT |
| TTGTACTCAATAATCAACTCCTTGTCCCGGTATTTGCAGAGA |
| CTACTTAAACAGGTAAAGTGACAATCCTGGCGAAGTTGTCT |
| GTTTCTTAGCTCTGAACCCATCATTCAGGTAAGATTAAGTAT |
| TTAAGAAGAAATTTTGTTTTTACCTAAAATGAATGATCTTGT |
| GTAACTGCTTGCTTCTTGCATTAAATAAGAACTTTCTGCTGC |
| ATATGTGACAGTTACATCCACAAAAAAGTTGGAGGTTTGTTC |
| AGGGATTGGAAATGAAGGTACTTCAGAATTCCTGGAATGTT |
| TATGAATGCTCCAGACTTCAGAGTCTTTAATGGAAAATTCGA |
| GTCACTAAAAAAACATTATTCCTATCATCAGAGCTTTGAAGT |
| TCCTCTATACAAGGTCAACTGAGTTCCTCTTTGCCTCTTGTTT |
| AATTGTATTTACTTGTACCTTAATTATAATCTGTATATTGTTT |
| TAGTTAAGTTCTAAAACAGGTTATTATTCATCATTTGTGCAG |
| CATATTGCTGGAATCAAGAATCTAGTGCTTCTTCTTCCTGAC |
| TTCACTGTCAAAATAGCAGTTCCCATGCTGGAAATAAGCGC |
| GCTAGCAATGTAATTGATGACATGGATGTTGCTGCTTCTGAG |
| TTTTGATCATAAAAAGCTGTTATGTGTTTCTTGAATGTAATG |
| AAGGAGAGGAGAAAACTGAAAACTCTTGGCAAAAACGTGA |
| AATTGCAGTGCCTCGGGGTGGTAGGGATCACCCGGATTCAG |
| TTCAGACGATACTTTTTTCAACCCGGTTTGTTCCGGTTTTCAG |
| CTTCGGGTTTTCCTTGTACTTTTGGGGCACACATACAAGGCT |
| ACTTCATGTTTGAGAAACCTAATTGAGGCTATCTTGTAGCAA |
| ATGCACACCACACTCTTTCTCTCTTCTCTCCTTTTTTCACCTT |
| CCATTTGTAAAAATCCTCTTTTAAAGGTTAATAAAAAAAAGC |
| TTCAAGTCTCGTAGGGTGGATGTAGGTCACATTGACCGAACC |
| ACGGTAAACTCTTTGTGTTCTTTCTTCTCTCTTTGTTTCTCATT |
| TTTACGGCAAGTGTTTATGGTTAACCATGCATCTTAGAATAG |
| CTTAAGGCATTAACATAATAACATCAATGTTCTCCAAAGATT |
| CACCTTACTTGTTGTACATAATCACAATGTTAAGCCTATGAA |
| GGTAGAATGCTCTCATGATTTGGTTTAACCAAAAAATAAACT |
| CTAAAATAATACGGAGTAATAAAAATTGGCCATAAATTATT |
| TACAAAGTTTGATTTTTGTATAGGGTATCTTGTACTTGTGAT |
| AAAAAAAATTAAAAAAAAAAAAATTACTTATTTCTTCTATTT |
| TTACTTGTTACACTTTTCTACAACAGAAACATCAAAACGCCC |
| GCAACACACTATAAATGAAAAACCATTTTGTATGCAATGAT |
| ATTTACGTTCTCACTTTATTCTCTTTAATAACTCCTACTACGT |
| AATTCTCACCAATCAAATAAAATTATAGAAATTTTCATTTAT |
| ACCCTCTTAAAATGATGTTGATTTNNNNNNNNNNNNNNNNN |
| NNNNNNNNNNNNNNNNNNNNNNNNNAGGTGTGAAAAAGTT |
| TGTGTTATAAGTTACAACAATTTAAAAACGGAGAACATACTT |
| ATAATACTAGTGTAATCTTTGGCCGGATTATGGTCGTTGACA |
| AAAAAACTCCGGCCTTGACCCTCCACGTGCCGGTCAAGTGA |
| CTTAATAAACCTTTTATTCCACCCTTTTTTCATTCTTCTTTTTA |
| TTCTTCTTTTT |

TABLE 1-continued

| Sequence information. | |
|---|---|
| SEQ ID NO: 2: cds alpha-CMV | ATGGCCGAAATCGGATACTCGGTTTGTGCGAAACTCATCGA<br>AGTGATTGGCAGTGAGCTGATCAAAGAGATTTGTGACACAT<br>GGGGTTACAAATCTCTTCTTGAGGACCTCAACAAAACTGTAT<br>TGACGGTCAGGAACGTTCTCATTCAAGCCGGGGTGATGCGG<br>GAGCTTACTAGTGAACAACAAGGTTTCATTGCAGACCTTAA<br>AGATGTTGTTTATGATGCTGATGACTTGTTCGACAAGTTACT<br>CACTCGTGCTGAGCGAAAACAGATTGATGGAAACGAAATCT<br>CTGAAAAGGTACGTCGTTTCTTTTCCTCTAGTAACAAGATCG<br>GTCAAGCTTACTACATGTCTCGTAAGGTTAAGGAAATTAAG<br>AAGCAGTTGGATGAAATTGTTGATAGGCATACAAAATTTGG<br>GTTTAGTGCTGAGTTTATACCTGTTTGTAGGGGAAGGGGAAA<br>CGAGAGGGAAACACGTTCATATATAGATGTCAAGAATATTC<br>TTGGGAGGGATAAAGATAAGAATGATATCATAGATAGGTTG<br>CTTAATCGTAATGGTAATGAAGCTTGTAGTTTCCTGACCATA<br>GTGGGAGCGGGAGGATTGGGAAAAACTGCTCTTGCACAACT<br>TGTGTTCAATGATGAAAGGGTCAAAATTGAGTTCCATGATTT<br>GAGGTATTGGGTTTGTGTCTCTGATCAAGATGGGGGCCAATT<br>TGATGTGAAAGAAATCCTTTGTAAGATTTTAGAGGTGGTTAC<br>TAAGGAGAAAGTTGATAATAGTTCCACATTGGAATTGGTAC<br>AAAGCCAATTTCAAGAGAAGTTAAGAGGAAAGAAGTACTTC<br>CTTGTTCTTGATGATGTATGGAACGAAGATCGTGAGAAGTG<br>GCTTCCTTTGGAAGAGTTGTTAATGTTGGGTCAAGGGGGAA<br>GCAAGGTTGTAGTGACCACACGTTCAGAGAAGACAGCAAAT<br>GTCATAGGGAAAAGACATTTTTATACACTGGAATGTTTGTCA<br>CCAGATTATTCATGGAGCTTATTTGAAATGTCGGCTTTTCAG<br>AAAGGGCATGAGCAGGAAAACCATCACGAACTAGTTGATAT<br>TGGGAAAAAGATTGTTGAAAAATGTTATAACAATCCACTTG<br>CTATAACGGTGGTAGGAAGTCTTCTTTATGGAGAGGAGATA<br>AGTAAGTGGCGGTCATTTGAAATGAGTGAGTTGGCCAAAAT<br>TGGCAATGGGGATAATAAGATTTTGCCGATATTAAAGCTCA<br>GTTACCATAATCTTATACCCTCGTTGAAGAGTTGTTTTAGTT<br>ATTGTGCAGTGTTTCCCAAGGATCATGAAATAAAGAAGGAG<br>ATGTTGATTGAACTTTGGATGGCACAAGGATATGTTGTGCCG<br>TTGGATGGAGGTCAAAGTATAGAAGATGCTGCCGAGGAACA<br>TTTTGTAATTTTGTTACGAAGGTGTTTCTTTCAAGATGTAAA<br>GAAGGATAAATATGGTGATGTTGATTCTGTTAAAATCCACG<br>ACTTGATGCACGATGTCGCCCAAGAAGTGGGGAGGGAGGAA<br>TTATGTGTAGTGAATGATAATACAAAGAACTTGGGTGATAA<br>AATCCGTCATGTACATCGTGATGTCATTAGATATGCACAAAG<br>AGTCTCTCTGTGTAGCCATAGCCATAAGATTCGTTCGTATAT<br>TGGTGGTAATTGTGAAAAACGTTGTGTGGATACACTAATAG<br>ACAAGTGGATGTGTCTTAGGATGTTGGACTTGTCATGGTCGG<br>ATGTTAAAAATTTGCCTAATTCAATAGGTAAATTGTTGCACT<br>TGAGGTGTCTTAACCTGTCTTATAATAAAGATCTGTTGATAC<br>TCCCTGATGCAATTACAAGACTGCATAATTTGCAGACACTGC<br>TTTTAAAAGAGTGCAGAAGTTTAAAGGAGTTGCCAAAAGAT<br>TTTTGCAAATTGGTCAAACTGAGGCACTTGGATTTAAGGTGT<br>TCTGATTTGAAGGAGTTGCCAAAAGATTTTTGCAAATTGGTC<br>AAACTGAGGCACTTGGATTTATGGGGTTGTGATGATTTGATT<br>GGTGTGCCATTGGGAATGGATAGGCTAATTAGTCTTAGAGT<br>ACTGCCATTCTTTGTGGTGGGTAGGAAGGAACAAAGTGATG<br>ATGATGAGCTGAAAGCCCTAAAAGGCCTCACCGAGATAAAA<br>GGCTCCATTCGTATTAGAATCTATTCAAAGTATAGAATAGTT<br>GAAGGCATGAATGACACAGGAGGAGCTGGGTATTTAAAGAG<br>CATGAAACATCTCACGGGGGTTGATATTACATTTGATGGTGG<br>ATGTGTTAACCCTGAAGCTGTGTTGGCAACCCTAGAGCCACC<br>TTCAAATATCAAGAGGTTAGAGATGTGGCATTACAGTGGTA<br>CAACAATTCCAGTATGGGGAAGAGCAGAGATTAATTGGGCA<br>ATCTCCCTCTCACATCTTGTCGACATCCAGCTTTGGCATTGTC<br>GTAATTTGCAGGAGATGCCAGTGCTGAGTAAACTGCCTCATT<br>TGAAATCACTGGAACTTTATAATTTGATTAGTTTAGAGTACA<br>TGGAGAGCACAAGCAGAAGCAGTAGCAGTGACACAGAAGC<br>AGCAACACCAGAATTACCAACATTCTTCCCTTCCCTTGAAAA<br>ACTTACACTTTGGCGTCTGGACAAGTTGAAGGGTTTTGGGAA<br>CAGGAGATCGAGTAGTTTTCCCCGCCTCTCTAAATTGGAAAT<br>CTGGAAATGCCCAGATCTAACGTCATTTCCTTCTTGTCCAAG<br>CCTTGAAGAGTTGGAATTGAAAGAAAACAATGAAGCATTGC<br>AAATAATAGTAAAAATAACAACAACAAGAGGTAAAGAAGA<br>AAAAGAAGAAGACAAGAATGCTGGTGTTGGAAATTCACAAG<br>ATGATGACAATGTCAAATTATGGACGGTGGAAATAGACAAT<br>CTGGGTTATCTCAAATCACTGCCCACAAATTGTCTTACTCTG<br>TTGGACTCACTCGAACTTTCAAATATAGAAGACCAGGAAGA<br>TGAGGGCGAAGACAACATCATATTCTGGAAATCCTTTCCTCA<br>AAACCTCCGCAGTTTGGAAATTGAAAACTCTTACAAAATGA<br>CAAGTTTGCCCATGGGGATGCAGTACTTAACCTCCCTCCAAA<br>CCCTCTATCTACACCATTGTTATGAATTGAATTCCCTTCCAG<br>AATGGATAAGCAGCTTATCATCTCTTCAATCCCTGCACATAG |

TABLE 1-continued

| Sequence information. | |
|---|---|
| | GAAAATGTCCAGCCCTAAAATCACTACCAGAAGCAATGCGG<br>AACCTCACCTCCCTTCAGACACTTGGGATATCGCGGTGTCCA<br>GACCTAATTGAAAGATGCGAAGAACCCAACGGCGAGGACTA<br>TCCCAAAATTCAACACATCCCCAAAATTGTACTAAATGAATA<br>TTGGTGA |
| SEQ ID NO: 3: cds of alpha-CMV (isoform 1) | ATGGCCGAAATCGGATACTCGGTTTGTGCGAAACTCATCGA<br>AGTGATTGGCAGTGAGCTGATCAAAGAGATTTGTGACACAT<br>GGGGTTACAAATCTCTTCTTGAGGACCTCAACAAAACTGTAT<br>TGACGGTCAGGAACGTTCTCATTCAAGCCGGGGTGATGCGG<br>GAGCTTACTAGTGAACAACAAGGTTTCATTGCAGACCTTAA<br>AGATGTTGTTTATGATGCTGATGACTTGTTCGACAAGTTACT<br>CACTCGTGCTGAGCGAAAACAGATTGATGGAAACGAAATCT<br>CTGAAAAGGTACGTCGTTTCTTTTCCTCTAGTAACAAGATCG<br>GTCAAGCTTACTACATGTCTCGTAAGGTTAAGGAAATTAAG<br>AAGCAGTTGGATGAAATTGTTGATAGGCATACAAAATTTGG<br>GTTTAGTGCTGAGTTTATACCTGTTTGTAGGGGAAGGGGAAA<br>CGAGAGGGAAACACGTTCATATATAGATGTCAAGAATATTC<br>TTGGGAGGGATAAAGATAAGAATGATATCATAGATAGGTTG<br>CTTAATCGTAATGGTAATGAAGCTTGTAGTTTCCTGACCATA<br>GTGGGAGCGGGAGGATTGGGAAAAACTGCTCTTGCACAACT<br>TGTGTTCAATGATGAAAGGGTCAAAATTGAGTTCCATGATTT<br>GAGGTATTGGGTTTGTGTCTCTGATCAAGATGGGGGCCAATT<br>TGATGTGAAAGAAATCCTTTGTAAGATTTTAGAGGTGGTTAC<br>TAAGGAGAAAGTTGATAATAGTTCCACATTGGAATTGGTAC<br>AAAGCCAATTTCAAGAGAAGTTAAGAGGAAAGAAGTACTTC<br>CTTGTTCTTGATGATGTATGGAACGAAGATCGTGAGAAGTG<br>GCTTCCTTTGGAAGAGTTGTTAATGTTGGGTCAAGGGGGAA<br>GCAAGGTTGTAGTGACCACACGTTCAGAGAAGACAGCAAAT<br>GTCATAGGGAAAAGACATTTTTATACACTGGAATGTTTGTCA<br>CCAGATTATTCATGGAGCTTATTTGAAATGTCGGCTTTTCAG<br>AAAGGGCATGAGCAGGAAAACCATCACGAACTAGTTGATAT<br>TGGGAAAAAGATTGTTGAAAAATGTTATAACAATCCACTTG<br>CTATAACGGTGGTAGGAAGTCTTCTTTATGGAGAGGAGATA<br>AGTAAGTGGCGGTCATTTGAAATGAGTGAGTTGGCCAAAAT<br>TGGCAATGGGGATAATAAGATTTTGCCGATATTAAAGCTCA<br>GTTACCATAATCTTATACCCTCGTTGAAGAGTTGTTTTAGTT<br>ATTGTGCAGTGTTTCCCAAGGATCATGAAATAAAGAAGGAG<br>ATGTTGATTGAACTTTGGATGGCACAAGGATATGTTGTGCCG<br>TTGGATGGAGGTCAAAGTATAGAAGATGCTGCCGAGGAACA<br>TTTTGTAATTTTGTTACGAAGGTGTTTCTTTCAAGATGTAAA<br>GAAGGATAAATATGGTGATGTTGATTCTGTTAAAATCCACG<br>ACTTGATGCACGATGTCGCCCAAGAAGTGGGGAGGGAGGAA<br>TTATGTGTAGTGAATGATAATACAAAGAACTTGGGTGATAA<br>AATCCGTCATGTACATCGTGATGTCATTAGATATGCACAAAG<br>AGTCTCTCTGTGTAGCCATAGCCATAAGATTCGTTCGTATAT<br>TGGTGGTAATTGTGAAAAACGTTGTGTGGATACACTAATAG<br>ACAAGTGGATGTGTCTTAGGATGTTGGACTTGTCATGGTCGG<br>ATGTTAAAAATTTGCCTAATTCAATAGGTAAATTGTTGCACT<br>TGAGGTGTCTTAACCTGTCTTATAATAAAGATCTGTTGATAC<br>TCCCTGATGCAATTACAAGACTGCATAATTTGCAGACACTGC<br>TTTTAAAAGAGTGCAGAAGTTTAAAGGAGTTGCCAAAAGAT<br>TTTTGCAAATTGGTCAAACTGAGGCACTTGGATTTAAGGTGT<br>TCTGATTTGAAGGAGTTGCCAAAAGATTTTTGCAAATTGGTC<br>AAACTGAGGCACTTGGATTTATGGGGTTGTGATGATTTGATT<br>GGTGTGCCATTGGGAATGGATAGGCTAATTAGTCTTAGAGT<br>ACTGCCATTCTTTGTGGTGGGTAGGAAGGAACAAAGTGATG<br>ATGATGAGCTGAAAGCCCTAAAAGGCCTCACCGAGATAAAA<br>GGCTCCATTCGTATTAGAATCTATTCAAAGTATAGAATAGTT<br>GAAGGCATGAATGACACAGGAGGAGCTGGGTATTTAAAGAG<br>CATGAAACATCTCACGGGGGTTGATATTACATTTGATGGTGG<br>ATGTGTTAACCCTGAAGCTGTGTTGGCAACCCTAGAGCCACC<br>TTCAAATATCAAGAGGTTAGAGATGTGGCATTACAGTGGTA<br>CAACAATTCCAGTATGGGGAAGAGCAGAGATTAATTGGGCA<br>ATCTCCCTCTCACATCTTGTCGACATCCAGCTTTGGCATTGTC<br>GTAATTTGCAGGAGATGCCAGTGCTGAGTAAACTGCCTCATT<br>TGAAATCACTGGAACTTTATAATTTGATTAGTTTAGAGTACA<br>TGGAGAGCACAAGCAGAAGCAGTAGCAGTGACACAGAAGC<br>AGCAACACCAGAATTACCAACATTCTTCCCTTCCCTTGAAAA<br>ACTTACACTTTGGCGTCTGGACAAGTTGAAGGGTTTTGGGAA<br>CAGGAGATCGAGTAGTTTTCCCCGCCTCTCTAAATTGGAAAT<br>CTGGAAATGCCCAGATCTAACGTCATTTCCTTCTTGTCCAAG<br>CCTTGAAGAGTTGGAATTGAAAGAAAACAATGAAGCATTGC<br>AAATAATAGTAAAAATAACAACAACAAGAGGTAAAGAAGA<br>AAAAGAAGAAGACAAGAATGCTGGTGTTGGAAATTCACAAG<br>ATGATGACAATGTCAAATTATGGACGGTGGAAATAGACAAT<br>CTGGGTTATCTCAAATCACTGCCCACAAATTGTCTTACTCTG<br>TTGGACTCACTCGAACTTTCAAATATAGAAGACCAGGAAGA |

TABLE 1-continued

| Sequence information. | |
|---|---|
| | TGAGGGCGAAGACAACATCATATTCTGGAAATCCTTTCCTCA AAACCTCCGCAGTTTGGAAATTGAAAACTCTTACAAAATGA CAAGTTTGCCCATGGGGATGCAGTACTTAACCTCCCTCCAAA CCCTCTATCTACACCATTGTTATGAATTGAATTCCCTTCCAG AATGGATAAGCAGCTTATCATCTCTTCAATCCCTGCACATAG GAAAATGTCCAGCCCTAAAATCACTACCAGAAGCAATGCGG AACCTCACCTCCCTTCAGACACTTGGGATATCGCGGTGTCCA GACCTAATTGAAAGATGCGAAGAACCCAACGGCGAGGACTA TCCCAAAATTCAACACATCCCCAAAATTTTACTCAACACTAG CTTGATCCTGAACGCACCCAACCTTCAGGACATGGATTGA |
| SEQ ID NO: 4: protein sequence of alpha-CMV | MAEIGYSVCAKLIEVIGSELIKEICDTWGYKSLLEDLNKTVLTV RNVLIQAGVMRELTSEQQGFIADLKDVVYDADDLFDKLLTRAE RKQIDGNEISEKVRRFFSSSNKIGQAYYMSRKVKEIKKQLDEIV DRHTKFGFSAEFIPVCRGRGNERETRSYIDVKNILGRDKDKNDII DRLLNRNGNEACSFLTIVGAGGLGKTALAQLVFNDERVKIEFH DLRYWVCVSDQDGGQFDVKEILCKILEVVTKEKVDNSSTLELV QSQFQEKLRGKKYFLVLDDVWNEDREKWLPLEELLMLGQGGS KVVVTTRSEKTANVIGKRHFYTLECLSPDYSWSLFEMSAFQKG HEQENHHELVDIGKKIVEKCYNNPLAITVVGSLLYGEEISKWRS FEMSELAKIGNGDNKILPILKLSYHNLIPSLKSCFSYCAVFPKDH EIKKEMLIELWMAQGYVVPLDGGQSIEDAAEEHFVILLRRCFFQ DVKKDKYGDVDSVKIHDLMEDVAQEVGREELCVVNDNTKNL GDKIRHVHRDVIRYAQRVSLCSHSHKIRSYIGGNCEKRCVDTLI DKWMCLRMLDLSWSDVKNLPNSIGKLLHLRCLNLSYNKDLLI LPDAITRLHNLQTLLLKECRSLKELPKDFCKLVKLRHLDLRCSD LKELPKDFCKLVKLRHLDLWGCDDLIGVPLGMDRLISLRVLPFF VVGRKEQSDDDELKALKGLTEIKGSIRIRIYSKYRIVEGMNDTG GAGYLKSMKHLTGVDITFDGGCVNPEAVLATLEPPSNIKRLEM WHYSGTTIPVWGRAEINWAISLSHLVDIQLWHCRNLQEMPVLS KLPHLKSLELYNLISLEYMESTSRSSSSDTEAATPELPTFFPSLEK LTLWRLDKLKGFGNRRSSSFPRLSKLEIWKCPDLTSFPSCPSLEE LELKENNEALQIIVKITTTRGKEEKEEDKNAGVGNSQDDDNVK LWTVEIDNLGYLKSLPTNCLTLLDSLELSNIEDQEDEGEDNIIFW KSFPQNLRSLEIENSYKMTSLPMGMQYLTSLQTLYLHHCYELN SLPEWISSLSSLQSLHIGKCPALKSLPEAMRNLTSLQTLGISRCPD LIERCEEPNGEDYPKIQHIPKIVLNEYW* |
| SEQ ID NO: 5: protein sequence of alpha-CMV (isoform 1) | MAEIGYSVCAKLIEVIGSELIKEICDTWGYKSLLEDLNKTVLTV RNVLIQAGVMRELTSEQQGFIADLKDVVYDADDLFDKLLTRAE RKQIDGNEISEKVRRFFSSSNKIGQAYYMSRKVKEIKKQLDEIV DRHTKFGFSAEFIPVCRGRGNERETRSYIDVKNILGRDKDKNDII DRLLNRNGNEACSFLTIVGAGGLGKTALAQLVFNDERVKIEFH DLRYWVCVSDQDGGQFDVKEILCKILEVVTKEKVDNSSTLELV QSQFQEKLRGKKYFLVLDDVWNEDREKWLPLEELLMLGQGGS KVVVTTRSEKTANVIGKRHFYTLECLSPDYSWSLFEMSAFQKG HEQENHHELVDIGKKIVEKCYNNPLAITVVGSLLYGEEISKWRS FEMSELAKIGNGDNKILPILKLSYHNLIPSLKSCFSYCAVFPKDH EIKKEMLIELWMAQGYVVPLDGGQSIEDAAEEHFVILLRRCFFQ DVKKDKYGDVDSVKIHDLMHDVAQEVGREELCVVNDNTKNL GDKIRHVHRDVIRYAQRVSLCSHSHKIRSYIGGNCEKRCVDTLI DKWMCLRMLDLSWSDVKNLPNSIGKLLHLRCLNLSYNKDLLI LPDAITRLHNLQTLLLKECRSLKELPKDFCKLVKLRHLDLRCSD LKELPKDFCKLVKLRHLDLWGCDDLIGVPLGMDRLISLRVLPFF VVGRKEQSDDDELKALKGLTEIKGSIRIRIYSKYRIVEGMNDTG GAGYLKSMKHLTGVDITFDGGCVNPEAVLATLEPPSNIKRLEM WHYSGTTIPVWGRAEINWAISLSHLVDIQLWHCRNLQEMPVLS KLPHLKSLELYNLISLEYMESTSRSSSSDTEAATPELPTFFPSLEK LTLWRLDKLKGFGNRRSSSFPRLSKLEIWKCPDLTSFPSCPSLEE LELKENNEALQIIVKITTTRGKEEKEEDKNAGVGNSQDDDNVK LWTVEIDNLGYLKSLPTNCLTLLDSLELSNIEDQEDEGEDNIIFW KSFPQNLRSLEIENSYKMTSLPMGMQYLTSLQTLYLHHCYELN SLPEWISSLSSLQSLHIGKCPALKSLPEAMRNLTSLQTLGISRCPD LIERCEEPNGEDYPKIQHIPKILLNTSLILNAPNLQDMD* |
| SEQ ID NO: 6: Forward primer LRR domain (Alpha) | ACAAGTGGATGTGTCTTAGG |
| SEQ ID NO: 7: Reverse primer LRR domain | TTCGCCCTCATCTTCCTGG |

TABLE 1-continued

| Sequence information. | |
|---|---|
| SEQ ID NO: 8: Forward primer LRR domain (Beta) | TCACGTGGGTTGTGTTGT |
| SEQ ID NO: 9: Amplicon of LRR domain of the alpha-CMV allele | ACAAGTGGATGTGTCTTAGGATGTTGGACTTGTCATGGTCGG<br>ATGTTAAAAATTTGCCTAATTCAATAGGTAAATTGTTGCACT<br>TGAGGTGTCTTAACCTGTCTTATAATAAAGATCTGTTGATAC<br>TCCCTGATGCAATTACAAGACTGCATAATTTGCAGACACTGC<br>TTTTAAAAGAGTGCAGAAGTTTAAAGGAGTTGCCAAAAGAT<br>TTTTGCAAATTGGTCAAACTGAGGCACTTGGATTTAAGGTGT<br>TCTGATTTGAAGGAGTTGCCAAAAGATTTTTGCAAATTGGTC<br>AAACTGAGGCACTTGGATTTATGGGGTTGTGATGATTTGATT<br>GGTGTGCCATTGGGAATGGATAGGCTAATTAGTCTTAGAGT<br>ACTGCCATTCTTTGTGGTGGGTAGGAAGGAACAAAGTGATG<br>ATGATGAGCTGAAAGCCCTAAAAGGCCTCACCGAGATAAAA<br>GGCTCCATTCGTATTAGAATCTATTCAAAGTATAGAATAGTT<br>GAAGGCATGAATGACACAGGAGGAGCTGGGTATTTAAAGAG<br>CATGAAACATCTCACGGGGGTTGATATTACATTTGATGGTGG<br>ATGTGTTAACCCTGAAGCTGTGTTGGCAACCCTAGAGCCACC<br>TTCAAATATCAAGAGGTTAGAGATGTGGCATTACAGTGGTA<br>CAACAATTCCAGTATGGGGAAGAGCAGAGATTAATTGGGCA<br>ATCTCCCTCTCACATCTTGTCGACATCCAGCTTTGGCATTGTC<br>GTAATTTGCAGGAGATGCCAGTGCTGAGTAAACTGCCTCATT<br>TGAAATCACTGGAACTTTATAATTTGATTAGTTTAGAGTACA<br>TGGAGAGCACAAGCAGAAGCAGTAGCAGTGACACAGAAGC<br>AGCAACACCAGAATTACCAACATTCTTCCCTTCCCTTGAAAA<br>ACTTACACTTTGGCGTCTGGACAAGTTGAAGGGTTTTGGGAA<br>CAGGAGATCGAGTAGTTTTCCCCGCCTCTCTAAATTGGAAAT<br>CTGGAAATGCCCAGATCTAACGTCATTTCCTTCTTGTCCAAG<br>CCTTGAAGAGTTGGAATTGAAAGAAAACAATGAAGCATTGC<br>AAATAATAGTAAAAATAACAACAACAAGAGGTAAAGAAGA<br>AAAAGAAGAAGACAAGAATGCTGGTGTTGGAAATTCACAAG<br>ATGATGACAATGTCAAATTATGGACGGTGGAAATAGACAAT<br>CTGGGTTATCTCAAATCACTGCCCACAAATTGTCTTACTCTG<br>TTGGACTCACTCGAACTTTCAAATATAGAAGACCAGGAAGA<br>TGAGGGCGAA |
| SEQ ID NO: 10: amino acid sequence encoded by amplicon of LRR domain of alpha-CMV | KWMCLRMLDLSWSDVKNLPNSIGKLLHLRCLNLSYNKDLLILP<br>DAITRLHNLQTLLLKECRSLKELPKDFCKLVKLRHLDLRCSDLK<br>ELPKDFCKLVKLRHLDLWGCDDLIGVPLGMDRLISLRVLPFFV<br>VGRKEQSDDDELKALKGLTEIKGSIRIRIYSKYRIVEGMNDTGG<br>AGYLKSMKHLTGVDITFDGGCVNPEAVLATLEPPSNIKRLEMW<br>HYSGTTIPVWGRAEINWAISLSHLVDIQLWHCRNLQEMPVLSK<br>LPHLKSLELYNLISLEYMESTSRSSSSDTEAATPELPTFFPSLEKL<br>TLWRLDKLKGFGNRRSSSFPRLSKLEIWKCPDLTSFPSCPSLEEL<br>ELKENNEALQIIVKITTTRGKEEKEEDKNAGVGNSQDDDNVKL<br>WTVEIDNLGYLKSLPTNCLTLLDSLELSNIEDQEDEGE |
| SEQ ID NO: 11: Amplicon of LRR domain of the beta-WOLF 0 allele | TCACGTGGGTTGTGTTGTCGATAGAGATCCAGAAATAGTCTT<br>TTTATGTAGCAATAAGATTCGTTCGTATATTAGCGGTCGCTG<br>CATAAAGAATCCGGTGGATTCACAAATAGACAACTGGATGT<br>GCCTTAGGGTGTTGGACTTGTCAGATTCATGTGTTAAAGATT<br>TGTCTGATTCAATAGGTAAGCTGCTGCACTTAAGGTATCTTA<br>ACCTCTCTTCTAATATAAAGTTGGAGATAATCCCTGATGCAA<br>TTACAAGACTGCATAACTTGCAGACACTACTTTTAGAAGATT<br>GCAGAAGTTTAAAGGAGTTGCCAAAAGATTTTTGCAAATTG<br>GTCAAACTGAGGCACTTGGAATTACAGGGTTGTCATGATTTG<br>ATTGGTATGTCATTTGGAATGGATAAGCTAACTAGTCTTAGA<br>ATACTACCAAACATTGTGGTGGGTAGGAAGGAACAAAGTGT<br>TGATGATGAGCTGAAAGCCCTAAAAGGCCTCACCGAGATAA<br>AAGGCTCCATTGATATCACAATCTATTCAAAATATAGAAGA<br>GTTGAAGGCATGAATGGCACAGGAGGAGGAGCTGGGTATTT<br>GAAGAGCATGAAACATCTCACGGGGGTTAATATTACATTTG<br>ATGAAGGTGGATGTGTTAACCCTGAAGCTGTGTATTTGAAG<br>AGCATGAAACATCTCACGAGGGTTATTATTATATTTGATTAT<br>AAAGGTGGATGTGTTAACCCTGAAGCTGTGTTGGCAACCCT<br>AGAGCCACCTTCAAATATCAAGAGGTTAGAGATGTGGCATT<br>ACAGTGGTACAACAATTCCAGTATGGGGAAGAGCAGAGATT<br>AATTGGGCAATCTCCCTCTCACATCTTGTCGACATCACGCTT<br>GAAGATTGTTACAATTTGCAGGAGATGCCAGTGCTGAGTAA<br>ACTGCCTCATTTGAAATCACTGGAACTTACAGAGTTGGATAA<br>CTTAGAGTACATGGAGAGTAGAAGCAGCAGCAGTAGCAGTG<br>ACACAGAAGCAGCAACACCAGAATTACCAACATTCTTCCCT<br>TCCCTTGAAAAACTTACACTTTGGCGTCTGGACAAGTTGAAG<br>GGTTTTGGGAACAGGAGATCGAGTAGTTTTCCCCGCCTCTCT |

TABLE 1-continued

| Sequence information. | |
|---|---|
| | AAATTGGAAATCTGGAAATGTCCAGATCTAACGTCATTTCCT<br>TCTTGTCCAAGCCTTGAAGAGTTGGAATTGAAAGAAAACAA<br>TGAAGCGTTGCAAATAATAGTAAAAATAACAACAACAAGAG<br>GTAAAGAAGAAAAAGAAGAAGACAAGAATGCTGGTGTTGG<br>AAATTCACAAGATGATGACAATGTCAAATTATGGAAGGTGG<br>AAATAGACAATCTGGGTTATCTCAAATCACTGCCCACAAATT<br>GTCTGACTCACCTCGACCTTACAATAAGTGATTCCAAGGAGG<br>GGGAGGGTGAATGGGAAGTTGGGGATGCATTTCAGAAGTGT<br>GTATCTTCTTTGAGAAGCCTCACCATAATCGGAAATCACGGA<br>ATAAATAAAGTGAAGAGACTGTCTGGAAGAACAGGGTTGGA<br>GCATTTCACTCTGTTGGAATCACTCAAACTTTCAGATATAGA<br>AGACCAGGAAGATGAGGGCGAA |
| SEQ ID NO: 12: amino acid sequence encoded by amplicon of LRR domain Beta Wolf 0 (Viroflay) | HVGCVVDRDPEIVFLCSNKIRSYISGRCIKNPVDSQIDNWMCLR<br>VLDLSDSCVKDLSDSIGKLLHLRYLNLSSNIKLEIIPDAITRLHNL<br>QTLLLEDCRSLKELPKDFCKLVKLRHLELQGCHDLIGMSFGMD<br>KLTSLRILPNIVVGRKEQSVDDELKALKGLTEIKGSIDITIYSKYR<br>RVEGMNGTGGGAGYLKSMKHLTGVNITFDEGGCVNPEAVYL<br>KSMKHLTRVIIIFDYKGGCVNPEAVLATLEPPSNIKRLEMWHYS<br>GTTIPVWGRAEINWAISLSHLVDITLEDCYNLQEMPVLSKLPHL<br>KSLELTELDNLEYMESRSSSSSDTEAATPELPTFFPSLEKLTLW<br>RLDKLKGFGNRRSSSFPRLSKLEIWKCPDLTSFPSCPSLEELELK<br>ENNEALQIIVKITTTRGKEEKEEDKNAGVGNSQDDDNVKLWK<br>VEIDNLGYLKSLPTNCLTHLDLTISDSKEGEGEWEVGDAFQKC<br>VSSLRSLTIIGNHGINKVKRLSGRTGLEHFTLLESLKLSDIEDQE<br>DEGE |
| SEQ ID NO: 13: Genomic sequence comprising beta-WOLF 3 allele (with a 2 kb region upstream of the start codon) | TGGTCCACAACTCCACACTAAGAGGAACTCCAATGCTTAGTT<br>ACAAGGTGGTGTAGTTAAAAAGTAATTCCAATAGTTAACTA<br>CACGGTATTATAGTTAAATTTGCCAACTCAAATTTCTAACTA<br>CAATATATTTAAGCTACAAAGTTTCTCATTGGCTGACTACAA<br>TACGTTGTAGCGCCTTATAATATTTTATTCAATATACAATTTT<br>ATTTATTTTACCTTTTTAACAATTTTTTTTTGATCTACCTGCTG<br>TCCTGTTCATATGAGCTACACTAATTTGATAGCTGCTTACGC<br>AATTCTTATATCAACGGTTGGCTACTTGTTCAAATATTTTTAT<br>TTTTTTACGAGTAAGTCATTTTATGATCATTGAAGTGGCTCT<br>ATTATTATTATCATGCACCGATTAACGCAAGAATAATTAACT<br>CGGTACGAATTAGTTTCAAAATAAAATCCCTCAAAAAAAAA<br>AGTTTCAAAATAAAATTAACAGAAAACCAACCTTCTCCGGTT<br>TACTGTTGTTAGAGCATGGAATTTTCCAGTAATCGCAGACCC<br>CAAATTATCTTCCAGTTGAATCAATCCTTGATTTTTGGATTTG<br>CCAGAAAACTCCTTGAATTTTAGGGTTCATATTTGATCCGTA<br>ATTGGGAAAATTTTCAGCAATTGATCTTCCAAATCAGCCCTA<br>CTTGTTTCCAGACTGCAAATGAAAGGTGCGAACTTTATACTG<br>CATTTTGGTTTTCCATTAGTGTAATTTATTAAGATGAACTGC<br>ATTTTGCAATTGTTTTATTCGACTACTCATTTTTAAATCAAAT<br>TGCTTAATTGCTAGTTAGTTTTCTTATCATATTGCCAAAAAA<br>AATTATTTTTGTTTAATTGGTGAAAAAGGGTAAATTATACCT<br>AGTGTACAAGATTTTCTTGCACACCACCCTTAATTTGTTGAC<br>ACATCATCAAACGTACTGAAAAATGAGAATGAAAGACAATA<br>AATATGTCATTTTAACCAATAGAAAAACATGATGTAGTAAG<br>ATCCTTAATTGATAGATAAATAATTAAATATCAGTCCATTAG<br>TTGAATATTCAATGAAAATGTATGGTCCAAAAATGGCGTTTA<br>ATAGTCAATGTCATGCTTTATGGGGTGGTGGAGTACTATGTG<br>ACTGTGTGTGGACTTGGAGAAGACTAGAGAGTATGATTATC<br>AACCTATGGACCCTCAAAATGAAAATGAAAATGATGTTTTT<br>ACACTTTAAAATCGTCAAGAAACAACAATCCTTTTTAGCAAT<br>AGTATTTACACGCGCTAGTTGCACGAACTTTAATGCAAATAG<br>TATAAATTTACGGTCAAAGTTTTCATACTTTAGACACATACT<br>CTCTCCGTCCCTTAATACTCGCACCGCTTTCCTTTTCGGGCCG<br>TCCCTTAATACTTGCACCGCTTCTATAAATGGAAATCTATTT<br>CTCACAATTACCTACTAACCCACCTACACTCATCGTCCCTAC<br>AAAAAATCATTTAAAAATTCACACCCCACACTCACCACTCCT<br>CACCCATTACACATTTCCTACTAACTATATTAAAAAAATATC<br>CCACTATAAACTAACACTCATTAAATTAATAAGTCAATTCAA<br>ATATCTTAAACTCCGCACCGGTCAAATCGGTGCGAGTATTAA<br>GGGACGGAGGGAGTATTATAGAGTGTAAATAACTTTCATGA<br>ATGGAGGGAGTAAAAAATTGTTTTACTTGGCTAAAATACTTT<br>TGTTCTTATTGGCAGATAAACATGAGTCCATTATTGGCCAAC<br>TTGAACATATACCTCCAAACAATAATCAATGATGTCGATTAT<br>GAAGTTTGTGAATGCAATTTATTATCACTTTCATTGCAAGTT<br>GTCATCTGTGCTGAGTGTTGATTTATAAAAAGGACTACTTGA<br>TTAACACATACAATATTACTCCACCTTTCTCCAGACAACCTT<br>TCTTTTCTGCTTTTATCTTGTTTTCTCATCTTAATTCATCTCTT<br>CATCTTTCTGAAAAACCCAACCCA**ATG**GCTGAAATCGGATA<br>CTCGGTTTGTTCAAAACTTATTGAAGTGATGGGCAGTAAGAT<br>CATTAAAGAGATTTGTGACATGTGGGGTTACAAATCTCATCT<br>TGAAGACCTCAACAAATCTGTCTTGACGATCAAGGATGTGCT |

TABLE 1-continued

| Sequence information. |
|---|
| CTTGGATGCTGAGGCGAAGCGGGATCTTTCCCGTGAACAAC<br>AGAGTTACATTGCAGAACTTAAGGATGTTGTTTACGATGCTG<br>ATGATTTGTTCGATGAGTTCCTCACTCTTGCTGAGCTCAAAC<br>AGATTGATGGCAACAACAAGGGTGGTGGTAAATTCTCCAAA<br>AAGGTACGTCGTTTCTTTTCTTCTAATAAGGAGAAGATGGGT<br>CAAGCTTACAAGATGTCTCATATGGTTAAAGAAATTAAGAA<br>GCAGTTGGGTGAAATTGTTGATAGGTATACCAAATTTGGGTT<br>TATTGTTGATTATAAACCTATTATTAGGAGAAGGGAGGAAA<br>CATGTTCTTATTTTGTAGGTGCCAAGGAGATTGTTGGGAGGG<br>ATAAGGATAAAGATGTTATCATAGGCATGTTGCTAGATCAT<br>GATAACGATTGTAGTTTCTTGGCTGTTGTGGGGGTTGGAGGG<br>GTGGGAAAAACTACTCTTGCCCAACTTGTGTATAATGATGAA<br>AGAGTCAAAAGTGAGTTCCAAGATTTGAGGTATTGGGTTTGT<br>GTCTCTGATCAAGATGGGGGACAATTTGATGACAAAAGAAT<br>TCTTTGTAAGATTATAGAGTTAGTTACGGGCCAGATTCCTCC<br>GAGTAACGAGAGCATGGAATCGGTGCGTAAGAAATTTCAAG<br>AGGAATTAGGAGGAAAGAAGTACTTCCTTGTTCTTGATGAT<br>GTATGGAACGAGGATCGCCAGAAGTGGCTTCATCTAGAAAA<br>TTTCTTGAAATTGGGTCAAGGGGGAAGCAAGATTGTGGTAA<br>CCACACGTTCAGAGAAGACGGCAAATGTTATAGGGAAAAGA<br>CAAGACTATAAACTAGAATGTTTGTCAGCAGAGGATTCATG<br>GCGCTTATTTGAAATGTCAGCTTTTGACGAAGGGCATGGCCA<br>GGAAAACTATGACGAATTAGTGACGATTGGCAAGAAGATTG<br>TTGAAAAATGTTATAACAATCCACTTGCTATAACAGTGGTAG<br>GAAGCCTTCTTTTTGGACAAGAGATAAATAAGTGGCGGTCG<br>TTTGAAAGCAGTGGATTAGCCCAAATTGCCAATGGTGATAA<br>TCAGATTTTCCCGATATTAAAGCTCAGTTACCACAATCTTCC<br>ACACTCCTTGAAGAGCTGCTTTAGCTATTGTGCAGTGTTTCC<br>CAAAGATTATGAAATAAAGAAGGAGATGTTGATTGATCTTT<br>GGATAGCACAAGGATACATTATACCGTTGGATGGAGGTCAA<br>AGTATAGAAGATGCTGCCGAGGAACATTTTGTAATTTTGTTA<br>AGAAGATGTTTCTTTCAAGATGTAAAGAAGGATTCTCTTGGT<br>AATGTTGATTATGTTAAAATCCACGACTTAATGCACGATGTC<br>GCTCAAGAAGTGGGGAAGGAGGAAATCTGTGTAGTGACTTC<br>AGGTACAAAGAAGTTGGCTGATAAAATCCGTCACGTGGGTT<br>GTGTTGTCGATAGAGATCCAGAAATAGTCTTTTTATGTAGCA<br>ATAAGATTCGTTCGTATATTAGCGGTCGTTGTATAAAGAATC<br>CGGTGGATTCACAAATAGACAACTGGATGCGCCTTAGGGTG<br>TTGGACTTGTCAGATTCATGTGTTAAAGATTTGTCTGATTCA<br>ATAGGTAAGCTGCTGCACTTAAGGTATCTTAACCTCTCTTCT<br>AATATAAAGTTGGAGATAATCCCTGATGCAATTACAAGACT<br>GCATAACTTGCAGACACTACTTTTAGAATATTGCAGAAGTTT<br>AAAGGAGTTGCCAAAAGATTTTTGCAAATTGGTCAAACTGA<br>GACACTTGGATTTAAGGGGTTGTCAGTGTTTGATTGGTATGC<br>CATTGGGAATGGATAGGCTAATTAGTCTTAGAGTACTACCA<br>AAAGTTGTGGTGGGTAAGAAGGAACAAAGTGATGATCAGCT<br>GAAAGCCCTAAAAGGCCTCACCGAGATAAAAGGCTCCATTG<br>ATATCACAATCTATTCAAAGTATAGAATAGTTGAAGGCATG<br>AATGACACAGGAGGAGCTGGGTATTTGAAGAGCATGAAACA<br>TCTCACGGGGGTTGATATTAGATTTGATGATAGAGAAGGTG<br>GATGTGTTAACCCTGAAGCTGTGTTGGCAACCCTAGAGCCAC<br>CTTCAAATATCAAGAGGTTAGAGATGTGGCATTACAGTGGT<br>ACAACAATTCCAGTATGGGGAAGAGCAGAGATTAATTGGGC<br>AATCTCCCTCTCACATCTTGTCGACATCCAGCTTAGTTTTTGT<br>AGAAATTTGCAGGAGATGCCAGTGCTGAGTAAACTGCCTCA<br>TTTGAAATCACTGGAACTTACAGAGTTGGATAACTTAGAGTA<br>CATGGAGAGTAGAAGCAGCAGCAGTAGCAGTGACACAGAA<br>GCAGCAACACCAGAATTACCAACATTCTTCCCTTCCCTTGAA<br>AAACTTTCACTTTGGGGTCTGGAAAAGTTGAAGGGTTTGGG<br>GAACAGGAGATCGAGTAGTTTTCCCCGCCTCTCTAAATTGGA<br>AATCTGGGAATGCCCAGATCTAACGTCATTTCCTTCTTGTCC<br>AAGCCTTGAAAAGTTGGAATTGAAAGAAAACAATGAAGCGT<br>TGCAAATAATAGTAAAAATAACAACAACAAGAGGTAAAGA<br>AGAAAAAGAAGAAGACAAGAATGCTGGTGTTGGAAATTCAC<br>AAGATGATGACAATGTCAAATTATGGAAGGTGGAAATAGAC<br>AATCTGGGTTATCTCAAATCACTGCCCACAAATTGTCTTACT<br>CACCTCGACCTTACAATAAGAGATTCCAAGGAGGGGGAGGG<br>TGAATGGGAAGTTGGGGAGGCATTTCAGAAGTGTGTATCTT<br>CTTTGAGAAAGCTCAGCATAATCGGAAATCACGGAATAAAT<br>AAAGTGAAGAGACTGTCTGGAAGAACAGGGTTGGAGCATTT<br>CACTCTGTTGGACTCACTCGAACTTTCAAATATAGAAGACCA<br>GGAAGATGAGGGCGAAGACAACATCATGTTCTGGAAATCCT<br>TTCCTCAAAACCTCCGCAATTTGGAAATTAATTACTCTGACA<br>AAATGACAAGTTTTCCCATGGGGATGCAGTACTTAACCTCCC<br>TCCAAACCATCCATCTTTATGATTGTTATAAATTGAATTCCA<br>TTCCAGAATGGATAAGCAGCTTATCATCTCTTCAATCCCTGC<br>ACATAGGAAAATGTCCAGCCCTAAAATCACTACCAGAAGCA<br>ATGCGGAACCTCACCTCCCTTCAGAGACTTACGATATGGCAG |

TABLE 1-continued

| Sequence information. | |
|---|---|
| | TGTCCAGACCTAATTGAAAGATGCAAAGAACCTAACGGGGA |
| | GGACTATCCCAAAATTGTAAGTCATTGCAGAAAGTAATTTAT |
| | TCATTTATATTTATTTTATGCTTAGAATGATATACGCAGTCGT |
| | CCTTTGGTTTCAAATCTTGAATTTGGTTTTTGTTTTCTTTCTTT |
| | GTTTCTTTATTCAACACCAGTCCATTTATGATTGATTCATTAA |
| | AAAAAGGATGGAGTTTTATGGATTTGAAGAAGACAACGAAT |
| | TGAGATTCCTGGGGTTTTTTTTTCGTTGGGGTTGGTTTTCATG |
| | TATATGTTGCTGATTAAATACCAGACTGATGATGATGATGTG |
| | TTTATGGGTTTTAAATCAGATTAAATATATGGGAAATGTAAG |
| | TTAATTGGGGATGCACATAAGGTGTTTGATGAAATGTCTATT |
| | AGAAATGTTGTTTCTTGGACTTAGAATGATATACACTGTCGT |
| | CCTTTGGTTTCCAATCTGGAATTTGGTTTTTGTTTTCTTAGTT |
| | TGTTTCTTTATTCCACACTAGCCCATTTTTTTTAAACTACCTG |
| | CAACTACTGAATTTCATTTACCCTGTATCTCAGATTATATGG |
| | TAGTAATTCTCATTTACTCAACACTAGCTTGATCCTGAACGC |
| | AGCCAACCTTCAGGTTAGAATCCGCCTTACTCATCCTTTTGT |
| | CATGAATTGTTTTAAGTTGTTTTGCTTGCTTGTGTAATCATAA |
| | TTCATAGTATACGATTCATCATTCACTATGTCTATAGGCAAG |
| | ATATTGGAATTGTTCACGATTTCCTGAAGTTTCTTTGTTTTTG |
| | TTGATACCACCATATTGCAGCTTATAGTGACTAAGTTAATGA |
| | ATGTTTCCAAAAATTAGTCATATAAATTCTTCTTCTCTCTCTA |
| | TTACATAAACTCTTTTTCTCTTTCTAACTTATCATGTTCATGT |
| | CTAAAACGTATACATGCTCACATCATTGTTCGTTTCAGCTGA |
| | CTTACTTATGTAAGAGAGCTATCTAGTTAACAACTCTTGTAA |
| | CTTTTTATTTGCTAGTCAGAACATGGATTGGTGCAAGCATGG |
| | GAATTTGCCAACACTCTACCAAATCGATTGGAGTTTGGACTT |
| | AGTTTCACCAGAAGCCATACCCGGACACTTACTGGGGACTG |
| | TCAACAAAGCCGCATTGTGATGTACTTGGATGTTTCACGTGC |
| | CTGAGGTGTGAGTTACTTGGAAGGGAAGCGGTTTATTTAATT |
| | GTTTTCCTAAGTAGATTTTGCTTACAAGCTTTTACTTTTCACT |
| | TGGAAGGGTTTTCTTGTTTTAAGCTTTTCGAATTAGAGTTTCG |
| | GTTGCATTAAGAGTAGTCGTATTAGTCTTTTTTACCTAAGAC |
| | TCTTTTTTGTAATTTTCAGACTATGCAATTCAAGTTTTGAGTG |
| | TTTTCTTGCTTGTGTGATTGTGAGTTGGTGAATTCGTCTTTCA |
| | TACATTTTGAGATTATCAGAAGCTTTATGCTCCACCGGTAGT |
| | CTAGTACCTTTTCTGTTACTGTACGTGCAGGGAAGTAATCTG |
| | GTACCTTCTATATATATGGAAAAACATACATTATACATTACG |
| | CAAAATTCTTACAGGTTAGTTACTTCCTGGAACTTCATTTAC |
| | ACTTGGTTTTTTTTGTTCCATTCCCTCGGAAGACTATTCCCTC |
| | TGAGAAATATGTAATGAATTTCTGTATTCAGCTGCATTTACA |
| | ATGAAGTTTAAGCAGACACTCTCTTTATATAGTGCCTCTTTC |
| | TGGAGCACCGTAGAGCTGTCTGTGGTTGATCACCATATGCTG |
| | CCGAGAGATTCAGCAATCGCGTGTTTGATCAGGTAAAAGTTT |
| | TTATGTCAATGTGTTTTTTTTTTCCGTTTGATCAATTTATGTCT |
| | GTATTCAGATTCTTATCTTCTTACAGTAGCATAACACATTGTT |
| | TCTTTCATTTATGTAAACTGTTTCAAGATTACAGAGATGTAT |
| | GCTTCAGTCGACATTGATGATAACTTAAGATGGCATTCCTAC |
| | AACAGTTGCAGGCGCATTCTAACTCCGGCAATTCTAGTTAGG |
| | CAAGAGGAGCATTGCCAATACCTGCCACCTCTGGGATTTACT |
| | ATACCAGGGTTGAAGTTTATGGAAGACACCAGCTATGCACA |
| | AGCCTTCAAGGGGTCATCCTACATAACAAGTTGAACCAACC |
| | AATTGCTTGTTGGTTCAGTGGTAATTGGAGCTGAATTCGGTA |
| | GGGATGGCCCGTGTTCGATCCCCACAACAACAATTGGGAGG |
| | GGACTGGAACCTATCCACACAGAACTCGCCCTGAATCCGGA |
| | TTAGCCCTAAGGGTGAACGGGGTGCTAACACCAAAAAAAAA |
| | ACATAACAAGTTGAATCAAACATACTTTGTTTGAATTGAAGA |
| | TTTAGTGATTTCATTTGATCGATTGAGATGTCTTATTATAAGC |
| | GTATATGCTCTTGGATTTGGCCACTTAGGTGTTGTTTGACAA |
| | TTGGTCATTAACTCGCTTTTATATTTTCGTTTCTCTTAGGAAA |
| | GGTGATCCTGAGAATTTATATTGAAACACTTTTTTTATCTCTC |
| | ACTAGCTTTAAAAAAGTGTTCTGTGTTACCTGCAATTCAACT |
| | TGATTATTTTTCACATAGTTTTACCTGAAAAAGTGTTATCTG |
| | AAAATCAACTGACATAAATTTTTGTTTGGATCAAATTAAGGA |
| | TACTAGATAAATCGGAAAAAATAATCAACCAATTAAGTACT |
| | TCATAATTAAATATGAAGTATATTATTATCTTATGCTTGTG |
| SEQ ID | TTTGAAGTTAGGCTTAACTTGCTCACCAATTCTTAAATAGAC |
| NO: 14: | TCGACTTACACTGAATTTATTGTGTACTATGTCTAGAAAGTA |
| Genomic | AGGTCAACAACTTTCTTCTAAATTATTTTGGCATGTTTATTAG |
| sequence | GGTTATTATGAAAAACATATCAAATTGGTGTTGTTAGTTAGG |
| comprising | CTTGAATAATATGATTTTAAGTCACGAGACTTTTATAAATTA |
| alpha-WOLF | GGTAATTTGATTTAAAAAATTGTTACATATCTAAGAAAATGG |
| 6 allele | ATGTTAAATTTATCAGTCAATGTATAAACAATAAAAGTCAAT |
| (with a 2 | ATGTATGTAAAAGGGTTGCTAGATAAAATCTTTGGTTTTTTG |
| kb region | GTCCACAACTCCACACTAAGAGGAACTCCAATGCTTAGTTAC |
| upstream | AAGGTGGTGTAGTTAAAAGTAACTCCAATAGTTAACTACA |
| of the | CGGTATTATAGTTAAATTTGCCAACTCAAATTTCTAACTACA |

TABLE 1-continued

| Sequence information. | |
|---|---|
| start<br>codon) | ATATATTTAAGCTACAAAGTTTCTCATTGGCTGACTACAATA<br>CGTTGTAGCGCCTTATAATATTTTATTCAATATACAATTTTAT<br>TTATTTTACCTTTTTAACAATTTTTTTTTGATCTACCTGCTGTC<br>CTGTTCATATGAGCTACACTAATTTGATAGCTGCTTACGCAA<br>TTCTTATATCAACGGTTGGCTACTTGTTCAAATATTTTTATTT<br>TTTTACGAGTAAGTCATTTTATGATCATTGAAGTGGCTCTAT<br>TATTATTATCATGCACCGATTAACGCAAGAATAATTAACTCG<br>GTACGAATTAGTTTCAAAATAAAATCCCTCAAAAAAAAAAG<br>TTTCAAAATAAAATTAACAGAAAACCAACCTTCTCCGGTTTA<br>CTGTTGTTAGAGCATGGAATTTTCCAGTAATCGCAGACCCCA<br>AATTATCTTCCAGTTGAATCAATCCTTGATTTTTGGATTTGCC<br>AGAAAACTCCTTGAATTTTAGGGTTCATATTTGATCCGTAAT<br>TGGGAAAATTTTCAGCAATTGATCTTCCAAATCAGCCCTACT<br>TGTTTCCAGACTGCAAATGAAAGGTGCGAACTTTATACTGCA<br>TTTTGGTTTTCCATTAGTGTAATTTATTAAGATGAACTGCATT<br>TTGCAATTGTTTTATTCGACTACTCATTTTTAAATCAAATTGC<br>TTAATTGCTAGTTAGTTTTCTTATCATATTGCCAAAAAAAAT<br>TATTTTTGTTTAATTGGTGAAAAAGGGTAAATTATACCTAGT<br>GTACAAGATTTTCTTGCACACCACCGTTAATTTGTTGACACA<br>TCATCAAACGTACTGAAAAATGAGAATGAAAGACAATAAAT<br>ATGTCATTTTAACCAATAGAAAAACATGATGTAGTAAGATC<br>CTTAATTGATAGATAAATAATTAAATATCAGTCCATTAGTTG<br>AATATTCAATGAAAATGTATGGTCCAAAAATGGCGTTTAAT<br>AGTCAATGTCATGCTTTATGGGGTGGTGGAGTACTATGTGAC<br>TGTGTGTGGACTTGGAGAAGACTAGAGAGTATGATTATCAA<br>CCTATGGACCCTCAAAATGAAAATGAAAATGATGTTTACAC<br>GTGCTATTTGCACGGACTTCAATGCAAATAGTATAAATTTAC<br>GGTCAAAGTTTTCATTCTAAAGCGTAAATAACTTTCATGAAT<br>GGAGGACGGTAGTATAAGTATAACGTTATAGCCTACCATTTT<br>CTTATCATATTCACATAAATTTGTTGCTGAAATTTGTTTTACT<br>TGGCTAAAATACTTTTGTTCTTATTGGCAGATAAACATCAGT<br>ACGTCCATTATTGGCCAACTTGCTGAGTCCATTATTGGCCAA<br>CTTGAACATATACCTCCAAACAATAATCAATAATGTCGATTA<br>TGAAGTTTGTGAATGCAATTTATTATCACTTTCATTTATAAA<br>ATGACTACTTGATTAACACATACAATATTACCTTTCTCCAAA<br>CACCCTTTCAATTCTGCTTAATCTTGTTTTCTCATCATCTCTT<br>CATCTTTCTGAAAACACAACCCA**ATG**GCCGAAATCGGATAC<br>TCGGTTTGTGCGAAACTCATCGAAGTGATTGGCAGTGAGCTG<br>ATCAAAGAGATTTGTGACACATGGGGTTACAAATCTCTTCTT<br>GAGGACCTCAACAAAACTGTATTGACGGTCAGGAACGTTCT<br>CATTCAAGCCGGGGTGATGCGGGAGCTTACTAGTGAACAAC<br>AAGGTTTCATTGCAGACCTTAAAGATGTTGTTTATGATGCTG<br>ATGACTTGTTCGACAAGTTACTCACTCGTGCTGAGCGAAAAC<br>AGATTGATGGAAACGAAATCTCTGAAAAGGTACGTCGTTTC<br>TTTTCCTCTAGTAACAAGATCGGTCAAGCTTACTACATGTCT<br>CGTAAGGTTAAGGAAATTAAGAAGCAGTTGGATGAAATTGT<br>TGATAGGCATACAAAATTTGGGTTTAGTGCTGAGTTTATACC<br>TGTTTGTAGGGGAAGGGGAAACGAGAGGGAAACACGTTCAT<br>ATATAGATGTCAAGAATATTCTTGGGAGGGATAAAGATAAG<br>AATGATATCATAGATAGGTTGCTTAATCGTAATGGTAATGAA<br>GCTTGTAGTTTCCTGACCATAGTGGGAGCGGGAGGATTGGG<br>AAAAACTGCTCTTGCACAACTTGTGTTCAATGATGAAAGGGT<br>CAAAATTGAGTTCCATGATTTGAGGTATTGGGTTTGTGTCTC<br>TGATCAAGATGGGGGCCAATTTGATGTGAAAGAAATCCTTT<br>GTAAGATTTTAGAGGTGGTTACTAAGGAGAAAGTTGATAAT<br>AGTTCCACATTGGAATTGGTACAAAGCCAATTTCAAGAGAA<br>GTTAAGAGGAAAGAAGTACTTCCTTGTTCTTGATGATGTATG<br>GAACGAAGATCGTGAGAAGTGGCTTCCTTTGGAAGAGTTGT<br>TAATGTTGGGTCAAGGGGGAAGCAAGGTTGTAGTGACCACA<br>CGTTCAGAGAAGACAGCAAATGTCATAGGGAAAAGACATTT<br>TTATACACTGGAATGTTTGTCACCAGATTATTCATGGAGCTT<br>ATTTGAAATGTCGGCTTTTCAGAAAGGGCATGAGCAGGAAA<br>ACCATCACGAACTAGTTGATATTGGGAAAAAGATTGTTGAA<br>AAATGTTATAACAATCCACTTGCTATAACGGTGGTAGGAAG<br>TCTTCTTTATGGAGAGGAGATAAGTAAGTGGCGGTCATTTGA<br>AATGAGTGAGTTGGCCAAAATTGGCAATGGGGATAATAAGA<br>TTTTGCCGATATTAAAGCTCAGTTACCATAATCTTATACCCT<br>CGTTGAAGAGTTGTTTTAGTTATTGTGCAGTGTTTCCCAAGG<br>ATCATGAAATAAAGAAGGAGATGTTGATTGAACTTTGGATG<br>GCACAAGGATATGTTGTGCCGTTGGATGGAGGTCAAAGTAT<br>AGAAGATGCTGCCGAGGAACATTTTGTAATTTTGTTACGAAG<br>GTGTTTCTTTCAAGATGTAAAGAAGGATAAATATGGTGATGT<br>TGATTCTGTTAAAATCCACGACTTGATGCACGATGTCGCCCA<br>AGAAGTGGGGAGGGAGGAATTATGTGTAGTGAATGATAATA<br>CAAAGAACTTGGGTGATAAAATCCGTCATGTACATCGTGAT<br>GTCATTAGATATGCACAAAGAGTCTCTCTGTGTAGCCATAGC<br>CATAAGATTCGTTCGTATATTGGTGGTAATTGTGAAAAACGT<br>TGTGTGGATACACTAATAGACAAGTGGATGTGTCTTAGGAT |

TABLE 1-continued

| Sequence information. |
|---|
| GTTGGACTTGTCATGGTCGGATGTTAAAAATTTGCCTAATTC<br>AATAGGTAAATTGTTGCACTTGAGGTGTCTTAACCTGTCTTA<br>TAATAAAGATCTGTTGATACTCCCTGATGCAATTACAAGACT<br>GCATAATTTGCAGACACTGCTTTTAAAAGAGTGCAGAAGTTT<br>AAAGGAGTTGCCAAAAGATTTTTGCAAATTGGTCAAACTGA<br>GGCACTTGGATTTAAGGTGTTCTGATTTGAAGGAGTTGCCAA<br>AAGATTTTTGCAAATTGGTCAAACTGAGGCACTTGGATTTAT<br>GGGGTTGTGATGATTTGATTGGTGTGCCATTGGGAATGGATA<br>GGCTAATTAGTCTTAGAGTACTGCCATTCTTTGTGGTGGGTA<br>GGAAGGAACAAAGTGATGATGATGAGCTGAAAGCCCTAAA<br>AGGCCTCACCGAGATAAAAGGCTCCATTCGTATTAGAATCT<br>ATTCAAAGTATAGAATAGTTGAAGGCATGAATGACACAGGA<br>GGAGCTGGGTATTTAAAGAGCATGAAACATCTCACGGGGGT<br>TGATATTACATTTGATGGTGGATGTGTTAACCCTGAAGCTGT<br>GTTGGCAACCCTAGAGCCACCTTCAAATATCAAGAGGTTAG<br>AGATGTGGCATTACAGTGGTACAACAATTCCAGTATGGGGA<br>AGAGCAGAGATTAATTGGGCAATCTCCCTCTCACATCTTGTC<br>GACATCCAGCTTTGGCATTGTCGTAATTTGCAGGAGATGCCA<br>GTGCTGAGTAAACTGCCTCATTTGAAATCACTGGAACTTTAT<br>AATTTGATTAGTTTAGAGTACATGGAGAGCACAAGCAGAAG<br>CAGTAGCAGTGACACAGAAGCAGCAACACCAGAATTACCAA<br>CATTCTTCCCTTCCCTTGAAAAACTTACACTTTGGCGTCTGG<br>ACAAGTTGAAGGGTTTTGGGAACAGGAGATCGAGTAGTTTT<br>CCCCGCCTCTCTAAATTGGAAATCTGGAAATGCCCAGATCTA<br>ACGTCATTTCCTTCTTGTCCAAGCCTTGAAGAGTTGGAATTG<br>AAAGAAAACAATGAAGCATTGCAAATAATAGTAAAAATAAC<br>AACAACAAGAGGTAAAGAAGAAAAAGAAGAAGACAAGAAT<br>GCTGGTGTTGGAAATTCACAAGATGATGACAATGTCAAATT<br>ACGGAAGGTGGAAATAGACAATGTGAGTTATCTCAAATCAC<br>TGCCCACAAATTGTCTTACTCACCTCGACCTTACAATAAGAG<br>ATTCCAAGGAGGGGGAGGGTGAATGGGAAGTTGGGGATGC<br>ATTTCAGAAGTGTGTATCTTCTTTGAGAAGCCTCACCATAAT<br>CGGAAATCACGGAATAAATAAAGTGAAGAGACTGTCTGGAA<br>GAACAGGGTTGGAGCATTTCACTCTGTTGGAATCACTCAAAC<br>TTTCAGATATAGAAGACCAGGAAGATGAGGGCGAAGACAAC<br>ATCATATTCTGGAAATCCTTTCCTCAAAACCTCCGCAGTTTG<br>AGAATTAAAGACTCTGACAAAATGACAAGTTTGCCCATGGG<br>GATGCAGTACTTAACCTCCCTCCAAACCCTCTATCTACACCA<br>TTGTTATGAATTGAATTCCCTTCCAGAATGGATAAGCAGCTT<br>ATCATCTCTTCAATCCCTGCACATAGGAAAATGTCCAGCCCT<br>AAAATCACTACCAGAAGCAATGCGGAACCTCACCTCCCTTC<br>AGAGACTTACGATATGGCAGTGTCCAGACCTAATTGAAAGA<br>TGCAAAGAACCTAACGGGGAGGACTATCCCAAAATTCAACA<br>CATCCCCAAAATTGTAAGTCATTGCAGAAAGTAATTTATTCA<br>TTTATATTTATTTTATGCTTAGAATGATATACACCGTCGTCCT<br>TTGGTTTCAAATCTTGAATTTGGTTTTTGTTTTCTTTCTTTGTT<br>TCTTTATTCAACACCAGCCCATTTATGATTGATTCATTAAAA<br>AAAGGATGGAGTTTTGTGGATTTGAAGAAGACAACGAATTG<br>AGATTCCTGGGGTTTTCTTTTTGTTGGGGTTGGATTTCATGTA<br>TATGTTGCTGATTAAATACGAGACTGATGATGATGATGATGT<br>GTTTATGGGTTTTAAATCAGATTAAATATATGGGAAATGTAA<br>GTTAATTTGGGATGCACATAAGGTGTTTGCTGAAATGTCTAT<br>GAGAAATGTTGTTTCTTGGACTTAGAATGATATACACTGTCG<br>TCCATTGGTTTCCAATCTTACATTTGGTTTGTGTTTTCTTAGT<br>TTGTTTCTTTAATCAACACCAACCCATTTTTTTAAAACTACCT<br>GCAACTACTAATTTACGTTGACCCTGTATCTCAGGTACTAAA<br>TAAATATTGGTGATTTTCAGTTACTCAACACTAGCTTGATCC<br>TGAACGCACCCAACCTTCAGGTTAGAATCCGGCTTACTCATC<br>CTTTTGTCCAGTTTTCAAGTAATTGTTTTGGCAGGATCAATTC<br>TCTAATTGTTGTACACCGTATATTGCAATTTATAGTGACTAC<br>AGTTAATGAATGTTTACAAAAAATTAGTCATGTAAAAACTTC<br>TTCTCTGTCCATTACATAAACTCTTTTTCTCTTTCTAACTTAT<br>CATGTTCATGTCTAAAAAATTAAACATGCTCACATCAATGTT<br>CATTTAAGCTAACTTACTTCTGTAAGAGAGCGAGCTAGTTAA<br>AAACTCCTTTAACTTTCTGTTTTATACTCAGGACATGGATTG<br>ATGCAAGCATGAAGAACTTCGGGAATTTGCTAAAACTCTAC<br>CAAAGCGATGAGAGTTTGGACTTTGTTTCACTTGAAGTCAGG<br>GACTGTCAACAAAGCCACAGTGTGCATGTTGGCTGTTTCACT<br>TGGACGATAAAAAGGTTTATTTAATTGTTTTCCTAAGTGTAT<br>TTGGCTTACAAGCTTTTACTTTTCGCTTGAAAGGGTTTTTCTT<br>GTTTTAAGCTTTTTGAATTAGAGTTTCGGTTGAAGTAAGAGT<br>AGTCGTATTAGTCTTTTACTTTGCAGGAGTCTATGCCTATAT<br>AAGGTAAGACTCGTATTTGTAATTTTCAGATTATGCAATTCA<br>AGTTTTCGAGTGTTTTCTTAAAAAAACATATCATACCTGTGT<br>GTAGCATAAAGATAAATTCTGATGCTGTGCTTCTTGTTATGG<br>CTCACATTGGTTTTCATTGTTTGGATTGTTTCACAGGGAAGC<br>AGAGAATACCTGGAACCTGTAAAGGACGCTATATCTATAGC<br>AGCTTTCACAGGCCAAGTAATATAATGTTCTTTATCAATCAC |

TABLE 1-continued

| | Sequence information. |
|---|---|
| | TCAATACCTGGAGATTGTTTGAACACATAATTCACCTCTTTT |
| | TTTCCATCTCAAATTGCAGACTTTTACTGGGATTTGAATGAC |
| | AGCAAACATTTGATTGTCACGAGGATTGATCTAACTGGTGA |
| | ATGTTGTGATCACCATATTGGTCTTTCTCATTCAAACAAACT |
| | TGCATACCGTTCTTTTGAAGTTTGAAGACAAGCAGGCGATAA |
| | TCAACTCAGGTCGAAGCTCATGTGCAGGAGAGAATAGAATA |
| | TAGAGGAGATTATTTTTAAAAGAAACGCTCAAAGGTATTGT |
| | AGCACCTTTCCTATTTGCTACTGCAGTGATGTTTTTATTTCTT |
| | GTTTGCAGCGCTTGTTTCTCATATTTCAACCTACTTTTAGAAA |
| | AAAAAACATCTCCGAACATAACCAAAAATAAAGTTCCCTTA |
| | TCAGTGCTTTCCCTGCTTTCTTCTAAACAACATATACAATTAT |
| | AAACCCTTTTTCTCTCTTACCTTTGTTATTCTTCCTTGCTTCAT |
| | TGAGATAACACTCTCCTGTTTTTGTTTTGTTGTTAGTCATTAC |
| | ATGGATATATCAAGGACAACAGTTCTGTAGTCCGTCAACTGT |
| | GGTTAGGAAGGCTAAACTGGAGCACAATAACCCCATGTCAA |
| | TTGAATAGTAAAGGTGTGCTATATCAGTTTCGTTTGGCTTGG |
| | CTTACCTGAAAAATGGCTGGTTATTTATCCTTGTCTCTTTCTA |
| | TGACGTGCAGTGGCTTGTTAATGTGTCTCGGACAACAATTCC |
| | TCACTTTCCAAGTTCCATACACGCTGATGTAACTATCTTCTG |
| | CAGTCTGTTCTTTCATTTTTGCCACGTGCTCTAATTATAACTT |
| | TTTGTACTCAATAATCAACTCCTTGTCCCGGTATTTGCAGAG |
| | ACTACTTAAACAGGTAAAGTGACAATCCTGGCGAAGTTGTC |
| | TGTTTCTTAGCTCTGAACCCATCATTCAGGTAAGATTAAGTA |
| | TTTAAGAAGAAATTTTGTTTTTACCTAAAATGAATGATCTTG |
| | TGTAACTGCTTGCTTCTTGCATTAAATAAGAACTTTCTGCTG |
| | CATATGTGACAGTTACATCCACAAAAAAGTTGGAGGTTTGTT |
| | CAGGGATTGGAAATGAAGGTACTTCAGAATTCCTGGAATGT |
| | TTATGAATGCTCCAGACTTCAGAGTCTTTAATGGAAAATTCG |
| | AGTCACTAAAAAAACATTATTCCTATCATCAGAGCTTTGAAG |
| | TTCCTCTATACAAGGTCAACTGAGTTCCTCTTTGCCTCTTGTT |
| | TAATTGTATTTACTTGTACCTTAATTATAATCTGTATATTGTT |
| | TTAGTTAAGTTCTAAAACAGGTTATTATTCATCATTTGTGCA |
| | GCATATTGCTGGAATCAAGAATCTAGTGCTTCTTCTTCCTGA |
| | CTTCACTGTCAAAATAGCAGTTCCCATGCTGGAAATAAGCGC |
| | GCTAGCAATGTAATTGATGACATGGATGTTGCTGCTTCTGAG |
| | TTTTGATCATAAAAAGCTGTTATGTGTTTCTTGAATGTAATG |
| | AAGGAGAGGAGAAAACTGAAAACTCTTGGCAAAAACGTGA |
| | AATTGCAGTGCCTCGGGGTGGTAGGGATCACCCGGATTCAG |
| | TTCAGACGATACTTTTTCAACCCGGTTTGTTCCGGTTTTCAG |
| | CTTCGGGTTTTCCTTGTACTTTTGGGGCACACATACAAGGCT |
| | ACTTCATGTTTGAGAAACCTAATTGAGGCTATCTTGTAGCAA |
| | ATGCACACCACACTCTTTCTCTCTTCTCTCCTTTTTTCACCTT |
| | CCATTTGTAAAAATCCTCTTTTAAAGGTTAATAAAAAAAAGC |
| | TTCAAGTCTCGTAGGGTGGATGTAGGTCACATTGACCGAACC |
| | ACGGTAAACTCTTTGTGTTCTTTCTTCTCTCTTTGTTTCTCATT |
| | TTTACGGCAAGTGTTTATGGTTAACCATGCATCTTAGAATAG |
| | CTTAAGGCATTAACATAATAACATCAATGTTCTCCAAAGATT |
| | CACCTTACTTGTTGTACATAATCACAATGTTAAGCCTATGAA |
| | GGTAGAATGCTCTCATGATTTGGTTTAACCAAAAAATAAACT |
| | CTAAAATAATACGGAGTAATAAAAATTGGCCATAAACTAAT |
| | TACAAAGTTTGATTTTTGTATAGGGTATCTTGTACTTGTGAT |
| | AAAAAAAATTTTAAAAAAATTAAAAAGTAAATAAATTACTT |
| | ATTCCTTCTATTTTTACTTGTTACACTTTTCTACAACAGAAAC |
| | ATCAAAACGCCCGCAACACACTATAAATGAAAAACCATTTT |
| | GTATGCAATGATATTTACGTTCTCACTTTATTCTCTTTAATAA |
| | CTCCTACTACGTAATTCTCACCAATCAAATAAAATTATAGAA |
| | ATTTTCATTTATACCCTCTTAAAATGATGTTGATTTTTTTTTTT |
| | TTTTTTAAGGTGTGAAAAAGTTTGTGTTATACTTACAACAAT |
| | TTAAAAACGGAGAACATACTTATAATACTAGTGTAATCTTTG |
| | GCCGGATTATGGTCGTTGACAAAAAAACTCCGGCCTTGACC |
| | CTCCACGTGCCGGTCAAGTTCTTCTTTTTTCATTCTTCTTTTT |
| | ATTCTTCTTTTTCTCTCCATTAATACAAATCAAGTGATTATGT |
| | CGATCCGATCCTTCTGTTCTCTACTGTAATTGATTACACCAA |
| | CAACAACCAAGCGAAACAGTCAATGTTACCGAATTGAATTG |
| | CGGAAAATAGTTTATGATTGATTCATTAAAAAAGGATGGAG |
| | TTTTGTGGATTTGAATAAGACAACGAATTGAGATTCCTGGGG |
| | TTTTCTTTCTGTTGGGGTTGGATTTCATGTACTTGTT |
| SEQ ID | TTTGAAGTTAGGCTTAACTTGCTCACCAATTCTTAAATAGAC |
| NO: 15: | TCGACTTACACTGAATTTATTGTGTACTATGTCTAGAAAGTA |
| Genomic | AGGTCAACAACTTTCTTCTAAATTATTTTGGCATGTTTATTAG |
| sequence | GGTTATTATGAAAAACATATCAAATTGGTGTTGTTAGTTAGG |
| comprising | CTTGAATAATATGATTTTAAGTCACGAGACTTTTATAAATTA |
| alpha-WOLF | GGTAATTTGATTTAAAAAATTGTTACATATCTAAGAAAATGG |
| 6 b allele | ATGTTAAATTTATCAGTCAATGTATAAACAATAAAAGTCAAT |
| (with a 2 | ATGTATGTAAAAGGGTTGCTAGATAAAATCTTTGGTTTTTTG |
| kb region | GTCCACAACTCCACACTAAGAGGAACTCCAATGCTTAGTTAC |
| upstream | AAGGTGGTGTAGTTAAAAAGTAACTCCAATAGTTAACTACA |

TABLE 1-continued

| Sequence information. | |
|---|---|
| of the | CGGTATTATAGTTAAATTTGCCAACTCAAATTTCTAACTACA |
| start | ATATATTTAAGCTACAAAGTTTCTCATTGGCTGACTACAATA |
| codon) | CGTTGTAGCGCCTTATAATATTTTATTCAATATACAATTTTAT |
| | TTATTTTACCTTTTTAACAATTTTTTTTTGATCTACCTGCTGTC |
| | CTGTTCATATGAGCTACACTAATTTGATAGCTGCTTACGCAA |
| | TTCTTATATCAACGGTTGGCTACTTGTTCAAATATTTTTATTT |
| | TTTTACGAGTAAGTCATTTTATGATCATTGAAGTGGCTCTAT |
| | TATTATTATCATGCACCGATTAACGCAAGAATAATTAACTCG |
| | GTACGAATTAGTTTCAAAATAAAATCCCTCAAAAAAAAAAG |
| | TTTCAAAATAAAATTAACAGAAAACCAACCTTCTCCGGTTTA |
| | CTGTTGTTAGAGCATGGAATTTTCCAGTAATCGCAGACCCCA |
| | AATTATCTTCCAGTTGAATCAATCCTTGATTTTTGGATTTGCC |
| | AGAAAACTCCTTGAATTTTAGGGTTCATATTTGATCCGTAAT |
| | TGGGAAAATTTTCAGCAATTGATCTTCCAAATCAGCCCTACT |
| | TGTTTCCAGACTGCAAATGAAAGGTGCGAACTTTATACTGCA |
| | TTTTGGTTTTCCATTAGTGTAATTTATTAAGATGAACTGCATT |
| | TTGCAATTGTTTTATTCGACTACTCATTTTTAAATCAAATTGC |
| | TTAATTGCTAGTTAGTTTTCTTATCATATTGCCAAAAAAAAT |
| | TATTTTTGTTTAATTGGTGAAAAAGGGTAAATTATACCTAGT |
| | GTACAAGATTTTCTTGCACACCACCGTTAATTTGTTGACACA |
| | TCATCAAACGTACTGAAAAATGAGAATGAAAGACAATAAAT |
| | ATGTCATTTTAACCAATAGAAAAACATGATGTAGTAAGATC |
| | CTTAATTGATAGATAAATAATTAAATATCAGTCCATTAGTTG |
| | AATATTCAATGAAAATGTATGGTCCAAAAATGGCGTTTAAT |
| | AGTCAATGTCATGCTTTATGGGGTGGTGGAGTACTATGTGAC |
| | TGTGTGTGGACTTGGAGAAGACTAGAGAGTATGATTATCAA |
| | CCTATGGACCCTCAAAATGAAAATGAAAATGATGTTTACAC |
| | GTGCTATTTGCACGGACTTCAATGCAAATAGTATAAATTTAC |
| | GGTCAAAGTTTTCATTCTAAAGCGTAAATAACTTTCATGAAT |
| | GGAGGACGGTAGTATAAGTATAACGTTATAGCCTACCATTTT |
| | CTTATCATATTCACATAAATTTGTTGCTGAAATTTGTTTTACT |
| | TGGCTAAAATACTTTTGTTCTTATTGGCAGATAAACATCAGT |
| | ACGTCCATTATTGGCCAACTTGCTGAGTCCATTATTGGCCAA |
| | CTTGAACATATACCTCCAAACAATAATCAATAATGTCGATTA |
| | TGAAGTTTGTGAATGCAATTTATTATCACTTTCATTTATAAA |
| | ATGACTACTTGATTAACACATACAATATTACCTTTCTCCAAA |
| | CACCCTTTCAATTCTGCTTAATCTTGTTTTCTCATCATCTCTT |
| | CATCTTTCTGAAAACACAACCCA**ATG**GCCGAAATCGGATAC |
| | TCGGTTTGTGCGAAACTCATCGAAGTGATTGGCAGTGAGCTG |
| | ATCAAAGAGATTTGTGACACATGGGGTTACAAATCTCTTCTT |
| | GAGGACCTCAACAAAACTGTATTGACGGTCAGGAACGTTCT |
| | CATTCAAGCCGGGGTGATGCGGGAGCTTACTAGTGAACAAC |
| | AAGGTTTCATTGCAGACCTTAAAGATGTTGTTTATGATGCTG |
| | ATGACTTGTTCGACAAGTTACTCACTCGTGCTGAGCGAAAAC |
| | AGATTGATGGAAACGAAATCTCTGAAAAGGTACGTCGTTTC |
| | TTTTCCTCTAGTAACAAGATCGGTCAAGCTTACTACATGTCT |
| | CGTAAGGTTAAGGAAATTAAGAAGCAGTTGGATGAAATTGT |
| | TGATAGGCATACAAAATTTGGGTTTAGTGCTGAGTTTATACC |
| | TGTTTGTAGGGGAAGGGGAAACGAGAGGGAAACACGTTCAT |
| | ATATAGATGTCAAGAATATTCTTGGGAGGGATAAAGATAAG |
| | AATGATATCATAGATAGGTTGCTTAATCGTAATGGTAATGAA |
| | GCTTGTAGTTTCCTGACCATAGTGGGAGCGGGAGGATTGGG |
| | AAAAACTGCTCTTGCACAACTTGTGTTCAATGATGAAAGGGT |
| | CAAAATTGAGTTCCATGATTTGAGGTATTGGGTTTGTGTCTC |
| | TGATCAAGATGGGGGCCAATTTGATGTGAAAGAAATCCTTT |
| | GTAAGATTTTAGAGGTGGTTACTAAGGAGAAAGTTGATAAT |
| | AGTTCCACATTGGAATTGGTACAAAGCCAATTTCAAGAGAA |
| | GTTAAGAGGAAAGAAGTACTTCCTTGTTCTTGATGATGTATG |
| | GAACGAAGATCGTGAGAAGTGGCTTCCTTTGGAAGAGTTGT |
| | TAATGTTGGGTCAAGGGGGAAGCAAGGTTGTAGTGACCACA |
| | CGTTCAGAGAAGACAGCAAATGTCATAGGGAAAAGACATTT |
| | TTATACACTGGAATGTTTGTCACCAGATTATTCATGGAGCTT |
| | ATTTGAAATGTCGGCTTTTCAGAAAGGGCATGAGCAGGAAA |
| | ACCATCACGAACTAGTTGATATTGGGAAAAAGATTGTTGAA |
| | AAATGTTATAACAATCCACTTGCTATAACGGTGGTAGGAAG |
| | TCTTCTTTATGGAGAGGAGATAAGTAAGTGGCGGTCATTTGA |
| | AATGAGTGAGTTGGCCAAAATTGGCAATGGGGATAATAAGA |
| | TTTTGCCGATATTAAAGCTCAGTTACCATAATCTTATACCCT |
| | CGTTGAAGAGTTGTTTTAGTTATTGTGCAGTGTTTCCCAAGG |
| | ATCATGAAATAAAGAAGGAGATGTTGATTGAACTTTGGATG |
| | GCACAAGGATATGTTGTGCCGTTGGATGGAGGTCAAAGTAT |
| | AGAAGATGCTGCCGAGGAACATTTTGTAATTTTGTTACGAAG |
| | GTGTTTCTTTCAAGATGTAAAGAAGGATAAATATGGTGATGT |
| | TGATTCTGTTAAAATCCACGACTTGATGCACGATGTCGCCCA |
| | AGAAGTGGGGAGGGAGGAATTATGTGTAGTGAATGATAATA |
| | CAAAGAACTTGGGTGATAAAATCCGTCATGTACATCGTGAT |
| | GTCATTAGATATGCACAAAGAGTCTCTCTGTGTAGCCATAGC |
| | CATAAGATTCGTTCGTATATTGGTGGTAATTGTGAAAAACGT |

TABLE 1-continued

| Sequence information. |
|---|
| TGTGTGGATACACTAATAGACAAGTGGATGTGTCTTAGGAT<br>GTTGGACTTGTCATGGTCGGATGTTAAAAATTTGCCTAATTC<br>AATAGGTAAATTGTTGCACTTGAGGTGTCTTAACCTGTCTTA<br>TAATAAAGATCTGTTGATACTCCCTGATGCAATTACAAGACT<br>GCATAATTTGCAGACACTGCTTTTAAAAGAGTGCAGAAGTTT<br>AAAGGAGTTGCCAAAAGATTTTTGCAAATTGGTCAAACTGA<br>GGCACTTGGATTTAAGGTGTTCTGATTTGAAGGAGTTGCCAA<br>AAGATTTTTGCAAATTGGTCAAACTGAGGCACTTGGATTTAT<br>GGGGTTGTGATGATTTGATTGGTGTGCCATTGGGAATGGATA<br>GGCTAATTAGTCTTAGAGTACTGCCATTCTTTGTGGTGGGTA<br>GGAAGGAACAAAGTGATGATGATGAGCTGAAAGCCCTAAA<br>AGGCCTCACCGAGATAAAAGGCTCCATTCGTATTAGAATCT<br>ATTCAAAGTATAGAATAGTTGAAGGCATGAATGACACAGGA<br>GGAGCTGGGTATTTAAAGAGCATGAAACATCTCACGGGGGT<br>TGATATTACATTTGATGGTGGATGTGTTAACCCTGAAGCTGT<br>GTTGGCAACCCTAGAGCCACCTTCAAATATCAAGAGGTTAG<br>AGATGTGGCATTACAGTGGTACAACAATTCCAGTATGGGGA<br>AGAGCAGAGATTAATTGGGCAATCTCCCTCTCACATCTTGTC<br>GACATCCAGCTTTGGCATTGTCGTAATTTGCAGGAGATGCCA<br>GTGCTGAGTAAACTGCCTCATTTGAAATCACTGGAACTTTAT<br>AATTTGATTAGTTTAGAGTACATGGAGAGCACAAGCAGAAG<br>CAGTAGCAGTGACACAGAAGCAGCAACACCAGAATTACCAA<br>CATTCTTCCCTTCCCTTGAAAAACTTAGACTTTGGCGTCTGG<br>ACAAGTTGAAGGGTTTTGGGAACAGGAGATCGAGTAGTTTT<br>CCCCGCCTCTCTAAATTGGAAATCTGGAAATGCCCAGATCTA<br>ACGTCATTTCCTTCTTGTCCAAGCCTTGAAGAGTTGGAATTG<br>AAAGAAAACAATGAAGCATTGCAAATAATAGTAAAAATAAC<br>AACAACAAGAGGTAAAGAAGAAAAAGAAGAAGACAAGAAT<br>GCTGGTGTTGGAAATTCACAAGATGATGACAATGTCAAATT<br>ACGGAAGGTGGAAATAGACAATGTGAGTTATCTCAAATCAC<br>TGCCCACAAATTGTCTTACTCACCTCGACCTTACAATAAGAG<br>ATTCCAAGGAGGGGGAGGGTGAATGGGAAGTTGGGGATGC<br>ATTTCAGAAGTGTGTATCTTCTTTGAGAAGCCTCACCATAAT<br>CGGAAATCACGGAATAAATAAAGTGAAGAGACTGTCTGGAA<br>GAACAGGGTTGGAGCATTTCACTCTGTTGGAATCACTCAAAC<br>TTTCAGATATAGAAGACCAGGAAGATGAGGGCGAAGACAAC<br>ATCATATTCTGGAAATCCTTTCCTCAAAACCTCCGCAGTTTG<br>AGAATTAAAGACTCTGACAAAATGACAAGTTTGCCCATGGG<br>GATGCAGTACTTAACCTCCCTCCAAACCCTCTATCTACACCA<br>TTGTTATGAATTGAATTCCCTTCCAGAATGGATAAGCAGCTT<br>ATCATCTCTTCAATCCCTGCACATAGGAAAATGTCCAGCCCT<br>AAAATCACTACCAGAAGCAATGCGGAACCTCACCTCCCTTC<br>AGAGACTTACGATATGGCAGTGTCCAGACCTAATTGAAAGA<br>TGCAAAGAACCTAACGGGGAGGACTATCCCAAAATTCAACA<br>CATCCCCAAAATTGTAAGTCATTGCAGAAAGTAATTTATTCA<br>TTTATATTTATTTTATGCTTAGAATGATATACACCGTCGTCCT<br>TTGGTTTCAAATCTTGAATTTGGTTTTTGTTTTCTTTCTTTGTT<br>TCTTTATTCAACACCAGCCCATTTATGATTGATTCATTAAAA<br>AAAGGATGGAGTTTTGTGGATTTGAAGAAGACAACGAATTG<br>AGATTCCTGGGGTTTTCTTTTTGTTGGGGTTGGATTTCATGTA<br>TATGTTGCTGATTAAATACGAGACTGATGATGATGATGATGT<br>GTTTATGGGTTTTAAATCAGATTAAATATATGGGAAATGTAA<br>GTTAATTTGGGATGCACATAAGGTGTTTGCTGAAATGTCTAT<br>GAGAAATGTTGTTTCTTGGACTTAGAATGATATACACTGTCG<br>TCCATTGGTTTCCAATCTTACATTTGGTTTGTGTTTTCTTAGT<br>TTGTTTCTTTAATCAACACCAACCCATTTTTTTAAAACTACCT<br>GCAACTACTAATTTACGTTGACCCTGTATCTCAGGTACTAAA<br>TGAATATTGGTGATTTTCAGTTACTCAACACTAGCTTGATCC<br>TGAACGCACCCAACCTTCAGGTTAGAATCCGGCTTACTCATC<br>CTTTTGTCCAGTTTTCAAGTAATTGTTTTGGCAGGATCAATTC<br>TCTAATTGTTGTACACCGTATATTGCAATTTATAGTGACTAC<br>AGTTAATGAATGTTTACAAAAAATTAGTCATGTAAAAACTTC<br>TTCTCTGTCCATTACATAAACTCTTTTTCTCTTTCTAACTTAT<br>CATGTTCATGTCTAAAAAATTAAACATGCTCACATCAATGTT<br>CATTTAAGCTAACTTACTTCTGTAAGAGAGCGAGCTAGTTAA<br>AAACTCCTTTAACTTTCTGTTTTATACTCAGGACATGGATTG<br>ATGCAAGCATGAAGAACTTCGGGAATTTGCTAAAACTCTAC<br>CAAAGCGATGAGAGTTTGGACTTTGTTTCACTTGAAGTCAGG<br>GACTGTCAACAAAGCCACAGTGTGCATGTTGGCTGTTTCACT<br>TGGACGATAAAAAGGTTTATTTAATTGTTTTCCTAAGTGTAT<br>TTGGCTTACAAGCTTTTACTTTTCGCTTGAAAGGGTTTTTCTT<br>GTTTTAAGCTTTTTGAATTAGAGTTTCGGTTGAAGTAAGAGT<br>AGTCGTATTAGTCTTTTACTTTGCAGGAGTCTATGCCTATAT<br>AAGGTAAGACTCGTATTTGTAATTTTCAGATTATGCAATTCA<br>AGTTTTCGAGTGTTTTCTTAAAAAAACATATCATACCTGTGT<br>GTAGCATAAAGATAAATTCTGATGCTGTGCTTCTTGTTATGG<br>CTCACATTGGTTTTCATTGTTTGGATTGTTTCACAGGGAAGC<br>AGAGAATACCTGGAACCTGTAAAGGACGCTATATCTATAGC |

TABLE 1-continued

| | Sequence information. |
|---|---|
| | AGCTTTCACAGGCCAAGTAATATAATGTTCTTTATCAATCAC<br>TCAATACCTGGAGATTGTTTGAACACATAATTCACCTCTTTT<br>TTTCCATCTCAAATTGCAGACTTTTACTGGGATTTGAATGAC<br>AGCAAACATTTGATTGTCACGAGGATTGATCTAACTGGTGA<br>ATGTTGTGATCACCATATTGGTCTTTCTCATTCAAACAAACT<br>TGCATACCGTTCTTTTGAAGTTTGAAGACAAGCAGGCGATAA<br>TCAACTCAGGTCGAAGCTCATGTGCAGGAGAGAATAGAATA<br>TAGAGGAGATTATTTTTAAAAGAAACGCTCAAAGGTATTGT<br>AGCACCTTTCCTATTTGCTACTGCAGTGATGTTTTTATTTCTT<br>GTTTGCAGCGCTTGTTTCTCATATTTCAACCTACTTTTAGAAA<br>AAAAAACATCTCCGAACATAACCAAAAATAAAGTTCCCTTA<br>TCAGTGCTTTCCCTGCTTTCTTCTAAACAACATATACAATTAT<br>AAACCCTTTTTCTCTCTTACCTTTGTTATTCTTCCTTGCTTCAT<br>TGAGATAACACTCTCCTGTTTTTGTTTTGTTGTTAGTCATTAC<br>ATGGATATATCAAGGACAACAGTTCTGTAGTCCGTCAACTGT<br>GGTTAGGAAGGCTAAACTGGAGCACAATAACCCCATGTCAA<br>TTGAATAGTAAAGGTGTGCTATATCAGTTTCGTTTGGCTTGG<br>CTTACCTGAAAAATGGCTGGTTATTTATCCTTGTCTCTTTCTA<br>TGACGTGCAGTGGCTTGTTAATGTGTCTCGGACAACAATTCC<br>TCACTTTCCAAGTTCCATACACGCTGATGTAACTATCTTCTG<br>CAGTCTGTTCTTTCATTTTTGCCACGTGCTCTAATTATAACTT<br>TTTGTACTCAATAATCAACTCCTTGTCCCGGTATTTGCAGAG<br>ACTACTTAAACAGGTAAAGTGACAATCCTGGCGAAGTTGTC<br>TGTTTCTTAGCTCTGAACCCATCATTCAGGTAAGATTAAGTA<br>TTTAAGAAGAAATTTTGTTTTTACCTAAAATGAATGATCTTG<br>TGTAACTGCTTGCTTCTTGCATTAAATAAGAACTTTCTGCTG<br>CATATGTGACAGTTACATCCACAAAAAAGTTGGAGGTTTGTT<br>CAGGGATTGGAAATGAAGGTACTTCAGAATTCCTGGAATGT<br>TTATGAATGCTCCAGACTTCAGAGTCTTTAATGGAAAATTCG<br>AGTCACTAAAAAAACATTATTCCTATCATCAGAGCTTTGAAG<br>TTCCTCTATACAAGGTCAACTGAGTTCCTCTTTGCCTCTTGTT<br>TAATTGTATTTACTTGTACCTTAATTATAATCTGTATATTGTT<br>TTAGTTAAGTTCTAAAACAGGTTATTATTCATCATTTGTGCA<br>GCATATTGCTGGAATCAAGAATCTAGTGCTTCTTCTTCCTGA<br>CTTCACTGTCAAAATAGCAGTTCCCATGCTGGAAATAAGCGC<br>GCTAGCAATGTAATTGATGACATGGATGTTGCTGCTTCTGAG<br>TTTTGATCATAAAAAGCTGTTATGTGTTTCTTGAATGTAATG<br>AAGGAGAGGAGAAAACTGAAAACTCTTGGCAAAAACGTGA<br>AATTGCAGTGCCTCGGGGTGGTAGGGATCACCCGGATTCAG<br>TTCAGACGATACTTTTTTCAACCCGGTTTGTTCCGGTTTTCAG<br>CTTCGGGTTTTCCTTGTACTTTTGGGGCACACATACAAGGCT<br>ACTTCATGTTTGAGAAACCTAATTGAGGCTATCTTGTAGCAA<br>ATGCACACCACACTCTTTCTCTCTTCTCTCCTTTTTTCACCTT<br>CCATTTGTAAAAATCCTCTTTTAAAGGTTAATAAAAAAAAGC<br>TTCAAGTCTCGTAGGGTGGATGTAGGTCACATTGACCGAACC<br>ACGGTAAACTCTTTGTGTTCTTTCTTCTCTCTTTGTTTCTCATT<br>TTTACGGCAAGTGTTTATGGTTAACCATGCATCTTAGAATAG<br>CTTAAGGCATTAACATAATAACATCAATGTTCTCCAAAGATT<br>CACCTTACTTGTTGTACATAATCACAATGTTAAGCCTATGAA<br>GGTAGAATGCTCTCATGATTTGGTTTAACCAAAAAATAAACT<br>CTAAAATAATACGGAGTAATAAAAATTGGCCATAAATTATT<br>TACAAAGTTTGATTTTTGTATAGGGTATCTTG |
| SEQ ID NO: 16: Genomic sequence of alpha-WOLF 8 allele | ATGGCCGAAATCGGATACTCGGTTTGTGCGAAACTCATCGA<br>AGTGATTGGCAGTGAGCTGATCAAAGAGATTTGTGACACAT<br>GGGGTTACAAATCTCTTCTTGAGGACCTCAACAAAACTGTAT<br>TGACGGTCAGGAACGTTCTCATTCAAGCCGGGGTGATGCGG<br>GAGCTTACTAGTGAACAACAAGGTTTCATTGCAGACCTTAA<br>AGATGTTGTTTATGATGCTGATGACTTGTTCGACAAGTTACT<br>CACTCGTGCTGAGCGAAAACAGATTGATGGAAACGAAATCT<br>CTGAAAAGGTACGTCGTTTCTTTTCCTCTAGTAACAAGATCG<br>GTCAAGCTTACTACATGTCTCGTAAGGTTAAGGAAATTAAG<br>AAGCAGTTGGATGAAATTGTTGATAGGCATACAAAATTTGG<br>GTTTAGTGCCGAGTTTATACCTGTTTGTAGGGAAAGGGGGA<br>ACGAGAGGGAAACACGTTCATATATAGATGTCAAGAATATT<br>CTTGGGAGGGATAAAGATAAGAATGATATCATAGATAGGTT<br>GCTTAATCGTAATGGTAATGAAGCTTGTAGTTTCCTGACCAT<br>AGTGGGAGCGGGAGGATTGGGAAAAACTGCTCTTGCACAAC<br>TTGTGTTCAATGATGAAAGGGTCAAAATTGAGTTCCATGATT<br>TGAGGTATTGGGTTTGTGTCTCTGATCAAGATGGGGGCCAAT<br>TTGATGTGAAAGAAATCCTTTGTAAGATTTTAGAGGTGGTTA<br>CTAAGGAGAAAGTTGATAATAGTTCCACATTGGAATTGGTA<br>CAAAGCCAATTTCAAGAGAAGTTAAGAGGAAAGAAGTACTT<br>CCTTGTTCTTGATGATGTATGGAACGAAGATCGTGAGAAGTG<br>GCTTCCTTTGGAAGAGTTGTTAATGTTGGGTCAAGGGGGAA<br>GCAAGGTTGTAGTGACCGCACGTTCAGAGAAGACAGCAAAT<br>GTCATAGGGAAAAGACATTTTTATACACTGGAATGTTTGTCA<br>CCAGATTATTCATGGAGCTTATTTGAAATGTCGGCTTTTCAG |

TABLE 1-continued

| Sequence information. |
|---|
| AAAGGGCATGAGCAGGAAAACCATCACGAACTAGTTGATAT<br>TGGGAAAAAGATTGTTGAAAAATGTTATAACAATCCACTTG<br>CTATAACGGTGGTAGGAAGTCTTCTTTATGGAGAGGAGATA<br>AGTAAGTGGCGGTCATTTGAAATGAGTGAGTTGGCCAAAAT<br>TGGCAATGGGGATAATAAGATTTTGCCGATATTAAAGCTCA<br>GTTACCATAATCTTATACCCTCGTTGAAGAGTTGCTTCAGTT<br>ATTGTGCAGTGTTTCCCAAGGATCATGAAATAAAGAAGGAG<br>ATGTTGATTGATCTTTGGATAGCACAAGGATACGTTGTGGCA<br>CTTGATGGAGGTCAAAGTATAGAAGATGCTGCCGAAGAACA<br>TTTTGTAATTTTGTTACGGAGATGTTTCTTTCAAGATGTAAA<br>GAAGGATGAATATGGTGATGTTGATTCTGTTAAAATCCACG<br>ACTTGATGCACGATGTCGCCCAAGAAGTGGGGAGGGAGGAA<br>ATATGTGTAGTGAATGATAATACAAAGAACTTGGGTGATAA<br>AATCCGTCATGTACATGGTGATGTCAATAGATATGCACAAA<br>GAGTCTCTCTGTGTAGCCATAGCCATAAGATTCGTTCGTATA<br>TTGGTGGTGATTGTGAAAAACGTTGTGTGGATACACTAATAG<br>ACAAGTGGATGTGTCTTAGGATGTTGGACTTGTCATGGTCGG<br>ATGTTAAAAATTTGCCTAATTCAATAGGTAAATTGTTGCACT<br>TGAGGTATCTTAACCTGTCAGATAATAGAAATCTAAAGATA<br>CTTCCTGATGCAATTACAAGACTGCATAATTTGCAGACACTG<br>CTTTTAAAAGATTGCAGAAGTTTAAAGGAGTTGCCAAAAGA<br>TTTTTGCAAATTGGTCAAACTGAGACACTTGGATTTATGGGG<br>TTGTGATGATTTGATTGGTATGCCATTTGGAATGGATAAGCT<br>AACTAGTCTTAGAATACTACCAAACATTGTGGTGGGTAGGA<br>AGGAACAAAGTGTTGATGATGAGCTGAAAGCCCTTAAAGGC<br>CTCACCGAGATAAAAGGCGACATTGATATCAAAATCTGTGA<br>AAATTATAGAATAGTTGAAGGCATGAATGACACAGGAGGAG<br>CTGGGTATTTGAAGAGCATGAAACATCTCAGGGAGATTGGT<br>ATTACATTTGATGGTGGATGTGTTAACCCTGAAGCTGTGTTG<br>GCAACCCTAGAGCCACCTTCAAATATCAAGAGCTTATCTATA<br>CATCGTTTTGATGGTAAAACACTTCCAGTATGGGGAAGAGC<br>AGAGATTAATTGGGCAATCTCCCTCTCACATCTTGTCGACAT<br>CCAGCTTTGGCATTGTCGTAATTTGCAGGAGATGCCAGTGCT<br>GAGTAAACTGCCTCATTTGAAATCACTGGAACTTTATAATTT<br>GATTAGTTTAGAGTACATGGAGAGCACAAGCAGAAGCAGTA<br>GCAGTGACACAGAAGCAGCAACACCAGAATTACCAACATTC<br>TTCCCTTCCCTTGAAAAACTTACACTTTGGGGTCTGGAAAAG<br>TTGAAGGGTTTGGGGAACAGGAGATCGAGTAGTTTTCCCCG<br>CCTCTCTGAATTGAAAATCATGGAATGCCCAGATCTAACGTG<br>GTTTCCTCCCTGTCCAAGCCTTGAAAAACTTACACTTTGGCG<br>TCTGGACAAGTTGAAGGGTTTTGGGAACCGGAGATCGAGTA<br>CTTTTCCCCGCCTCTCTGAATTGGAAATCAAGAAATGCCCAG<br>ATCTAACGTCATTTCCTTCTTGTCCAAGCCTTGAGAAGTTGG<br>AATTGAAAGAAAGCAATGAAGCATTGCAAATAATAGTAAAA<br>ATAACAACAAGAGGTAAAGAAAAAGAAGAGAACAATAATG<br>CTGGTGTTAGAAATTCACAAGATGATGACAAAGTCAAATTA<br>CGGAAGATGGTGATAGACAATCTGGGTTATCTCAAATCACT<br>GCCCACAAATTGTCTTACTCACCTCGACCTTACAATAAGTGA<br>TTCCAAGGAGGGGGAGGGTGAATGGGAAGTTGGGGATGCAT<br>TTCAGAAGTGTGTATCTTCTTTGAGAAGCCTCACCATAATCG<br>GAAATCACGGAATAAATAAAGTGAAGAGACTGTCTGGAAGA<br>ACAGGGTTGGAGCATTTCACTCTGTTGGAATCACTCAAACTT<br>TCAGATATAGAAGACCAGGAAGATGAGGGCGAAGACAACA<br>TCATATTCTGGAAATCCTTTCCTCAAAACCTCCGCAGTTTGA<br>GAATTAAAGACTCTGACAAAATGACAAGTTTGCCCATGGGG<br>ATGCAGTACTTAACCTCCCTCCAAACCCTCTATCTACACCAT<br>TGTTATGAATTGAATTCCCTTCCAGAATGGATAAGCAGCTTA<br>TCATCTCTTCAATACCTGCGCATATACTACTGTCCAGCCCTG<br>AAATCACTACCAGAAGCAATGCGGAACCTCACCTCCCTTCA<br>GACACTTGGGATATCGGATTGTCCAGACCTAGTTAAAAGAT<br>GCAGAAAACCCAACGGCAAGGACTATCCCAAAATTCAACAC<br>ATCCCCTATTGGAGTATAGAACATCAGGTTATAACTAGCTTG<br>TAACTAACTTGTAACTACCTAGTATAAATACAGTAGTTTGTA<br>CTATTTTACATTCAATTACACAATTAATAAAATGTAGACTCT<br>CACTCTCTCTCTCTAAGCCACGAGCTCCAAGCTCGTCAATGG<br>CTTCCCTTCTCTGTTCTTGCTTTCTTCTTTCCTCTTCAATTCAC<br>AAATTCAACATGGTATCAGAGCGGGACGATCCTTGCTCTTCA<br>CTTCCGCACAAAATTTTCGTTCAATTCAACCCATCAAATTTTT<br>TTTTTCCCCCAAATTTTCTCGAATTCGGTCAAAATTCGACGA<br>ATTAGGGATTCAATTTACCCTGATTTCTTCTGATTCCATTCAA<br>TGATTGTTCATTTCGAATCTTGAATCAAATAATTGTTGATTCT<br>GGATTCCCCAAATTCTAGGGTTCTTGAAGGATTTACAAGAAT<br>CTGGCATTGCTGATAGATTCTTGAAGCAATTTGCGTCTCCGT<br>GTTCCTCGGTGGTCTTGAGTTTGTTTCCGTATTCGCTGCTCTC<br>ATCTTTACTGGGGATTGTGGTCTGATTTCTTGGCTTCCTCTGT<br>CGATGATGTGATTGGTAATACTTAAAACCCCTCTCTCTCTTT<br>CCGAAATTATTGATGCTGGTTCGTCATTTTTTTTTTTGGAATC<br>ATCTCAGTTTATCGCCGCAATTTGAGTTGTTGTTGGGTAATT |

TABLE 1-continued

| Sequence information. |
| --- |
| GTTGTTGCTGCCGATGATGTTTTGTGAATTTGAGAATTGTTA<br>GAATGATTCTTGTTCAATCAATTTGGTTCTCATACTCTAATG<br>GAAGCCTGTTTTGGAGCGACGAATTATGCAATTCTGAGATTT<br>CTTTTGATCCTTATTTCTTTTCTTCACTTGAATTTCTGGTGTTT<br>GTGAGTAATTCTTGGTTAATGTTTGATCTGGGTAGTTCTTGG<br>GTTTACTGAAGACGTTTCTTGAAGGTTTTGACAGAAAAGCTG<br>AGGTTTAATTCCAAAATTCTTCTGTCCAATTACATTTTTATTG<br>TTGATGGTTCTTATGTGAGAACTAGACTGAGTTTTTTTATG<br>AAATTGTTTCGACCTTCAGATGGATTCGAGAGATTTGAGTTC<br>ATTTTCTTTGATGAATGTGTTAGAAAAGGTTTTGGTGCAGTG<br>ACCATTTTAAACCAAATAGAGTTACATAAATATTGGGATTCT<br>TTTCTGGGAATGTAGTTAGGAGTTGAAATCTTTTGGAGCTGC<br>TTTACCATAAAACCCAGCCTCAGAGTCTGTTAACCAGTTAGG<br>ACCGTGTAAACATGATCCCAGGCTGCATTTGCGTTATCAGAT<br>TTGATTCAGTTTTGGAATTGTGGATTTTGAGGGTTTAAAAGC<br>TTACAGTTGCTCCTGGAGAATGGTGTGAGCAATATAGGAATT<br>CAGCACTAGTATTGCAGAAAATGAAGCTTGGTTGTTGATTGT<br>TGGCATGTTTTGTTGCCATTGTTTTGGGTTGATGTTTTCCTTT<br>TCTTTTGAATGTTGGCACGATTCAACATTTCTTTCCTGCAACA<br>GATTTGGAGTTCAGTACCTGTATAATCAGGTCAATTTTGTTC<br>ATTTTTCCCAGCAACAGATCTGGAGAATCAGAACCTGTAAA<br>ANNNNNNNNNNNNNNNNNNNNNNNNNNNNNNNNNNNNNNN<br>NNNNNNNNNNNNNNNNNNNNNNACCCAAAGAGGTCAGTTT<br>TCATTGATCCATTGTGATCATTCTTTTGATGAGACCCATTGA<br>GGCTCATTTCTTCAAGGCAATATTGGAAGTTGTAGATTGATA<br>TGAGCAGTTGGTACAACAGCAACAAAAGTGGCCAGCATCTA<br>TGCTTGTTCATGAGGAGTTCTTGGTGCAGAGTTAATGAAGAG<br>TCTGTTTTGAAGCTTTCAAACTGAAGATGTTTATCACCATCT<br>CCAGTTTGAGGGGGGGTATTGGAGTATAGAACATCAGGTTA<br>TAACTAGCTTGTAACTAACTTGTAACTACCTAGTATAAATAC<br>AGTAGTTTGTACNNNNNNNNNNNNNNNNNNNNNNNNNNNNN<br>NNNNNNNNNNNNNNNNNNNNNNCCACGAGCTCCAAGCTCG<br>TCAATGGCTTCCCTTCTCTGTTCTTGCTTTCTTCTTTCCTCTTC<br>AATTCACAAATTCAACATCCCCAAAATTGTAAGTCATTGCAG<br>AAAGTAATTTATTCATTTATATTTATTTTATGCTTAGAATGAT<br>ATACGCAGTCGTCCTTTGGTTTCAAATCTTGAATTTGGTTTTT<br>GTTTTCTTTCTTTGTTTCTTTATTCAACACCAGCCCATTTATG<br>ATTGATTCATTAAAAAAAGGATGGAGTTTTATGGATTTGAAG<br>AAGACAACGAATTGAGATTCCTGGGGTTTTCTTTTTGTTGGG<br>GTTGGATTTCATGTATATGTTGCTGATTAAATACGAGACTGA<br>TGATGATGATGTGTTTATGGGTTTTAAATCAGATTAAATATA<br>TGGGAAATGCAAGTTAATTTGGGATGCACATAAGGTGTTTG<br>CTGAAATGTCTATGAGAAATGTTGTTTCTTGGACTTAGAATG<br>ATATACACTGTCGTCCTTTGGTTTCCAATCTTACATTTGGTTT<br>GTGTTTTCTTAGTTTGTTTCTTTAATCAACACCAACCCGTTTT<br>TTTTAAACTACCTGCAACTACTAATTTACGTTTACCCTGTATC<br>TCAGGTACTAAATGAATATTGGTGATTTTCAGTTACTCAACA<br>CTAGCTTGATCCTGAACGCACCCAACCTTCAGGTTAGAATCC<br>GGCTTACTCATCCTTTTGTCCAGTTTTCAAGTAATTGTTTTGG<br>CAGGATCAATTCTCTAATTGTTGTACACCGTATATTGCAATT<br>TATAGTGACTACAGTTAATGAATGTTTACAAAAAATTAGTCA<br>TGTAAAAACTTCTTCTCTGTCCATTACATAAACTCTTTTTCTC<br>TTTCTAACTTATCATGTTCATGTCTAAACAATTAAACATGCT<br>CACATCAATGTTCATTTAAGCTAACTTACTTCTGTAAGAGAG<br>CGAGCTAGTTAAAAACTCCTTTAACTTTCTGTTTTATACTCA<br>GGACATGGATTGATGCAAGCATGAAGAACTTCGGGAATTTG<br>CTAAAACTCTACCAAAGCGATGAGAGTTTGGACTTTATTTCA<br>CTTGAAGTCAGGGACTGTCAACAAAGCCACAGTGTGCATGT<br>TGGCTGTTTCACTTGGACGATAAAAAGGTTTATTTAATTGTT<br>TTCCTAAGTGTATTTGGCTTACAAGCTTTTACTTTTCACTTGA<br>AAGGGTTTTTCTTGTTTTAAGCTTTTCGAATTAGAGTTTTCGG<br>TTGAAGTAAGAGTAGTCGTATTAGTCTTTTACCTAAGGAAGA<br>CTCTTTTTTGTAATTTTCAGACTATGCAATTCAAGTTTTCGAG<br>TGTTTTCTTGCTTGTGTGATTGTGAGTTGGTGAATTCGTCTTT<br>CATACATTTTGAGATTATCAGAAGCTTTATGCTCCACCGGTA<br>GTCTAGTACCTTTTCTGTTACTGTGCAGGGAAGTAATCTGGT<br>ACCTTCTATATATATGGAAAAACATACATTATACATTATGCA<br>AAATTCTTACAGGTTAGTTACTTCCTGGAACTTCATTTACAC<br>TTAGTTTTTTTTGTTCCATTCCCTCGGAATCAAGTCATTCCCT<br>CTGAGAAATATGTAATGAACTTCTGTATGTTGCTGTTTGGTT<br>CCTGTTTTAATCTTCAATTTTCTTGTATAGTTACAGCTGCATT<br>TACAATGAAGTTTAAGCAGACACTCTCTTTATATAGTGCCTC<br>TTTCTGGAGCACCGTAGAGCTGTCTGTGGTTGATCACCATCT<br>GCTGCCGAGAGATTCAGCAATCGCGTGTTTGATCAGGTAAA<br>AGTTTTTATGTCAATGTGTTTTTTTTTCCGTTTGATCAATTTA<br>TGTCTGTATTCAGATTCTTATCTTCTTACAGTAGCATAACAC<br>ATTGTTTCTTTCATTTATGTAAACTGTTTCAAGATTACAGAG<br>ATGTATGCTTCAGTCGACATTGATGATAACTTAAGATGGCAT |

TABLE 1-continued

| Sequence information. | |
|---|---|
| | TCCTACAACAGTTGCAGGCGCATTCTAACTCCGGCAATTCTA<br>GTTAGGCAAGAGGAGCATTGCCAATACCTGCCACCTCTGGG<br>ATTTACTATACCAGGGTTGAAGTTTATGGAAGACACCAGCTA<br>TGCACAAGCCTTCAAGGGGTCATCCTACATAACAAGTTGAA<br>CCAACCAATTGCTTGTTGGTTCAGTGGTAATTGAAGCTGAAT<br>TTGGTAGGGATGGCCCGTGTTCGATCCCCACAACAACAATTG<br>GGAGGGGACTGGAACCTATCCACACAGAACTCGCCCTGAAT<br>CCGGATTAGCCCTAAGGGTGAACGGGGTGCTAACACCAAAA<br>AAAAAAACATAACAAGTTGAACCAAACATACTTTGTTTGAA<br>TTGAAGATTTAGTGATTTCATTTGATCGATTGAGATGTCTTA<br>TTATAAGCGTATATGCTCTTGGATTTGGCCACTTAGGTGTTG<br>TTTGACAATTGGACATTAACTCGCTTTTATATTTTCTTTTCTC<br>TTAGGAAAGGTGATCCTGAGAATTTATATTGGAACACTTTTT<br>TTTTCTCACTAGCTTTAAAAAAGTGTTCTGTGTTACCTGCAAT<br>TCAATTTGATTATTTTTCACATAGTTTTACCTGAAAAAGTGTT<br>ACCTGAAAAAGTGTTACCTGAAAATCAACTGACATAAGTTTT<br>TGTTTGGATCCAATTAAGGACACTAGATAAATCGGAATAAA<br>TAATCAACCAATTAAGTACTTCATAATTAAATATGAAGTGTA<br>TTATTATCTTATGCTTGTGACATTGAAGGATGTTATGATATTT<br>TAACTCAATACCTTGCAAAATATACTGG |
| SEQ ID NO: 17: Genomic sequence comprising alpha-WOLF 9 allele (with a 2 kb region upstream of the start codon) | TTTGAAGTTAGGCTTAACTTGCTCACCAATTCTTAAATAGAC<br>TCGACTTACACTGAATTTATTGTGTACTATGTCTAGAAAGTA<br>AGGTCAACAACTTTCTTCTAAATTATTTTGGCATGTTTATTAG<br>GGTTATTATGAAAAACATATCAAATTGGTGTTGTTAGTTAGG<br>CTTGAATAATATGATTTTAAGTCACGAGACTTTTATAAATTA<br>GGTAATTTGATTTAAAAAATTGTTACATATCTAAGAAAATGG<br>ATGTTAAATTTATCAGTCAATGTATAAACAATAAAAGTCAAT<br>ATGTATGTAAAAGGGTTGCTAGATAAAATCTTTGGTTTTTTG<br>GTCCACAACTCCACACTAAGAGGAACTCCAATGCTTAGTTAC<br>AAGGTGGTGTAGTTAAAAAGTAACTCCAATAGTTAACTACA<br>CGGTATTATAGTTAAATTTGCCAACTCAAATTTCTAACTACA<br>ATATATTTAAGCTACAAAGTTTCTCATTGGCTGACTACAATA<br>CGTTGTAGCGCCTTATAATATTTTATTCAATATACAATTTTAT<br>TTATTTTACCTTTTTAACAATTTTTTTTTGATCTACCTGCTGTC<br>CTGTTCATATGAGCTACACTAATTTGATAGCTGCTTACGCAA<br>TTCTTATATCAACGGTTGGCTACTTGTTCAAATATTTTTATTT<br>TTTTACGAGTAAGTCATTTTATGATCATTGAAGTGGCTCTAT<br>TATTATTATCATGCACCGATTAACGCAAGAATAATTAACTCG<br>GTACGAATTAGTTTCAAAATAAAATCCCTCAAAAAAAAAAG<br>TTTCAAAATAAAATTAACAGAAAACCAACCTTCTCCGGTTTA<br>CTGTTGTTAGAGCATGGAATTTTCCAGTAATCGCAGACCCCA<br>AATTATCTTCCAGTTGAATCAATCCTTGATTTTTGGATTTGCC<br>AGAAAACTCCTTGAATTTTAGGGTTCATATTTGATCCGTAAT<br>TGGGAAAATTTTCAGCAATTGATCTTCCAAATCAGCCCTACT<br>TGTTTCCAGACTGCAAATGAAAGGTGCGAACTTTATACTGCA<br>TTTTGGTTTTCCATTAGTGTAATTTATTAAGATGAACTGCATT<br>TTGCAATTGTTTTATTCGACTACTCATTTTTAAATCAAATTGC<br>TTAATTGCTAGTTAGTTTTCTTATCATATTGCCAAAAAAAAT<br>TATTTTTGTTTAATTGGTGAAAAAGGGTAAATTATACCTAGT<br>GTACAAGATTTTCTTGCACACCACCGTTAATTTGTTGACACA<br>TCATCAAACGTACTGAAAAATGAGAATGAAAGACAATAAAT<br>ATGTCATTTTAACCAATAGAAAAACATGATGTAGTAAGATC<br>CTTAATTGATAGATAAATAATTAAATATCAGTCCATTAGTTG<br>AATATTCAATGAAAATGTATGGTCCAAAAATGGCGTTTAAT<br>AGTCAATGTCATGCTTTATGGGGTGGTGGAGTACTATGTGAC<br>TGTGTGTGGACTTGGAGAAGACTAGAGAGTATGATTATCAA<br>CCTATGGACCCTCAAAATGAAAATGAAAATGATGTTTACAC<br>GTGCTATTTGCACGGACTTCAATGCAAATAGTATAAATTTAC<br>GGTCAAAGTTTTCATTCTAAAGCGTAAATAACTTTCATGAAT<br>GGAGGACGGTAGTATAAGTATAACGTTATAGCCTACCATTTT<br>CTTATCATATTCACATAAATTTGTTGCTGAAATTTGTTTTACT<br>TGGCTAAAATACTTTTGTTCTTATTGGCAGATAAACATCAGT<br>ACGTCCATTATTGGCCAACTTGCTGAGTCCATTATTGGCCAA<br>CTTGAACATATACCTCCAAACAATAATCAATAATGTCGATTA<br>TGAAGTTTGTGAATGCAATTTATTATCACTTTCATTTATAAA<br>ATGACTACTTGATTAACACATACAATATTACCTTTCTCCAAA<br>CACCCTTTCAATTCTGCTTAATCTTGTTTTCTCATCATCTCTT<br>CATCTTTCTGAAAACACAACCCA**ATG**GCCGAAATCGGATAC<br>TCGGTTTGTGCGAAACTCATCGAAGTGATTGGCAGTGAGCTG<br>ATCAAAGAGATTTGTGACACATGGGGTTACAAATCTCTTCTT<br>GAGGACCTCAACAAAACTGTATTGACGGTCAGGAACGTTCT<br>CATTCAAGCCGGGGTGATGCGGGAGCTTACTAGTGAACAAC<br>AAGGTTTCATTGCAGACCTTAAAGATGTTGTTTATGATGCTG<br>ATGACTTGTTCGACAAGTTACTCACTCGTGCTGAGCGAAAAC<br>AGATTGATGGAAACGAAATCTCTGAAAAGGTACGTCGTTTC<br>TTTTCCTCTAGTAACAAGATCGGTCAAGCTTACTACATGTCT<br>CGTAAGGTTAAGGAAATTAAGAAGCAGTTGGATGAAATTGT |

TABLE 1-continued

| Sequence information. |
|---|
| TGATAGGCATACAAAATTTGGGTTTAGTGCCGAGTTTATACC<br>TGTTTGTAGGGAAAGGGGGAACGAGAGGGAAACACGTTCAT<br>ATATAGATGTCAAGAATATTCTTGGGAGGGATAAAGATAAG<br>AATGATATCATAGATAGGTTGCTTAATCGTAATGGTAATGAA<br>GCTTGTAGTTTCCTGACCATAGTGGGAGCGGGAGGATTGGG<br>AAAAACTGCTCTTGCACAACTTGTGTTCAATGATGAAAGGGT<br>CAAAATTGAGTTCCATGATTTGAGGTATTGGGTTTGTGTCTC<br>TGATCAAGATGGGGGCCAATTTGATGTGAAAGAAATCCTTT<br>GTAAGATTTTAGAGGTGGTTACTAAGGAGAAAGTTGATAAT<br>AGTTCCACATTGGAATTGGTACAAAGCCAATTTCAAGAGAA<br>GTTAAGAGGAAAGAAGTACTTCCTTGTTCTTGATGATGTATG<br>GAACGAAGATCGTGAGAAGTGGCTTCCTTTGGAAGAGTTGT<br>TAATGTTGGGTCAAGGGGGAAGCAAGGTTGTAGTGACCGCA<br>CGTTCAGAGAAGACAGCAAATGTCATAGGGAAAAGACATTT<br>TTATACACTGGAATGTTTGTCACCAGATTATTCATGGAGCTT<br>ATTTGAAATGTCGGCTTTTCAGAAAGGGCATGAGCAGGAAA<br>ACCATCACGAACTAGTTGATATTGGGAAAAAGATTGTTGAA<br>AAATGTTATAACAATCCACTTGCTATAACGGTGGTAGGAAG<br>TCTTCTTTATGGAGAGGAGATAAGTAAGTGGCGGTCATTTGA<br>AATGAGTGAGTTGGCCAAAATTGGCAATGGGGATAATAAGA<br>TTTTGCCGATATTAAAGCTCAGTTACCATAATCTTATACCCT<br>CGTTGAAGAGTTGCTTCAGTTATTGTGCAGTGTTTCCCAAGG<br>ATCATGAAATAAAGAAGGAGATGTTGATTGATCTTTGGATA<br>GCACAAGGATACGTTGTGGCACTTGATGGAGGTCAAAGTAT<br>AGAAGATGCTGCCGAAGAACATTTTGTAATTTTGTTACGGAG<br>ATGTTTCTTTCAAGATGTAAAGAAGGATGAATATGGTGATGT<br>TGATTCTGTTAAAATCCACGACTTGATGCACGATGTCGCCCA<br>AGAAGTGGGGAGGGAGGAAATATGTGTAGTGAATGATAATA<br>CAAAGAACTTGGGTGATAAAATCCGTCATGTACATCGTGAT<br>GTCATTAGATATGCACAAAGAGTCTCTCTGTGTAGCCATAGC<br>CATAAGATTCGTTCGTATATTGGTGGTAATTGTGAAAAACGT<br>TGTGTGGATACACTAATAGACAAGTGGATGTGTCTTAGGAT<br>GTTGGACTTGTCATGGTCGGATGTTAAAAATTTGCCTAATTC<br>AATAGGTAAATTGTTGCACTTGAGGTGTCTTAACCTGTCTTA<br>TAATAAAGATCTGTTGATACTCCCTGATGCAATTACAAGACT<br>GCATAATTTGCAGACACTGCTTTTAAAAGAGTGCAGAAGTTT<br>AAAGGAGTTGCCAAAAGATTTTTGCAAATTGGTCAAACTGA<br>GGCACTTGGATTTAAGGTGTTCTGATTTGAAGGAGTTGCCAA<br>AAGATTTTTGCAAATTGGTCAAACTGAGGCACTTGGATTTAA<br>GGTGTTCTGATTTGAAGGAGTTGCCAAAAGATTTTTGCAAAT<br>TGGTCAAACTGAGGCACTTGGATTTATGGGGTTGTGATGATT<br>TGATTGGTGTGCCATTGGGAATGGATAGGCTAATTAGTCTTA<br>GAGTACTGCCATTCTTTGTGGTGGGTAGGAAGGAACAAAGT<br>GATGATGATGAGCTGAAAGCCCTAAAAGGCCTCACCGAGAT<br>AAAAGGCTCCATTCGTATTAGAATCTATTCAAAGTATAGAAT<br>AGTTGAAGGCATGAATGACACAGGAGGAGCTGGGTATTTAA<br>AGAGCATGAAACATCTCACGGGGGTTGATATTACATTTGAT<br>GGTGGATGTGTTAACCCTGAAGCTGTGTTGGCAACCCTAGA<br>GCCACCTTCAAATATCAAGAGGTTAGAGATGTGGCATTACA<br>GTGGTACAACAATTCCAGTATGGGGAAGAGCAGAGATTAAT<br>TGGGCAATCTCCCTCTCACATCTTGTCGACATCCAGCTTTGG<br>TGTTGTAGTAATTTGCAGGAGATGCCAGTGCTGAGTAAACTG<br>CCTCATTTGAAATCACTGTATCTTTTTAAGTTTTGTAAGTTAG<br>AGTACATGGAGAGTAGAAGCAGCAGCAGTAGCAGTGACAC<br>AGAAGCAGCAACACCAGAATTACCAACATTCTTCCCTTCCCT<br>TGAAAAACTTAGACTTTGGTATCTGGAAAAGTTGAAGGGTTT<br>GGGGAACAGGAGACCGAGTAGTTTTCCCCGCCTCTCTGAATT<br>GGAAATCTGGGAATGCCCAGATCTAACGTGGTTTCCTCCCTG<br>TCCAAGCCTTGAAAAACTTACACTTTGGCGTCTGGACAAGTT<br>GAAGGGTTTGGGGAACAGGAGATCGAGTAGTTTTCCCCGCC<br>TCTCTAAATTGGTAATCTGGAAATGCCCAGATCTAACGTGGT<br>TTCCTCCCTGTCCAAGCCTTGAAAAACTTACACTTTGGCGTC<br>TGGACAAGTTGAAGGGTTTGGGGAACAGGAGATCGAGTAGT<br>TTTCCCCGCCTCTCTGAATTGGAAATCAAGAAATGCCCAGAT<br>CTAACGTGGTTTCCTCCTTGTCCAAGCCTTGAAACGTTGAAA<br>TTGGAAAAAAACAATGAAGCGTTGCAAATAATAGTAAAAAT<br>AACAACAACAAGAGGTAAAGAAGAAAAAGAAGAAGACAAG<br>AATGCTGGTGTTGGAAATTCACAAGATGATGACAATGTCAA<br>ATTATGGACGGTGGAAATAGACAATCTGGGTTATCTCAAAT<br>CACTGCCCACAAATTGTCTTACTCACCTCAAAATAACTGGAA<br>TAGATTACAGGGAGGGGGAGATTGAATCAGATTCCGTGGAG<br>GAGGAGATTGAATTGGAAGTTGGGGAGGCATTTCAGAAGTG<br>TGCATCTTCTTTGAGAAGCCTCATCATAATCGGAAATCACGG<br>AATAAATAAAGTGATGAGACTGTCTGGAAGAACAGGGTTGG<br>AGCATTTCACTCTGTTGGACTCACTCAAACTTTCAAATATAG<br>AAGACCAGGAAGATGAGGGCGAAGACAACATCATATTCTGG<br>AAATCCTTTCCTCAAAACCTTCGCAGTTTGAGAATTAAAGAC<br>TCTGACAAAATGACAAGTTTGCCCATGGGGATGCAGTACTT |

TABLE 1-continued

| Sequence information. |
|---|
| AACCTCCCTCCAAACCCTCGAACTATCATATTGTGATGAATT<br>GAATTCCCTTCCAGAATGGATAAGCAGCTTATCATCTCTTCA<br>ATACCTGCGCATATACAACTGTCCAGCCCTGAAATCACTACC<br>AGAAGCAATGCGGAACCTCACCTCCCTTCAGACACTTGGGA<br>TATCGGATTGTCCAGACCTAGTTAAAATATGCAGAAAACCC<br>AACGGCGAGGACTATCCCAAAATTCAACACATCCCCGGCAT<br>TGTAAGTGATTGCAGAAAGTATTTTATTCATTTATATTTATTT<br>TATGCTTAGAATGATATACGCCGTCGTCCTTAGGTTTCCAAT<br>CTTGAATTTGGTTTTTGTTTTCTTTCTTTGTTTCTTTATTCAAC<br>ACCAGCCCATTTATGATTGATTCATTAAAAAAAGGAAGAAG<br>ACAACGAATTGAGATTCCTGGGGTTTTTTTTTCGTTGGGGTT<br>GGTTTTCATGTATATGTTGCTGATTAAATACGAGACTGATGA<br>TGATTATGTGTTTATGGGTTTTAAATCAGATTAAATATATGG<br>AAAATGTAAGTTAGTTGGGGATGCACATAAGGTGTTTGATG<br>AAATGTCTTTTAGAAATGTTGTTTCTTGGACTTAGAATGATA<br>TACACTGTCGTCCTTTGGTTTCCAATCTTACATTTGGTTTGTG<br>TTTTCTTAGTTTGTTTCTTTAATCAACACCAACCCATTTTTTTT<br>AAACTACCTGCAACTACTAATTTACGTTTACCCTTTATCTCA<br>GGTACTAAATGAATATTGGTGATTTTCAGTTACTCAACACTA<br>GCTTGATCCTGAACGCACCCAACCTTCAGGTTAGAATCCGGC<br>TTACTCATCCTTTTGTCCAGTTTTCAAGTAATTGTTTTGGCAG<br>GATCAATTCTCTAATTGTTGTACACCGTATATTGCAATTTAT<br>AGTGACTACAGTTAATGAATGTTTACAAAAAATTAGTCATGT<br>AAAAACTTCTTCTCTGTCCATTACATAAACTCTTTTTCTCTTT<br>CTAACTTATCATGTTCATGTCTAAAAAATTAAACATGCTCAC<br>ATCAATGTTCATTTAAGCTAACTTACTTCTGTAAGAGAGCGA<br>GCTAGTTAAAAACTCCTTTAACTTTCTGTTTTATACTCAGGA<br>GTCAGGAAGGATATGGATTGATGCAGCTTTCACAGGCCAAG<br>TAATATAATGTTCTTTATCAATCACTCAATACCTGGAGATTG<br>TTTGAACACATAATTCACCTCTTTTTTTCCATCTCAAATTGCA<br>GCCTTTTACTGGGATTTGAATGACAGCAAACATTTGATTGTC<br>ACGAGGATTGATCTAACTGGTGAATGTTGTGATCACCATATT<br>GGTCTTTCTCATTCAAACAAACTTGCATACCGTTCTTTTGAA<br>GTTTGAAGACAAGCAGGCGATAATCAACTCAGGTCGAAGCT<br>CATGTGCAGGAGAGAATAGAATATAGAGGAGATTATTTTA<br>AAAGAAACGCTCAAAGGTATTGTAGCACCTTTCCTATTTGCT<br>ACTGCAGTGATGTTTTTATTTCTTGTTTGCAGCGCTTGTTTCT<br>CATATTTCAACCTACTTTTAGAAAAAAAAACATCTCCGAACA<br>TAACCAAAAATAAAGTTCCCTTATCAGTGCTTTCCCTGCTTT<br>CTTCTGAACAACATATACAATTATAAACCCTTTTTCTCTCTTA<br>CCTTTGTTATTCTTCCTTGCTTCATTGAGATAACACTCTCCTG<br>TTTTTGTTTTGTTGTTAGTCATTACATGGATATATCAAGGACA<br>ACAGTTCTGTAGTCCGTCAACTGTGGTTAGGAAGGCTAAACT<br>GGAGCACAATAACCCCATGTCAATTGAATAGTAAAGGTGTG<br>CTATATCAGTTTCGTTTGGCTTGGCTTGTTTACCTGAAAAAT<br>GGCTGGTTATTTATCCTTGTCTCTTTCTATGACGTGCAGTGGC<br>TTGTTAATGTGTCTCGGACAACAATTCCTCACTTTCCAAGTT<br>CCATACACGCTGATGTAACTATCTTCTGCAGTCTGTTCTTTCA<br>TTTTTGCCACGTGCTCTAATTATAACTTTTTGTACTCAATAAT<br>CAACTCCTTGTCCCGGTATTTGCAGAGACTACTTAAACAGGT<br>AAAGTGACAATCCTGGCGAAGTTGTCTGTTTCTTAGCTCTGA<br>TCCCATCATTCAGGTAAGATTAAGTAGTTAAGAAGAAACAT<br>TTATTTTTACCTAATTTGAATGAACTTGTGTAACTGCTTGCTT<br>CCTGCATTAAATAAGAAATTTCTGCTGCATATGTGACAGTTA<br>CATCCACAAAAAAGTTGGAGGTTTGTTCAGGGATTGGAAAT<br>GAAGGTACTTCAGAATTTGTTTATGAATGCTCCAGACTTCAG<br>AGTCTTTAATGGAAAATTCGAGTCACTAAAAATACATTATTC<br>CTATCATCAGAGCTTTCAAGTTCCTCTATACAAGGTCAACTG<br>AGTTCCTCTTTGCCTCTTGTTTAATTGTATTTACTTGTACCTT<br>AATTATAATCTGTATATTGTTTTAGTTAAGTTCTAAAACAGG<br>TTACTATTCATCATTTGTGCAGCATATTGCTGGAATCAAGAA<br>TCTAGTGCTTCTTCTTCCTGACTTCACTGTCAAAATAGCAGTT<br>CCCATGCTGGAAATAAGCGCGCTAGCAATGTAATTGATGAC<br>ATGGATGTTGCTGCTTCTGAGTTTTGATCATAAAAAGCTGTT<br>ATGTGTTTCTTGAATGTAATGTAGAAGAGGAGAAAACTGAA<br>AACTCTTGGCAAAAACGTGAAATTGCAGTGCCTCGGGGTGG<br>GAGGGATCACCCGGATTCAGTTCAGACGATACTTTTTTCAAC<br>CCGGTTTGTTCCGGTTTTCAGCTTCAGGTTTTCCTTGTACTTT<br>TGGGGGACACAGACAAGGCTACTTCATGTTTGAGAAACCTA<br>ATTGAGGCTATCTTGTAGCAAATGCACACCACACTCTTTCTC<br>TCTTCTCTCCTTTTTTCACCTTCCATTTGTAAAAATCCTCCTTT<br>AAAGGTTAATAAAAAAAAAGCTCCAAGTCTCGTAGGGTGGA<br>TGTAGGTCACATTGACCGAACCACGGTAAACTCTTTGTGTTC<br>TTTCTTCTCTCTTTGTTTCTCATTTTTACGGCAAGTGTTTATG<br>GTTAACCATGCATCTTAGAATAGCTTAAGGCATTAACATAAT<br>AACATCAATGTTCTCCAAAGATTCACCTTACTTGTTGTACAT<br>AATCACAATGTTAAGCCTATGAAGGTAGAATGCTCTCATGAT |

TABLE 1-continued

| Sequence information. | |
|---|---|
| | TTGGTTTAACCAAAAAATAAACTCTAAAATAATACGGAGTA<br>ATAAAAATTGGCCATAAACTAATTACAAAGTTTGATTTTTGT |
| SEQ ID NO: 18: Genomic sequence comprising alpha-WOLF 11 allele (with a 2 kb region upstream of the start codon) | GGCTTAACTTGCTCACCAATTCTTAAATAGACTCGACTTACA<br>CTGAATTTATTGTGTACTATGTCTAGAAAGTAAGGTCAACAA<br>CTTTCTTCTAAATTATTTTGGCATGTTTATTAGGGTTATTATG<br>AAAAACATATCAAATTGGTGTTGTTAGTTAGGCTTGAATAAT<br>ATGATTTTAAGTCACGAGACTTTTATAAATTAGGTAATTTGA<br>TTTAAAAAATTGTTACATATCTAAGAAAATGGATGTTAAATT<br>TATCAGTCAATGTATAAACAATAAAAGTCAATATGTATGTA<br>AAAGGGTTGCTAGATAAAATCTTTGGTTTTTTGGTCCACAAC<br>TCCACACTAAGAGGAACTCCAATGCTTAGTTACAAGGTGGT<br>GTAGTTAAAAAGTAACTCCAATAGTTAACTACACGGTATTAT<br>AGTTAAATTTGCCAACTCAAATTTCTAACTACAATATATTTA<br>AGCTACAAAGTTTCTCATTGGCTGACTACAATACGTTGTAGC<br>GCCTTATAATATTTTATTCAATATACAATTTTATTTATTTTAC<br>CTTTTTAACAATTTTTTTTTGATCTACCTGCTGTCCTGTTCAT<br>ATGAGCTACACTAATTTGATAGCTGCTTACGCAATTCTTATA<br>TCAACGGTTGGCTACTTGTTCAAATATTTTTATTTTTTTACGA<br>GTAAGTCATTTTATGATCATTGAAGTGGCTCTATTATTATTAT<br>CATGCACCGATTAACGCAAGAATAATTAACTCGGTACGAAT<br>TAGTTTCAAAATAAAATCCCTCAAAAAAAAAAGTTTCAAAA<br>TAAAATTAACAGAAAACCAACCTTCTCCGGTTTACTGTTGTT<br>AGAGCATGGAATTTTCCAGTAATCGCAGACCCCAAATTATCT<br>TCCAGTTGAATCAATCCTTGATTTTTGGATTTGCCAGAAAAC<br>TCCTTGAATTTTAGGGTTCATATTTGATCCGTAATTGGGAAA<br>ATTTTCAGCAATTGATCTTCCAAATCAGCCCTACTTGTTTCCA<br>GACTGCAAATGAAAGGTGCGAACTTTATACTGCATTTTGGTT<br>TTCCATTAGTGTAATTTAGTGTAATTTATTAAGATAAACTGC<br>ATTTTGCAATTGTTTTATTCGACTACTCATTTTTAAATCAAAT<br>TGCTTAATTGCTAGTTAGTTTTCTTATCATATTGCCAAAAAA<br>AATTATTTTTGTTTAATTGGTGAAAAAGGGTAAATTATACCT<br>AGTGTACAAGATTTTCTTGCACACCACCGTTAATTTGTTGAC<br>ACATCATCAAACGTACTGAAAAATGAGAATGAAAGACAATA<br>AATATGTCATTTTAACCAATAGAAAAACATGATGTAGTAAG<br>ATCCTTAATTGATAGATAAATAATTAAATATCAGTCCATTAG<br>TTGAATATTCAATGAAAATGTATGGTCCAAAAATGGCGTTTA<br>ATAGTCAATGTCATGCTTTATGGGGTGGTGGAGTACTATGTG<br>ACTGTGTGTGGACTTGGAGAAGACTAGAGAGTATGATTATC<br>AACCTATGGACCCTCAAAATGAAAATGAAAATGATGTTTAC<br>ACGTGCTATTTGCACGGACTTCAATGCAAATAGTATAAATTT<br>ACGGTCAAAGTTTTCATTCTAAAGCGTAAATAACTTTCATGA<br>ATGGAGGACGGTAGTATAAGTATAACGTTATAGCCTACCAT<br>TTTCTTATCATATTCACATAAATTTGTTGCTGAAATTTGTTTT<br>ACTTGGCTAAAATACTTTTGTTCTTATTGGCAGATAAACATC<br>AGTACGTCCATTATTGGCCAACTTGCTGAGTCCATTATTGGC<br>CAACTTGAACATATACCTCCAAACAATAATCAATAATGTCG<br>ATTATGAAGTTTGTGAATGCAATTTATTATCACTTTCATTTAT<br>AAAATGACTACTTGATTAACACATACAATATTACCTTTCTCC<br>AAACACCCTTTCAATTCTGCTTAATCTTGTTTTCTCATCATCT<br>CTTCATCTTTCTGAAAACACAACCCA**ATG**GCCGAAATCGGA<br>TACTCGGTTTGTGCGAAACTCATCGAAGTGATTGGCAGTGAG<br>CTGATCAAAGAGATTTGTGACACATGGGGTTACAAATCTCTT<br>CTTGAGGACCTCAACAAAACTGTATTGACGGTCAGGAACGT<br>TCTCATTCAAGCCGGGGTGATGCGGGAGCTTACTAGTGAAC<br>AACAAGGTTTCATTGCAGACCTTAAAGATGTTGTTTATGATG<br>CTGATGACTTGTTCGACAAGTTACTCACTCGTGCTGAGCGAA<br>AACAGATTGATGGAAACGAAATCTCTGAAAAGGTACGTCGT<br>TTCTTTTCCTCTAGTAACAAGATCGGTCAAGCTTACTACATG<br>TCTCGTAAGGTTAAGGAAATTAAGAAGCAGTTGGATGAAAT<br>TGTTGATAGGCATACAAAATTTGGGTTTAGTGCCGAGTTTAT<br>ACCTGTTTGTAGGGAAAGGGGGAACGAGAGGGAAACACGTT<br>CATATATAGATGTCAAGAATATTCTTGGGAGGGATAAAGAT<br>AAGAATGATATCATAGATAGGTTGCTTAATCGTAATGGTAAT<br>GAAGCTTGTAGTTTCCTGACCATAGTGGGAGCGGGAGGATT<br>GGGAAAAACTGCTCTTGCACAACTTGTGTTCAATGATGAAA<br>GGGTCAAAATTGAGTTCCATGATTTGAGGTATTGGGTTTGTG<br>TCTCTGATCAAGATGGGGGCCAATTTGATGTGAAAGAAATC<br>CTTTGTAAGATTTTAGAGGTGGTTACTAAGGAGAAAGTTGAT<br>AATAGTTCCACATTGGAATTGGTACAAAGCCAATTTCAAGA<br>GAAGTTAAGAGGAAAGAAGTACTTCCTTGTTCTTGATGATGT<br>ATGGAACGAAGATCGTGAGAAGTGGCTTCCTTTGGAAGAGT<br>TGTTAATGTTGGGTCAAGGGGGAAGCAAGGTTGTAGTGACC<br>GCACGTTCAGAGAAGACAGCAAATGTCATAGGGAAAAGAC<br>ATTTTTATACACTGGAATGTTTGTCACCAGATTATTCATGGA<br>GCTTATTTGAAATGTCGGCTTTTCAGAAAGGGCATGAGCAG<br>GAAAACCATCACGAACTAGTTGATATTGGGAAAAAGATTGT<br>TGAAAAATGTTATAACAATCCACTTGCTATAACGGTGGTAG |

TABLE 1-continued

| Sequence information. |
|---|
| GAAGTCTTCTTTATGGAGAGGAGATAAGTAAGTGGCGGTCA<br>TTTGAAATGAGTGAGTTGGCCAAAATTGGCAATGGGGATAA<br>TAAGATTTTGCCGATATTAAAGCTCAGTTACCATAATCTTAT<br>ACCCTCGTTGAAGAGTTGCTTCAGTTATTGTGCAGTGTTTCC<br>CAAGGATCATGAAATAAAGAAGGAGATGTTGATTGATCTTT<br>GGATAGCACAAGGATACGTTGTGGCACTTGATGGAGGTCAA<br>AGTATAGAAGATGCTGCCGAAGAACATTTTGTAATTTTGTTA<br>CGGAGATGTTTCTTTCAAGATGTAAAGAAGGATGAATATGG<br>TGATGTTGATTCTGTTAAAATCCACGACTTGATGCACGATGT<br>CGCCCAAGAAGTGGGGAGGGAGGAAATATGTGTAGTGAATG<br>ATAATACAAAGAACTTGGGTGATAAAATCCGTCATGTACAT<br>GGTGATGTCAATAGATATGCACAAAGAGTCTCTCTGTGTAGC<br>CATAGCCATAAGATTCGTTCGTATATTGGTGGTGATTGTGAA<br>AAACGTTGTGTGGATACACTAATAGACAAGTGGATGTGTCTT<br>AGGATGTTGGACTTGTCATGGTCGGATGTTAAAAATTTGCCT<br>AATTCAATAGGTAAATTGTTGCACTTGAGGTATCTTAACCTG<br>TCAGATAATAGAAATCTAAAGATACTTCCTGATGCAATTACA<br>AGACTGCATAATTTGCAGACACTGCTTTAGAAGATTGCAGA<br>AGTTTAAAGGAGTTGCCAAAAGATTTTTGCAAATTGGTCAA<br>ACTGAGACACTTGGATTTATGGGGTTGTGATGATTTGATTGG<br>TATGCCATTTGGAATGGATAAGCTAACTAGTCTTAGAATACT<br>ACCAAACATTGTGGTGGGTAGGAAGGAACAAAGTGTTGATG<br>ATGAGCTGAAAGCCCTTAAAGGCCTCACCGAGATAAAAGGC<br>GACATTGATATCAAAATCTGTGAAAATTATAGAATAGTTGA<br>AGGCATGAATGACACAGGAGGAGCTGGGTATTTGAAGAGCA<br>TGAAACATCTCAGGGAGATTGGTATTACATTTGATGGTGGAT<br>GTGTTAACCCTGAAGCTGTGTTGGCAACCCTAGAGCCACCTT<br>CAAATATCAAGAGCTTATCTATAGATAATTACGATGGTACA<br>ACAATTCCAGTATGGGGAAGAGCAGAGATTAATTGGGCAAT<br>CTCCCTCTCACATCTTGTCGACATCACGCTTGAAGATTGTTA<br>CAATTTGCAGGAGATGCCAGTGCTGAGTAAACTGCCTCATTT<br>GAAATCACTGTATCTTTTTAAGTTTTGTAAGTTAGAGTACAT<br>GGAGAGTAGAAGCAGCAGCAGTAGCAGTGACACAGAAGCA<br>GCAACACCAGAATTACCAACATTCTTCCCTTCCCTTGAAAAA<br>CTTAGACTTTGGTATCTGGAAAAGTTGAAGGGTTTGGGGAA<br>CAGGAGACCGAGTAGTTTTCCCCGCCTCTCTGAATTGGAAAT<br>CTGGGAATGCCCAGATCTAACGTGGTTTCCTCCTTGTCCAAG<br>CCTTAAAACGTTGAAATTGGAAAAAAACAATGAAGCGTTGC<br>AAATAATAGTAAAAATAACAACAACAAGAGGTAAAGAAGA<br>AAAAGAAGAAGACAAGAATGCTGGTGTTGGAAATTCACAAG<br>ATGATGACAATGTCAAATTACGGAAGGTGGAAATAGACAAT<br>GTGAGTTATCTCAAATCACTGCCCACAAATTGTCTTACTCAC<br>CTCAAAATAACTGGAATAGATTACAGGGAGGGGGAGATTGA<br>ATCAGATTCCGTGGAGGAGGAGATTGAATTGGAAGTTGGGG<br>AGGCATTTCAGAAGTGTGCATCTTCTTTGAGAAGCCTCATCA<br>TAATCGGAAATCACGGAATAAATAAAGTGATGAGACTGTCT<br>GGAAGAACAGGGTTGGAGCATTTCACTCTGTTGGACTCACTC<br>AAATTTTCAAAGATAGAAGACCAGGAAGATGAGGGCGAAG<br>ACAACATCATATTCTGGAAATCCTTTCCTCAAAACCTCCGCA<br>GTTTGGAAATTAAAGGCTCTTGCAAAATGACAAGTTTGCCCA<br>TGGGGATGCAGTACTTAACCTCCCTCCAAACCCTCGAACTAT<br>CATATTGTGATGAATTGAATTCCCTTCCAGAATGGATAAGCA<br>GCTTATCATCTCTTCAATACCTGCGCATATACAACTGTCCAG<br>CCCTGAAATCACTACCAGAAGCAATGCGGAACCTCACCTCC<br>CTTCAGACACTTGGGATATCGGATTGTCCAGACCTAGTTAAA<br>ATATGCAGAAAACCCAACGGCGAGGACTATCCCAAAATTCA<br>ACACATCCCCGGCATTGTAAGTGATTGCAGAAAGTATTTTAT<br>TCATTTATATTTATTTTATGCTTAGAATGATATACGCCGTCGT<br>CCTTAGGTTTCCAATCTTGAATTTGGTTTTTGTTTTCTTTCTTT<br>GTTTCTTTATTCAACACCAGCCCATTTATGATTGATTCATTAA<br>AAAAAGGAAGAAGACAACGAATTGAGATTCCTGGGGTTTTT<br>TTTTCGTTGGGGTTGGTTTTCATGTATATGTTGCTGATTAAAT<br>ACGAGACTGATGATGATTATGTGTTTATGGGTTTTAAATCAG<br>ATTAAATATATGGAAAATGTAAGTTAGTTGGGGATGCACAT<br>AAGGTGTTTGATGAAATGTCTATTAGAAATGTTGTTTCTTGG<br>ACTTAGAATGATATACACTGTCGTCCTTTGGTTTCCAATCTT<br>ACATTTGGTTTGTGTTTTCTTAGTTTGTTTCTTTAATCAACAC<br>CAACCCATTTTTTTTAAACTACCTGCAACTACTAATTTACGTT<br>TACCCTTTATCTCAGGTACTAAATGAATATTGGTGATTTTCA<br>GTTACTCAACACTAGCTTGATCCTGAACGCACCCAACCTTCA<br>GGTTAGAATCCGGCTTACTCATCCTTTTGTCCAGTTTTCAAGT<br>AATTGTTTTGGCAGGATCAATTCTCTAATTGTTGTACACCGT<br>ATATTGCAATTTATAGTGACTACAGTTAATGAATGTTTACAA<br>AAAATTAGTCATGTAAAAACTTCTTCTCTGTCCATTACATAA<br>ACTCATTTTCTCTTTCTAACTTATCATGTTCATGTTTAAAAAA<br>TTAAACATGCTCACATCATTGTTCATTTGAGCTAACTTACTTC<br>TGTAAGAGAGCGAGCTAGTTAACAACTCCTTTAACTTTCTGT<br>TTTATACTCAGGACATGGATTGATGCAAGCATGAAGAACTTC |

TABLE 1-continued

| Sequence information. |
|---|
| TGGAATTTGCTAAAACTCTACCAAAGCGATGAGAGTTTGGA<br>CTTTGTTTCACTTGAAGTCAGGGATTGTCAACAAAGCCACAG<br>TGTGCATGTTGGCTGTGTCACTTGGACGATAAAAAGGTTTAT<br>TTAATTGTTTTCCTAAGTGTATTTGGCTTACAAGCTTTTACTT<br>TTCACTTGAAAGGGTTTTTTTTGTTTTAAGCTTTTTGAATTAG<br>AGTTTCGGTTGAAGTAAGAGTAGTCGTATTAGTCTTTTACTT<br>TGCAGGAGTCTATGCCTATATAAGGTAAGACTCGTATTTGTA<br>ATTTTCAGATTATGCAATTCAAGTTTTCGAGTGTTTTCTTAAA<br>AAAACATATCATACCTGTGTGTAGCATAAAGATAAATTCTG<br>ATGCTGTGCTTCTTGTTATGGCTCACATTGGTTTTCATTGTTT<br>GGATTGTTTCACAGGGAAGCAGAGAATACCTGGAACCTATG<br>AAGGACGCTATATCTATAGCAGCTTTCACAGGCCAAGTAAT<br>ATAATGTTCTTTATCAATCACTCAATACCTGGAGATTGTTTG<br>AACACATAATTCACCTCTTTTTTTCCATCTCAAATTGCAGACT<br>TTTACTGGGATTTGAATGACAGCAAACATTTGATTGTCACGA<br>GGATTGATCTAACTGGTGAATGTTGTGATCACCATATTGGTC<br>TTTCTCATTCAAACAAACTTGCATACCGTTCTTTTGAATTTTG<br>AAGACAAGCAGGCGATAATCAACTCAGGTCGAAGCTCATGT<br>GCAGGAGAGAATCGAATATAGAGGAGATTATTTTTAAAAGA<br>AACGCTCAAAGGTATTGTAGCACCTTTCCTATTTGCTACTGC<br>AGTGATGTTTTTATTTCTTGTTTGCAGCGCTTGTTTCTCATAT<br>TTCAACCTACTTTTAGAAAAAAAAACATCTCCGAACATAACC<br>AAAAATAAAGTTCCCTTATCAGTGCTTTCCCTGCTTTCTTCTA<br>AACAACATATACAATTATAAACCCTTTTTCTCTCTTACCTTTG<br>TTATTCTTCCTTGCTTCATTGAGATAACACTCTCCTGTTTTTG<br>TTTTGTTGTTAGTCATTACATGGATATATCAAGGACAACAGT<br>TCTGTAGTCCGTCAACTGTGGTTAGGAAGGCTAAACTGGAG<br>CACAATAACCCCATGTCAATTGAATAGTAAAGGTGTGCTAT<br>ATCAGTTTCGTTTGGCTTGGCTTGTTTACCTGAAAAATGGCT<br>GGTTATTTATCCTTGTCTCTTTCTATGACGTGCAGTGGCTTGT<br>TAATGTGTCTCGGACAACAATTCCTCACTTTCCAAGTTCCAT<br>ACACGCTGATGTAACTATCTTCTGCAGTCTGTTCTTTCATTTT<br>TGCCACGTGCTCTAATTATAACTTTTTGTACTCAATAATCAA<br>CTCCTTGTCCCGGTATTTGCAGAGACTACTTAAACAGGTAAA<br>GTGACAATCCTGGCGAAGTTGTCTGTTTCTTAGCTCTGAACC<br>CATCATTCAGGTAAGATTAAGTATTTAAGAAGAAATTTTGTT<br>TTTACCTAAAATGAATGATCTTGTGTAACTGCTTGCTTCTTGC<br>ATTAAATAAGAACTTTCTGCTGCATATGTGACAGTTACATCC<br>ACAAAAAAGTTGGAGGTTTGTTCAGGGATTGGAAATGAAGG<br>TACTTCAGAATTCCTGGAATGTTTATGAATGCTCCAGACTTC<br>AGAGTCTTTAATGGAAAATTCGAGTCACTAAAAATACATTAT<br>TCCTATCATCAGAGCTTTCAAGTTCCTCTATACAAGGTCAAC<br>TGAGTTCCTCTTTGCCTCTTGTTTAATTGTATTTACTTGTACC<br>TTAACTATAATCTGTATATTGTTTTAGTTAAGTTCTAAAACA<br>GGTTACTATTCATCATTTGTGCAGCATATTGCTGGAATCAAG<br>AATCTAGTGCTTCTTCTTCCTGACTTCACTGTAAACCTTAATC<br>TGTTGCTGAATTTTTTTAATCGAAAGACTTTCTGTTTAATTAT<br>ATTCTAAATCTATTACGATGTCTTAAACAGCTTGAAAATGAC<br>ACAAAATATAATAGCTCCACACCTAGATAAGACCCTCAAAT<br>GGAAATGTCAGTAACTTGTTACATAGAGACAATATGCTGAT<br>ATATAGTTCCACATAGATCACTCTTCTTTACTAAAAACACAT<br>TATTTTTATAACCTGGACATTAGTCGAGAGGGGGATGTCACG<br>TCATGAGAAATCTTCATCAGAGCCTTCATTACTCGGAATTTT<br>ATTTTCTCCCAAAGCTGGTGAATTTGCCATAGATGTTGCTGT<br>ACTTCATTCTTATGATGTTCAGGTGACTTGTCAGGCCTCACT<br>GCCTCAGACTAACACTCTCGTGTTTCTTTTCTGTTGTTAGTCA<br>TGACATGGATACATCACGAACAACAGTTCTGTAGTCCAGCA<br>ACTGTGGTGTAGGAAGACTAAACTGGAGCACAATAACTCCA<br>TGTCAATTGAATGGTAAAGATGTGCTATCTCAGTTTCTTTTG<br>GCTTGTTTACATGAAAAACGGCTCGTTTTTTATCTGTGTCTTT<br>CTATGACGTTCAGGTGCAGTGGCTTGTTAATGTGTCTCAGAC<br>AACAATTTTCTCACTTTCCAAGTTCCATACATGCTGATGTAA<br>CTATCTTCTGCACTCTGTTCTTTCATTTTGCCTTTTGCTCTAAT<br>TATAACTTTTTGTACTCAATAATCAACTCCTTGTCGCGTATTT<br>GCAGGGATTACTTAAATAGGTATAGTGACAATCCTGGTGAA<br>GTTGTCTGTTTCTTAGCTCTGATCCCATCATTCAGGTAAGATT<br>AAGTAGTTAAGAAGAAACATTTATTTTTACCTAATTTGAATG<br>AACTTGTGTTAACTGCTTGCTTCCTGCATTAAATAAGAACTT<br>TCTGCTGCATATGTGACAGTTACATCCACAAAAAAGTTGGA<br>GGTTTGTTCAGGGATTGGAAATGAAGGTACTTCAGAATTCCT<br>GGAATGTTTATGAATGCTCCAGACTTCAGAGTCTTTAATGGA<br>AAATTCGAGTCACTAAAAATACATTATTCCTATCATCAGAGC<br>TTTCAAGTTCCTCTATACAAGGTCAACTGAGTTCCTCTTTGCC<br>TCTTGTTTAATTGTATTTACTCGTACCTTAATTATAATCTGTA<br>TATTGTTTTAGTTAAGTTCTAAAACAGGTTACTATTCATCATT<br>TGTGCAGCATATTGCTGGAATCAAGAATCTAGTGCTTCATCT<br>TCCTGACTTCACTGTCAAAATAGTAGTTCCCATGCTGGAAAT<br>AAGCGCGCTAGCAATGTAATTGATGACATGGATGTTGCTGCT |

TABLE 1-continued

Sequence information.

TCTGAGTTTTGATCATAAAAAGCTGTTATGTGTTTCTTGAAT
GTAATGAAGGAGAGGAGAAAACTGAAAACTCTTGGCAAAA
ACGTGAAATTGCAGTGCCTCGGGGTGGTAGGGATCACCCGG
ATTCAGTTCAGACGATACTTTTTTCAACCCGGTTTGTTCCGGT
TTTCAGCTTCGGGTTTTCCTTGTACTTTTGGGGCACACATACA
AGGCTACTTCATGTTTGAGAAACCTAATTGAGGCTATCTTGT
AGCAAATGCACACCACACTCTTTCTCTCTTCTCTCCTTTTTTC
ACCTTCCATTTGTAAAAATCCTCTTTTAAAGGTTAATAAAAA
AAAGCTTCAAGTCTCGTAGGGTGGATGTAGGTCACATTGAC
CGAACCACGGTAAACTCTTTGTGTTCTTTCTTCTCTCTTTGTT
TCTCATTTTTACGGCAAGTGTTTATGGTTAACCATGCATCTTA
GAATAGCTTAAGGCATTAACATAATAACATCAATGTTCTCCA
AAGATTCACCTTACTTGTTGTACATAATCACAATGTTAAGCC
TATGAAGGTAGAATGCTCTCATGATTTGGTTTAACCAAAAAA
TAAACTCTAAAATAATACGGAGTAATAAAAATTGGCCATAA
ACTAATTACAAAGTTTGATTTTTGTATAGGGTATCTTGTACTT
GTGATAAAAAAAATTAAAAAAAAAAAATTACTTATTTCTTC
TATTTTTACTTGTTACACTTTTCTACA

SEQ ID NO: 19: Genomic sequence comprising alpha-WOLF 12 allele (with a 2 kb region upstream of the start codon)

TTTGAAGTTAGGCTTAACTTGCTCACCAATTCTTAAATAGAC
TCGACTTACACTGAATTTATTGTGTACTATGTCTAGAAAGTA
AGGTCAACAACTTTCTTCTAAATTATTTTGGCATGTTTATTAG
GGTTATTATGAAAAACATATCAAATTGGTGTTGTTAGTTAGG
CTTGAATAATATGATTTTAAGTCACGAGACTTTTATAAATTA
GGTAATTTGATTTAAAAAATTGTTACATATCTAAGAAAATGG
ATGTTAAATTTATCAGTCAATGTATAAACAATAAAAGTCAAT
ATGTATGTAAAAGGGTTGCTAGATAAAATCTTTGGTTTTTTG
GTCCACAACTCCACACTAAGAGGAACTCCAATGCTTAGTTAC
AAGGTGGTGTAGTTAAAAAGTAACTCCAATAGTTAACTACA
CGGTATTATAGTTAAATTTGCCAACTCAAATTTCTAACTACA
ATATATTTAAGCTACAAAGTTTCTCATTGGCTGACTACAATA
CGTTGTAGCGCCTTATAATATTTTATTCAATATACAATTTTAT
TTATTTTACCTTTTTAACAATTTTTTTTTGATCTACCTGCTGTC
CTGTTCATATGAGCTACACTAATTTGATAGCTGCTTACGCAA
TTCTTATATCAACGGTTGGCTACTTGTTCAAATATTTTTATTT
TTTTACGAGTAAGTCATTTTATGATCATTGAAGTGGCTCTAT
TATTATTATCATGCACCGATTAACGCAAGAATAATTAACTCG
GTACGAATTAGTTTCAAAATAAAATCCCTCAAAAAAAAAAG
TTTCAAAATAAAATTAACAGAAAACCAACCTTCTCCGGTTTA
CTGTTGTTAGAGCATGGAATTTTCCAGTAATCGCAGACCCCA
AATTATCTTCCAGTTGAATCAATCCTTGATTTTTGGATTTGCC
AGAAAACTCCTTGAATTTTAGGGTTCATATTTGATCCGTAAT
TGGGAAAATTTTCAGCAATTGATCTTCCAAATCAGCCCTACT
TGTTTCCAGACTGCAAATGAAAGGTGCGAACTTTATACTGCA
TTTTGGTTTTCCATTAGTGTAATTTATTAAGATGAACTGCATT
TTGCAATTGTTTTATTCGACTACTCATTTTTAAATCAAATTGC
TTAATTGCTAGTTAGTTTTCTTATCATATTGCCAAAAAAAAT
TATTTTTGTTTAATTGGTGAAAAAGGGTAAATTATACCTAGT
GTACAAGATTTTCTTGCACACCACCGTTAATTTGTTGACACA
TCATCAAACGTACTGAAAAATGAGAATGAAAGACAATAAAT
ATGTCATTTTAACCAATAGAAAAACATGATGTAGTAAGATC
CTTAATTGATAGATAAATAATTAAATATCAGTCCATTAGTTG
AATATTCAATGAAAATGTATGGTCCAAAAATGGCGTTTAAT
AGTCAATGTCATGCTTTATGGGGTGGTGGAGTACTATGTGAC
TGTGTGTGGACTTGGAGAAGACTAGAGAGTATGATTATCAA
CCTATGGACCCTCAAAATGAAAATGAAAATGATGTTTACAC
GTGCTATTTGCACGGACTTCAATGCAAATAGTATAAATTTAC
GGTCAAAGTTTTCATTCTAAAGCGTAAATAACTTTCATGAAT
GGAGGACGGTAGTATAAGTATAACGTTATAGCCTACAATTTT
CTTATCATATTCATATAAATTTGTTTCTAAAAGTTGTTTTACT
TGGCTAAAATACTTTTGTTCTTATTGGCAGATAAACATCAGT
ACGTCCATTATTGGCCAACTTGCTGAGTCCATTATTGGCCAA
CTTGAACATATACCTCCAAACAATAATCAATAATGTCGATTA
TGAAGTTTGTGAATGCAATTTATTATCACTTTCATTTATAAA
ATGACTACTTGATTAACACATACAATATTACCTTTCTCCAAA
CACCCTTTCAATTCTGCTTAATCTTGTTTTCTCATCATCTCTT
CATCTTTCTGAAAACACAACCCAATGGCCGAAATCGGATAC
TCGGTTTGTGCGAAACTCATCGAAGTGATTGGCAGTGAGCTG
ATCAAAGAGATTTGTGACACATGGGGTTACAAATCTCTTCTT
GAGGACCTCAACAAAACTGTATTGACGGTCAGGAACGTTCT
CATTCAAGCCGGGGTGATGCGGGAGCTTACTAGTGAACAAC
AAGGTTTCATTGCAGACCTTAAAGATGTTGTTTATGATGCTG
ATGACTTGTTCGACAAGTTACTCACTCGTGCTGAGCGAAAAC
AGATTGATGGAAACGAAATCTCTGAAAAGGTACGTCGTTTC
TTTTCCTCTAGTAACAAGATCGGTCAAGCTTACTACATGTCT
CGTAAGGTTAAGGAAATTAAGAAGCAGTTGGATGAAATTGT
TGATAGGCATACAAAATTTGGGTTTAGTGCTGAGTTTATACC
TGTTTGTAGGGGAAGGGGAAACGAGAGGGAAACACGTTCAT

TABLE 1-continued

| Sequence information. |
|---|
| ATATAGATGTCAAGAATATTCTTGGGAGGGATAAAGATAAG<br>AATGATATCATAGATAGGTTGCTTAATCGTAATGGTAATGAA<br>GCTTGTAGTTTCCTGACCATAGTGGGAGCGGGAGGATTGGG<br>AAAAACTGCTCTTGCACAACTTGTGTTCAATGATGAAAGGGT<br>CAAAATTGAGTTCCATGATTTGAGGTATTGGGTTTGTGTCTC<br>TGATCAAGATGGGGGCCAATTTGATGTGAAAGAAATCCTTT<br>GTAAGATTTTAGAGGTGGTTACTAAGGAGAAAGTTGATAAT<br>AGTTCCACATTGGAATTGGTACAAAGCCAATTTCAAGAGAA<br>GTTAAGAGGAAAGAAGTACTTCCTTGTTCTTGATGATGTATG<br>GAACGAGGATCGTGAGAAGTGGCTTCCTTTGGAAGAGTTGT<br>TAATGTTGGGTCAAGGGGGAAGCAAGGTTGTAGTGACCACA<br>CGTTCAGAGAAGACAGCAAATGTCATAGGGAAAAGACATTT<br>TTATACACTGGAATGTTTGTCACCAGATTATTCATGGAGCTT<br>ATTTGAAATGTCGGCTTTTCAGAAAGGGCATGAGCAGGAAA<br>ACCATCACGAACTAGTTGATATTGGGAAAAAGATTGTTGAA<br>AAATGTTATAACAATCCACTTGCTATAACGGTGGTAGGAAG<br>TCTTCTTTATGGAGAGGAGATAAGTAAGTGGCGGTCATTTGA<br>AATGAGTGAGTTGGCCAAAATTGGCAATGGGGATAATAAGA<br>TTTTGCCGATATTAAAGCTCAGTTACCATAATCTTATACCCT<br>CGTTGAAGAGTTGTTTTAGTTATTGTGCAGTGTTTCCCAAGG<br>ATCATGAAATAAAGAAGGAGATGTTGATTGAACTTTGGATG<br>GCACAAGGATATGTTGTGCCGTTGGATGGAGGTCAAAGTAT<br>AGAAGATGCTGCCGAGGAACATTTTGTAATTTTGTTACGAAG<br>GTGTTTCTTTCAAGATGTAAAGAAGGATAAATATGGTGATGT<br>TGATTCTGTTAAAATCCACGACTTGATGCACGATGTCGCCCA<br>AGAAGTGGGGAGGGAGGAATTATGTGTAGTGAATGATAATA<br>CAAAGAACTTGGGTGATAAAATCCGTCATGTACATCGTGAT<br>GTCATTAGATATGCACAAAGAGTCTCTCTGTGTAGCCATAGC<br>CATAAGATTCGTTCGTATATTGGTGGTAATTGTGAAAAACGT<br>TGTGTGGATACACTAATAGACAAGTGGATGTGTCTTAGGAT<br>GTTGGACTTGTCAAGGTCGGATGTTAAAAATTTGCCTAATTC<br>AATAGGTAAATTGTTGCACTTGAGGTATCTTAACCTGTCAGA<br>TAATAGAAATCTAAAGATACTTCCTGATGCAATTACAAGACT<br>GCATAATTTGCAGACACTACTTTTAGAACGTTGCGAAAGTTT<br>AAAGGAGTTGCCAAAAGATTTTTGCAAATTGGTCAAACTGA<br>GACACTTGGATTTAAGGGGATGTTTTTCTTTGATTGGTATGC<br>CATTGGGAATGGATAGGCTAATTAGTCTTAGAATACTACCA<br>AACATTGTGGTGGGTAGGAAGGAACAAAGTGATGATGATGA<br>GCTGAAAGCCCTAAAAGGCCTCACCGAGATAAAAGGCTCCA<br>TTCGTATTAGAATCTATTCAAAGTATAGAATAGTTGAAGGCA<br>TGAATGACACAGGAGGAGCTGGGTATTTAAAGAGCATGAAA<br>CATCTCACGGGGGTTGATATTACATTTGATGGTGGATGTGTT<br>AACCCTGAAGCTGTGTTGGCAACCCTAGAGCCACCTTCAAAT<br>ATCAAGAGGTTAGAGATGTGGCATTACAGTGGTACAACAAT<br>TCCAGTATGGGGAAGAGCAGAGATTAATTGGGCAATCTCCC<br>TCTCACATCTTGTCGACATCCAGCTTTGGCATTGTCGTAATTT<br>GCAGGAGATGCCAGTGCTGAGTAAACTGCCTCATTTGAAAT<br>CACTGGAACTTTATAATTTGATTAGTTTAGAGTACATGGAGA<br>GCACAAGCAGAAGCAGTAGCAGTGACACAGAAGCAGCAAC<br>ACCAGAATTACCAACATTCTTCCCTTCCCTTGAAAAACTTAC<br>ACTTTGGCGTCTGGACAAGTTGAAGGGTTTTGGGAACAGGA<br>GATCGAGTAGTTTTCCCCGCCTCTCTAAATTGGAAATCTGGG<br>AATGCCCAGATCTAACGTGGTTTCCTCCTTGTCCAAGCCTTA<br>AAACGTTGAAATTGGAAAAAAACAATGAAGCGTTGCAAATA<br>ATAGTAAAAATAACAACAACAAGAGGTAAAGAAGAAAAAG<br>AAGAAGACAAGAATGCTGGTGTTGGAAATTCACAAGATGAT<br>GACAATGTCAAATTACGGAAGGTGGAAATAGACAATGTGAG<br>TTATCTCAAATCACTGCCCACAAATTGTCTTACTCACCTCAA<br>AATAACTGGAATAGATTACAGGGAGGGGGAGATTGAATCAG<br>ATTCCGTGGAGGAGGAGATTGAATTGGAAGTTGGGGAGGCA<br>TTTCAGAAGTGTGCATCTTCTTTGAGAAGCCTCATCATAATC<br>GGAAATCACGGAATAAATAAAGTGATGAGACTGTCTGGAAG<br>AACAGGGTTGGAGCATTTCACTCTGTTGGACTCACTCGAACT<br>TTCAAAGATAGAAGACCAGGAAGATGAGGGCGAAGACAAC<br>ATCATATTCTGGAAATCCTTTCCTCAAAACCTCCGCAGTTTG<br>GAAATTAAAGGCTCTTGCAAAATGACAAGTTTGCCCATGGG<br>GATGCAGTACTTAACCTCCCTCCAAACCCTCAAACTAGAAA<br>ATTGTGATGAATTGAATTCCCTTCCAGAATGGATAAGCAGCT<br>TATCATCTCTTCAATACCTGGGCATATTCAACTGTCCAGCCC<br>TAGAATCACTACCAGAAGCAATGCGGAACCTCACCTCCCTTC<br>AGAGACTTGTGATACGGCTGTGTCCAGACCTAGTTAAAAGA<br>TGCGGAAAACCCAAAGGCAAGGACTATCCCAAAATTCAACA<br>CATCCCCGAAATTGTAAGTGATTGCAGAAAGTATTTTATTCA<br>TTTATATTTATTTTATGCTTAGAATGATATACACCGTCGTCCT<br>TTGGTTTCAAATCTTGAATTTGGTTTTTGTTTTCTTTCTTTGTT<br>TCTTTATTCAACACCAGCCCATTTATGATTGATTCATTAAAA<br>AAAGGATGGAGTTTTGTGTATTTGAAGAAGACAACGAATTG<br>AGATTCCTGGGGTTTTCTTTTTGTTGGGGTTGGATTTCATGTA |

TABLE 1-continued

| Sequence information. |
|---|
| TATGTTGCTGATTAAATACGAGACTGATGATGATGATGATGT<br>GTTTATGGGTTTTAAATCAGATTAAATATATGGAAATGTAA<br>GTTAATTTGGGATGCACATAAGGTGTTTGCTGAAATGTCTAT<br>GAGAAATGTTGTTTCTTGGACTTAGAATGATATACACTGTCG<br>TCCATTGGTTTCCAATCTTACATTTGGTTTGTGTTTTCTTAGT<br>TTGTTTCTTTAATCAACACCAACCCATTTTTTTAAAACTACCT<br>GCAACTACTAATTTACGTTGACCCTGTATCTCAGGTACTAAA<br>TGAATATTGGTGATTTTCAGTTACTCAACACTAGCTTGATCC<br>TGAACGCACCCAACCTTCAGGTTAGAATCCGGCTTACTCATC<br>CTTTTGTCCAGTTTTCAAGTAATTGTTTTGGCAGGATCAATTC<br>TCTAATTGTTGTACACCGTATATTGCAATTTATAGTGACTAC<br>AGTTAATGAATGTTTACAAAAAATTAGTCATGTAAAAACTTC<br>TTCTCTGTCCATTACATAAACTCTTTTTCTCTTTCTAACTTAT<br>CATGTTCATGTCTAAAAAATTAAACATGCTCACATCAATGTT<br>CATTTAAGCTAACTTACTTCTGTAAGAGAGCGAGCTAGTTAA<br>AAACTCCTTTAACTTTCTGTTTTATACTCAGGACATGGATTG<br>ATGCAAGCATGAAGAACTTCGGGAATTTGCTAAAACTCTAC<br>CAAAGCGATGAGAGTTTGGACTTTGTTTCACTTGAAGTCAGG<br>GACTGTCAACAAAGCCACAGTGTGCATGTTGGCTGTTTCACT<br>TGGACGATAAAAAGGTTTATTTAATTGTTTTCCTAAGTGTAT<br>TTGGCTTACAAGCTTTTACTTTTCGCTTGAAAGGGTTTTTCTT<br>GTTTTAAGCTTTTTGAATTAGAGTTTCGGTTGAAGTAAGAGT<br>AGTCGTATTAGTCTTTTACTTTGCAGGAGTCTATGCCTATAT<br>AAGGTAAGACTCGTATTTGTAATTTTCAGATTATGCAATTCA<br>AGTTTTCGAGTGTTTTCTTAAAAAAACATATCATACCTGTGT<br>GTAGCATAAAGATAAATTCTGATGCTGTGCTTCTTGTTATGG<br>CTCACATTGGTTTTCATTGTTTGGATTGTTTCACAGGGAAGC<br>AGAGAATACCTGGAACCTGTAAAGGACGCTATATCTATAGC<br>AGCTTTCACAGGCCAAGTAATATAATGTTCTTTATCAATCAC<br>TCAATACCTGGAGATTGTTTGAACACATAATTCACCTCTTTT<br>TTTCCATCTCAAATTGCAGACTTTTACTGGGATTTGAATGAC<br>AGCAAACATTTGATTGTCACGAGGATTGATCTAACTGGTGA<br>ATGTTGTGATCACCATATTGGTCTTTCTCATTCAAACAAACT<br>TGCATACCGTTCTTTTGAAGTTTGAAGACAAGCAGGCGATAA<br>TCAACTCAGGTCGAAGCTCATGTGCAGGAGAGAATAGAATA<br>TAGAGGAGATTATTTTTAAAAGAAACGCTCAAAGGTATTGT<br>AGCACCTTTCCTATTTGCTACTGCAGTGATGTTTTTATTTCTT<br>GTTTGCAGCGCTTGTTTCTCATATTTCAACCTACTTTTAGAAA<br>AAAAAACATCTCCGAACATAACCAAAAATAAAGTTCCCTTA<br>TCAGTGCTTTCCCTGCTTTCTTCTAAACAACATATACAATTAT<br>AAACCCTTTTTCTCTCTTACCTTTGTTATTCTTCCTTGCTTCAT<br>TGAGATAACACTCTCCTGTTTTTGTTTTGTTGTTAGTCATTAC<br>ATGGATATATCAAGGACAACAGTTCTGTAGTCCGTCAACTGT<br>GGTTAGGAAGGCTAAACTGGAGCACAATAACCCCATGTCAA<br>TTGAATAGTAAAGGTGTGCTATATCAGTTTCGTTTGGCTTGG<br>CTTACCTGAAAAATGGCTGGTTATTTATCCTTGTCTCTTTCTA<br>TGACGTGCAGTGGCTTGTTAATGTGTCTCGGACAACAATTCC<br>TCACTTTCCAAGTTCCATACACGCTGATGTAACTATCTTCTG<br>CAGTCTGTTCTTTCATTTTTGCCACGTGCTCTAATTATAACTT<br>TTTGTACTCAATAATCAACTCCTTGTCCCGGTATTTGCAGAG<br>ACTACTTAAACAGGTAAAGTGACAATCCTGGCGAAGTTGTC<br>TGTTTCTTAGCTCTGAACCCATCATTCAGGTAAGATTAAGTA<br>TTTAAGAAGAAATTTTGTTTTTACCTAAAATGAATGATCTTG<br>TGTAACTGCTTGCTTCTTGCATTAAATAAGAACTTTCTGCTG<br>CATATGTGACAGTTACATCCACAAAAAAGTTGGAGGTTTGTT<br>CAGGGATTGGAAATGAAGGTACTTCAGAATTCCTGGAATGT<br>TTATGAATGCTCCAGACTTCAGAGTCTTTAATGGAAAATTCG<br>AGTCACTAAAAAAACATTATTCCTATCATCAGAGCTTTGAAG<br>TTCCTCTATACAAGGTCAACTGAGTTCCTCTTTGCCTCTTGTT<br>TAATTGTATTTACTTGTACCTTAATTATAATCTGTATATTGTT<br>TTAGTTAAGTTCTAAAACAGGTTATTATTCATCATTTGTGCA<br>GCATATTGCTGGAATCAAGAATCTAGTGCTTCTTCTTCCTGA<br>CTTCACTGTCAAAATAGCAGTTCCCATGCTGGAAATAAGCGC<br>GCTAGCAATGTAATTGATGACATGGATGTTGCTGCTTCTGAG<br>TTTTGATCATAAAAAGCTGTTATGTGTTTCTTGAATGTAATG<br>AAGGAGAGGAGAAAACTGAAAACTCTTGGCAAAAACGTGA<br>AATTGCAGTGCCTCGGGGTGGTAGGGATCACCCGGATTCAG<br>TTCAGACGATACTTTTTTCAACCCGGTTTGTTCCGGTTTTCAG<br>CTTCGGGTTTTCCTTGTACTTTTGGGGCACACATACAAGGCT<br>ACTTCATGTTTGAGAAACCTAATTGAGGCTATCTTGTAGCAA<br>ATGCACACCACACTCTTTCTCTCTTCTCTCCTTTTTTCACCTT<br>CCATTTGTAAAAATCCTCTTTTAAAGGTTAATAAAAAAAAGC<br>TTCAAGTCTCGTAGGGTGGATGTAGGTCACATTGACCGAACC<br>ACGGTAAACTCTTTGTGTTCTTTCTTCTCTCTTTGTTTCTCATT<br>TTTACGGCAAGTGTTTATGGTTAACCATGCATCTTAGAATAG<br>CTTAAGGCATTAACATAATAACATCAATGTTCTCCAAAGATT<br>CACCTTACTTGTTGTACATAATCACAATGTTAAGCCTATGAA<br>GGTAGAATGCTCTCATGATTTGGTTTAACCAAAAAATAAACT |

TABLE 1-continued

| Sequence information. | |
|---|---|
| | CTAAAATAATACGGAGTAATAAAAATTGGCCATAAATTATT |
| | TACAAAGTTTGATTTTTGTATAGGGTATCTTGTACTTGTGAT |
| | AAAAAAAATTAAAAAAAAAAAAAATTACTTATTTCTTC |
| SEQ ID | ATGGCCGAAATCGGATACTCGGTTTGTGCGAAACTCATCGA |
| NO: 20: | AGTGATTGGCAGTGAGCTGATCAAAGAGATTTGTGACACAT |
| Genomic | GGGGTTACAAATCTCTTCTTGAGGACCTCAACAAAACTGTAT |
| sequence of | TGACGGTCAGGAACGTTCTCATTCAAGCCGGGGTGATGCGG |
| alpha-WOLF | GAGCTTACTAGTGAACAACAAGGTTTCATTGCAGACCTTAA |
| 15 allele | AGATGTTGTTTATGATGCTGATGACTTGTTCGACAAGTTACT |
| | CACTCGTGCTGAGCGAAAACAGATTGATGGAAACGAAATCT |
| | CTGAAAAGGTACGTCGTTTCTTTTCCTCTAGTAACAAGATCG |
| | GTCAAGCTTACTACATGTCTCGTAAGGTTAAGGAAATTAAG |
| | AAGCAGTTGGATGAAATTGTTGATAGGCATACAAAATTTGG |
| | GTTTAGTGCCGAGTTTATACCTGTTTGTAGGGAAAGGGGGA |
| | ACGAGAGGGAAACACGTTCATATATAGATGTCAAGAATATT |
| | CTTGGGAGGGATAAAGATAAGAATGATATCATAGATAGGTT |
| | GCTTAATCGTAATGGTAATGAAGCTTGTAGTTTCCTGACCAT |
| | AGTGGGAGCGGGAGGATTGGGAAAAACTGCTCTTGCACAAC |
| | TTGTGTTCAATGATGAAAGGGTCAAAATTGAGTTCCATGATT |
| | TGAGGTATTGGGTTTGTGTCTCTGATCAAGATGGGGGCCAAT |
| | TTGATGTGAAAGAAATCCTTTGTAAGATTTTAGAGGTGGTTA |
| | CTAAGGAGAAAGTTGATAATAGTTCCACATTGGAATTGGTA |
| | CAAAGCCAATTTCAAGAGAAGTTAAGAGGAAAGAAGTACTT |
| | CCTTGTTCTTGATGATGTATGGAACGAAGATCGTGAGAAGTG |
| | GCTTCCTTTGGAAGAGTTGTTAATGTTGGGTCAAGGGGGAA |
| | GCAAGGTTGTAGTGACCGCACGTTCAGAGAAGACAGCAAAT |
| | GTCATAGGGAAAAGACATTTTTATACACTGGAATGTTTGTCA |
| | CCAGATTATTCATGGAGCTTATTTGAAATGTCGGCTTTTCAG |
| | AAAGGGCATGAGCAGGAAAACCATCACGAACTAGTTGATAT |
| | TGGGAAAAAGATTGTTGAAAAATGTTATAACAATCCACTTG |
| | CTATAACGGTGGTAGGAAGTCTTCTTTATGGAGAGGAGATA |
| | AGTAAGTGGCGGTCATTTGAAATGAGTGAGTTGGCCAAAAT |
| | TGGCAATGGGGATAATAAGATTTTGCCGATATTAAAGCTCA |
| | GTTACCATAATCTTATACCCTCGTTGAAGAGTTGCTTCAGTT |
| | ATTGTGCAGTGTTTCCCAAGGATCATGAAATAAAGAAGGAG |
| | ATGTTGATTGATCTTTGGATAGCACAAGGATACGTTGTGGCA |
| | CTTGATGGAGGTCAAAGTATAGAAGATGCTGCCGAAGAACA |
| | TTTTGTAATTTTGTTACGGAGATGTTTCTTTCAAGATGTAAA |
| | GAAGGATGAATATGGTGATGTTGATTCTGTTAAAATCCACG |
| | ACTTGATGCACGATGTCGCCCAAGAAGTGGGGAGGGAGGAA |
| | ATATGTGTAGTGAATGATAATACAAAGAACTTGGGTGATAA |
| | AATCCGTCATGTACATGGTGATGTCAATAGATATGCACAAA |
| | GAGTCTCTCTGTGTAGCCATAGCCATAAGATTCGTTCGTATA |
| | TTGGTGGTGATTGTGAAAAACGTTGTGTGGATACACTAATAG |
| | ACAAGTGGATGTGTCTTAGGATGTTGGACTTGTCATGGTCGG |
| | ATGTTAAAAATTTGCCTAATTCAATAGGTAAATTGTTGCACT |
| | TGAGGTATCTTAACCTGTCAGATAATAGAAATCTAAAGATA |
| | CTTCCTGATGCAATTACAAGACTGCATAATTTGCAGACACTG |
| | CTTTTAGAAGATTGCAGAAGTTTAAAGGAGTTGCCAAAAGA |
| | TTTTTGCAAATTGGTCAAACTGAGGCACTTGGAATTACAGGG |
| | TTGTCATGATTTGATTGGTATGCCATTTGGAATGGATAAGCT |
| | AACTAGTCTTAGAATACTACCAAACATTGTGGTGGGTAGGA |
| | AGGAACAAAGTGATGATGAGCTGAAAGCCCTAAAAGGCCTC |
| | ACCGAGATAAAAGGCTCCATTTCTATCAGAATCTATTCAAAG |
| | TATAGAATAGTTGAAGGCATGAATGACACAGGAGGAGCTGC |
| | TTATTTGAAGAGCATGAAACATCTCAGGGAGATTGATATTAC |
| | ATTTTTGGGTGAATGTGTTGGCCCTGAAGCTGTATTGGAAAC |
| | CTTAGAGCCACCTTCAAATATCAAGAGCTTATATATATATAA |
| | TTACAGTGGTACAACAATTCCAGTATGGGGAAGAGCAGAGA |
| | TTAATTGGGCAATCTCCCTCTCACATCTCGTCGACATCCAGC |
| | TTAGTTGTTGTAGTAATTTGCAGGAGATGCCAGTGCTGAGTA |
| | AACTGCCTCATTTGAAATCGCTGAAACTTGGATGGTTGGATA |
| | ACTTAGAGTACATGGAGAGTAGCAGTAGCAGTGACACAGAA |
| | GCAGCAACACCAGAATTACCAACATTCTTCCCTTCCCTTGAA |
| | AAACTTACTTTACAGCATCTGGAAAAGTTGAAGGGTTTTGGG |
| | AACAGGAGATCGAGTAGTTTTCCCCGCCTCTCTGAATTGGAA |
| | ATCAAGAAATGCCCAGATCTAACGTCATTTCCTTCTTGTCCA |
| | AGCCTTGAGAAGTTGGAATTGAAAGAAAGCAATGAAGCATT |
| | GCAAATAATAGTAAAAATAACAACAAGAGGTAAAGAAAAA |
| | GAAGAGAACAATAATGCTGGTGTTAGAAATTCACAAGATGA |
| | TGACAAAGTCAAATTACGGAAGATGGTGATAGACAATCTGG |
| | GTTATCTCACGGGGGTTGATATTAGATTTGATGATAGAGAAG |
| | GTGGATTTGTTAACCCTGAAGCTGTGTTGGCAACCCTAGAGC |
| | CACCTTCAAATATCAAGAGCTTATCTATACATCGTTTTGATG |
| | GTAAAACACTTCCAGTATGGGGAAGAGCAGAGATTAATTGG |
| | GCAATCTCCCTCTCACATCTTGTCGACATCCAGCTTTGGCAT |
| | TGTCGTAATTTGCAGGAGATGCCAGTGCTGAGTAAACTGCCT |

TABLE 1-continued

| Sequence information. |
| --- |
| CATTTGAAATCACTGGAACTTTATAATTTGATTAGTTTAGAG<br>TACATGGAGAGCACAAGCAGAAGCAGTAGCAGTGACACAG<br>AAGCAGCAACACCAGAATTACCAACATTCTTCCCTTCCCTTG<br>AAAAACTTAGACTTTGGTATCTGGAAAAGTTGAAGGGTTTG<br>GGGAACAGGAGACCGAGTAGTTTTCCCCGCCTCTCTGAATTG<br>GAAATCTGGGAATGCCCAGATCTAACGTGGTTTCCTCCTTGT<br>CCAAGCCTTAAAACGTTGAAATTGGAAAAAAACAATGAAGC<br>GTTGCAAATAATAGTAAAAATAACAACAACAAGAGGTAAAG<br>AAGAAAAAGAAGAAGACAAGAATGCTGGTGTTGGAAATTC<br>ACAAGATGATGACAATGTCAAATTACGGAAGGTGGAAATAG<br>ACAATGTGAGTTATCTCAAATCACTGCCCACAAATTGTCTTA<br>CTCACCTCAAAATAACTGGAATAGATTACAGGGAGGGGGAG<br>ATTGAATCAGATTCCGTGGAGGAGGAGATTGAATTGGAAGT<br>TGGGGAGGCATTTCAGAAGTGTGCATCTTCTTTGAGAAGCCT<br>CATCATAATCGGAAATCACGGAATAAATAAAGTGATGAGAC<br>TGTCTGGAAGAACAGGGTTGGAGCATTTCACTCTGTTGGACT<br>CACTCAAATTTTCAAAGATAGAAGACCAGGAAGATGAGGGC<br>GAAGACAACATCATATTCTGGAAATCCTTTCCTCAAAACCTT<br>CGCAGTTTGAGAATTAAAGACTCTGACAAAATGACAAGTTT<br>GCCCATGGGGATGCAGTACTTAACCTCCCTCCAAACCCTCGA<br>ACTATCATATTGTGATGAATTGAATTCCCTTCCAGAATGGAT<br>AAGCAGCTTATCATCTCTTCAATACCTGCGCATATACTACTG<br>TCCAGCCCTGAAATCACTACCAGAAGCAATGCGGAACCTCA<br>CCTCCCTTCAGACACTTGGGATATCGGATTGTCCAGACCTAG<br>TTAAAAGATGCAGAAAACCCAACGGCAAGGACTATCCCAAA<br>ATTCAACACATCCCCAAAATTGTAAGTCATTGCAGAAAGTA<br>ATTTATTCATTTATATTTATTTTATGCTTAGAATGATATACGC<br>AGTCGTCCTTTGGTTTCAAATCTTGAATTTGGTTTTTGTTTTC<br>TTTCTTTGTTTCTTTATTCAACACCAGCCCATTTATGATTGAT<br>TCATTAAAAAAAGGATGGAGTTTTATGGATTTGAAGAAGAC<br>AACGAATTGAGATTCCTGGGGTTTTCTTTTTGTTGGGGTTGG<br>ATTTCATGTATATGTTGCTGATTAAATACGAGACTGATGATG<br>ATGATGTGTTTATGGGTTTTAAATCAGATTAAATATATGGGA<br>AATGCAAGTTAATTTGGGATGCACATAAGGTGTTTGCTGAA<br>ATGTCTATGAGAAATGTTGTTTCTTGGACTTAGAATGATATA<br>CACTGTCGTCCTTTGGTTTCCAATCTTACATTTGGTTTGTGTT<br>TTCTTAGTTTGTTTCTTTAATCAACACCAACCCGTTTTTTTTA<br>AACTACCTGCAACTACTAATTTACGTTTACCCTGTATCTCAG<br>GTACTAAATGAATATTGGTGATTTTCAGTTACTCAACACTAG<br>CTTGATCCTGAACGCACCCAACCTTCAGGTTAGAATCCGGCT<br>TACTCATCCTTTTGTCCAGTTTTCAAGTAATTGTTTTGGCAGG<br>ATCAATTCTCTAATTGTTGTACACCGTATATTGCAATTTATA<br>GTGACTACAGTTAATGAATGTTTACAAAAAATTAGTCATGTA<br>AAAACTTCTTCTCTGTCCATTACATAAACTCTTTTTCTCTTTC<br>TAACTTATCATGTTCATGTCTAAACAATTAAACATGCTCACA<br>TCAATGTTCATTTAAGCTAACTTACTTCTGTAAGAGAGCGAG<br>CTAGTTAAAAACTCCTTTAACTTTCTGTTTTATACTCAGGAC<br>ATGGATTGATGCAAGCATGAAGAACTTCGGGAATTTGCTAA<br>AACTCTACCAAAGCGATGAGAGTTTGGACTTTATTTCACTTG<br>AAGTCAGGGACTGTCAACAAAGCCACAGTGTGCATGTTGGC<br>TGTTTCACTTGGACGATAAAAAGGTTTATTTAATTGTTTTCCT<br>AAGTGTATTTGGCTTACAAGCTTTTACTTTTCACTTGAAAGG<br>GTTTTTCTTGTTTTAAGCTTTTCGAATTAGAGTTTTCGGTTGA<br>AGTAAGAGTAGTCGTATTAGTCTTTTACCTAAGGAAGACTCT<br>TTTTTGTAATTTTCAGACTATGCAATTCAAGTTTTCGAGTGTT<br>TTCTTGCTTGTGTGATTGTGAGTTGGTGAATTCGTCTTTCATA<br>CATTTTGAGATTATCAGAAGCTTTATGCTCCACCGGTAGTCT<br>AGTACCTTTTCTGTTACTGTGCAGGGAAGTAATCTGGTACCT<br>TCTATATATATGGAAAAACATACATTATACATTATGCAAAAT<br>TCTTACAGGTTAGTTACTTCCTGGAACTTCATTTACACTTAGT<br>TTTTTTTGTTCCATTCCCTCGGAATCAAGTCATTCCCTCTGAG<br>AAATATGTAATGAACTTCTGTATGTTGCTGTTTGGTTCCTGTT<br>TTAATCTTCAATTTTCTTGTATAGTTACAGCTGCATTTACAAT<br>GAAGTTTAAGCAGACACTCTCTTTATATAGTGCCTCTTTCTG<br>GAGCACCGTAGAGCTGTCTGTGGTTGATCACCATCTGCTGCC<br>GAGAGATTCAGCAATCGCGTGTTTGATCAGGTAAAAGTTTTT<br>ATGTCAATGTGTTTTTTTTTCCGTTTGATCAATTTATGTCTGT<br>ATTCAGATTCTTATCTTCTTACAGTAGCATAACACATTGTTTC<br>TTTCATTTATGTAAACTGTTTCAAGATTACAGAGATGTATGC<br>TTCAGTCGACATTGATGATAACTTAAGATGGCATTCCTACAA<br>CAGTTGCAGGCGCATTCTAACTCCGGCAATTCTAGTTAGGCA<br>AGAGGAGCATTGCCAATACCTGCCACCTCTGGGATTTACTAT<br>ACCAGGGTTGAAGTTTATGGAAGACACCAGCTATGCACAAG<br>CCTTCAAGGGGTCATCCTACATAACAAGTTGAACCAACCAA<br>TTGCTTGTTGGTTCAGTGGTAATTGAAGCTGAATTTGGTAGG<br>GATGGCCCGTGTTCGATCCCCACAACAACAATTGGGAGGGG<br>ACTGGAACCTATCCACACAGAACTCGCCCTGAATCCGGATT<br>AGCCCTAAGGGTGAACGGGGTGCTAACACCAAAAAAAAAA |

TABLE 1-continued

| Sequence information. | |
|---|---|
| | ACATAACAAGTTGAACCAAACATACTTTGTTTGAATTGAAG<br>ATTTAGTGATTTCATTTGATCGATTGAGATGTCTTATTATAA<br>GCGTATATGCTCTTGGATTTGGCCACTTAGGTGTTGTTTGAC<br>AATTGGACATTAACTCGCTTTTATATTTTCTTTTCTCTTAGGA<br>AAGGTGATCCTGAGAATTTATATTGGAACACTTTTTTTTTCTC<br>ACTAGCTTTAAAAAAGTGTTCTGTGTTACCTGCAATTCAATT<br>TGATTATTTTTCACATAGTTTTACCTGAAAAAGTGTTACCTG<br>AAAAAGTGTTACCTGAAAATCAACTGACATAAGTTTTTGTTT<br>GGATCCAATTAAGGACACTAGATAAATCGGAATAAATAATC<br>AACCAATTAAGTACTTCATAATTAAATATGAAGTGTATTATT<br>ATCTTATGCTTGTGACATTGAAGGATGTTATGATATTTTAAC<br>TCAATACCTTGCAAAATATACTGGTTAAATTTCTTAACAAGG<br>TAACTTGGCAACA |
| SEQ ID NO: 21 Genomic sequence of alpha-CMV (with 2 kb upstream of the start codon) and adjacent beta-CMV | TTTGAAGTTAGGCTTAACTTGCTCACCAATTCTTAAATAGAC<br>TCGACTTACACTGAATTTATTGTGTACTATGTCTAGAAAGTA<br>AGGTCAACAACTTTCTTCTAAATTATTTTGGCATGTTTATTAG<br>GGTTATTATGAAAAACATATCAAATTGGTGTTGTTAGTTAGG<br>CTTGAATAATATGATTTTAAGTCACGAGACTTTTATAAATTA<br>GGTAATTTGATTTAAAAAATTGTTACATATCTAAGAAAATGG<br>ATGTTAAATTTATCAGTCAATGTATAAACAATAAAAGTCAAT<br>ATGTATGTAAAAGGGTTGCTAGATAAAATCTTTGGTTTTTTG<br>GTCCACAACTCCACACTAAGAGGAACTCCAATGCTTAGTTAC<br>AAGGTGGTGTAGTTAAAAAGTAACTCCAATAGTTAACTACA<br>CGGTATTATAGTTAAATTTGCCAACTCAAATTTCTAACTACA<br>ATATATTTAAGCTACAAAGTTTCTCATTGGCTGACTACAATA<br>CGTTGTAGCGCCTTATAATATTTTATTCAATATACAATTTTAT<br>TTATTTTACCTTTTTAACAATTTTTTTTTGATCTACCTGCTGTC<br>CTGTTCATATGAGCTACACTAATTTGATAGCTGCTTACGCAA<br>TTCTTATATCAACGGTTGGCTACTTGTTCAAATATTTTTATTT<br>TTTTACGAGTAAGTCATTTTATGATCATTGAAGTGGCTCTAT<br>TATTATTATCATGCACCGATTAACGCAAGAATAATTAACTCG<br>GTACGAATTAGTTTCAAAATAAAATCCCTCAAAAAAAAAAG<br>TTTCAAAATAAAATTAACAGAAAACCAACCTTCTCCGGTTTA<br>CTGTTGTTAGAGCATGGAATTTTCCAGTAATCGCAGACCCCA<br>AATTATCTTCCAGTTGAATCAATCCTTGATTTTTGGATTTGCC<br>AGAAAACTCCTTGAATTTTAGGGTTCATATTTGATCCGTAAT<br>TGGGAAAATTTTCAGCAATTGATCTTCCAAATCAGCCCTACT<br>TGTTTCCAGACTGCAAATGAAAGGTGCGAACTTTATACTGCA<br>TTTTGGTTTTCCATTAGTGTAATTTATTAAGATGAACTGCATT<br>TTGCAATTGTTTTATTCGACTACTCATTTTTAAATCAAATTGC<br>TTAATTGCTAGTTAGTTTTCTTATCATATTGCCAAAAAAAAT<br>TATTTTTGTTTAATTGGTGAAAAAGGGTAAATTATACCTAGT<br>GTACAAGATTTTCTTGCACACCACCGTTAATTTGTTGACACA<br>TCATCAAACGTACTGAAAAATGAGAATGAAAGACAATAAAT<br>ATGTCATTTTAACCAATAGAAAAACATGATGTAGTAAGATC<br>CTTAATTGATAGATAAATAATTAAATATCAGTCCATTAGTTG<br>AATATTCAATGAAAATGTATGGTCCAAAAATGGCGTTTAAT<br>AGTCAATGTCATGCTTTATGGGGTGGTGGAGTACTATGTGAC<br>TGTGTGTGGACTTGGAGAAGACTAGAGAGTATGATTATCAA<br>CCTATGGACCCTCAAAATGAAAATGAAAATGATGTTTACAC<br>GTGCTATTTGCACGGACTTCAATGCAAATAGTATAAATTTAC<br>GGTCAAAGTTTTCATTCTAAAGCGTAAATAACTTTCATGAAT<br>GGAGGACGGTAGTATAAGTATAACGTTATAGCCTACCATTTT<br>CTTATCATATTCACATAAATTTGTTGCTGAAATTTGTTTTACT<br>TGGCTAAAATACTTTTGTTCTTATTGGCAGATAAACATCAGT<br>ACGTCCATTATTGGCCAACTTGCTGAGTCCATTATTGGCCAA<br>CTTGAACATATACCTCCAAACAATAATCAATAATGTCGATTA<br>TGAAGTTTGTGAATGCAATTTATTATCACTTTCATTTATAAA<br>ATGACTACTTGATTAACACATACAATATTACCTTTCTCCAAA<br>CACCCTTTCAATTCTGCTTAATCTTGTTTTCTCATCATCTCTT<br>CATCTTTCTGAAAACACAACCCA**ATG**GCCGAAATCGGATAC<br>TCGGTTTGTGCGAAACTCATCGAAGTGATTGGCAGTGAGCTG<br>ATCAAAGAGATTTGTGACACATGGGGTTACAAATCTCTTCTT<br>GAGGACCTCAACAAAACTGTATTGACGGTCAGGAACGTTCT<br>CATTCAAGCCGGGGTGATGCGGGAGCTTACTAGTGAACAAC<br>AAGGTTTCATTGCAGACCTTAAAGATGTTGTTTATGATGCTG<br>ATGACTTGTTCGACAAGTTACTCACTCGTGCTGAGCGAAAAC<br>AGATTGATGGAAACGAAATCTCTGAAAAGGTACGTCGTTTC<br>TTTTCCTCTAGTAACAAGATCGGTCAAGCTTACTACATGTCT<br>CGTAAGGTTAAGGAAATTAAGAAGCAGTTGGATGAAATTGT<br>TGATAGGCATACAAAATTTGGGTTTAGTGCTGAGTTTATACC<br>TGTTTGTAGGGGAAGGGGAAACGAGAGGGAAACACGTTCAT<br>ATATAGATGTCAAGAATATTCTTGGGAGGGATAAAGATAAG<br>AATGATATCATAGATAGGTTGCTTAATCGTAATGGTAATGAA<br>GCTTGTAGTTTCCTGACCATAGTGGGAGCGGGAGGATTGGG<br>AAAAACTGCTCTTGCACAACTTGTGTTCAATGATGAAAGGGT<br>CAAAATTGAGTTCCATGATTTGAGGTATTGGGTTTGTGTCTC |

TABLE 1-continued

| Sequence information. |
|---|
| TGATCAAGATGGGGGCCAATTTGATGTGAAAGAAATCCTTT<br>GTAAGATTTTAGAGGTGGTTACTAAGGAGAAAGTTGATAAT<br>AGTTCCACATTGGAATTGGTACAAAGCCAATTTCAAGAGAA<br>GTTAAGAGGAAAGAAGTACTTCCTTGTTCTTGATGATGTATG<br>GAACGAAGATCGTGAGAAGTGGCTTCCTTTGGAAGAGTTGT<br>TAATGTTGGGTCAAGGGGGAAGCAAGGTTGTAGTGACCACA<br>CGTTCAGAGAAGACAGCAAATGTCATAGGGAAAAGACATTT<br>TTATACACTGGAATGTTTGTCACCAGATTATTCATGGAGCTT<br>ATTTGAAATGTCGGCTTTTCAGAAAGGGCATGAGCAGGAAA<br>ACCATCACGAACTAGTTGATATTGGGAAAAAGATTGTTGAA<br>AAATGTTATAACAATCCACTTGCTATAACGGTGGTAGGAAG<br>TCTTCTTTATGGAGAGGAGATAAGTAAGTGGCGGTCATTTGA<br>AATGAGTGAGTTGGCCAAAATTGGCAATGGGGATAATAAGA<br>TTTTGCCGATATTAAAGCTCAGTTACCATAATCTTATACCCT<br>CGTTGAAGAGTTGTTTTAGTTATTGTGCAGTGTTTCCCAAGG<br>ATCATGAAATAAAGAAGGAGATGTTGATTGAACTTTGGATG<br>GCACAAGGATATGTTGTGCCGTTGGATGGAGGTCAAAGTAT<br>AGAAGATGCTGCCGAGGAACATTTTGTAATTTTGTTACGAAG<br>GTGTTTCTTTCAAGATGTAAAGAAGGATAAATATGGTGATGT<br>TGATTCTGTTAAAATCCACGACTTGATGCACGATGTCGCCCA<br>AGAAGTGGGGAGGGAGGAATTATGTGTAGTGAATGATAATA<br>CAAAGAACTTGGGTGATAAAATCCGTCATGTACATCGTGAT<br>GTCATTAGATATGCACAAAGAGTCTCTCTGTGTAGCCATAGC<br>CATAAGATTCGTTCGTATATTGGTGGTAATTGTGAAAAACGT<br>TGTGTGGATACACTAATAGACAAGTGGATGTGTCTTAGGAT<br>GTTGGACTTGTCATGGTCGGATGTTAAAAATTTGCCTAATTC<br>AATAGGTAAATTGTTGCACTTGAGGTGTCTTAACCTGTCTTA<br>TAATAAAGATCTGTTGATACTCCCTGATGCAATTACAAGACT<br>GCATAATTTGCAGACACTGCTTTTAAAAGAGTGCAGAAGTTT<br>AAAGGAGTTGCCAAAAGATTTTTGCAAATTGGTCAAACTGA<br>GGCACTTGGATTTAAGGTGTTCTGATTTGAAGGAGTTGCCAA<br>AAGATTTTTGCAAATTGGTCAAACTGAGGCACTTGGATTTAT<br>GGGGTTGTGATGATTTGATTGGTGTGCCATTGGGAATGGATA<br>GGCTAATTAGTCTTAGAGTACTGCCATTCTTTGTGGTGGGTA<br>GGAAGGAACAAAGTGATGATGATGAGCTGAAAGCCCTAAA<br>AGGCCTCACCGAGATAAAAGGCTCCATTCGTATTAGAATCT<br>ATTCAAAGTATAGAATAGTTGAAGGCATGAATGACACAGGA<br>GGAGCTGGGTATTTAAAGAGCATGAAACATCTCACGGGGGT<br>TGATATTACATTTGATGGTGGATGTGTTAACCCTGAAGCTGT<br>GTTGGCAACCCTAGAGCCACCTTCAAATATCAAGAGGTTAG<br>AGATGTGGCATTACAGTGGTACAACAATTCCAGTATGGGGA<br>AGAGCAGAGATTAATTGGGCAATCTCCCTCTCACATCTTGTC<br>GACATCCAGCTTTGGCATTGTCGTAATTTGCAGGAGATGCCA<br>GTGCTGAGTAAACTGCCTCATTTGAAATCACTGGAACTTTAT<br>AATTTGATTAGTTTAGAGTACATGGAGAGCACAAGCAGAAG<br>CAGTAGCAGTGACACAGAAGCAGCAACACCAGAATTACCAA<br>CATTCTTCCCTTCCCTTGAAAAACTTACACTTTGGCGTCTGG<br>ACAAGTTGAAGGGTTTTGGGAACAGGAGATCGAGTAGTTTT<br>CCCCGCCTCTCTAAATTGGAAATCTGGAAATGCCCAGATCTA<br>ACGTCATTTCCTTCTTGTCCAAGCCTTGAAGAGTTGGAATTG<br>AAAGAAAACAATGAAGCATTGCAAATAATAGTAAAAATAAC<br>AACAACAAGAGGTAAAGAAGAAAAAGAAGAAGACAAGAAT<br>GCTGGTGTTGGAAATTCACAAGATGATGACAATGTCAAATT<br>ATGGACGGTGGAAATAGACAATCTGGGTTATCTCAAATCAC<br>TGCCCACAAATTGTCTTACTCTGTTGGACTCACTCGAACTTT<br>CAAATATAGAAGACCAGGAAGATGAGGGCGAAGACAACAT<br>CATATTCTGGAAATCCTTTCCTCAAAACCTCCGCAGTTTGGA<br>AATTGAAAACTCTTACAAAATGACAAGTTTGCCCATGGGGA<br>TGCAGTACTTAACCTCCCTCCAAACCCTCTATCTACACCATT<br>GTTATGAATTGAATTCCCTTCCAGAATGGATAAGCAGCTTAT<br>CATCTCTTCAATCCCTGCACATAGGAAAATGTCCAGCCCTAA<br>AATCACTACCAGAAGCAATGCGGAACCTCACCTCCCTTCAG<br>ACACTTGGGATATCGCGGTGTCCAGACCTAATTGAAAGATG<br>CGAAGAACCCAACGGCGAGGACTATCCCAAAATTCAACACA<br>TCCCCAAAATTGTAAGTCATTGCAGAAAGTAATTTATTCATT<br>TATATTTATTTTATGCTTAGAATGATATACACCGTCGTCCTTT<br>GGTTTCAAATCTTGAATTTGGTTTTTGTTTTCTTTCTTTGTTTC<br>TTTATTCAACACCAGCCCATTTATGATTGATTCATTAAAAAA<br>AGGATGGAGTTTTGTGGATTTGAAGAAGACAACGAATTGAG<br>ATTCCTGGGGTTTTCTTTTTGTTGGGGTTGGATTTCATGTATA<br>TGTTGCTGATTAAATACGAGACTGATGATGATGATGATGTGT<br>TTATGGGTTTTAAATCAGATTAAATATATGGGAAATGTAAGT<br>TAATTTGGGATGCACATAAGGTGTTTGCTGAAATGTCTATGA<br>GAAATGTTGTTTCTTGGACTTAGAATGATATACACTGTCGTC<br>CATTGGTTTCCAATCTTACATTTGGTTTGTGTTTTCTTAGTTT<br>GTTTCTTTAATCAACACCAACCCATTTTTTTAAAACTACCTGC<br>AACTACTAATTTACGTTGACCCTGTATCTCAGGTACTAAATG<br>AATATTGGTGATTTTCAGTTACTCAACACTAGCTTGATCCTG |

TABLE 1-continued

| Sequence information. |
|---|
| AACGCACCCAACCTTCAGGTTAGAATCCGGCTTACTCATCCT<br>TTTGTCCAGTTTTCAAGTAATTGTTTTGGCAGGATCAATTCTC<br>TAATTGTTGTACACCGTATATTGCAATTTATAGTGACTACAG<br>TTAATGAATGTTTACAAAAAATTAGTCATGTAAAAACTTCTT<br>CTCTGTCCATTACATAAACTCTTTTTCTCTTTCTAACTTATCA<br>TGTTCATGTCTAAAAAATTAAACATGCTCACATCAATGTTCA<br>TTTAAGCTAACTTACTTCTGTAAGAGAGCGAGCTAGTTAAAA<br>ACTCCTTTAACTTTCTGTTTTATACTCAGGACATGGATTGATG<br>CAAGCATGAAGAACTTCGGGAATTTGCTAAAACTCTACCAA<br>AGCGATGAGAGTTTGGACTTTGTTTCACTTGAAGTCAGGGAC<br>TGTCAACAAAGCCACAGTGTGCATGTTGGCTGTTTCACTTGG<br>ACGATAAAAAGGTTTATTTAATTGTTTTCCTAAGTGTATTTG<br>GCTTACAAGCTTTTACTTTTCGCTTGAAAGGGTTTTTCTTGTT<br>TTAAGCTTTTTGAATTAGAGTTTCGGTTGAAGTAAGAGTAGT<br>CGTATTAGTCTTTTACTTTGCAGGAGTCTATGCCTATATAAG<br>GTAAGACTCGTATTTGTAATTTTCAGATTATGCAATTCAAGT<br>TTTCGAGTGTTTTCTTAAAAAAACATATCATACCTGTGTGTA<br>GCATAAAGATAAATTCTGATGCTGTGCTTCTTGTTATGGCTC<br>ACATTGGTTTTCATTGTTTGGATTGTTTCACAGGGAAGCAGA<br>GAATACCTGGAACCTGTAAAGGACGCTATATCTATAGCAGC<br>TTTCACAGGCCAAGTAATATAATGTTCTTTATCAATCACTCA<br>ATACCTGGAGATTGTTTGAACACATAATTCACCTCTTTTTTTC<br>CATCTCAAATTGCAGACTTTTACTGGGATTTGAATGACAGCA<br>AACATTTGATTGTCACGAGGATTGATCTAACTGGTGAATGTT<br>GTGATCACCATATTGGTCTTTCTCATTCAAACAAACTTGCAT<br>ACCGTTCTTTTGAAGTTTGAAGACAAGCAGGCGATAATCAA<br>CTCAGGTCGAAGCTCATGTGCAGGAGAGAATAGAATATAGA<br>GGAGATTATTTTTAAAAGAAACGCTCAAAGGTATTGTAGCA<br>CCTTTCCTATTTGCTACTGCAGTGATGTTTTTATTTCTTGTTT<br>GCAGCGCTTGTTTCTCATATTTCAACCTACTTTTAGAAAAAA<br>AAACATCTCCGAACATAACCAAAAATAAAGTTCCCTTATCA<br>GTGCTTTCCCTGCTTTCTTCTAAACAACATATACAATTATAA<br>ACCCTTTTTCTCTCTTACCTTTGTTATTCTTCCTTGCTTCATTG<br>AGATAACACTCTCCTGTTTTTGTTTTGTTGTTAGTCATTACAT<br>GGATATATCAAGGACAACAGTTCTGTAGTCCGTCAACTGTG<br>GTTAGGAAGGCTAAACTGGAGCACAATAACCCCATGTCAAT<br>TGAATAGTAAAGGTGTGCTATATCAGTTTCGTTTGGCTTGGC<br>TTACCTGAAAAATGGCTGGTTATTTATCCTTGTCTCTTTCTAT<br>GACGTGCAGTGGCTTGTTAATGTGTCTCGGACAACAATTCCT<br>CACTTTCCAAGTTCCATACACGCTGATGTAACTATCTTCTGC<br>AGTCTGTTCTTTCATTTTTGCCACGTGCTCTAATTATAACTTT<br>TTGTACTCAATAATCAACTCCTTGTCCCGGTATTTGCAGAGA<br>CTACTTAAACAGGTAAAGTGACAATCCTGGCGAAGTTGTCT<br>GTTTCTTAGCTCTGAACCCATCATTCAGGTAAGATTAAGTAT<br>TTAAGAAGAAATTTTGTTTTTACCTAAAATGAATGATCTTGT<br>GTAACTGCTTGCTTCTTGCATTAAATAAGAACTTTCTGCTGC<br>ATATGTGACAGTTACATCCACAAAAAAGTTGGAGGTTTGTTC<br>AGGGATTGGAAATGAAGGTACTTCAGAATTCCTGGAATGTT<br>TATGAATGCTCCAGACTTCAGAGTCTTTAATGGAAAATTCGA<br>GTCACTAAAAAAACATTATTCCTATCATCAGAGCTTTGAAGT<br>TCCTCTATACAAGGTCAACTGAGTTCCTCTTTGCCTCTTGTTT<br>AATTGTATTTACTTGTACCTTAATTATAATCTGTATATTGTTT<br>TAGTTAAGTTCTAAAACAGGTTATTATTCATCATTTGTGCAG<br>CATATTGCTGGAATCAAGAATCTAGTGCTTCTTCTTCCTGAC<br>TTCACTGTCAAAATAGCAGTTCCCATGCTGGAAATAAGCGC<br>GCTAGCAATGTAATTGATGACATGGATGTTGCTGCTTCTGAG<br>TTTTGATCATAAAAAGCTGTTATGTGTTTCTTGAATGTAATG<br>AAGGAGAGGAGAAAACTGAAAACTCTTGGCAAAAACGTGA<br>AATTGCAGTGCCTCGGGGTGGTAGGGATCACCCGGATTCAG<br>TTCAGACGATACTTTTTTCAACCCGGTTTGTTCCGGTTTTCAG<br>CTTCGGGTTTTCCTTGTACTTTTGGGGCACACATACAAGGCT<br>ACTTCATGTTTGAGAAACCTAATTGAGGCTATCTTGTAGCAA<br>ATGCACACCACACTCTTTCTCTCTTCTCTCCTTTTTTCACCTT<br>CCATTTGTAAAAATCCTCTTTTAAAGGTTAATAAAAAAAAGC<br>TTCAAGTCTCGTAGGGTGGATGTAGGTCACATTGACCGAACC<br>ACGGTAAACTCTTTGTGTTCTTTCTTCTCTCTTTGTTTCTCATT<br>TTTACGGCAAGTGTTTATGGTTAACCATGCATCTTAGAATAG<br>CTTAAGGCATTAACATAATAACATCAATGTTCTCCAAAGATT<br>CACCTTACTTGTTGTACATAATCACAATGTTAAGCCTATGAA<br>GGTAGAATGCTCTCATGATTTGGTTTAACCAAAAAATAAACT<br>CTAAAATAATACGGAGTAATAAAAATTGGCCATAAATTATT<br>TACAAAGTTTGATTTTTGTATAGGGTATCTTGTACTTGTGAT<br>AAAAAAAATTAAAAAAAAAAAAATTACTTATTTCTTCTATTT<br>TTACTTGTTACACTTTTCTACAACAGAAACATCAAAACGCCC<br>GCAACACACTATAAATGAAAAACCATTTTGTATGCAATGAT<br>ATTTACGTTCTCACTTTATTCTCTTTAATAACTCCTACTACGT<br>AATTCTCACCAATCAAATAAAATTATAGAAATTTTCATTTAT<br>ACCCTCTTAAAATGATGTTGATTTNNNNNNNNNNNNNNNNN |

TABLE 1-continued

| Sequence information. |
|---|
| NNNNNNNNNNNNNNNNNNNNNNNNNAGGTGTGAAAAAGTT<br>TGTGTTATAAGTTACAACAATTTAAAAACGGAGAACATACTT<br>ATAATACTAGTGTAATCTTTGGCCGGATTATGGTCGTTGACA<br>AAAAAACTCCGGCCTTGACCCTCCACGTGCCGGTCAAGTGA<br>CTTAATAAACCTTTTATTCCACCCTTTTTTCATTCTTCTTTTTA<br>TTCTTCTTTTTCTCTCCATTAATACAAATCAAGTGATTATGTC<br>GATCCGATCCTTCTGTTCTCTACTGTAATTGATTACACCAAC<br>AACAACCAAGCGAAACAGTCAATGTTACCGAATTGAATTGC<br>GGAAAATAGTTTATGATTGATTCATTAAAAAAGGATGGAGT<br>TTTGTGGATTTGAATAAGACAACGAATTGAGATTCCTGGGGT<br>TTTCTTTCTGTTGGGGTTGGATTTCATGTACTTGTTGCTGATC<br>AAATATGTGATTGAAGATTGAAGATGATGATGTGTTTATGG<br>GTTTGAAATCGGATTAAATTTATGGGAAATGTAAGTGAATTG<br>GGGATGCACATAAGGTGTTTGATGAAATGTCTATGAGAAAT<br>ATTGTTTCTTGCACTTGTATGATAATTTGTGGGGATTTGATTA<br>GTTCATGGTGCGAGTTTGATGCAACGCCGAAGAGAAATCAG<br>GTCTTTAGAGAAACTCAAATGGTTGAATAGGCTTCCAACAAT<br>GTTGTTTCGTAGTACACTGCCATGATTGATAGAGAAGGAAG<br>CAGATGAAGGAGAAGGCTCATGTGACCGGCACATGGGTAGT<br>AAGTCAACGCCGGAAATCGTGGTCAACGTCCAAAACCGAGC<br>TAAGGTAACATATTGGAGTACAAGTAATTACAACAAAAAGT<br>GTTACTTCCTTGTACATTATTATTTTACTTGAAATGCTAGTTG<br>TGTTTGTGCATCTGTGGAACTCTAAATTAATTAATTAACAAT<br>CAACCAAACAACTTTAGTGTAAATTGGCCAACCTTTTGCCAT<br>CAGCCACAGAAAAGTGAAATATCACCCCATTATTGCCCATTC<br>TGTATTTGCACTTTTTTTTAAGGCATAGCACAGCCGGTTTTCC<br>GGATCTTAGCTCCGTCTACATTCGGATCCGATCCATTTCGCA<br>CACCTTATTTGTGGTGGATGAGTCTCCCAACAAGAATTTCTC<br>GCTCGAAACTGAGAACCCCCTTAAGCGGCATCAAGTTGCTT<br>ACCACTTGAGCCAACTCTATGTTGGTTTCTGCATTTGCAGTT<br>AGTTAGGTCGTCTGAGTGCGAAATGGGAATGCTTTATCACAC<br>ACTCCACAGTTTAGTCAGGCTGATGGAAACGTAATAATTGA<br>GTTATTTGAGTGTTCAAACTTAAAGTCACTCACTCACTCAAA<br>CACTCAATACTTTCTCCATCTTGTTTTCTCATTACATATGAAA<br>ACCCAAACACCTTTCATTTCTGCTTAATCTTCTTTCTCTCATC<br>TTTCAGTTATTCACCTGTTCATCTTTCTGAAAACAACCCAAA<br>CACCCTTCATTTCTGTTTAATCTTCTTTCCTCATCTTCATCCA<br>CCTGTTTATCTTTCTGTAAACACAACCCAAACACCTTTCATTT<br>CTGATTTATCTTGTTATCTCATCTTCATTCACCTGTTCATCTTT<br>CTGAAAATCTAAACACCCTTCATTTCTGCTAATCTTCTTTTCT<br>CATCTCCCCCTAAATCATCTTTCTGAAAACCCAAACACCTTT<br>CTTTTCTGCTTTTATCTTGTTTTCTCATCTTAATTCATCTCTTC<br>ATCTTTCTGAAAAACCCAACCCAATGGCTGAAATCGGATACT<br>CGGTTTGTTCAAAACTTATTGAAGTGATGGGCAGTAATATCA<br>TTAAAGAGATTCGCGACATGTGGGGTTACAATTCTCATCTTG<br>AAGACCTCAACAAATCTGTCTTGACGATCAAGGATGTGCTCT<br>TGGATGCTGAGGCGAAGCGGGATCTTTCCCGTGAACAACAG<br>AGTTACATTGCAGAACTTAAGGATGTTGTTTACGATGCTGAT<br>GATTTGTTCGATGAGTTCCTCACTCTTGCTGAGCTCAAACAG<br>ATTGATGGAAACAAGGGTGGTGGTAAATTCTCCAAAAAGGT<br>ACGTCGTTTCTTTTCTTCTAATAAGGAGAAGATGGGTCAAGC<br>TTACAAGATGTCTCATATGGTTAAAGAAATTAAGAAGCAGT<br>TGGGTGAAATTGTTGATAGGTATACCAAATTTGGGTTTATTG<br>TTGATTATAAACCTATTATTAGGAGAAGGGAGGAAACATGT<br>TCTTATTTTGTAGGTGCCAAGGAGATTGTTGGGAGGGATAAG<br>GATAAAGATGTTATCATAGGCATGTTGCTAGATCATGATAAC<br>GATTGTAGTTTCTTGGCTGTTGTGGGGGTTGGAGGGGTGGGA<br>AAAACTACTCTTGCCCAACTTGTGTATAATGATGAAAGAGTC<br>AAAAGTGAGTTCCAAGATTTGAGGTATTGGGTTTGTGTCTCT<br>GATCAAGATGGGGGACAATTTGATGACAAAAGAATTCTTTG<br>TAAGATTATAGAGTTAGTTACGGGCCAGATTCCTCCGAGTAA<br>CGAGAGCATGGAATCGGTGCGTAAGAAATTTCAAGAGGAAT<br>TAGGAGGAAAGAAGTACTTCCTTGTTCTTGATGATGTATGGA<br>ACGAGGATCGCCAGAAGTGGCTTCATCTAGAAAATTTCTTG<br>AAATTGGGTCAAGGGGGAAGCAAGGTTGTGGTAACCACACG<br>TTCAGAGAAGACGGCAAATGTTATAGGGAAAAGACAAGACT<br>ATAAACTAGAATGTTTGTCAGCAGAGGATTCATGGCGCTTAT<br>TTGAAATGTCAGCTTTTGACGAAGGGCATGGCCAGGAAAAC<br>TATGACGAATTAGTGACGATTGGCAAGAAGATTGTTGAAAA<br>ATGTTATAACAATCCACTTGCTATAACAGTGGTAGGAAGCCT<br>TCTTTTTGGACAAGAGATAAATAAGTGGCGGTCGTTTGAAA<br>ACAGTGGATTAGCCCAAATTGCCAATGGTGATAATCAGATTT<br>TCCCGATATTAAAGCTCAGTTACCACAATCTTCCACACTCCT<br>TGAAGAGCTGCTTTAGCTATTGTGCAGTGTTTCCCAAAGATA<br>ATGAAATAAAGAAGGAGATGTTGATTGATCTTTGGATAGCA<br>CAAGGATACATTATACCGTTGGATGGAGGTCAAAGTATAGA<br>AGATGCTGCCGAGGAACATTTTGTAATTTTGTTAAGAAGATG<br>TTTCTTTCAAGATGTAAAGAAGGATTCTCTTGGTAATGTTGA |

TABLE 1-continued

| Sequence information. |
|---|
| TTATGTTAAAATCCACGACTTAATGCACGATGTCGCTCAAGA<br>AGTGGGGAAGGAGGAAATTTGTGTAGTGACTTCAGGTACAA<br>AGAAGTTGGCTGATAAAATCCGTCACGTGGGTTGTGTTGTCG<br>ATAGAGATCCAGAAATAGTCTTTTTATGTAGCAATAAGATTC<br>GTTCGTATATTAGCGGTCGTTGTATAAAGAATCCGGTGGATT<br>CACAAATAGACAACTGGATGCGCCTTAGGGTGTTGGACTTG<br>TCAGATTCATGTGTTAAAGATTTGTCTGATTCAATAGGTAAG<br>CTGCTGCACTTAAGGTATCTTAACCTCTCTTCTAATATAAAG<br>TTGGAGATAATCCCTGATGCAATTACAAGACTGCATAACTTG<br>CAGACACTACTTTTAGAAGATTGCAGAAGTTTAAAGGAGTT<br>GCCAAAAGATTTTTGCAAATTGGTCAAACTGAGGCACTTGG<br>AATTACAGGGTTGTCATGATTTGATTGGTATGCCATTTGGAA<br>TGGATAAGCTAACTAGTCTTAGAATACTACCAAACATTGTGG<br>TGGGTAGGAAGGAACAAAGTGATGATGAGCTGAAAGCCCTA<br>AAAGGCCTCATCGAGATAAAAGGCTCCATTTCTATCAGAAT<br>CTATTCAAAGTATAGAATAGTTGAAGGCATGAATGACACAG<br>GAGGAGCTGCTTATTTGAAGAGCATGAAACATCTCAGGGAG<br>ATTGATATTACATTTTTGGGTGAATGTGTTAGCCCTGAAGCT<br>GTATTGGAAACCTTAGAGCCACCTTCAAATATCAAGAGCTTA<br>TATATATATAATTACAGTGGTACAACAATTCCAGTATGGGGA<br>AGAGCAGAGATTAATTGGGCAATCTCCCTCTCACATCTCGTC<br>GACATCCAGCTTAGTTGTTGTAGTAATTTGCAGGAGATGCCA<br>GTGCTGAGTAAACTGCCTCATTTGAAATCGCTGAAACTTGGA<br>TGGTTGGATAACTTAGAGTACATGGAGAGTAGCAGTAGCAG<br>TGACACAGAAGCAGCAACACCAGAATTACCAACATTCTTCC<br>CTTCCCTTGAAAAACTTACTTTACAGCATCTGGAAAAGTTGA<br>AGGGTTTTGGGAACAGGAGATCGAGTAGTTTTCCCCGCCTCT<br>CTGAATTGGAAATCAAGAAATGCCCAGATCTAACGTCATTTC<br>CTTCTTGTCCAAGCCTTGAGAAGTTGGAATTGAAAGAAAGC<br>AATGAAGCGTTGCAAATAATAGTAAAAATAACAACAAGAGG<br>TAAAGAAAAAGAAGAGAACAATAATGCTGGTGTTGGAAATT<br>CACAAGATGATGACAAAGTCAAATTACGGAAGATGGTGATA<br>GACAATCTGGGTTATCTCAAATCACTGCCCACAAATTGTCTT<br>ACTCACCTTGAAATTGAGGAGTTTATTGAATCAGATTCCGAG<br>GAAGAGATTGAATCAGAAGTCGGGGAGGAGGAGGTTGAATT<br>GGAAGTTGTGGAGGCATTTCAGAAGTCTGCATCTTCTCTGCA<br>AAGCCTCGAAATATACAGAATAAATAAACTGAATAGACTAA<br>CTGGAACAACAGGATTAGTGCATTTCAGTGCCTTGGACGAA<br>CTCACATTGAATTTTGTCGACGATTTTGAAGTATCCTTTCCTC<br>AAAGCCTCCGCAGTTTGAAAATTGAATACTCTTATAAAATGA<br>CAAGTCTGCCCATGGGGATGCAGTACTTAACCTCCCTCCAAA<br>CCCTCGAACTAAAATGTTGTGATGAATTGAATTCCCTTCCAG<br>AATGGATAAGCAACTTATCATCTCTTCAATCCCTGTCCATAT<br>CCTACTGTGAAGCCCTGAAATCACTACCAGAAGCAATGCAG<br>AACCTCACCTCCCTTCAGAGACTTGTGATAAGAGAATGTCGA<br>GACCTAGCTGAAAGATGCGAAGAACCCAATGGGGAAGACTA<br>TCACAAAATTCAACACATCCCCAAAATTGTAAGTGATTGCG<br>GAAAGTGTTTCTTTTATTTATTTTTAATTTTATGCTTAGAATG<br>ATATACATCAGCATTCAGCGTCCATTGGTTTCCAATCTTACA<br>TTTGGTTTTTGTTTCTTAGTTTGTTTCTTTAATCAACACCAGC<br>CCATTTTTTTTAAACTACCTGCAACTACTAATTTTCATTTACC<br>CTGTATCTCAGGAAATATGGTAGTATTCTCATTTACTCAACA<br>CTAGCTTGATCCTGAACGCAGCCAACCTTCAGGTTAGAATCC<br>GCCTTACTCATCCTTTTGTCATGCATTGTTTTAAGTTGTTTTG<br>CTTGCTTGTGTAATCATAATTCATAGTATACGATTCATCATTC<br>ACTATGTCTACAGGCAAGATATTGGAATTGTTCACGATTCCC<br>TGAAGTTTCTTTGTTTTTGTTGATACCACCATATTGCAGCTTA<br>TAGTGACTAAGTTAATGAATGTTTCCAAAAAATTAGTCATAT<br>AAATTCTTCTTCTCTCTCTATTACATAAACTCTTTTTCTCTTTC<br>TAACTATCATGTTCATGTCTAAAACTTATACATGCTCACATC<br>ATTGTTCGTTTCAGCTGACTTACTTCTGTAAGAGAGCTATCT<br>AGTTAACAACTCTTGTAACATTTTATTTGCTAGTCAGAACAT<br>GGATTGGTGCAAGCATGGGAATTTGCCAACACTCTACCAAA<br>TCGATTGGAGTTTGGACTTAGTTTCACCAGAAGCCATACCCG<br>GACACTTACTGGGGACTGTCAACAAAGCCGCATTATGATGT<br>ACTTGGATGTTTCACGTGCCTGAGGTGTGAGTTACTTGGAAG<br>GGAAGCGGTTTATTTAATTGTTTTCCTAAGTAGATTTTGCTTA<br>GAAGCTTTTACTTTTCACTTGAAAGGGTTTTTCTTGTTTTAAG<br>CTTTTCGAATTAGAGTTTCGGTTGCATTAAGAGTAGTCGTAT<br>TAGTCTTTTTTTACCTAAGGAAGACTTTTTTGTAATTTTCAGA<br>CGATGCAATTCAACTTTTCGAGTGTTTTGTTGCTTGTGTGATT<br>GTGAGTTTGTGAATTTGTCTTTCATAAATATTGAGTTCATCA<br>GAAGCTTTATGCTCCACCGGTAGTCTAGTACCTTTTGTTATT<br>GTTCAGGGAAGTAATCTGGTACCTTCTATATATATGAGAAAA<br>CATACATTATGCAAAATTCTTACAGGTTAGTTACTTCCTAGA<br>ACTTCAGTTATACTTTTTTTTTGTTCCATGTCCTTGGAATCAA<br>GTCATTCCCTCTGAAAAATGTGTACTGAACTTTTGAAAGTTG<br>CTGTTTGATTCCTGTTTGAATCTTCACTTTTCTTGCATCGTGA |

TABLE 1-continued

Sequence information.

```
CAGCTGTGTTTACAATGAAGTTTAAGCAGACACTCTCTTTAT
ATAGTGCCTCCTTTTGGAGCATCGGAGAGTTGTGGCTGATCA
CTATGTGCGACCAAGAGATTCATTAATCGCGTGTTTGATCAG
GTAAAAGTTTTTATGTCAATGTGTTTTATTTTTCTTTCTGTTT
GATCAGTTTATGTCTGTATTCAGATTCTTATCTTCTTCTAGTA
GCATAACAAATTTGTTTGTTTCATTATATAAACCGTTTCAGG
ATTACAAATGATCGGACAGAGATGTATGCTTCAGTCGATATT
GATGATAACTTAAGGTAGTATTGCTAGAACAGTTACAGAGC
TGTGGCTGATCACTATGTGCTGCAAACAGATTCATCAATCAC
GTGTTTGATAAGGTAGAGTTTTCATGTCAACGCGTTTTTTCT
GTTTGATCAATTTATGTCTGTATTCAGATTCTTATCTACTTCT
AGTAGCATAACATATCTGTTTCTATCATTATATAATTGTTTCA
GGGTTACAAATGACCGGACAGAGATGTATGCTTCAGTCGAT
ATTGATGCTAACTTAAGATAGCATTGCTAGAACAGTTTCAGG
TTGCCATTGAAATTTGAAAACAGAAAGACACCATCAGGTAG
AGTTTTCATGTCAATGCTTTTTTTTTTTGATCAATTTATGTTT
GTATAAAAATTTGTATCTTCTTCTATACTATAAATTCTATATA
ACGTATCTGTTTATTTCATTATAATAAACCGTTTCAGGATTA
CAAATGATCGAACAGTGATGTATGCTTCAGTCGATAACTTCA
GGTAGCATTGCCAGAAGAATTGCAGACACATCCTAACTTAA
GAGGGTTATGGTTGATTGACTAACTCTCGAAATTCTAGTTAG
GCAAGAGGAGCATTGCAGTACCTGCCTTAAAAGGGGTCGTC
TTATATAGATATCTCTATCAGTAGTCATTTACGTCTTAAGTCC
TGAAATAAGTTGAACTAAACATACTTTGTTTGAATCGAAGAT
TTAGTGAATTTTACTTTGTATTTGATTGTGTTGAGATGACCGT
AGGGAAAAGTTAACTAATTATAAGCGTAAATTATGTTCTTGG
ATTCGGCTTTTATATTTTCTTTTCGTTTAATAAAAGTGGTCAT
AGAGATATTCTACAATGTATTTTGGTAAGTTACCTAAAATTT
AATTTGATTATTTTTCACATAATTAATCAACTGATAAAATTTT
ATTTGGATCAACCGATCAAGAAGTGAAAACGTAAAGAACAA
AAAGAAACAGAGGGAGTATATTATTATCTTTTACTTTTGATA
GTGAAGGATGTTATGATATTTTAACTCAATCCCTTACAAAAT
ATACTGGTTAAATTTCTTAACAATGTAGTACTTTGGCAACAA
GTTCAGGTTGAAAGCTTTGAGAAATAGAGTTAGGAAACATA
AGAATCACAAAATTTATGCTTCTCTCATCTGTGAATCAAAAC
ACAAATTCTTATTTACAAAGGTTGTACAATAATTATTGTACA
CCGAAGTAAAAGTTAACTCAAAATGCTTAAAAGTTAGGCTT
ATATATGTAAAAGTTATCTATTGTTTAGTGATAAAAAATTTC
ATTTTAATAAAACTTATTTTTTCAAAATCACTAATAATGTAT
AAAATTAATCATTTAATTATTTAAAATATTTATCTATCAAAT
TTTTTTACTAATATAAAAGTTACTCAAAACTAGGTTAAAATT
ACAAAAAAATGGATTAAAGTTATTTTGGTGTACAATAAATTT
ATTGTATACTTTGTGCGCGC
```

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1: Testing for Resistance to CMV in Spinach Plants

The resistance to CMV infection was assayed as described in the CPVO protocol for tests on distinctness, uniformity, and stability for spinach as available on: www.cpvo.europa.eu/documents/TP/vegetales/TP_055-5Rev_Spinacia_oleracea_pdf.

Spinach seeds of the invention together with seeds of varieties Viroflay and Polka were sown in 5×5 cm soil blocks and under a cultivation regime with a day temperature of 20° C. and a night temperature of 18° C. and receiving at least 16 hours of light. When the plants had developed three true leaves they were inoculated with CMV. Inoculation was done by dusting the leaves of the plants with carborundum powder and subsequently rubbing the leaves with a sponge soaked in inoculum. The inoculum was a dilution (1:10) of isolates NL 16 and SP 43 in water. After inoculation plants were slightly rinsed with water.

Symptoms may be observed 7 to 9 days after inoculation. A resistant plant, i.e. a plant comprising the allele of the invention, shows no symptoms, while a susceptible plant typically shows dwarf growth and mosaic symptoms in the heart of the plant.

Plants for this specific test were scored as resistant or susceptible based on the development of symptoms. Plants exhibiting no symptoms were in this specific test considered as resistant. Plants that showed symptoms of infection were in this test scored a susceptible.

All plants of varieties Viroflay and Polka were scored as susceptible since they showed symptoms such as dwarf growth and mosaic symptoms in the heart of the plant, while plants of the invention showed no symptoms and were scored resistant.

Example 2: Transferring CMV Resistance into a Plant of Variety Viroflay

In seeds of deposit NCIMB 42651 the alpha-CMV allele is heterozygously present. Seed of this deposit was grown into mature spinach plants which were individually selfed to produce an F2 population.

Fifty F2 seeds were used to develop plants for a disease test as described in Example 1. F2 plants that scored resistant in the disease test were further grown to maturity and again individually selfed to obtain for each plant a F3 population. Each F3 population was again subjected to a disease test as described in Example 1. Plants of the F3 populations that scored completely resistant in the CMV disease test can be considered to comprise the alpha CMV allele homozygously.

One of the plants that is homozygous for the alpha CMV allele was used to cross with a plant of variety Viroflay which is susceptible to CMV to obtain F1 seed and a subsequent F1 plant grown from the F1 seed. The F1 plant was selfed to obtain an F2 population of seeds and plants. This population was again subjected to the disease test as described in Example 1. The disease test showed that the segregation pattern for CMV resistance is 3:1 which is consistent with that of a dominant inheritance.

Example 3: Amplification of the LRR Domain-Encoding Region

Identification and selection of CMV resistant spinach plants carrying the Alpha CMV allele can also be efficiently done by screening the DNA for the presence of the alpha CMV allele. For example by amplifying and optionally determining the sequence of the LRR domain of alpha CMV allele as described below.

The isolated genomic DNA of spinach plants from the F2 population as obtained in Example 2 was amplified using forward primer ACAAGTGGATGTGTCTTAGG (SEQ ID NO:6) and reverse primer TTCGCCCTCATCTTCCTGG (SEQ ID NO:7). The primer pair amplifies the LRR domain-encoding region of an alpha-WOLF gene to which the alpha-CMV allele belongs, and has been designed for selectively amplifying part of an alpha-WOLF gene, and not of other CC-NBS-LRR protein-encoding genes.

PCR conditions for amplifying the LRR domain-encoding region of an alpha-WOLF gene using primers having SEQ ID NO:6 and SEQ ID NO:7 were as follows, using Platinum Taq enzyme (Thermo Fisher Scientific):
 3 minutes at 95° C. (initial denaturing step)
 40 amplification cycles, each cycle consisting of: 30 seconds denaturation at 95° C., 30 seconds annealing at 60° C., and 30 seconds extension at 72° C.
 2 minutes at 72° C. (final extension step)

The isolated genomic DNA of spinach plants from the F2 population as obtained in Example 2 was in parallel amplified using forward primer TCACGTGGGTTGTGTTGT (SEQ ID NO:8) and reverse primer TTCGCCCTCATCTTCCTGG (SEQ ID NO:7). This primer pair amplifies the LRR domain-encoding region of a beta-WOLF gene, to which the beta-WOLF 0 allele of Viroflay belongs, and has been designed for selectively amplifying part of a beta-WOLF gene, and not of other CC-NBS-LRR protein-encoding genes.

PCR conditions for amplifying the LRR domain-encoding region of a beta-WOLF gene using primers having SEQ ID NO:7 and SEQ ID NO:8 were as follows, using a Taq enzyme:
 3 minutes at 95° C. (initial denaturing step)
 40 amplification cycles, each cycle consisting of: 30 seconds denaturation at 95° C., 50 seconds annealing at 58° C. and 50 seconds extension at 72° C.
 2 minutes at 72° C. (final extension step)

The PCR products were visualized on agarose gel (not shown), and DNA was purified from the PCR reaction. Subsequently the sequence of the PCR products was determined using methods well known in the art.

The sequence of the LRR domain of the alpha-CMV allele amplified by primers having SEQ ID NO:6 and SEQ ID NO:7 is provided in Table 1 under SEQ ID NO:9.

The sequence of the LRR domain of the beta-WOLF 0 allele amplified by primers having SEQ ID NO:7 and SEQ ID NO:8 is provided in Table 1 under SEQ ID NO:11.

The PCR products were visualized on agarose gel (not shown), this demonstrated that approximately 25% of the plant only contained an alpha-WOLF fragment, approximately 50% contained both an alpha- and a beta-WOLF fragment, and that the remaining approximately 25% of the plants only contained a beta-WOLF fragment. The plants containing the alpha-WOLF fragment completely correlated with the plants that scored resistant for CMV. The plants only comprising the beta-WOLF fragment completely correlated with the plants that scored susceptible for CMV.

DNA from the PCR reaction was purified, and subsequently the sequence of the PCR products was determined. The alpha-WOLF PCR products gave a sequence that corresponded to the sequence of SEQ ID NO:9, the genomic sequence of the LRR domain of the alpha-CMV allele. The beta-WOLF PCR products gave a sequence that corresponded to the sequence of SEQ ID NO:11 the genomic sequence of the LRR domain of the beta-WOLF 0 allele.

Finally, the obtained sequences were translated into the corresponding amino acid sequence of the LRR domain having SEQ ID NO:10 and SEQ ID NO:12 for the alpha-CMV allele and the beta-WOLF 0, respectively (See also Table 2).

Example 4: Creating Hybrid and Parent Lines with CMV Resistance

One of the WOLF alleles present in Racoon (51-317 RZ) is beta-WOLF 3 having SEQ ID NO:13, which confers resistance to *Peronospora farinosa* f. sp. *spinaciae* races Pfs:1, Pfs:3, Pfs5, Pfs:9, Pfs:11, Pfs:12, Pfs:14, and Pfs:16. Next to the full resistance against these races, Beta-WOLF 3 provides intermediate resistance against Pfs:8. The goal of this experiment was to create a stable hybrid in which the beta-WOLF 3 allele is combined with the alpha-CMV allele of the invention.

A plant comprising the alpha-CMV allele homozygously, e.g. a plant as obtained in Example 2, was crossed with a plant of the male parent line of hybrid Racoon. F1 Plants were subjected to a CMV disease test as described in Example 1 and a resistant plant was selected. The selected plant was crossed again with a plant of the male parent line of hybrid Racoon to obtain a $BC_1$ population. The $BC_1$ population was subjected to a CMV disease test as described in Example 1 and again a CMV resistant plant was selected. This was repeated three more times until a $BC_4$ population was obtained.

Again, a resistant plant was selected from a CMV disease test and this plant was selfed. From the obtained $S_1BC_4$ population a plant homozygous for the alpha-CMV allele was selected by determining the sequence of the LRR domain of the WOLF gene as mentioned in Example 3.

The selected homozygous plant was further inbred to obtain a population that could serve as an alternative CMV resistant parent line for Racoon.

Plants from this CMV resistant parent line were crossed with the female parent line of hybrid Racoon to produce seed for a new hybrid variety resistant to CMV conferred by the alpha-CMV allele of the invention in combination with downy mildew resistance conferred by the beta-WOLF 3 allele.

In a similar fashion hybrids can be created in which the alpha-CMV allele is combined with an alpha/beta-WOLF allele conferring resistance against one or more downy mildew races.

The invention is further described by the following numbered paragraphs:

1. An allele designated alpha-CMV which confers resistance to CMV when present in a spinach plant, wherein the protein encoded by said allele is a CC-NBS-LRR protein that comprises in its amino acid sequence: a) the motif "MAEIGYSVC" (SEQ ID NO: 22) at its N-terminus; b) the motif "KWMCLR" (SEQ ID NO: 23); and c) an LRR domain that has in order of increased preference at least 95%, 96%, 97%, 98%, 99%, 100% sequence similarity to SEQ ID NO:10.

2. The allele of paragraph 1, wherein the allele has a genomic nucleotide sequence which in order of increased preference has at least 80%, 81%, 82%, 83%, 84%, 85%, 86%, 87%, 88%, 89%, 90%, 91%, 92%, 93%, 94%, 95%, 96%, 97%, 98%, 99%, 100% sequence similarity to SEQ ID NO:1.

3. The allele of paragraph 1, wherein the allele has a coding sequence which in order of increased preference has at least 80%, 81%, 82%, 83%, 84%, 85%, 86%, 87%, 88%, 89%, 90%, 91%, 92%, 93%, 94%, 95%, 96%, 97%, 98%, 99%, 100% sequence similarity to SEQ ID NO:2.

4. The allele of paragraph 1, wherein the allele has a coding sequence which in order of increased preference has at least 80%, 81%, 82%, 83%, 84%, 85%, 86%, 87%, 88%, 89%, 90%, 91%, 92%, 93%, 94%, 95%, 96%, 97%, 98%, 99%, 100% sequence similarity to SEQ ID NO:3.

5. The allele of paragraph 1, wherein the allele encodes a protein having an amino acid sequence which in order of increased preference has at least 95%, 96%, 97%, 98%, 99%, 100% sequence similarity to SEQ ID NO:4.

6. The allele of paragraph 1, wherein the allele encodes for a protein having an amino acid sequence which in order of increased preference has at least 95%, 96%, 97%, 98%, 99%, 100% sequence similarity to SEQ ID NO:5.

7. Nucleic acid encoding a CC-NBS-LRR protein that comprises in its amino acid sequence: a) the motif "MAEIGYSVC" (SEQ ID NO: 22) at its N-terminus; b) the motif "KWMCLR" (SEQ ID NO: 23); and c) an LRR domain that has in order of increased preference at least 95%, 96%, 97%, 98%, 99%, 100% sequence similarity to SEQ ID NO:10.

8. Nucleic acid of paragraph 7 having a genomic nucleotide sequence which in order of increased preference has at least 80%, 81%, 82%, 83%, 84%, 85%, 86%, 87%, 88%, 89%, 90%, 91%, 92%, 93%, 94%, 95%, 96%, 97%, 98%, 99%, 100% sequence similarity to SEQ ID NO:1.

9. A spinach plant comprising the alpha-CMV allele of any one of the paragraphs 1 to 6 or a nucleic acid of paragraph 7 or 8 and optionally further comprising a downy mildew resistance conferring allele of the alpha/beta-WOLF gene.

10. The plant of paragraph 9, wherein the downy mildew resistance conferring allele of the alpha/beta-WOLF gene is beta-WOLF 3 having a genomic sequence which in order of increased preference has at least 95%, 96%, 97%, 98%, 99%, 100% sequence similarity to SEQ ID NO:13, and wherein the plant is at least resistant to CMV and *Peronospora farinosa* f sp. *spinaciae* races Pfs:1, Pfs:3, Pfs:5, Pfs:9, Pfs:11, Pfs:12, Pfs:14, and Pfs:16.

11. The plant of paragraph 9, wherein the downy mildew resistance conferring allele of the alpha/beta-WOLF gene is alpha-WOLF 6 having a genomic sequence which in order of increased preference has at least 95%, 96%, 97%, 98%, 99%, 100% sequence similarity to SEQ ID NO:14, and wherein the plant is at least resistant to CMV and *Peronospora farinosa* f sp. *spinaciae* races Pfs:1, Pfs:2, Pfs:3, Pfs:4, Pfs:5, Pfs:6, Pfs:9, Pfs:11, Pfs:12, Pfs:14, Pfs:15, and Pfs:16.

12. The plant of paragraph 9, wherein the downy mildew resistance conferring allele of the alpha/beta-WOLF gene is alpha-WOLF 6b having a genomic sequence which in order of increased preference has at least 95%, 96%, 97%, 98%, 99%, 100% sequence similarity to SEQ ID NO:15, and wherein the plant is at least resistant to CMV and *Peronospora farinosa* f sp. *spinaciae* races Pfs:1, Pfs:2, Pfs:3, Pfs:4, Pfs:5, Pfs:6, Pfs:9, Pfs:11, Pfs:12, Pfs:14, Pfs:15, Pfs:16 and isolate US1508.

13. The plant of paragraph 9, wherein the downy mildew resistance conferring allele of the alpha/beta-WOLF gene is alpha-WOLF 8 having a genomic sequence which in order of increased preference has at least 95%, 96%, 97%, 98%, 99%, 100% sequence similarity to SEQ ID NO:16, and wherein the plant shows at least resistance to CMV and *Peronospora farinosa* f. sp. *spinaciae* races Pfs:1, Pfs:2, Pfs:6, Pfs:8, Pfs:15, and intermediate resistance to Pfs:16.

14. The plant of paragraph 9, wherein the downy mildew resistance conferring allele of the alpha/beta-WOLF gene is alpha-WOLF 9 having a genomic sequence which in order of increased preference has at least 95%, 96%, 97%, 98%, 99%, 100% sequence similarity to SEQ ID NO:17, and wherein the plant is at least resistant to CMV and *Peronospora farinosa* f sp. *spinaciae* races Pfs:1, Pfs:2, Pfs:3, Pfs:4, Pfs:5, Pfs:6, Pfs:7, Pfs:8, Pfs:9, Pfs:10, Pfs:11, Pfs:12, and Pfs:13.

15. The plant of paragraph 9, wherein the downy mildew resistance conferring allele of the alpha/beta-WOLF gene is alpha-WOLF 11 having a genomic sequence which in order of increased preference has at least 95%, 96%, 97%, 98%, 99%, 100% sequence similarity to SEQ ID NO:18, and wherein the plant is at least resistant to CMV and *Peronospora farinosa* f sp. *spinaciae* races Pfs:1, Pfs:3, Pfs:4, Pfs:5, Pfs:7, Pfs:11, Pfs:13, Pfs:15, Pfs:16 and isolate US1508.

16. The plant of paragraph 9, wherein the downy mildew resistance conferring allele of the alpha/beta-WOLF gene is alpha-WOLF 12 having a genomic sequence which in order of increased preference has at least 95%, 96%, 97%, 98%, 99%, 100% sequence similarity to SEQ ID NO:19, and wherein the plant is at least resistant to CMV and *Peronospora farinosa* f sp. *spinaciae* races Pfs:1, Pfs:2, Pfs:3, Pfs:4, Pfs:6, Pfs:7, Pfs:8, Pfs:9, Pfs:10, Pfs:11, Pfs:12 and isolate Pfs:13.

17. The plant of paragraph 9, wherein the downy mildew resistance conferring allele of the alpha/beta-WOLF gene is alpha-WOLF 15 having a genomic sequence which in order of increased preference has at least 95%, 96%, 97%, 98%, 99%, 100% sequence similarity to SEQ ID NO:20, and wherein the plant is at least resistant to CMV and *Peronospora farinosa* f sp. *spinaciae* races Pfs:1, Pfs:2, Pfs:3, Pfs:4, Pfs:5, Pfs:6, Pfs:9, Pfs:11, Pfs:12, Pfs:13, Pfs:14, and Pfs:15.

18. The plant of any of the paragraphs 9 to 17, wherein the plant is an F1 hybrid variety.

19. A method of producing a hybrid spinach seed comprising crossing a first parent spinach plant with a second parent spinach plant and harvesting the resultant hybrid spinach seed, wherein said first and/or second parent spinach plant comprises the allele of any of the paragraphs 1 to 6 or the nucleic acid of paragraph 7 or 8.

20. The method of paragraph 19, wherein the first and/or second parent is a plant of an inbred line.

21. A hybrid spinach plant grown from the seed produced by the method of paragraph 19 or paragraph 20.

22. Method for identifying or selecting a spinach plant carrying the allele of any of the paragraphs 1 to 6 or a nucleic acid of paragraph 7 or 8, comprising determining the presence of a genomic nucleotide sequence or a part thereof in the genome of a plant, wherein said sequence has in order of increased preference 80%, 81%, 82%, 83%, 84%, 85%, 86%, 87%, 88%, 89%, 90%, 91%, 92%, 93%, 94%, 95%, 96%, 97%, 98%, 99%, 100% sequence similarity to SEQ ID NO:1.

23. Method for identifying or selecting a spinach plant carrying the allele of any of the paragraphs 1-3 and 5 or a nucleic acid of paragraph 7 or 8, comprising determining the presence of a coding sequence or a part thereof in the genome of a plant, wherein said sequence has in order of increased preference 80%, 81%, 82%, 83%, 84%, 85%, 86%, 87%, 88%, 89%, 90%, 91%, 92%, 93%, 94%, 95%, 96%, 97%, 98%, 99%, 100% sequence similarity to SEQ ID NO:2.

24. Method for identifying or selecting a spinach plant carrying the allele of any of the paragraphs 1-2, 4 and 6 a nucleic acid of paragraph 7 or 8, comprising determining the presence of a coding sequence or a part thereof in the genome of a plant, wherein said sequence has in order of increased preference 80%, 81%, 82%, 83%, 84%, 85%, 86%, 87%, 88%, 89%, 90%, 91%, 92%, 93%, 94%, 95%, 96%, 97%, 98%, 99%, 100% sequence similarity to SEQ ID NO:3.

25. The method of any of the paragraphs 22 to 24, comprising determining the presence of the LRR domain as defined in paragraph 1.

26. The method of paragraph 25, wherein the LRR domain is determined by using a primer pair to amplify the LRR domain, wherein the forward primer is a nucleic acid molecule comprising the sequence of SEQ ID NO:6.

27. The method of paragraph 25, wherein the LRR domain is determined by using a primer pair to amplify the LRR domain, wherein the reverse primer is a nucleic acid molecule comprising the sequence of SEQ ID NO:7.

28. Primer pair comprising a forward primer which is a nucleic acid molecule comprising the sequence of SEQ ID NO:6 and a reverse primer which is a nucleic acid molecule comprising the sequence of SEQ ID NO:7.

29. A method for producing a spinach plant showing resistance to CMV comprising: (a) crossing a plant comprising the allele of any one of the paragraphs 1 to 6 or the nucleic acid of paragraph 7 or 8, with another plant; (b) optionally performing one or more rounds of selfing and/or crossing; (c) selecting after one or more rounds of selfing and/or crossing for a plant that comprises said allele of any of the paragraphs 1 to 6 or the nucleic acid of paragraph 7 or 8.

30. The method of paragraph 29, wherein the selection of a plant comprising the allele comprises determining the presence of the allele according to the method of anyone of the paragraphs 22 to 27.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A spinach plant comprising: an alpha-CMV allele which confers resistance to Cucumber Mosaic Virus (CMV) when present in a spinach plant, and a downy mildew resistance conferring allele of the alpha/beta-WOLF gene, wherein the downy mildew resistance conferring allele of the alpha/beta-WOLF gene has: a genomic sequence comprising SEQ ID NO: 13, or a genomic sequence having at least 96% sequence similarity to SEQ ID NO: 14, 15, 18, or 19, or, a genomic sequence having at least 95% sequence similarity to SEQ ID NO: 16 or 17; or a genomic sequence having at least 99% sequence similarity to SEQ ID NO: 20;

and wherein the alpha-CMV allele is as present in seed which was deposited with the NCIMB under NCIMB accession number 42651.

2. The plant of claim 1, wherein the plant is an F1 hybrid variety.

3. The plant of claim 1, wherein the downy mildew resistance conferring allele of the alpha/beta-WOLF gene is beta-WOLF 3 having a genomic sequence comprising SEQ ID NO: 13.

4. The plant of claim 1, wherein the downy mildew resistance conferring allele of the alpha/beta-WOLF gene is alpha-WOLF 6 having a genomic sequence which has at least 96% sequence similarity to SEQ ID NO: 14.

5. The plant of claim 1, wherein the downy mildew resistance conferring allele of the alpha/beta-WOLF gene is alpha-WOLF 6b having a genomic sequence which has at least 96% sequence similarity to SEQ ID NO: 15.

6. The plant of claim 1, wherein the downy mildew resistance conferring allele of the alpha/beta-WOLF gene is alpha-WOLF 8 having a genomic sequence which has at least 95% sequence similarity to SEQ ID NO: 16.

7. The plant of claim 1, wherein the downy mildew resistance conferring allele of the alpha/beta-WOLF gene is alpha-WOLF 9 having a genomic sequence which has at least 95% sequence similarity to SEQ ID NO: 17.

8. The plant of claim 1, wherein the downy mildew resistance conferring allele of the alpha/beta-WOLF gene is alpha-WOLF 11 having a genomic sequence which has at least 96% sequence similarity to SEQ ID NO: 18.

9. The plant of claim 1, wherein the downy mildew resistance conferring allele of the alpha/beta-WOLF gene is alpha-WOLF 12 having a genomic sequence which has at least 96% sequence similarity to SEQ ID NO: 19.

10. The plant of claim 1, wherein the downy mildew resistance conferring allele of the alpha/beta-WOLF gene is alpha-WOLF 15 having a genomic sequence which has at least 99% sequence similarity to SEQ ID NO: 20.

11. The plant of claim 4, wherein the downy mildew resistance conferring allele of the alpha/beta-WOLF gene is alpha-WOLF 6 having a genomic sequence comprising SEQ ID NO: 14.

12. The plant of claim 5, wherein the downy mildew resistance conferring allele of the alpha/beta-WOLF gene is alpha-WOLF 6b having a genomic sequence comprising SEQ ID NO: 15.

13. The plant of claim 6, wherein the downy mildew resistance conferring allele of the alpha/beta-WOLF gene is alpha-WOLF 8 having a genomic sequence comprising SEQ ID NO: 16.

14. The plant of claim 7, wherein the downy mildew resistance conferring allele of the alpha/beta-WOLF gene is alpha-WOLF 9 having a genomic sequence comprising SEQ ID NO: 17.

15. The plant of claim 8, wherein the downy mildew resistance conferring allele of the alpha/beta-WOLF gene is alpha-WOLF 11 having a genomic sequence comprising SEQ ID NO: 18.

16. The plant of claim 9, wherein the downy mildew resistance conferring allele of the alpha/beta-WOLF gene is alpha-WOLF 12 having a genomic sequence comprising SEQ ID NO: 19.

17. The plant of claim 10, wherein the downy mildew resistance conferring allele of the alpha/beta-WOLF gene is alpha-WOLF 15 having a genomic sequence comprising SEQ ID NO: 20.

* * * * *

SEQUENCE LISTING

```
<160> NUMBER OF SEQ ID NOS: 25

<210> SEQ ID NO 1
<211> LENGTH: 9424
<212> TYPE: DNA
<213> ORGANISM: Spinacia oleracea
<220> FEATURE:
<223> OTHER INFORMATION: 9188..9229
<220> FEATURE:
<221> NAME/KEY: misc_feature
<222> LOCATION: 9188..9229
<223> OTHER INFORMATION: /note="n = a or t or c or g"

<400> SEQUENCE: 1

tttgaagtta ggcttaactt gctcaccaat tcttaaatag actcgactta cactgaattt     60

attgtgtact atgtctagaa agtaaggtca acaactttct tctaaattat tttggcatgt    120

ttattagggt tattatgaaa aacatatcaa attggtgttg ttagttaggc ttgaataata    180

tgattttaag tcacgagact tttataaatt aggtaatttg atttaaaaaa ttgttacata    240

tctaagaaaa tggatgttaa atttatcagt caatgtataa acaataaaag tcaatatgta    300

tgtaaaaggg ttgctagata aaatctttgg ttttttggtc cacaactcca cactaagagg    360

aactccaatg cttagttaca aggtggtgta gttaaaaagt aactccaata gttaactaca    420

cggtattata gttaaatttg ccaactcaaa tttctaacta caatatattt aagctacaaa    480

gtttctcatt ggctgactac aatacgttgt agcgccttat aatattttat tcaatataca    540

attttattta ttttaccttt ttaacaattt ttttttgatc tacctgctgt cctgttcata    600

tgagctacac taatttgata gctgcttacg caattcttat atcaacggtt ggctacttgt    660
```

```
tcaaatattt ttattttttt acgagtaagt cattttatga tcattgaagt ggctctatta    720
ttattatcat gcaccgatta acgcaagaat aattaactcg gtacgaatta gtttcaaaat    780
aaaatccctc aaaaaaaaaa gtttcaaaat aaaattaaca gaaaaccaac cttctccggt    840
ttactgttgt tagagcatgg aattttccag taatcgcaga ccccaaatta tcttccagtt    900
gaatcaatcc ttgatttttg gatttgccag aaaactcctt gaattttagg gttcatattt    960
gatccgtaat tgggaaaatt ttcagcaatt gatcttccaa atcagcccta cttgtttcca   1020
gactgcaaat gaaaggtgcg aactttatac tgcattttgg ttttccatta gtgtaattta   1080
ttaagatgaa ctgcattttg caattgtttt attcgactac tcatttttaa atcaaattgc   1140
ttaattgcta gttagtttc ttatcatatt gccaaaaaaa attattttttg tttaattggt   1200
gaaaaagggt aaattatacc tagtgtacaa gattttcttg cacaccaccg ttaatttgtt   1260
gacacatcat caaacgtact gaaaaatgag aatgaaagac aataaatatg tcattttaac   1320
caatagaaaa acatgatgta gtaagatcct taattgatag ataaataatt aaatatcagt   1380
ccattagttg aatattcaat gaaaatgtat ggtccaaaaa tggcgtttaa tagtcaatgt   1440
catgctttat ggggtggtgg agtactatgt gactgtgtgt ggacttggag aagactagag   1500
agtatgatta tcaacctatg gaccctcaaa atgaaaatga aaatgatgtt tacacgtgct   1560
atttgcacgg acttcaatgc aaatagtata aatttacggt caaagttttc attctaaagc   1620
gtaaataact ttcatgaatg gaggacggta gtataagtat aacgttatag cctaccattt   1680
tcttatcata ttcacataaa tttgttgctg aaatttgttt tacttggcta aaatactttt   1740
gttcttattg gcagataaac atcagtacgt ccattattgg ccaacttgct gagtccatta   1800
ttggccaact tgaacatata cctccaaaca ataatcaata atgtcgatta tgaagtttgt   1860
gaatgcaatt tattatcact ttcatttata aaatgactac ttgattaaca catacaatat   1920
tacctttctc caaacaccct ttcaattctg cttaatcttg ttttctcatc atctcttcat   1980
ctttctgaaa acacaaccca atggccgaaa tcggatactc ggtttgtgcg aaactcatcg   2040
aagtgattgg cagtgagctg atcaaagaga tttgtgacac atggggttac aaatctcttc   2100
ttgaggacct caacaaaact gtattgacgg tcaggaacgt tctcattcaa gccggggtga   2160
tgcgggagct tactagtgaa caacaaggtt tcattgcaga ccttaaagat gttgtttatg   2220
atgctgatga cttgttcgac aagttactca ctcgtgctga gcgaaaacag attgatggaa   2280
acgaaatctc tgaaaaggta cgtcgtttct tttcctctag taacaagatc ggtcaagctt   2340
actacatgtc tcgtaaggtt aaggaaatta agaagcagtt ggatgaaatt gttgataggc   2400
atacaaaatt tgggtttagt gctgagttta tacctgtttg taggggaagg ggaaacgaga   2460
gggaaacacg ttcatatata gatgtcaaga atattcttgg gagggataaa gataagaatg   2520
atatcataga taggttgctt aatcgtaatg gtaatgaagc ttgtagtttc ctgaccatag   2580
tgggagcggg aggattggga aaaactgctc ttgcacaact tgtgttcaat gatgaaaggg   2640
tcaaaattga gttccatgat ttgaggtatt gggtttgtgt ctctgatcaa gatgggggcc   2700
aatttgatgt gaaagaaatc ctttgtaaga ttttagaggt ggttactaag gagaaagttg   2760
ataatagttc cacattggaa ttggtacaaa gccaatttca agagaagtta agaggaaaga   2820
agtacttcct tgttcttgat gatgtatgga acgaagatcg tgagaagtgg cttcctttgg   2880
aagagttgtt aatgttgggt caagggggaa gcaaggttgt agtgaccaca cgttcagaga   2940
agacagcaaa tgtcataggg aaaagacatt tttatacact ggaatgtttg tcaccagatt   3000
```

-continued

```
attcatggag cttatttgaa atgtcggctt ttcagaaagg gcatgagcag gaaaaccatc   3060
acgaactagt tgatattggg aaaaagattg ttgaaaaatg ttataacaat ccacttgcta   3120
taacggtggt aggaagtctt ctttatggag aggagataag taagtggcgg tcatttgaaa   3180
tgagtgagtt ggccaaaatt ggcaatgggg ataataagat tttgccgata ttaaagctca   3240
gttaccataa tcttataccc tcgttgaaga gttgttttag ttattgtgca gtgtttccca   3300
aggatcatga aataaagaag gagatgttga ttgaactttg gatggcacaa ggatatgttg   3360
tgccgttgga tggaggtcaa agtatagaag atgctgccga ggaacatttt gtaattttgt   3420
tacgaaggtg tttctttcaa gatgtaaaga aggataaata tggtgatgtt gattctgtta   3480
aaatccacga cttgatgcac gatgtcgccc aagaagtggg gagggaggaa ttatgtgtag   3540
tgaatgataa tacaaagaac ttgggtgata aaatccgtca tgtacatcgt gatgtcatta   3600
gatatgcaca aagagtctct ctgtgtagcc atagccataa gattcgttcg tatattggtg   3660
gtaattgtga aaaacgttgt gtggatacac taatagacaa gtggatgtgt cttaggatgt   3720
tggacttgtc atggtcggat gttaaaaatt tgcctaattc aataggtaaa ttgttgcact   3780
tgaggtgtct taacctgtct tataataaag atctgttgat actccctgat gcaattacaa   3840
gactgcataa tttgcagaca ctgcttttaa aagagtgcag aagtttaaag gagttgccaa   3900
aagatttttg caaattggtc aaactgaggc acttggattt aaggtgttct gatttgaagg   3960
agttgccaaa agatttttgc aaattggtca aactgaggca cttggattta tggggttgtg   4020
atgatttgat tggtgtgcca ttgggaatgg ataggctaat tagtcttaga gtactgccat   4080
tctttgtggt gggtaggaag gaacaaagtg atgatgatga gctgaaagcc ctaaaaggcc   4140
tcaccgagat aaaaggctcc attcgtatta gaatctattc aaagtataga atagttgaag   4200
gcatgaatga cacaggagga gctgggtatt taaagagcat gaaacatctc acgggggttg   4260
atattacatt tgatggtgga tgtgttaacc ctgaagctgt gttggcaacc ctagagccac   4320
cttcaaatat caagaggtta gagatgtggc attacagtgg tacaacaatt ccagtatggg   4380
gaagagcaga gattaattgg gcaatctccc tctcacatct tgtcgacatc cagctttggc   4440
attgtcgtaa tttgcaggag atgccagtgc tgagtaaact gcctcatttg aaatcactgg   4500
aactttataa tttgattagt ttagagtaca tggagagcac aagcagaagc agtagcagtg   4560
acacagaagc agcaacacca gaattaccaa cattcttccc ttcccttgaa aaacttacac   4620
tttggcgtct ggacaagttg aagggttttg ggaacaggag atcgagtagt tttccccgcc   4680
tctctaaatt ggaaatctgg aaatgcccag atctaacgtc atttccttct tgtccaagcc   4740
ttgaagagtt ggaattgaaa gaaaacaatg aagcattgca aataatagta aaaataacaa   4800
caacaagagg taaagaagaa aaagaagaag acaagaatgc tggtgttgga aattcacaag   4860
atgatgacaa tgtcaaatta tggacggtgg aaatagacaa tctgggttat ctcaaatcac   4920
tgcccacaaa ttgtcttact ctgttggact cactcgaact ttcaaatata gaagaccagg   4980
aagatgaggg cgaagacaac atcatattct ggaaatcctt tcctcaaaac ctccgcagtt   5040
tggaaattga aaactcttac aaaatgacaa gtttgcccat ggggatgcag tacttaacct   5100
ccctccaaac cctctatcta caccattgtt atgaattgaa ttcccttcca gaatggataa   5160
gcagcttatc atctcttcaa tccctgcaca taggaaaatg tccagcccta aaatcactac   5220
cagaagcaat gcggaacctc acctcccttc agacacttgg gatatcgcgg tgtccagacc   5280
taattgaaag atgcgaagaa cccaacggcg aggactatcc caaaattcaa cacatcccca   5340
aaattgtaag tcattgcaga aagtaattta ttcatttata tttattttat gcttagaatg   5400
```

-continued atatacaccg tcgtcctttg gtttcaaatc ttgaatttgg tttttgtttt ctttctttgt 5460
ttctttattc aacaccagcc catttatgat tgattcatta aaaaaaggat ggagttttgt 5520
ggatttgaag aagacaacga attgagattc ctggggtttt ctttttgttg gggttggatt 5580
tcatgtatat gttgctgatt aaatacgaga ctgatgatga tgatgatgtg tttatgggtt 5640
ttaaatcaga ttaaatatat gggaaatgta agttaatttg ggatgcacat aaggtgtttg 5700
ctgaaatgtc tatgagaaat gttgtttctt ggacttagaa tgatatacac tgtcgtccat 5760
tggtttccaa tcttacattt ggtttgtgtt ttcttagttt gtttctttaa tcaacaccaa 5820
cccatttttt taaaactacc tgcaactact aatttacgtt gaccctgtat ctcaggtact 5880
aaatgaatat tggtgatttt cagttactca acactagctt gatcctgaac gcacccaacc 5940
ttcaggttag aatccggctt actcatcctt ttgtccagtt ttcaagtaat tgttttggca 6000
ggatcaattc tctaattgtt gtacaccgta tattgcaatt tatagtgact acagttaatg 6060
aatgtttaca aaaaattagt catgtaaaaa cttcttctct gtccattaca taaactcttt 6120
ttctctttct aacttatcat gttcatgtct aaaaaattaa acatgctcac atcaatgttc 6180
atttaagcta acttacttct gtaagagagc gagctagtta aaaactcctt taactttctg 6240
ttttatactc aggacatgga ttgatgcaag catgaagaac ttcgggaatt tgctaaaact 6300
ctaccaaagc gatgagagtt tggactttgt ttcacttgaa gtcagggact gtcaacaaag 6360
ccacagtgtg catgttggct gtttcacttg gacgataaaa aggtttattt aattgttttc 6420
ctaagtgtat ttggcttaca agcttttact tttcgcttga aagggttttt cttgttttaa 6480
gctttttgaa ttagagtttc ggttgaagta agagtagtcg tattagtctt ttactttgca 6540
ggagtctatg cctatataag gtaagactcg tatttgtaat tttcagatta tgcaattcaa 6600
gttttcgagt gttttcttaa aaaaacatat catacctgtg tgtagcataa agataaattc 6660
tgatgctgtg cttcttgtta tggctcacat tggttttcat tgtttggatt gtttcacagg 6720
gaagcagaga atacctggaa cctgtaaagg acgctatatc tatagcagct ttcacaggcc 6780
aagtaatata atgttcttta tcaatcactc aatacctgga gattgtttga acacataatt 6840
cacctctttt tttccatctc aaattgcaga cttttactgg gatttgaatg acagcaaaca 6900
tttgattgtc acgaggattg atctaactgg tgaatgttgt gatcaccata ttggtctttc 6960
tcattcaaac aaacttgcat accgttcttt tgaagtttga agacaagcag gcgataatca 7020
actcaggtcg aagctcatgt gcaggagaga atagaatata gaggagatta tttttaaaag 7080
aaacgctcaa aggtattgta gcacctttcc tatttgctac tgcagtgatg tttttatttc 7140
ttgtttgcag cgcttgtttc tcatatttca acctactttt agaaaaaaaa acatctccga 7200
acataaccaa aaataaagtt cccttatcag tgctttccct gctttcttct aaacaacata 7260
tacaattata aaccctttttt ctctcttacc tttgttattc ttccttgctt cattgagata 7320
acactctcct gtttttgttt tgttgttagt cattacatgg atatatcaag gacaacagtt 7380
ctgtagtccg tcaactgtgg ttaggaaggc taaactggag cacaataacc ccatgtcaat 7440
tgaatagtaa aggtgtgcta tatcagtttc gtttggcttg gcttacctga aaaatggctg 7500
gttatttatc cttgtctctt tctatgacgt gcagtggctt gttaatgtgt ctcggacaac 7560
aattcctcac tttccaagtt ccatacacgc tgatgtaact atcttctgca gtctgttctt 7620
tcatttttgc cacgtgctct aattataact ttttgtactc aataatcaac tccttgtccc 7680
ggtatttgca gagactactt aaacaggtaa agtgacaatc ctggcgaagt tgtctgtttc 7740

```
ttagctctga acccatcatt caggtaagat taagtattta agaagaaatt ttgtttttac   7800
ctaaaatgaa tgatcttgtg taactgcttg cttcttgcat taaataagaa ctttctgctg   7860
catatgtgac agttacatcc acaaaaaagt tggaggtttg ttcagggatt ggaaatgaag   7920
gtacttcaga attcctggaa tgtttatgaa tgctccagac ttcagagtct ttaatggaaa   7980
attcgagtca ctaaaaaaac attattccta tcatcagagc tttgaagttc ctctatacaa   8040
ggtcaactga gttcctcttt gcctcttgtt taattgtatt tacttgtacc ttaattataa   8100
tctgtatatt gttttagtta agttctaaaa caggttatta ttcatcattt gtgcagcata   8160
ttgctggaat caagaatcta gtgcttcttc ttcctgactt cactgtcaaa atagcagttc   8220
ccatgctgga aataagcgcg ctagcaatgt aattgatgac atggatgttg ctgcttctga   8280
gttttgatca taaaaagctg ttatgtgttt cttgaatgta atgaaggaga ggagaaaact   8340
gaaaactctt ggcaaaaacg tgaaattgca gtgcctcggg gtggtaggga tcacccggat   8400
tcagttcaga cgatactttt ttcaacccgg tttgttccgg ttttcagctt cgggttttcc   8460
ttgtactttt ggggcacaca tacaaggcta cttcatgttt gagaaaccta attgaggcta   8520
tcttgtagca aatgcacacc acactctttc tctcttctct cctttttttca ccttccattt   8580
gtaaaaatcc tcttttaaag gttaataaaa aaaagcttca agtctcgtag ggtggatgta   8640
ggtcacattg accgaaccac ggtaaactct ttgtgttctt tcttctctct ttgtttctca   8700
tttttacggc aagtgtttat ggttaaccat gcatcttaga atagcttaag gcattaacat   8760
aataacatca atgttctcca aagattcacc ttacttgttg tacataatca caatgttaag   8820
cctatgaagg tagaatgctc tcatgatttg gtttaaccaa aaaataaact ctaaaataat   8880
acggagtaat aaaaattggc cataaattat ttacaaagtt tgatttttgt atagggtatc   8940
ttgtacttgt gataaaaaaa attaaaaaaa aaaaaattac ttatttcttc tatttttact   9000
tgttacactt ttctacaaca gaaacatcaa aacgcccgca acacactata aatgaaaaac   9060
cattttgtat gcaatgatat ttacgttctc actttattct ctttaataac tcctactacg   9120
taattctcac caatcaaata aaattataga aattttcatt tataccctct taaaatgatg   9180
ttgatttnnn nnnnnnnnnn nnnnnnnnnn nnnnnnnnnn nnnnnnnnna ggtgtgaaaa   9240
agtttgtgtt ataagttaca acaatttaaa aacggagaac atacttataa tactagtgta   9300
atctttggcc ggattatggt cgttgacaaa aaaactccgg ccttgaccct ccacgtgccg   9360
gtcaagtgac ttaataaacc ttttattcca cccttttttc attcttcttt ttattcttct   9420
tttt                                                                 9424
```

<210> SEQ ID NO 2
<211> LENGTH: 3366
<212> TYPE: DNA
<213> ORGANISM: Spinacia oleracea

<400> SEQUENCE: 2

```
atggccgaaa tcggatactc ggtttgtgcg aaactcatcg aagtgattgg cagtgagctg     60
atcaaagaga tttgtgacac atggggttac aaatctcttc ttgaggacct caacaaaact    120
gtattgacgg tcaggaacgt tctcattcaa gccggggtga tgcgggagct tactagtgaa    180
caacaaggtt tcattgcaga ccttaaagat gttgtttatg atgctgatga cttgttcgac    240
aagttactca ctcgtgctga gcgaaaacag attgatggaa acgaaatctc tgaaaaggta    300
cgtcgtttct tttcctctag taacaagatc ggtcaagctt actacatgtc tcgtaaggtt    360
aaggaaatta agaagcagtt ggatgaaatt gttgataggc atacaaaatt tgggtttagt    420
```

```
gctgagttta tacctgtttg taggggaagg ggaaacgaga gggaaacacg ttcatatata    480
gatgtcaaga atattcttgg gagggataaa gataagaatg atatcataga taggttgctt    540
aatcgtaatg gtaatgaagc ttgtagtttc ctgaccatag tgggagcggg aggattggga    600
aaaactgctc ttgcacaact tgtgttcaat gatgaaaggg tcaaaattga gttccatgat    660
ttgaggtatt gggtttgtgt ctctgatcaa gatgggggcc aatttgatgt gaaagaaatc    720
ctttgtaaga ttttagaggt ggttactaag gagaaagttg ataatagttc cacattggaa    780
ttggtacaaa gccaatttca agagaagtta agaggaaaga agtacttcct tgttcttgat    840
gatgtatgga acgaagatcg tgagaagtgg cttcctttgg aagagttgtt aatgttgggt    900
caagggggaa gcaaggttgt agtgaccaca cgttcagaga agacagcaaa tgtcataggg    960
aaaagacatt tttatacact ggaatgtttg tcaccagatt attcatggag cttatttgaa   1020
atgtcggctt ttcagaaagg gcatgagcag gaaaaccatc acgaactagt tgatattggg   1080
aaaaagattg ttgaaaaatg ttataacaat ccacttgcta taacggtggt aggaagtctt   1140
ctttatggag aggagataag taagtggcgg tcatttgaaa tgagtgagtt ggccaaaatt   1200
ggcaatgggg ataataagat tttgccgata ttaaagctca gttaccataa tcttataccc   1260
tcgttgaaga gttgttttag ttattgtgca gtgtttccca aggatcatga aataaagaag   1320
gagatgttga ttgaactttg gatggcacaa ggatatgttg tgccgttgga tggaggtcaa   1380
agtatagaag atgctgccga ggaacatttt gtaattttgt tacgaaggtg tttctttcaa   1440
gatgtaaaga aggataaata tggtgatgtt gattctgtta aaatccacga cttgatgcac   1500
gatgtcgccc aagaagtggg gagggaggaa ttatgtgtag tgaatgataa tacaaagaac   1560
ttgggtgata aaatccgtca tgtacatcgt gatgtcatta gatatgcaca aagagtctct   1620
ctgtgtagcc atagccataa gattcgttcg tatattggtg gtaattgtga aaaacgttgt   1680
gtggatacac taatagacaa gtggatgtgt cttaggatgt tggacttgtc atggtcggat   1740
gttaaaaatt tgcctaattc aataggtaaa ttgttgcact tgaggtgtct taacctgtct   1800
tataataaag atctgttgat actccctgat gcaattacaa gactgcataa tttgcagaca   1860
ctgcttttaa aagagtgcag aagtttaaag gagttgccaa aagatttttg caaattggtc   1920
aaactgaggc acttggattt aaggtgttct gatttgaagg agttgccaaa agatttttgc   1980
aaattggtca aactgaggca cttggattta tggggttgtg atgatttgat tggtgtgcca   2040
ttgggaatgg ataggctaat tagtcttaga gtactgccat tctttgtggt gggtaggaag   2100
gaacaaagtg atgatgatga gctgaaagcc ctaaaaggcc tcaccgagat aaaaggctcc   2160
attcgtatta gaatctattc aaagtataga atagttgaag gcatgaatga cacaggagga   2220
gctgggtatt taaagagcat gaaacatctc acgggggttg atattacatt tgatggtgga   2280
tgtgttaacc ctgaagctgt gttggcaacc ctagagccac cttcaaatat caagaggtta   2340
gagatgtggc attacagtgg tacaacaatt ccagtatggg gaagagcaga gattaattgg   2400
gcaatctccc tctcacatct tgtcgacatc cagctttggc attgtcgtaa tttgcaggag   2460
atgccagtgc tgagtaaact gcctcatttg aaatcactgg aactttataa tttgattagt   2520
ttagagtaca tggagagcac aagcagaagc agtagcagtg acacagaagc agcaacacca   2580
gaattaccaa cattcttccc ttcccttgaa aaacttacac tttggcgtct ggacaagttg   2640
aagggttttg ggaacaggag atcgagtagt tttccccgcc tctctaaatt ggaaatctgg   2700
aaatgcccag atctaacgtc atttccttct tgtccaagcc ttgaagagtt ggaattgaaa   2760
```

```
gaaaacaatg aagcattgca aataatagta aaaataacaa caacaagagg taaagaagaa   2820

aaagaagaag acaagaatgc tggtgttgga aattcacaag atgatgacaa tgtcaaatta   2880

tggacggtgg aaatagacaa tctgggttat ctcaaatcac tgcccacaaa ttgtcttact   2940

ctgttggact cactcgaact ttcaaatata gaagaccagg aagatgaggg cgaagacaac   3000

atcatattct ggaaatcctt tcctcaaaac ctccgcagtt tggaaattga aaactcttac   3060

aaaatgacaa gtttgcccat ggggatgcag tacttaacct ccctccaaac cctctatcta   3120

caccattgtt atgaattgaa ttcccttcca gaatggataa gcagcttatc atctcttcaa   3180

tccctgcaca taggaaaatg tccagcccta aaatcactac cagaagcaat gcggaacctc   3240

acctcccttc agacacttgg gatatcgcgg tgtccagacc taattgaaag atgcgaagaa   3300

cccaacggcg aggactatcc caaaattcaa cacatcccca aaattgtact aaatgaatat   3360

tggtga                                                              3366
```

<210> SEQ ID NO 3
<211> LENGTH: 3399
<212> TYPE: DNA
<213> ORGANISM: Spinacia oleracea

<400> SEQUENCE: 3

```
atggccgaaa tcggatactc ggtttgtgcg aaactcatcg aagtgattgg cagtgagctg     60

atcaaagaga tttgtgacac atggggttac aaatctcttc ttgaggacct caacaaaact    120

gtattgacgg tcaggaacgt tctcattcaa gccggggtga tgcgggagct tactagtgaa    180

caacaaggtt tcattgcaga ccttaaagat gttgtttatg atgctgatga cttgttcgac    240

aagttactca ctcgtgctga gcgaaaacag attgatggaa acgaaatctc tgaaaaggta    300

cgtcgtttct tttcctctag taacaagatc ggtcaagctt actacatgtc tcgtaaggtt    360

aaggaaatta agaagcagtt ggatgaaatt gttgataggc atacaaaatt tgggtttagt    420

gctgagttta tacctgtttg taggggaagg ggaaacgaga gggaaacacg ttcatatata    480

gatgtcaaga atattcttgg gagggataaa gataagaatg atatcataga taggttgctt    540

aatcgtaatg gtaatgaagc ttgtagtttc ctgaccatag tgggagcggg aggattggga    600

aaaactgctc ttgcacaact tgtgttcaat gatgaaaggg tcaaaattga gttccatgat    660

ttgaggtatt gggtttgtgt ctctgatcaa gatgggggcc aatttgatgt gaaagaaatc    720

ctttgtaaga ttttagaggt ggttactaag gagaaagttg ataatagttc cacattggaa    780

ttggtacaaa gccaatttca agagaagtta agaggaaaga agtacttcct tgttcttgat    840

gatgtatgga acgaagatcg tgagaagtgg cttcctttgg aagagttgtt aatgttgggt    900

caagggggaa gcaaggttgt agtgaccaca cgttcagaga agacagcaaa tgtcataggg    960

aaaagacatt tttatacact ggaatgtttg tcaccagatt attcatggag cttatttgaa   1020

atgtcggctt ttcagaaagg gcatgagcag gaaaaccatc acgaactagt tgatattggg   1080

aaaaagattg ttgaaaaatg ttataacaat ccacttgcta taacggtggt aggaagtctt   1140

ctttatggag aggagataag taagtggcgg tcatttgaaa tgagtgagtt ggccaaaatt   1200

ggcaatgggg ataataagat tttgccgata ttaaagctca gttaccataa tcttataccc   1260

tcgttgaaga gttgttttag ttattgtgca gtgtttccca aggatcatga aataaagaag   1320

gagatgttga ttgaactttg gatggcacaa ggatatgttg tgccgttgga tggaggtcaa   1380

agtatagaag atgctgccga ggaacatttt gtaattttgt tacgaaggtg tttctttcaa   1440

gatgtaaaga aggataaata tggtgatgtt gattctgtta aaatccacga cttgatgcac   1500
```

```
gatgtcgccc aagaagtggg gagggaggaa ttatgtgtag tgaatgataa tacaaagaac   1560
ttgggtgata aaatccgtca tgtacatcgt gatgtcatta gatatgcaca aagagtctct   1620
ctgtgtagcc atagccataa gattcgttcg tatattggtg gtaattgtga aaaacgttgt   1680
gtggatacac taatagacaa gtggatgtgt cttaggatgt tggacttgtc atggtcggat   1740
gttaaaaatt tgcctaattc aataggtaaa ttgttgcact tgaggtgtct taacctgtct   1800
tataataaag atctgttgat actccctgat gcaattacaa gactgcataa tttgcagaca   1860
ctgcttttaa aagagtgcag aagtttaaag gagttgccaa aagatttttg caaattggtc   1920
aaactgaggc acttggattt aaggtgttct gatttgaagg agttgccaaa agatttttgc   1980
aaattggtca aactgaggca cttggattta tggggttgtg atgatttgat tggtgtgcca   2040
ttgggaatgg ataggctaat tagtcttaga gtactgccat tctttgtggt gggtaggaag   2100
gaacaaagtg atgatgatga gctgaaagcc ctaaaaggcc tcaccgagat aaaaggctcc   2160
attcgtatta gaatctattc aaagtataga atagttgaag gcatgaatga cacaggagga   2220
gctgggtatt taaagagcat gaaacatctc acgggggttg atattacatt tgatggtgga   2280
tgtgttaacc ctgaagctgt gttggcaacc ctagagccac cttcaaatat caagaggtta   2340
gagatgtggc attacagtgg tacaacaatt ccagtatggg gaagagcaga gattaattgg   2400
gcaatctccc tctcacatct tgtcgacatc cagctttggc attgtcgtaa tttgcaggag   2460
atgccagtgc tgagtaaact gcctcatttg aaatcactgg aactttataa tttgattagt   2520
ttagagtaca tggagagcac aagcagaagc agtagcagtg acacagaagc agcaacacca   2580
gaattaccaa cattcttccc ttcccttgaa aaacttacac tttggcgtct ggacaagttg   2640
aagggttttg ggaacaggag atcgagtagt tttccccgcc tctctaaatt ggaaatctgg   2700
aaatgcccag atctaacgtc atttccttct tgtccaagcc ttgaagagtt ggaattgaaa   2760
gaaaacaatg aagcattgca aataatagta aaaataacaa caacaagagg taaagaagaa   2820
aaagaagaag acaagaatgc tggtgttgga aattcacaag atgatgacaa tgtcaaatta   2880
tggacggtgg aaatagacaa tctgggttat ctcaaatcac tgcccacaaa ttgtcttact   2940
ctgttggact cactcgaact ttcaaatata gaagaccagg aagatgaggg cgaagacaac   3000
atcatattct ggaaatcctt tcctcaaaac ctccgcagtt tggaaattga aaactcttac   3060
aaaatgacaa gtttgcccat ggggatgcag tacttaacct ccctccaaac cctctatcta   3120
caccattgtt atgaattgaa ttcccttcca gaatggataa gcagcttatc atctcttcaa   3180
tccctgcaca taggaaaatg tccagcccta aaatcactac cagaagcaat gcggaacctc   3240
acctcccttc agacacttgg gatatcgcgg tgtccagacc taattgaaag atgcgaagaa   3300
cccaacggcg aggactatcc caaaattcaa cacatcccca aaattttact caacactagc   3360
ttgatcctga acgcacccaa ccttcaggac atggattga                          3399
```

<210> SEQ ID NO 4
<211> LENGTH: 1121
<212> TYPE: PRT
<213> ORGANISM: Spinacia oleracea

<400> SEQUENCE: 4

```
Met Ala Glu Ile Gly Tyr Ser Val Cys Ala Lys Leu Ile Glu Val Ile
1               5                   10                  15

Gly Ser Glu Leu Ile Lys Glu Ile Cys Asp Thr Trp Gly Tyr Lys Ser
            20                  25                  30
```

```
Leu Leu Glu Asp Leu Asn Lys Thr Val Leu Thr Val Arg Asn Val Leu
        35                  40                  45

Ile Gln Ala Gly Val Met Arg Glu Leu Thr Ser Glu Gln Gln Gly Phe
    50                  55                  60

Ile Ala Asp Leu Lys Asp Val Val Tyr Asp Ala Asp Asp Leu Phe Asp
65                  70                  75                  80

Lys Leu Leu Thr Arg Ala Glu Arg Lys Gln Ile Asp Gly Asn Glu Ile
                85                  90                  95

Ser Glu Lys Val Arg Arg Phe Phe Ser Ser Ser Asn Lys Ile Gly Gln
            100                 105                 110

Ala Tyr Tyr Met Ser Arg Lys Val Lys Glu Ile Lys Lys Gln Leu Asp
        115                 120                 125

Glu Ile Val Asp Arg His Thr Lys Phe Gly Phe Ser Ala Glu Phe Ile
    130                 135                 140

Pro Val Cys Arg Gly Arg Gly Asn Glu Arg Glu Thr Arg Ser Tyr Ile
145                 150                 155                 160

Asp Val Lys Asn Ile Leu Gly Arg Asp Lys Asp Lys Asn Asp Ile Ile
                165                 170                 175

Asp Arg Leu Leu Asn Arg Asn Gly Asn Glu Ala Cys Ser Phe Leu Thr
            180                 185                 190

Ile Val Gly Ala Gly Gly Leu Gly Lys Thr Ala Leu Ala Gln Leu Val
        195                 200                 205

Phe Asn Asp Glu Arg Val Lys Ile Glu Phe His Asp Leu Arg Tyr Trp
    210                 215                 220

Val Cys Val Ser Asp Gln Asp Gly Gly Gln Phe Asp Val Lys Glu Ile
225                 230                 235                 240

Leu Cys Lys Ile Leu Glu Val Val Thr Lys Glu Lys Val Asp Asn Ser
                245                 250                 255

Ser Thr Leu Glu Leu Val Gln Ser Gln Phe Gln Glu Lys Leu Arg Gly
            260                 265                 270

Lys Lys Tyr Phe Leu Val Leu Asp Asp Val Trp Asn Glu Asp Arg Glu
        275                 280                 285

Lys Trp Leu Pro Leu Glu Glu Leu Leu Met Leu Gly Gln Gly Gly Ser
    290                 295                 300

Lys Val Val Val Thr Thr Arg Ser Glu Lys Thr Ala Asn Val Ile Gly
305                 310                 315                 320

Lys Arg His Phe Tyr Thr Leu Glu Cys Leu Ser Pro Asp Tyr Ser Trp
                325                 330                 335

Ser Leu Phe Glu Met Ser Ala Phe Gln Lys Gly His Glu Gln Glu Asn
            340                 345                 350

His His Glu Leu Val Asp Ile Gly Lys Lys Ile Val Glu Lys Cys Tyr
        355                 360                 365

Asn Asn Pro Leu Ala Ile Thr Val Val Gly Ser Leu Leu Tyr Gly Glu
    370                 375                 380

Glu Ile Ser Lys Trp Arg Ser Phe Glu Met Ser Glu Leu Ala Lys Ile
385                 390                 395                 400

Gly Asn Gly Asp Asn Lys Ile Leu Pro Ile Leu Lys Leu Ser Tyr His
                405                 410                 415

Asn Leu Ile Pro Ser Leu Lys Ser Cys Phe Ser Tyr Cys Ala Val Phe
            420                 425                 430

Pro Lys Asp His Glu Ile Lys Lys Glu Met Leu Ile Glu Leu Trp Met
        435                 440                 445

Ala Gln Gly Tyr Val Val Pro Leu Asp Gly Gly Gln Ser Ile Glu Asp
```

-continued

```
    450                 455                 460

Ala Ala Glu Glu His Phe Val Ile Leu Leu Arg Arg Cys Phe Phe Gln
465                 470                 475                 480

Asp Val Lys Lys Asp Lys Tyr Gly Asp Val Asp Ser Val Lys Ile His
                485                 490                 495

Asp Leu Met His Asp Val Ala Gln Glu Val Gly Arg Glu Glu Leu Cys
            500                 505                 510

Val Val Asn Asp Asn Thr Lys Asn Leu Gly Asp Lys Ile Arg His Val
        515                 520                 525

His Arg Asp Val Ile Arg Tyr Ala Gln Arg Val Ser Leu Cys Ser His
    530                 535                 540

Ser His Lys Ile Arg Ser Tyr Ile Gly Gly Asn Cys Glu Lys Arg Cys
545                 550                 555                 560

Val Asp Thr Leu Ile Asp Lys Trp Met Cys Leu Arg Met Leu Asp Leu
                565                 570                 575

Ser Trp Ser Asp Val Lys Asn Leu Pro Asn Ser Ile Gly Lys Leu Leu
            580                 585                 590

His Leu Arg Cys Leu Asn Leu Ser Tyr Asn Lys Asp Leu Leu Ile Leu
        595                 600                 605

Pro Asp Ala Ile Thr Arg Leu His Asn Leu Gln Thr Leu Leu Leu Lys
    610                 615                 620

Glu Cys Arg Ser Leu Lys Glu Leu Pro Lys Asp Phe Cys Lys Leu Val
625                 630                 635                 640

Lys Leu Arg His Leu Asp Leu Arg Cys Ser Asp Leu Lys Glu Leu Pro
                645                 650                 655

Lys Asp Phe Cys Lys Leu Val Lys Leu Arg His Leu Asp Leu Trp Gly
            660                 665                 670

Cys Asp Asp Leu Ile Gly Val Pro Leu Gly Met Asp Arg Leu Ile Ser
        675                 680                 685

Leu Arg Val Leu Pro Phe Phe Val Val Gly Arg Lys Glu Gln Ser Asp
    690                 695                 700

Asp Asp Glu Leu Lys Ala Leu Lys Gly Leu Thr Glu Ile Lys Gly Ser
705                 710                 715                 720

Ile Arg Ile Arg Ile Tyr Ser Lys Tyr Arg Ile Val Glu Gly Met Asn
                725                 730                 735

Asp Thr Gly Gly Ala Gly Tyr Leu Lys Ser Met Lys His Leu Thr Gly
            740                 745                 750

Val Asp Ile Thr Phe Asp Gly Gly Cys Val Asn Pro Glu Ala Val Leu
        755                 760                 765

Ala Thr Leu Glu Pro Pro Ser Asn Ile Lys Arg Leu Glu Met Trp His
    770                 775                 780

Tyr Ser Gly Thr Thr Ile Pro Val Trp Gly Arg Ala Glu Ile Asn Trp
785                 790                 795                 800

Ala Ile Ser Leu Ser His Leu Val Asp Ile Gln Leu Trp His Cys Arg
                805                 810                 815

Asn Leu Gln Glu Met Pro Val Leu Ser Lys Leu Pro His Leu Lys Ser
            820                 825                 830

Leu Glu Leu Tyr Asn Leu Ile Ser Leu Glu Tyr Met Glu Ser Thr Ser
        835                 840                 845

Arg Ser Ser Ser Ser Asp Thr Glu Ala Ala Thr Pro Glu Leu Pro Thr
    850                 855                 860

Phe Phe Pro Ser Leu Glu Lys Leu Thr Leu Trp Arg Leu Asp Lys Leu
865                 870                 875                 880
```

```
Lys Gly Phe Gly Asn Arg Arg Ser Ser Ser Phe Pro Arg Leu Ser Lys
                885                 890                 895

Leu Glu Ile Trp Lys Cys Pro Asp Leu Thr Ser Phe Pro Ser Cys Pro
            900                 905                 910

Ser Leu Glu Glu Leu Glu Leu Lys Glu Asn Asn Glu Ala Leu Gln Ile
        915                 920                 925

Ile Val Lys Ile Thr Thr Thr Arg Gly Lys Glu Glu Lys Glu Glu Asp
    930                 935                 940

Lys Asn Ala Gly Val Gly Asn Ser Gln Asp Asp Asp Asn Val Lys Leu
945                 950                 955                 960

Trp Thr Val Glu Ile Asp Asn Leu Gly Tyr Leu Lys Ser Leu Pro Thr
                965                 970                 975

Asn Cys Leu Thr Leu Leu Asp Ser Leu Glu Leu Ser Asn Ile Glu Asp
            980                 985                 990

Gln Glu Asp Glu Gly Glu Asp Asn Ile Ile Phe Trp Lys Ser Phe Pro
        995                 1000                1005

Gln Asn Leu Arg Ser Leu Glu Ile Glu Asn Ser Tyr Lys Met Thr Ser
    1010                1015                1020

Leu Pro Met Gly Met Gln Tyr Leu Thr Ser Leu Gln Thr Leu Tyr Leu
1025                1030                1035                1040

His His Cys Tyr Glu Leu Asn Ser Leu Pro Glu Trp Ile Ser Ser Leu
                1045                1050                1055

Ser Ser Leu Gln Ser Leu His Ile Gly Lys Cys Pro Ala Leu Lys Ser
            1060                1065                1070

Leu Pro Glu Ala Met Arg Asn Leu Thr Ser Leu Gln Thr Leu Gly Ile
        1075                1080                1085

Ser Arg Cys Pro Asp Leu Ile Glu Arg Cys Glu Glu Pro Asn Gly Glu
    1090                1095                1100

Asp Tyr Pro Lys Ile Gln His Ile Pro Lys Ile Val Leu Asn Glu Tyr
1105                1110                1115                1120

Trp


<210> SEQ ID NO 5
<211> LENGTH: 1132
<212> TYPE: PRT
<213> ORGANISM: Spinacia oleracea

<400> SEQUENCE: 5

Met Ala Glu Ile Gly Tyr Ser Val Cys Ala Lys Leu Ile Glu Val Ile
1               5                   10                  15

Gly Ser Glu Leu Ile Lys Glu Ile Cys Asp Thr Trp Gly Tyr Lys Ser
            20                  25                  30

Leu Leu Glu Asp Leu Asn Lys Thr Val Leu Thr Val Arg Asn Val Leu
        35                  40                  45

Ile Gln Ala Gly Val Met Arg Glu Leu Thr Ser Glu Gln Gln Gly Phe
    50                  55                  60

Ile Ala Asp Leu Lys Asp Val Val Tyr Asp Ala Asp Asp Leu Phe Asp
65                  70                  75                  80

Lys Leu Leu Thr Arg Ala Glu Arg Lys Gln Ile Asp Gly Asn Glu Ile
                85                  90                  95

Ser Glu Lys Val Arg Arg Phe Phe Ser Ser Ser Asn Lys Ile Gly Gln
            100                 105                 110

Ala Tyr Tyr Met Ser Arg Lys Val Lys Glu Ile Lys Lys Gln Leu Asp
        115                 120                 125
```

```
Glu Ile Val Asp Arg His Thr Lys Phe Gly Phe Ser Ala Glu Phe Ile
    130                 135                 140

Pro Val Cys Arg Gly Arg Gly Asn Glu Arg Glu Thr Arg Ser Tyr Ile
145                 150                 155                 160

Asp Val Lys Asn Ile Leu Gly Arg Asp Lys Asp Lys Asn Asp Ile Ile
                165                 170                 175

Asp Arg Leu Leu Asn Arg Asn Gly Asn Glu Ala Cys Ser Phe Leu Thr
            180                 185                 190

Ile Val Gly Ala Gly Gly Leu Gly Lys Thr Ala Leu Ala Gln Leu Val
        195                 200                 205

Phe Asn Asp Glu Arg Val Lys Ile Glu Phe His Asp Leu Arg Tyr Trp
    210                 215                 220

Val Cys Val Ser Asp Gln Asp Gly Gly Gln Phe Asp Val Lys Glu Ile
225                 230                 235                 240

Leu Cys Lys Ile Leu Glu Val Val Thr Lys Glu Lys Val Asp Asn Ser
                245                 250                 255

Ser Thr Leu Glu Leu Val Gln Ser Gln Phe Gln Glu Lys Leu Arg Gly
            260                 265                 270

Lys Lys Tyr Phe Leu Val Leu Asp Asp Val Trp Asn Glu Asp Arg Glu
        275                 280                 285

Lys Trp Leu Pro Leu Glu Glu Leu Leu Met Leu Gly Gln Gly Gly Ser
    290                 295                 300

Lys Val Val Val Thr Thr Arg Ser Glu Lys Thr Ala Asn Val Ile Gly
305                 310                 315                 320

Lys Arg His Phe Tyr Thr Leu Glu Cys Leu Ser Pro Asp Tyr Ser Trp
                325                 330                 335

Ser Leu Phe Glu Met Ser Ala Phe Gln Lys Gly His Glu Gln Glu Asn
            340                 345                 350

His His Glu Leu Val Asp Ile Gly Lys Lys Ile Val Glu Lys Cys Tyr
        355                 360                 365

Asn Asn Pro Leu Ala Ile Thr Val Val Gly Ser Leu Leu Tyr Gly Glu
    370                 375                 380

Glu Ile Ser Lys Trp Arg Ser Phe Glu Met Ser Glu Leu Ala Lys Ile
385                 390                 395                 400

Gly Asn Gly Asp Asn Lys Ile Leu Pro Ile Leu Lys Leu Ser Tyr His
                405                 410                 415

Asn Leu Ile Pro Ser Leu Lys Ser Cys Phe Ser Tyr Cys Ala Val Phe
            420                 425                 430

Pro Lys Asp His Glu Ile Lys Lys Glu Met Leu Ile Glu Leu Trp Met
        435                 440                 445

Ala Gln Gly Tyr Val Val Pro Leu Asp Gly Gly Gln Ser Ile Glu Asp
    450                 455                 460

Ala Ala Glu Glu His Phe Val Ile Leu Leu Arg Arg Cys Phe Phe Gln
465                 470                 475                 480

Asp Val Lys Lys Asp Lys Tyr Gly Asp Val Asp Ser Val Lys Ile His
                485                 490                 495

Asp Leu Met His Asp Val Ala Gln Glu Val Gly Arg Glu Glu Leu Cys
            500                 505                 510

Val Val Asn Asp Asn Thr Lys Asn Leu Gly Asp Lys Ile Arg His Val
        515                 520                 525

His Arg Asp Val Ile Arg Tyr Ala Gln Arg Val Ser Leu Cys Ser His
    530                 535                 540
```

-continued

```
Ser His Lys Ile Arg Ser Tyr Ile Gly Gly Asn Cys Glu Lys Arg Cys
545                 550                 555                 560

Val Asp Thr Leu Ile Asp Lys Trp Met Cys Leu Arg Met Leu Asp Leu
                565                 570                 575

Ser Trp Ser Asp Val Lys Asn Leu Pro Asn Ser Ile Gly Lys Leu Leu
            580                 585                 590

His Leu Arg Cys Leu Asn Leu Ser Tyr Asn Lys Asp Leu Leu Ile Leu
        595                 600                 605

Pro Asp Ala Ile Thr Arg Leu His Asn Leu Gln Thr Leu Leu Leu Lys
    610                 615                 620

Glu Cys Arg Ser Leu Lys Glu Leu Pro Lys Asp Phe Cys Lys Leu Val
625                 630                 635                 640

Lys Leu Arg His Leu Asp Leu Arg Cys Ser Asp Leu Lys Glu Leu Pro
                645                 650                 655

Lys Asp Phe Cys Lys Leu Val Lys Leu Arg His Leu Asp Leu Trp Gly
            660                 665                 670

Cys Asp Asp Leu Ile Gly Val Pro Leu Gly Met Asp Arg Leu Ile Ser
        675                 680                 685

Leu Arg Val Leu Pro Phe Phe Val Val Gly Arg Lys Glu Gln Ser Asp
    690                 695                 700

Asp Asp Glu Leu Lys Ala Leu Lys Gly Leu Thr Glu Ile Lys Gly Ser
705                 710                 715                 720

Ile Arg Ile Arg Ile Tyr Ser Lys Tyr Arg Ile Val Glu Gly Met Asn
                725                 730                 735

Asp Thr Gly Gly Ala Gly Tyr Leu Lys Ser Met Lys His Leu Thr Gly
            740                 745                 750

Val Asp Ile Thr Phe Asp Gly Gly Cys Val Asn Pro Glu Ala Val Leu
        755                 760                 765

Ala Thr Leu Glu Pro Pro Ser Asn Ile Lys Arg Leu Glu Met Trp His
    770                 775                 780

Tyr Ser Gly Thr Thr Ile Pro Val Trp Gly Arg Ala Glu Ile Asn Trp
785                 790                 795                 800

Ala Ile Ser Leu Ser His Leu Val Asp Ile Gln Leu Trp His Cys Arg
                805                 810                 815

Asn Leu Gln Glu Met Pro Val Leu Ser Lys Leu Pro His Leu Lys Ser
            820                 825                 830

Leu Glu Leu Tyr Asn Leu Ile Ser Leu Glu Tyr Met Glu Ser Thr Ser
        835                 840                 845

Arg Ser Ser Ser Ser Asp Thr Glu Ala Ala Thr Pro Glu Leu Pro Thr
    850                 855                 860

Phe Phe Pro Ser Leu Glu Lys Leu Thr Leu Trp Arg Leu Asp Lys Leu
865                 870                 875                 880

Lys Gly Phe Gly Asn Arg Arg Ser Ser Ser Phe Pro Arg Leu Ser Lys
                885                 890                 895

Leu Glu Ile Trp Lys Cys Pro Asp Leu Thr Ser Phe Pro Ser Cys Pro
            900                 905                 910

Ser Leu Glu Glu Leu Glu Leu Lys Glu Asn Asn Glu Ala Leu Gln Ile
        915                 920                 925

Ile Val Lys Ile Thr Thr Thr Arg Gly Lys Glu Glu Lys Glu Glu Asp
    930                 935                 940

Lys Asn Ala Gly Val Gly Asn Ser Gln Asp Asp Asp Asn Val Lys Leu
945                 950                 955                 960

Trp Thr Val Glu Ile Asp Asn Leu Gly Tyr Leu Lys Ser Leu Pro Thr
```

```
                965                 970                 975

Asn Cys Leu Thr Leu Leu Asp Ser Leu Glu Leu Ser Asn Ile Glu Asp
            980                 985                 990

Gln Glu Asp Glu Gly Glu Asp Asn Ile Ile Phe Trp Lys Ser Phe Pro
        995                 1000                1005

Gln Asn Leu Arg Ser Leu Glu Ile Glu Asn Ser Tyr Lys Met Thr Ser
    1010                1015                1020

Leu Pro Met Gly Met Gln Tyr Leu Thr Ser Leu Gln Thr Leu Tyr Leu
1025                1030                1035                1040

His His Cys Tyr Glu Leu Asn Ser Leu Pro Glu Trp Ile Ser Ser Leu
                1045                1050                1055

Ser Ser Leu Gln Ser Leu His Ile Gly Lys Cys Pro Ala Leu Lys Ser
            1060                1065                1070

Leu Pro Glu Ala Met Arg Asn Leu Thr Ser Leu Gln Thr Leu Gly Ile
        1075                1080                1085

Ser Arg Cys Pro Asp Leu Ile Glu Arg Cys Glu Glu Pro Asn Gly Glu
    1090                1095                1100

Asp Tyr Pro Lys Ile Gln His Ile Pro Lys Ile Leu Leu Asn Thr Ser
1105                1110                1115                1120

Leu Ile Leu Asn Ala Pro Asn Leu Gln Asp Met Asp
                1125                1130
```

<210> SEQ ID NO 6
<211> LENGTH: 20
<212> TYPE: DNA
<213> ORGANISM: Artificial Sequence
<220> FEATURE:
<223> OTHER INFORMATION: Forward primer

<400> SEQUENCE: 6
acaagtggat gtgtcttagg 20

<210> SEQ ID NO 7
<211> LENGTH: 19
<212> TYPE: DNA
<213> ORGANISM: Artificial Sequence
<220> FEATURE:
<223> OTHER INFORMATION: Reverse primer

<400> SEQUENCE: 7
ttcgccctca tcttcctgg 19

<210> SEQ ID NO 8
<211> LENGTH: 18
<212> TYPE: DNA
<213> ORGANISM: Artificial Sequence
<220> FEATURE:
<223> OTHER INFORMATION: Forward primer

<400> SEQUENCE: 8
tcacgtgggt tgtgttgt 18

<210> SEQ ID NO 9
<211> LENGTH: 1298
<212> TYPE: DNA
<213> ORGANISM: Spinacia oleracea

<400> SEQUENCE: 9
acaagtggat gtgtcttagg atgttggact tgtcatggtc ggatgttaaa aatttgccta 60
attcaatagg taaattgttg cacttgaggt gtcttaacct gtcttataat aaagatctgt 120

```
tgatactccc tgatgcaatt acaagactgc ataatttgca gacactgctt ttaaaagagt    180

gcagaagttt aaaggagttg ccaaaagatt tttgcaaatt ggtcaaactg aggcacttgg    240

atttaaggtg ttctgatttg aaggagttgc caaaagattt ttgcaaattg gtcaaactga    300

ggcacttgga tttatggggt tgtgatgatt tgattggtgt gccattggga atggataggc    360

taattagtct tagagtactg ccattctttg tggtgggtag gaaggaacaa agtgatgatg    420

atgagctgaa agccctaaaa ggcctcaccg agataaaagg ctccattcgt attagaatct    480

attcaaagta tagaatagtt gaaggcatga atgacacagg aggagctggg tatttaaaga    540

gcatgaaaca tctcacgggg gttgatatta catttgatgg tggatgtgtt aaccctgaag    600

ctgtgttggc aaccctagag ccaccttcaa atatcaagag gttagagatg tggcattaca    660

gtggtacaac aattccagta tggggaagag cagagattaa ttgggcaatc tccctctcac    720

atcttgtcga catccagctt tggcattgtc gtaatttgca ggagatgcca gtgctgagta    780

aactgcctca tttgaaatca ctggaacttt ataatttgat tagtttagag tacatggaga    840

gcacaagcag aagcagtagc agtgacacag aagcagcaac accagaatta ccaacattct    900

tcccttccct tgaaaaactt acactttggc gtctggacaa gttgaagggt tttgggaaca    960

ggagatcgag tagttttccc cgcctctcta aattggaaat ctggaaatgc ccagatctaa   1020

cgtcatttcc ttcttgtcca agccttgaag agttggaatt gaaagaaaac aatgaagcat   1080

tgcaaataat agtaaaaata acaacaacaa gaggtaaaga agaaaaagaa gaagacaaga   1140

atgctggtgt tggaaattca caagatgatg acaatgtcaa attatggacg gtggaaatag   1200

acaatctggg ttatctcaaa tcactgccca caaattgtct tactctgttg gactcactcg   1260

aactttcaaa tatagaagac caggaagatg agggcgaa                           1298
```

<210> SEQ ID NO 10
<211> LENGTH: 432
<212> TYPE: PRT
<213> ORGANISM: Spinacia oleracea

<400> SEQUENCE: 10

```
Lys Trp Met Cys Leu Arg Met Leu Asp Leu Ser Trp Ser Asp Val Lys
1               5                   10                  15

Asn Leu Pro Asn Ser Ile Gly Lys Leu Leu His Leu Arg Cys Leu Asn
            20                  25                  30

Leu Ser Tyr Asn Lys Asp Leu Leu Ile Leu Pro Asp Ala Ile Thr Arg
        35                  40                  45

Leu His Asn Leu Gln Thr Leu Leu Leu Lys Glu Cys Arg Ser Leu Lys
    50                  55                  60

Glu Leu Pro Lys Asp Phe Cys Lys Leu Val Lys Leu Arg His Leu Asp
65                  70                  75                  80

Leu Arg Cys Ser Asp Leu Lys Glu Leu Pro Lys Asp Phe Cys Lys Leu
                85                  90                  95

Val Lys Leu Arg His Leu Asp Leu Trp Gly Cys Asp Asp Leu Ile Gly
            100                 105                 110

Val Pro Leu Gly Met Asp Arg Leu Ile Ser Leu Arg Val Leu Pro Phe
        115                 120                 125

Phe Val Val Gly Arg Lys Glu Gln Ser Asp Asp Asp Glu Leu Lys Ala
    130                 135                 140

Leu Lys Gly Leu Thr Glu Ile Lys Gly Ser Ile Arg Ile Arg Ile Tyr
145                 150                 155                 160
```

-continued

```
Ser Lys Tyr Arg Ile Val Glu Gly Met Asn Asp Thr Gly Gly Ala Gly
            165                 170                 175

Tyr Leu Lys Ser Met Lys His Leu Thr Gly Val Asp Ile Thr Phe Asp
        180                 185                 190

Gly Gly Cys Val Asn Pro Glu Ala Val Leu Ala Thr Leu Glu Pro Pro
    195                 200                 205

Ser Asn Ile Lys Arg Leu Glu Met Trp His Tyr Ser Gly Thr Thr Ile
    210                 215                 220

Pro Val Trp Gly Arg Ala Glu Ile Asn Trp Ala Ile Ser Leu Ser His
225                 230                 235                 240

Leu Val Asp Ile Gln Leu Trp His Cys Arg Asn Leu Gln Glu Met Pro
                245                 250                 255

Val Leu Ser Lys Leu Pro His Leu Lys Ser Leu Glu Leu Tyr Asn Leu
            260                 265                 270

Ile Ser Leu Glu Tyr Met Glu Ser Thr Ser Arg Ser Ser Ser Ser Asp
        275                 280                 285

Thr Glu Ala Ala Thr Pro Glu Leu Pro Thr Phe Phe Pro Ser Leu Glu
    290                 295                 300

Lys Leu Thr Leu Trp Arg Leu Asp Lys Leu Lys Gly Phe Gly Asn Arg
305                 310                 315                 320

Arg Ser Ser Ser Phe Pro Arg Leu Ser Lys Leu Glu Ile Trp Lys Cys
                325                 330                 335

Pro Asp Leu Thr Ser Phe Pro Ser Cys Pro Ser Leu Glu Glu Leu Glu
            340                 345                 350

Leu Lys Glu Asn Asn Glu Ala Leu Gln Ile Ile Val Lys Ile Thr Thr
        355                 360                 365

Thr Arg Gly Lys Glu Glu Lys Glu Glu Asp Lys Asn Ala Gly Val Gly
    370                 375                 380

Asn Ser Gln Asp Asp Asp Asn Val Lys Leu Trp Thr Val Glu Ile Asp
385                 390                 395                 400

Asn Leu Gly Tyr Leu Lys Ser Leu Pro Thr Asn Cys Leu Thr Leu Leu
                405                 410                 415

Asp Ser Leu Glu Leu Ser Asn Ile Glu Asp Gln Glu Asp Glu Gly Glu
            420                 425                 430
```

<210> SEQ ID NO 11
<211> LENGTH: 1597
<212> TYPE: DNA
<213> ORGANISM: Spinacia oleracea

<400> SEQUENCE: 11

```
tcacgtgggt tgtgttgtcg atagagatcc agaaatagtc tttttatgta gcaataagat      60

tcgttcgtat attagcggtc gctgcataaa gaatccggtg gattcacaaa tagacaactg     120

gatgtgcctt agggtgttgg acttgtcaga ttcatgtgtt aaagatttgt ctgattcaat     180

aggtaagctg ctgcacttaa ggtatcttaa cctctcttct aatataaagt tggagataat     240

ccctgatgca attacaagac tgcataactt gcagacacta cttttagaag attgcagaag     300

tttaaaggag ttgccaaaag atttttgcaa attggtcaaa ctgaggcact tggaattaca     360

gggttgtcat gatttgattg gtatgtcatt tggaatggat aagctaacta gtcttagaat     420

actaccaaac attgtggtgg gtaggaagga acaaagtgtt gatgatgagc tgaaagccct     480

aaaaggcctc accgagataa aaggctccat tgatatcaca atctattcaa aatatagaag     540

agttgaaggc atgaatggca caggaggagg agctgggtat ttgaagagca tgaaacatct     600
```

```
cacgggggtt aatattacat ttgatgaagg tggatgtgtt aaccctgaag ctgtgtattt    660

gaagagcatg aaacatctca cgagggttat tattatattt gattataaag gtggatgtgt    720

taaccctgaa gctgtgttgg caaccctaga gccaccttca aatatcaaga ggttagagat    780

gtggcattac agtggtacaa caattccagt atggggaaga gcagagatta attgggcaat    840

ctccctctca catcttgtcg acatcacgct tgaagattgt tacaatttgc aggagatgcc    900

agtgctgagt aaactgcctc atttgaaatc actggaactt acagagttgg ataacttaga    960

gtacatggag agtagaagca gcagcagtag cagtgacaca gaagcagcaa caccagaatt   1020

accaacattc ttcccttccc ttgaaaaact tacactttgg cgtctggaca agttgaaggg   1080

ttttgggaac aggagatcga gtagttttcc ccgcctctct aaattggaaa tctggaaatg   1140

tccagatcta acgtcatttc cttcttgtcc aagccttgaa gagttggaat tgaaagaaaa   1200

caatgaagcg ttgcaaataa tagtaaaaat aacaacaaca agaggtaaag aagaaaaaga   1260

agaagacaag aatgctggtg ttggaaattc acaagatgat gacaatgtca aattatggaa   1320

ggtggaaata gacaatctgg gttatctcaa atcactgccc acaaattgtc tgactcacct   1380

cgaccttaca ataagtgatt ccaaggaggg ggagggtgaa tgggaagttg gggatgcatt   1440

tcagaagtgt gtatcttctt tgagaagcct caccataatc ggaaatcacg gaataaataa   1500

agtgaagaga ctgtctggaa gaacagggtt ggagcatttc actctgttgg aatcactcaa   1560

actttcagat atagaagacc aggaagatga gggcgaa                            1597
```

<210> SEQ ID NO 12
<211> LENGTH: 532
<212> TYPE: PRT
<213> ORGANISM: Spinacia oleracea

<400> SEQUENCE: 12

```
His Val Gly Cys Val Val Asp Arg Asp Pro Glu Ile Val Phe Leu Cys
1               5                   10                  15

Ser Asn Lys Ile Arg Ser Tyr Ile Ser Gly Arg Cys Ile Lys Asn Pro
            20                  25                  30

Val Asp Ser Gln Ile Asp Asn Trp Met Cys Leu Arg Val Leu Asp Leu
        35                  40                  45

Ser Asp Ser Cys Val Lys Asp Leu Ser Asp Ser Ile Gly Lys Leu Leu
    50                  55                  60

His Leu Arg Tyr Leu Asn Leu Ser Ser Asn Ile Lys Leu Glu Ile Ile
65                  70                  75                  80

Pro Asp Ala Ile Thr Arg Leu His Asn Leu Gln Thr Leu Leu Leu Glu
                85                  90                  95

Asp Cys Arg Ser Leu Lys Glu Leu Pro Lys Asp Phe Cys Lys Leu Val
            100                 105                 110

Lys Leu Arg His Leu Glu Leu Gln Gly Cys His Asp Leu Ile Gly Met
        115                 120                 125

Ser Phe Gly Met Asp Lys Leu Thr Ser Leu Arg Ile Leu Pro Asn Ile
    130                 135                 140

Val Val Gly Arg Lys Glu Gln Ser Val Asp Asp Glu Leu Lys Ala Leu
145                 150                 155                 160

Lys Gly Leu Thr Glu Ile Lys Gly Ser Ile Asp Ile Thr Ile Tyr Ser
                165                 170                 175

Lys Tyr Arg Arg Val Glu Gly Met Asn Gly Thr Gly Gly Gly Ala Gly
            180                 185                 190

Tyr Leu Lys Ser Met Lys His Leu Thr Gly Val Asn Ile Thr Phe Asp
```

-continued

```
        195                 200                 205

Glu Gly Gly Cys Val Asn Pro Glu Ala Val Tyr Leu Lys Ser Met Lys
    210                 215                 220

His Leu Thr Arg Val Ile Ile Ile Phe Asp Tyr Lys Gly Gly Cys Val
225                 230                 235                 240

Asn Pro Glu Ala Val Leu Ala Thr Leu Glu Pro Pro Ser Asn Ile Lys
                245                 250                 255

Arg Leu Glu Met Trp His Tyr Ser Gly Thr Thr Ile Pro Val Trp Gly
            260                 265                 270

Arg Ala Glu Ile Asn Trp Ala Ile Ser Leu Ser His Leu Val Asp Ile
        275                 280                 285

Thr Leu Glu Asp Cys Tyr Asn Leu Gln Glu Met Pro Val Leu Ser Lys
    290                 295                 300

Leu Pro His Leu Lys Ser Leu Glu Leu Thr Glu Leu Asp Asn Leu Glu
305                 310                 315                 320

Tyr Met Glu Ser Arg Ser Ser Ser Ser Ser Ser Asp Thr Glu Ala Ala
                325                 330                 335

Thr Pro Glu Leu Pro Thr Phe Phe Pro Ser Leu Glu Lys Leu Thr Leu
            340                 345                 350

Trp Arg Leu Asp Lys Leu Lys Gly Phe Gly Asn Arg Arg Ser Ser Ser
        355                 360                 365

Phe Pro Arg Leu Ser Lys Leu Glu Ile Trp Lys Cys Pro Asp Leu Thr
    370                 375                 380

Ser Phe Pro Ser Cys Pro Ser Leu Glu Glu Leu Glu Leu Lys Glu Asn
385                 390                 395                 400

Asn Glu Ala Leu Gln Ile Ile Val Lys Ile Thr Thr Thr Arg Gly Lys
                405                 410                 415

Glu Glu Lys Glu Glu Asp Lys Asn Ala Gly Val Gly Asn Ser Gln Asp
            420                 425                 430

Asp Asp Asn Val Lys Leu Trp Lys Val Glu Ile Asp Asn Leu Gly Tyr
        435                 440                 445

Leu Lys Ser Leu Pro Thr Asn Cys Leu Thr His Leu Asp Leu Thr Ile
    450                 455                 460

Ser Asp Ser Lys Glu Gly Glu Gly Glu Trp Glu Val Gly Asp Ala Phe
465                 470                 475                 480

Gln Lys Cys Val Ser Ser Leu Arg Ser Leu Thr Ile Ile Gly Asn His
                485                 490                 495

Gly Ile Asn Lys Val Lys Arg Leu Ser Gly Arg Thr Gly Leu Glu His
            500                 505                 510

Phe Thr Leu Leu Glu Ser Leu Lys Leu Ser Asp Ile Glu Asp Gln Glu
        515                 520                 525

Asp Glu Gly Glu
    530


<210> SEQ ID NO 13
<211> LENGTH: 8117
<212> TYPE: DNA
<213> ORGANISM: Spinacia oleracea

<400> SEQUENCE: 13

tggtccacaa ctccacacta agaggaactc caatgcttag ttacaaggtg gtgtagttaa      60

aaagtaattc caatagttaa ctacacggta ttatagttaa atttgccaac tcaaatttct     120

aactacaata tatttaagct acaaagtttc tcattggctg actacaatac gttgtagcgc     180
```

-continued

```
cttataatat tttattcaat atacaatttt atttatttta ccttttttaac aatttttttt    240
tgatctacct gctgtcctgt tcatatgagc tacactaatt tgatagctgc ttacgcaatt    300
cttatatcaa cggttggcta cttgttcaaa tatttttatt tttttacgag taagtcattt    360
tatgatcatt gaagtggctc tattattatt atcatgcacc gattaacgca agaataatta    420
actcggtacg aattagtttc aaaataaaat ccctcaaaaa aaaaagtttc aaaataaaat    480
taacagaaaa ccaaccttct ccggtttact gttgttagag catggaattt tccagtaatc    540
gcagacccca aattatcttc cagttgaatc aatccttgat ttttggattt gccagaaaac    600
tccttgaatt ttagggttca tatttgatcc gtaattggga aaattttcag caattgatct    660
tccaaatcag ccctacttgt ttccagactg caaatgaaag gtgcgaactt tatactgcat    720
tttggttttc cattagtgta atttattaag atgaactgca ttttgcaatt gttttattcg    780
actactcatt tttaaatcaa attgcttaat tgctagttag ttttcttatc atattgccaa    840
aaaaaattat ttttgtttaa ttggtgaaaa agggtaaatt atacctagtg tacaagattt    900
tcttgcacac caccccttaat ttgttgacac atcatcaaac gtactgaaaa atgagaatga    960
aagacaataa atatgtcatt ttaaccaata gaaaaacatg atgtagtaag atccttaatt   1020
gatagataaa taattaaata tcagtccatt agttgaatat tcaatgaaaa tgtatggtcc   1080
aaaaatggcg tttaatagtc aatgtcatgc tttatggggt ggtggagtac tatgtgactg   1140
tgtgtggact tggagaagac tagagagtat gattatcaac ctatggaccc tcaaaatgaa   1200
aatgaaaatg atgtttttac actttaaaat cgtcaagaaa caacaatcct ttttagcaat   1260
agtatttaca cgcgctagtt gcacgaactt taatgcaaat agtataaatt tacggtcaaa   1320
gttttcatac tttagacaca tactctctcc gtcccttaat actcgcaccg ctttcctttt   1380
cgggccgtcc cttaatactt gcaccgcttc tataaatgga aatctatttc tcacaattac   1440
ctactaaccc acctacactc atcgtcccta caaaaaatca tttaaaaatt cacaccccac   1500
actcaccact cctcacccat tacacatttc ctactaacta tattaaaaaa atatcccact   1560
ataaactaac actcattaaa ttaataagtc aattcaaata tcttaaactc cgcaccggtc   1620
aaatcggtgc gagtattaag ggacggaggg agtattatag agtgtaaata actttcatga   1680
atggagggag taaaaaattg ttttacttgg ctaaaatact tttgttctta ttggcagata   1740
aacatgagtc cattattggc caacttgaac atatacctcc aaacaataat caatgatgtc   1800
gattatgaag tttgtgaatg caatttatta tcactttcat tgcaagttgt catctgtgct   1860
gagtgttgat ttataaaaag gactacttga ttaacacata caatattact ccacctttct   1920
ccagacaacc tttcttttct gcttttatct tgttttctca tcttaattca tctcttcatc   1980
tttctgaaaa acccaaccca atggctgaaa tcggatactc ggtttgttca aaacttattg   2040
aagtgatggg cagtaagatc attaaagaga tttgtgacat gtggggttac aaatctcatc   2100
ttgaagacct caacaaatct gtcttgacga tcaaggatgt gctcttggat gctgaggcga   2160
agcgggatct ttcccgtgaa caacagagtt acattgcaga acttaaggat gttgtttacg   2220
atgctgatga tttgttcgat gagttcctca ctcttgctga gctcaaacag attgatggca   2280
acaacaaggg tggtggtaaa ttctccaaaa aggtacgtcg tttcttttct tctaataagg   2340
agaagatggg tcaagcttac aagatgtctc atatggttaa agaaattaag aagcagttgg   2400
gtgaaattgt tgataggtat accaaatttg ggtttattgt tgattataaa cctattatta   2460
ggagaaggga ggaaacatgt tcttattttg taggtgccaa ggagattgtt gggagggata   2520
aggataaaga tgttatcata ggcatgttgc tagatcatga taacgattgt agtttcttgg   2580
```

-continued

```
ctgttgtggg ggttggaggg gtgggaaaaa ctactcttgc ccaacttgtg tataatgatg   2640
aaagagtcaa aagtgagttc caagatttga ggtattgggt ttgtgtctct gatcaagatg   2700
ggggacaatt tgatgacaaa agaattcttt gtaagattat agagttagtt acgggccaga   2760
ttcctccgag taacgagagc atggaatcgg tgcgtaagaa atttcaagag gaattaggag   2820
gaaagaagta cttccttgtt cttgatgatg tatggaacga ggatcgccag aagtggcttc   2880
atctagaaaa tttcttgaaa ttgggtcaag gggaagcaa gattgtggta accacacgtt   2940
cagagaagac ggcaaatgtt atagggaaaa gacaagacta taaactagaa tgtttgtcag   3000
cagaggattc atggcgctta tttgaaatgt cagcttttga cgaagggcat ggccaggaaa   3060
actatgacga attagtgacg attggcaaga agattgttga aaaatgttat aacaatccac   3120
ttgctataac agtggtagga agccttcttt ttggacaaga gataaataag tggcggtcgt   3180
ttgaaagcag tggattagcc caaattgcca atggtgataa tcagattttc ccgatattaa   3240
agctcagtta ccacaatctt ccacactcct tgaagagctg ctttagctat tgtgcagtgt   3300
ttcccaaaga ttatgaaata aagaaggaga tgttgattga tctttggata gcacaaggat   3360
acattatacc gttggatgga ggtcaaagta tagaagatgc tgccgaggaa cattttgtaa   3420
ttttgttaag aagatgtttc tttcaagatg taaagaagga ttctcttggt aatgttgatt   3480
atgttaaaat ccacgactta atgcacgatg tcgctcaaga agtggggaag gaggaaatct   3540
gtgtagtgac ttcaggtaca aagaagttgg ctgataaaat ccgtcacgtg ggttgtgttg   3600
tcgatagaga tccagaaata gtctttttat gtagcaataa gattcgttcg tatattagcg   3660
gtcgttgtat aaagaatccg gtggattcac aaatagacaa ctggatgcgc cttagggtgt   3720
tggacttgtc agattcatgt gttaaagatt tgtctgattc aataggtaag ctgctgcact   3780
taaggtatct taacctctct tctaatataa agttggagat aatccctgat gcaattacaa   3840
gactgcataa cttgcagaca ctacttttag aatattgcag aagtttaaag gagttgccaa   3900
aagatttttg caaattggtc aaactgagac acttggattt aaggggttgt cagtgtttga   3960
ttggtatgcc attgggaatg gataggctaa ttagtcttag agtactacca aaagttgtgg   4020
tgggtaagaa ggaacaaagt gatgatcagc tgaaagccct aaaaggcctc accgagataa   4080
aaggctccat tgatatcaca atctattcaa agtatagaat agttgaaggc atgaatgaca   4140
caggaggagc tgggtatttg aagagcatga aacatctcac gggggttgat attagatttg   4200
atgatagaga aggtggatgt gttaaccctg aagctgtgtt ggcaacccta gagccacctt   4260
caaatatcaa gaggttagag atgtggcatt acagtggtac aacaattcca gtatggggaa   4320
gagcagagat taattgggca atctccctct cacatcttgt cgacatccag cttagttttt   4380
gtagaaattt gcaggagatg ccagtgctga gtaaactgcc tcatttgaaa tcactggaac   4440
ttacagagtt ggataactta gagtacatgg agagtagaag cagcagcagt agcagtgaca   4500
cagaagcagc aacaccagaa ttaccaacat tcttcccttc ccttgaaaaa ctttcacttt   4560
ggggtctgga aaagttgaag ggtttgggga acaggagatc gagtagtttt ccccgcctct   4620
ctaaattgga aatctgggaa tgcccagatc taacgtcatt tccttcttgt ccaagccttg   4680
aaaagttgga attgaaagaa aacaatgaag cgttgcaaat aatagtaaaa ataacaacaa   4740
caagaggtaa agaagaaaaa gaagaagaca agaatgctgg tgttggaaat tcacaagatg   4800
atgacaatgt caaattatgg aaggtggaaa tagacaatct gggttatctc aaatcactgc   4860
ccacaaattg tcttactcac ctcgacctta caataagaga ttccaaggag ggggagggtg   4920
```

aatgggaagt tggggaggca tttcagaagt gtgtatcttc tttgagaaag ctcagcataa 4980
tcggaaatca cggaataaat aaagtgaaga gactgtctgg aagaacaggg ttggagcatt 5040
tcactctgtt ggactcactc gaactttcaa atatagaaga ccaggaagat gagggcgaag 5100
acaacatcat gttctggaaa tcctttcctc aaaacctccg caatttggaa attaattact 5160
ctgacaaaat gacaagtttt cccatgggga tgcagtactt aacctccctc caaaccatcc 5220
atctttatga ttgttataaa ttgaattcca ttccagaatg gataagcagc ttatcatctc 5280
ttcaatccct gcacatagga aaatgtccag ccctaaaatc actaccagaa gcaatgcgga 5340
acctcacctc ccttcagaga cttacgatat ggcagtgtcc agacctaatt gaaagatgca 5400
aagaacctaa cggggaggac tatcccaaaa ttgtaagtca ttgcagaaag taatttattc 5460
atttatattt attttatgct tagaatgata tacgcagtcg tcctttggtt tcaaatcttg 5520
aatttggttt ttgttttctt tctttgtttc tttattcaac accagtccat ttatgattga 5580
ttcattaaaa aaaggatgga gttttatgga tttgaagaag acaacgaatt gagattcctg 5640
gggttttttt ttcgttgggg ttggttttca tgtatatgtt gctgattaaa taccagactg 5700
atgatgatga tgtgtttatg ggttttaaat cagattaaat atatgggaaa tgtaagttaa 5760
ttggggatgc acataaggtg tttgatgaaa tgtctattag aaatgttgtt tcttggactt 5820
agaatgatat acactgtcgt cctttggttt ccaatctgga atttggtttt tgttttctta 5880
gtttgtttct ttattccaca ctagcccatt ttttttaaac tacctgcaac tactgaattt 5940
catttaccct gtatctcaga ttatatggta gtaattctca tttactcaac actagcttga 6000
tcctgaacgc agccaacctt caggttagaa tccgccttac tcatcctttt gtcatgaatt 6060
gttttaagtt gttttgcttg cttgtgtaat cataattcat agtatacgat tcatcattca 6120
ctatgtctat aggcaagata ttggaattgt tcacgatttc ctgaagtttc tttgtttttg 6180
ttgataccac catattgcag cttatagtga ctaagttaat gaatgtttcc aaaaattagt 6240
catataaatt cttcttctct ctctattaca taaactcttt ttctctttct aacttatcat 6300
gttcatgtct aaaacgtata catgctcaca tcattgttcg tttcagctga cttacttatg 6360
taagagagct atctagttaa caactcttgt aactttttat ttgctagtca gaacatggat 6420
tggtgcaagc atgggaattt gccaacactc taccaaatcg attggagttt ggacttagtt 6480
tcaccagaag ccatacccgg acacttactg gggactgtca acaaagccgc attgtgatgt 6540
acttggatgt ttcacgtgcc tgaggtgtga gttacttgga agggaagcgg tttatttaat 6600
tgttttccta agtagatttt gcttacaagc ttttactttt cacttggaag ggtttcttg 6660 ttttaagctt ttcgaattag agtttcggtt gcattaagag tagtcgtatt agtctttttt 6720
acctaagact ctttttgta attttcagac tatgcaattc aagttttgag tgttttcttg 6780
cttgtgtgat tgtgagttgg tgaattcgtc tttcatacat tttgagatta tcagaagctt 6840
tatgctccac cggtagtcta gtacctttc tgttactgta cgtgcaggga agtaatctgg 6900
taccttctat atatatggaa aaacatacat tatacattac gcaaaattct tacaggttag 6960
ttacttcctg gaacttcatt tacacttggt ttttttgtt ccattccctc ggaagactat 7020
tccctctgag aaatatgtaa tgaatttctg tattcagctg catttacaat gaagtttaag 7080
cagacactct ctttatatag tgcctctttc tggagcaccg tagagctgtc tgtggttgat 7140
caccatatgc tgccgagaga ttcagcaatc gcgtgtttga tcaggtaaaa gtttttatgt 7200
caatgtgttt ttttttccg tttgatcaat ttatgtctgt attcagattc ttatcttctt 7260
acagtagcat aacacattgt ttctttcatt tatgtaaact gtttcaagat tacagagatg 7320

```
tatgcttcag tcgacattga tgataactta agatggcatt cctacaacag ttgcaggcgc   7380
attctaactc cggcaattct agttaggcaa gaggagcatt gccaatacct gccacctctg   7440
ggatttacta taccagggtt gaagtttatg gaagacacca gctatgcaca agccttcaag   7500
gggtcatcct acataacaag ttgaaccaac caattgcttg ttggttcagt ggtaattgga   7560
gctgaattcg gtagggatgg cccgtgttcg atccccacaa caacaattgg gaggggactg   7620
gaacctatcc acacagaact cgccctgaat ccggattagc cctaagggtg aacggggtgc   7680
taacaccaaa aaaaaaacat aacaagttga atcaaacata ctttgtttga attgaagatt   7740
tagtgatttc atttgatcga ttgagatgtc ttattataag cgtatatgct cttggatttg   7800
gccacttagg tgttgtttga caattggtca ttaactcgct tttatatttt cgtttctctt   7860
aggaaaggtg atcctgagaa tttatattga aacacttttt ttatctctca ctagctttaa   7920
aaaagtgttc tgtgttacct gcaattcaac ttgattattt ttcacatagt tttacctgaa   7980
aaagtgttat ctgaaaatca actgacataa atttttgttt ggatcaaatt aaggatacta   8040
gataaatcgg aaaaaataat caaccaatta agtacttcat aattaaatat gaagtatatt   8100
attatcttat gcttgtg                                                  8117
```

<210> SEQ ID NO 14
<211> LENGTH: 9789
<212> TYPE: DNA
<213> ORGANISM: Spinacia oleracea

<400> SEQUENCE: 14

```
tttgaagtta ggcttaactt gctcaccaat tcttaaatag actcgactta cactgaattt     60
attgtgtact atgtctagaa agtaaggtca acaactttct tctaaattat tttggcatgt    120
ttattagggt tattatgaaa aacatatcaa attggtgttg ttagttaggc ttgaataata    180
tgattttaag tcacgagact tttataaatt aggtaatttg atttaaaaaa ttgttacata    240
tctaagaaaa tggatgttaa atttatcagt caatgtataa acaataaaag tcaatatgta    300
tgtaaaaggg ttgctagata aaatctttgg ttttttggtc cacaactcca cactaagagg    360
aactccaatg cttagttaca aggtggtgta gttaaaaagt aactccaata gttaactaca    420
cggtattata gttaaatttg ccaactcaaa tttctaacta caatatattt aagctacaaa    480
gtttctcatt ggctgactac aatacgttgt agcgccttat aatattttat tcaatataca    540
attttattta ttttaccttt ttaacaattt ttttttgatc tacctgctgt cctgttcata    600
tgagctacac taatttgata gctgcttacg caattcttat atcaacggtt ggctacttgt    660
tcaaatattt ttattttttt acgagtaagt cattttatga tcattgaagt ggctctatta    720
ttattatcat gcaccgatta acgcaagaat aattaactcg gtacgaatta gtttcaaaat    780
aaaatccctc aaaaaaaaaa gtttcaaaat aaaattaaca gaaaaccaac cttctccggt    840
ttactgttgt tagagcatgg aattttccag taatcgcaga ccccaaatta tcttccagtt    900
gaatcaatcc ttgattttttg gatttgccag aaaactcctt gaattttagg gttcatattt    960
gatccgtaat tgggaaaatt ttcagcaatt gatcttccaa atcagcccta cttgtttcca   1020
gactgcaaat gaaaggtgcg aactttatac tgcattttgg ttttccatta gtgtaattta   1080
ttaagatgaa ctgcattttg caattgtttt attcgactac tcatttttaa atcaaattgc   1140
ttaattgcta gttagtttc ttatcatatt gccaaaaaaa attatttttg tttaattggt    1200
gaaaaagggt aaattatacc tagtgtacaa gattttcttg cacaccaccg ttaatttgtt   1260
```

gacacatcat caaacgtact gaaaaatgag aatgaaagac aataaatatg tcattttaac 1320
caatagaaaa acatgatgta gtaagatcct taattgatag ataaataatt aaatatcagt 1380
ccattagttg aatattcaat gaaaatgtat ggtccaaaaa tggcgtttaa tagtcaatgt 1440
catgctttat ggggtggtgg agtactatgt gactgtgtgt ggacttggag aagactagag 1500
agtatgatta tcaacctatg gaccctcaaa atgaaaatga aaatgatgtt tacacgtgct 1560
atttgcacgg acttcaatgc aaatagtata aatttacggt caaagttttc attctaaagc 1620
gtaaataact ttcatgaatg gaggacggta gtataagtat aacgttatag cctaccattt 1680
tcttatcata ttcacataaa tttgttgctg aaatttgttt tacttggcta aaatactttt 1740
gttcttattg gcagataaac atcagtacgt ccattattgg ccaacttgct gagtccatta 1800
ttggccaact tgaacatata cctccaaaca ataatcaata atgtcgatta tgaagtttgt 1860
gaatgcaatt tattatcact ttcatttata aaatgactac ttgattaaca catacaatat 1920
tacctttctc caaacaccct ttcaattctg cttaatcttg ttttctcatc atctcttcat 1980
ctttctgaaa acacaaccca atggccgaaa tcggatactc ggtttgtgcg aaactcatcg 2040
aagtgattgg cagtgagctg atcaaagaga tttgtgacac atggggttac aaatctcttc 2100
ttgaggacct caacaaaact gtattgacgg tcaggaacgt tctcattcaa gccggggtga 2160
tgcgggagct tactagtgaa caacaaggtt tcattgcaga ccttaaagat gttgtttatg 2220
atgctgatga cttgttcgac aagttactca ctcgtgctga gcgaaaacag attgatggaa 2280
acgaaatctc tgaaaaggta cgtcgtttct tttcctctag taacaagatc ggtcaagctt 2340
actacatgtc tcgtaaggtt aaggaaatta agaagcagtt ggatgaaatt gttgataggc 2400
atacaaaatt tgggtttagt gctgagttta tacctgtttg taggggaagg ggaaacgaga 2460
gggaaacacg ttcatatata gatgtcaaga atattcttgg gagggataaa gataagaatg 2520
atatcataga taggttgctt aatcgtaatg gtaatgaagc ttgtagtttc ctgaccatag 2580
tgggagcggg aggattggga aaaactgctc ttgcacaact tgtgttcaat gatgaaaggg 2640
tcaaaattga gttccatgat ttgaggtatt gggtttgtgt ctctgatcaa gatgggggcc 2700
aatttgatgt gaaagaaatc ctttgtaaga ttttagaggt ggttactaag gagaaagttg 2760
ataatagttc cacattggaa ttggtacaaa gccaatttca agagaagtta agaggaaaga 2820
agtacttcct tgttcttgat gatgtatgga acgaagatcg tgagaagtgg cttcctttgg 2880
aagagttgtt aatgttgggt caagggggaa gcaaggttgt agtgaccaca cgttcagaga 2940
agacagcaaa tgtcataggg aaaagacatt tttatacact ggaatgtttg tcaccagatt 3000
attcatggag cttatttgaa atgtcggctt ttcagaaagg gcatgagcag gaaaaccatc 3060
acgaactagt tgatattggg aaaaagattg ttgaaaaatg ttataacaat ccacttgcta 3120
taacggtggt aggaagtctt ctttatggag aggagataag taagtggcgg tcatttgaaa 3180
tgagtgagtt ggccaaaatt ggcaatgggg ataataagat tttgccgata ttaaagctca 3240
gttaccataa tcttataccc tcgttgaaga gttgttttag ttattgtgca gtgtttccca 3300
aggatcatga aataaagaag gagatgttga ttgaactttg gatggcacaa ggatatgttg 3360
tgccgttgga tggaggtcaa agtatagaag atgctgccga ggaacatttt gtaattttgt 3420
tacgaaggtg tttctttcaa gatgtaaaga aggataaata tggtgatgtt gattctgtta 3480
aaatccacga cttgatgcac gatgtcgccc aagaagtggg gagggaggaa ttatgtgtag 3540
tgaatgataa tacaaagaac ttgggtgata aaatccgtca tgtacatcgt gatgtcatta 3600
gatatgcaca aagagtctct ctgtgtagcc atagccataa gattcgttcg tatattggtg 3660

-continued

```
gtaattgtga aaaacgttgt gtggatacac taatagacaa gtggatgtgt cttaggatgt   3720
tggacttgtc atggtcggat gttaaaaatt tgcctaattc aataggtaaa ttgttgcact   3780
tgaggtgtct taacctgtct tataataaag atctgttgat actccctgat gcaattacaa   3840
gactgcataa tttgcagaca ctgcttttaa aagagtgcag aagtttaaag gagttgccaa   3900
aagatttttg caaattggtc aaactgaggc acttggattt aaggtgttct gatttgaagg   3960
agttgccaaa agatttttgc aaattggtca aactgaggca cttggattta tggggttgtg   4020
atgatttgat tggtgtgcca ttgggaatgg ataggctaat tagtcttaga gtactgccat   4080
tctttgtggt gggtaggaag gaacaaagtg atgatgatga gctgaaagcc ctaaaaggcc   4140
tcaccgagat aaaaggctcc attcgtatta gaatctattc aaagtataga atagttgaag   4200
gcatgaatga cacaggagga gctgggtatt taaagagcat gaaacatctc acgggggttg   4260
atattacatt tgatggtgga tgtgttaacc ctgaagctgt gttggcaacc ctagagccac   4320
cttcaaatat caagaggtta gagatgtggc attacagtgg tacaacaatt ccagtatggg   4380
gaagagcaga gattaattgg gcaatctccc tctcacatct tgtcgacatc cagctttggc   4440
attgtcgtaa tttgcaggag atgccagtgc tgagtaaact gcctcatttg aaatcactgg   4500
aactttataa tttgattagt ttagagtaca tggagagcac aagcagaagc agtagcagtg   4560
acacagaagc agcaacacca gaattaccaa cattcttccc ttcccttgaa aaacttacac   4620
tttggcgtct ggacaagttg aagggttttg ggaacaggag atcgagtagt tttccccgcc   4680
tctctaaatt ggaaatctgg aaatgcccag atctaacgtc atttccttct tgtccaagcc   4740
ttgaagagtt ggaattgaaa gaaaacaatg aagcattgca aataatagta aaaataacaa   4800
caacaagagg taaagaagaa aaagaagaag acaagaatgc tggtgttgga aattcacaag   4860
atgatgacaa tgtcaaatta cggaaggtgg aaatagacaa tgtgagttat ctcaaatcac   4920
tgcccacaaa ttgtcttact cacctcgacc ttacaataag agattccaag gagggggagg   4980
gtgaatggga agttggggat gcatttcaga agtgtgtatc ttctttgaga agcctcacca   5040
taatcggaaa tcacggaata aataaagtga agagactgtc tggaagaaca gggttggagc   5100
atttcactct gttggaatca ctcaaacttt cagatataga agaccaggaa gatgagggcg   5160
aagacaacat catattctgg aaatcctttc ctcaaaacct ccgcagtttg agaattaaag   5220
actctgacaa aatgacaagt ttgcccatgg ggatgcagta cttaacctcc ctccaaaccc   5280
tctatctaca ccattgttat gaattgaatt cccttccaga atggataagc agcttatcat   5340
ctcttcaatc cctgcacata ggaaaatgtc cagccctaaa atcactacca gaagcaatgc   5400
ggaacctcac ctcccttcag agacttacga tatggcagtg tccagaccta attgaaagat   5460
gcaaagaacc taacggggag gactatccca aaattcaaca catccccaaa attgtaagtc   5520
attgcagaaa gtaatttatt catttatatt tattttatgc ttagaatgat atacaccgtc   5580
gtcctttggt ttcaaatctt gaatttggtt tttgttttct ttctttgttt ctttattcaa   5640
caccagccca tttatgattg attcattaaa aaaaggatgg agttttgtgg atttgaagaa   5700
gacaacgaat tgagattcct ggggttttct ttttgttggg gttggatttc atgtatatgt   5760
tgctgattaa atacgagact gatgatgatg atgatgtgtt tatgggtttt aaatcagatt   5820
aaatatatgg gaaatgtaag ttaatttggg atgcacataa ggtgtttgct gaaatgtcta   5880
tgagaaatgt tgtttcttgg acttagaatg atatacactg tcgtccattg gtttccaatc   5940
ttacatttgg tttgtgtttt cttagtttgt ttctttaatc aacaccaacc catttttttta   6000
```

-continued

```
aaactacctg caactactaa tttacgttga ccctgtatct caggtactaa ataaatattg   6060
gtgattttca gttactcaac actagcttga tcctgaacgc acccaacctt caggttagaa   6120
tccggcttac tcatcctttt gtccagtttt caagtaattg ttttggcagg atcaattctc   6180
taattgttgt acaccgtata ttgcaattta tagtgactac agttaatgaa tgtttacaaa   6240
aaattagtca tgtaaaaact tcttctctgt ccattacata aactcttttt ctctttctaa   6300
cttatcatgt tcatgtctaa aaaattaaac atgctcacat caatgttcat ttaagctaac   6360
ttacttctgt aagagagcga gctagttaaa aactccttta actttctgtt ttatactcag   6420
gacatggatt gatgcaagca tgaagaactt cgggaatttg ctaaaactct accaaagcga   6480
tgagagtttg gactttgttt cacttgaagt cagggactgt caacaaagcc acagtgtgca   6540
tgttggctgt ttcacttgga cgataaaaag gtttatttaa ttgttttcct aagtgtattt   6600
ggcttacaag cttttacttt tcgcttgaaa gggtttttct tgttttaagc tttttgaatt   6660
agagtttcgg ttgaagtaag agtagtcgta ttagtctttt actttgcagg agtctatgcc   6720
tatataaggt aagactcgta tttgtaattt tcagattatg caattcaagt tttcgagtgt   6780
tttcttaaaa aaacatatca tacctgtgtg tagcataaag ataaattctg atgctgtgct   6840
tcttgttatg gctcacattg gttttcattg tttggattgt ttcacaggga agcagagaat   6900
acctggaacc tgtaaaggac gctatatcta tagcagcttt cacaggccaa gtaatataat   6960
gttctttatc aatcactcaa tacctggaga ttgtttgaac acataattca cctctttttt   7020
tccatctcaa attgcagact tttactggga tttgaatgac agcaaacatt tgattgtcac   7080
gaggattgat ctaactggtg aatgttgtga tcaccatatt ggtctttctc attcaaacaa   7140
acttgcatac cgttcttttg aagtttgaag acaagcaggc gataatcaac tcaggtcgaa   7200
gctcatgtgc aggagagaat agaatataga ggagattatt tttaaaagaa acgctcaaag   7260
gtattgtagc acctttccta tttgctactg cagtgatgtt tttatttctt gtttgcagcg   7320
cttgtttctc atatttcaac ctacttttag aaaaaaaaac atctccgaac ataaccaaaa   7380
ataaagttcc cttatcagtg ctttccctgc tttcttctaa acaacatata caattataaa   7440
cccttttctt ctcttacctt tgttattctt ccttgcttca ttgagataac actctcctgt   7500
ttttgttttg ttgttagtca ttacatggat atatcaagga caacagttct gtagtccgtc   7560
aactgtggtt aggaaggcta aactggagca caataacccc atgtcaattg aatagtaaag   7620
gtgtgctata tcagtttcgt ttggcttggc ttacctgaaa aatggctggt tatttatcct   7680
tgtctctttc tatgacgtgc agtggcttgt taatgtgtct cggacaacaa ttcctcactt   7740
tccaagttcc atacacgctg atgtaactat cttctgcagt ctgttctttc atttttgcca   7800
cgtgctctaa ttataacttt ttgtactcaa taatcaactc cttgtcccgg tatttgcaga   7860
gactacttaa acaggtaaag tgacaatcct ggcgaagttg tctgtttctt agctctgaac   7920
ccatcattca ggtaagatta agtatttaag aagaaatttt gtttttacct aaaatgaatg   7980
atcttgtgta actgcttgct tcttgcatta aataagaact ttctgctgca tatgtgacag   8040
ttacatccac aaaaaagttg gaggtttgtt cagggattgg aaatgaaggt acttcagaat   8100
tcctggaatg tttatgaatg ctccagactt cagagtcttt aatggaaaat tcgagtcact   8160
aaaaaaacat tattcctatc atcagagctt tgaagttcct ctatacaagg tcaactgagt   8220
tcctctttgc ctcttgttta attgtattta cttgtacctt aattataatc tgtatattgt   8280
tttagttaag ttctaaaaca ggttattatt catcatttgt gcagcatatt gctggaatca   8340
agaatctagt gcttcttctt cctgacttca ctgtcaaaat agcagttccc atgctggaaa   8400
```

taagcgcgct agcaatgtaa ttgatgacat ggatgttgct gcttctgagt tttgatcata 8460
aaaagctgtt atgtgtttct tgaatgtaat gaaggagagg agaaaactga aaactcttgg 8520
caaaaacgtg aaattgcagt gcctcggggt ggtagggatc acccggattc agttcagacg 8580
atactttttt caacccggtt tgttccggtt ttcagcttcg ggttttcctt gtacttttgg 8640
ggcacacata caaggctact tcatgtttga gaaacctaat tgaggctatc ttgtagcaaa 8700
tgcacaccac actctttctc tcttctctcc ttttttcacc ttccatttgt aaaaatcctc 8760
ttttaaaggt taataaaaaa aagcttcaag tctcgtaggg tggatgtagg tcacattgac 8820
cgaaccacgg taaactcttt gtgttctttc ttctctcttt gtttctcatt tttacggcaa 8880
gtgtttatgg ttaaccatgc atcttagaat agcttaaggc attaacataa taacatcaat 8940
gttctccaaa gattcacctt acttgttgta cataatcaca atgttaagcc tatgaaggta 9000
gaatgctctc atgatttggt ttaaccaaaa aataaactct aaaataatac ggagtaataa 9060
aaattggcca taaactaatt acaaagtttg atttttgtat agggtatctt gtacttgtga 9120
taaaaaaaat tttaaaaaaa ttaaaaagta aataaattac ttattccttc tatttttact 9180
tgttacactt ttctacaaca gaaacatcaa aacgcccgca acacactata aatgaaaaac 9240
cattttgtat gcaatgatat ttacgttctc actttattct ctttaataac tcctactacg 9300
taattctcac caatcaaata aaattataga aattttcatt tataccctct taaaatgatg 9360
ttgatttttt tttttttttt taaggtgtga aaaagtttgt gttatactta caacaattta 9420
aaaacggaga acatacttat aatactagtg taatctttgg ccggattatg gtcgttgaca 9480
aaaaaactcc ggccttgacc ctccacgtgc cggtcaagtt cttctttttt cattcttctt 9540
tttattcttc tttttctctc cattaataca aatcaagtga ttatgtcgat ccgatccttc 9600
tgttctctac tgtaattgat tacaccaaca acaaccaagc gaaacagtca atgttaccga 9660
attgaattgc ggaaaatagt ttatgattga ttcattaaaa aaggatggag ttttgtggat 9720
ttgaataaga caacgaattg agattcctgg ggttttcttt ctgttggggt tggatttcat 9780
gtacttgtt 9789

<210> SEQ ID NO 15
<211> LENGTH: 9111
<212> TYPE: DNA
<213> ORGANISM: Spinacia oleracea

<400> SEQUENCE: 15
tttgaagtta ggcttaactt gctcaccaat tcttaaatag actcgactta cactgaattt 60
attgtgtact atgtctagaa agtaaggtca acaactttct tctaaattat tttggcatgt 120
ttattagggt tattatgaaa aacatatcaa attggtgttg ttagttaggc ttgaataata 180
tgattttaag tcacgagact tttataaatt aggtaatttg atttaaaaaa ttgttacata 240
tctaagaaaa tggatgttaa atttatcagt caatgtataa acaataaaag tcaatatgta 300
tgtaaaaggg ttgctagata aaatctttgg ttttttggtc cacaactcca cactaagagg 360
aactccaatg cttagttaca aggtggtgta gttaaaaagt aactccaata gttaactaca 420
cggtattata gttaaatttg ccaactcaaa tttctaacta caatatattt aagctacaaa 480
gtttctcatt ggctgactac aatacgttgt agcgccttat aatattttat tcaatataca 540
attttattta ttttaccttt ttaacaattt ttttttgatc tacctgctgt cctgttcata 600
tgagctacac taatttgata gctgcttacg caattcttat atcaacggtt ggctacttgt 660

-continued

```
tcaaatattt ttattttttt acgagtaagt cattttatga tcattgaagt ggctctatta     720
ttattatcat gcaccgatta acgcaagaat aattaactcg gtacgaatta gtttcaaaat     780
aaaatccctc aaaaaaaaaa gtttcaaaat aaaattaaca gaaaaccaac cttctccggt     840
ttactgttgt tagagcatgg aattttccag taatcgcaga ccccaaatta tcttccagtt     900
gaatcaatcc ttgattttttg gatttgccag aaaactcctt gaattttagg gttcatattt     960
gatccgtaat tgggaaaatt ttcagcaatt gatcttccaa atcagcccta cttgtttcca    1020
gactgcaaat gaaaggtgcg aactttatac tgcattttgg ttttccatta gtgtaattta    1080
ttaagatgaa ctgcatttg caattgtttt attcgactac tcatttttaa atcaaattgc    1140
ttaattgcta gttagtttc ttatcatatt gccaaaaaaa attattttg tttaattggt     1200
gaaaaagggt aaattatacc tagtgtacaa gattttcttg cacaccaccg ttaatttgtt    1260
gacacatcat caaacgtact gaaaaatgag aatgaaagac aataaatatg tcattttaac    1320
caatagaaaa acatgatgta gtaagatcct taattgatag ataaataatt aaatatcagt    1380
ccattagttg aatattcaat gaaaatgtat ggtccaaaaa tggcgtttaa tagtcaatgt    1440
catgctttat ggggtggtgg agtactatgt gactgtgtgt ggacttggag aagactagag    1500
agtatgatta tcaacctatg gaccctcaaa atgaaaatga aaatgatgtt tacacgtgct    1560
atttgcacgg acttcaatgc aaatagtata aatttacggt caaagttttc attctaaagc    1620
gtaaataact ttcatgaatg gaggacggta gtataagtat aacgttatag cctaccattt    1680
tcttatcata ttcacataaa tttgttgctg aaatttgttt tacttggcta aaatactttt    1740
gttcttattg gcagataaac atcagtacgt ccattattgg ccaacttgct gagtccatta    1800
ttggccaact tgaacatata cctccaaaca ataatcaata atgtcgatta tgaagtttgt    1860
gaatgcaatt tattatcact ttcatttata aaatgactac ttgattaaca catacaatat    1920
tacctttctc caaacaccct ttcaattctg cttaatcttg ttttctcatc atctcttcat    1980
ctttctgaaa acacaaccca atggccgaaa tcggatactc ggtttgtgcg aaactcatcg    2040
aagtgattgg cagtgagctg atcaaagaga tttgtgacac atggggttac aaatctcttc    2100
ttgaggacct caacaaaact gtattgacgg tcaggaacgt tctcattcaa gccggggtga    2160
tgcgggagct tactagtgaa caacaaggtt tcattgcaga ccttaaagat gttgtttatg    2220
atgctgatga cttgttcgac aagttactca ctcgtgctga gcgaaaacag attgatggaa    2280
acgaaatctc tgaaaaggta cgtcgtttct tttcctctag taacaagatc ggtcaagctt    2340
actacatgtc tcgtaaggtt aaggaaatta agaagcagtt ggatgaaatt gttgataggc    2400
atacaaaatt tgggtttagt gctgagttta tacctgtttg taggggaagg ggaaacgaga    2460
gggaaacacg ttcatatata gatgtcaaga atattcttgg gagggataaa gataagaatg    2520
atatcataga taggttgctt aatcgtaatg gtaatgaagc ttgtagtttc ctgaccatag    2580
tgggagcggg aggattggga aaaactgctc ttgcacaact tgtgttcaat gatgaaaggg    2640
tcaaaattga gttccatgat ttgaggtatt gggtttgtgt ctctgatcaa gatgggggcc    2700
aatttgatgt gaaagaaatc ctttgtaaga ttttagaggt ggttactaag gagaaagttg    2760
ataatagttc cacattggaa ttggtacaaa gccaatttca agagaagtta agaggaaaga    2820
agtacttcct tgttcttgat gatgtatgga acgaagatcg tgagaagtgg cttcctttgg    2880
aagagttgtt aatgttgggt caagggggaa gcaaggttgt agtgaccaca cgttcagaga    2940
agacagcaaa tgtcataggg aaaagacatt tttatacact ggaatgtttg tcaccagatt    3000
attcatggag cttatttgaa atgtcggctt ttcagaaagg gcatgagcag gaaaaccatc    3060
```

-continued

```
acgaactagt tgatattggg aaaaagattg ttgaaaaatg ttataacaat ccacttgcta   3120
taacggtggt aggaagtctt ctttatggag aggagataag taagtggcgg tcatttgaaa   3180
tgagtgagtt ggccaaaatt ggcaatgggg ataataagat tttgccgata ttaaagctca   3240
gttaccataa tcttataccc tcgttgaaga gttgttttag ttattgtgca gtgtttccca   3300
aggatcatga aataaagaag gagatgttga ttgaactttg gatggcacaa ggatatgttg   3360
tgccgttgga tggaggtcaa agtatagaag atgctgccga ggaacatttt gtaattttgt   3420
tacgaaggtg tttctttcaa gatgtaaaga aggataaata tggtgatgtt gattctgtta   3480
aaatccacga cttgatgcac gatgtcgccc aagaagtggg gagggaggaa ttatgtgtag   3540
tgaatgataa tacaaagaac ttgggtgata aaatccgtca tgtacatcgt gatgtcatta   3600
gatatgcaca aagagtctct ctgtgtagcc atagccataa gattcgttcg tatattggtg   3660
gtaattgtga aaaacgttgt gtggatacac taatagacaa gtggatgtgt cttaggatgt   3720
tggacttgtc atggtcggat gttaaaaatt tgcctaattc aataggtaaa ttgttgcact   3780
tgaggtgtct taacctgtct tataataaag atctgttgat actccctgat gcaattacaa   3840
gactgcataa tttgcagaca ctgcttttaa aagagtgcag aagtttaaag gagttgccaa   3900
aagatttttg caaattggtc aaactgaggc acttggattt aaggtgttct gatttgaagg   3960
agttgccaaa agatttttgc aaattggtca aactgaggca cttggattta tggggttgtg   4020
atgatttgat tggtgtgcca ttgggaatgg ataggctaat tagtcttaga gtactgccat   4080
tctttgtggt gggtaggaag gaacaaagtg atgatgatga gctgaaagcc ctaaaaggcc   4140
tcaccgagat aaaaggctcc attcgtatta gaatctattc aaagtataga atagttgaag   4200
gcatgaatga cacaggagga gctgggtatt taaagagcat gaaacatctc acgggggttg   4260
atattacatt tgatggtgga tgtgttaacc ctgaagctgt gttggcaacc ctagagccac   4320
cttcaaatat caagaggtta gagatgtggc attacagtgg tacaacaatt ccagtatggg   4380
gaagagcaga gattaattgg gcaatctccc tctcacatct tgtcgacatc cagctttggc   4440
attgtcgtaa tttgcaggag atgccagtgc tgagtaaact gcctcatttg aaatcactgg   4500
aactttataa tttgattagt ttagagtaca tggagagcac aagcagaagc agtagcagtg   4560
acacagaagc agcaacacca gaattaccaa cattcttccc ttcccttgaa aaacttagac   4620
tttggcgtct ggacaagttg aagggttttg ggaacaggag atcgagtagt tttccccgcc   4680
tctctaaatt ggaaatctgg aaatgcccag atctaacgtc atttccttct tgtccaagcc   4740
ttgaagagtt ggaattgaaa gaaaacaatg aagcattgca aataatagta aaaataacaa   4800
caacaagagg taaagaagaa aaagaagaag acaagaatgc tggtgttgga aattcacaag   4860
atgatgacaa tgtcaaatta cggaaggtgg aaatagacaa tgtgagttat ctcaaatcac   4920
tgcccacaaa ttgtcttact cacctcgacc ttacaataag agattccaag gagggggagg   4980
gtgaatggga agttggggat gcatttcaga agtgtgtatc ttctttgaga agcctcacca   5040
taatcggaaa tcacggaata aataaagtga agagactgtc tggaagaaca gggttggagc   5100
atttcactct gttggaatca ctcaaacttt cagatataga agaccaggaa gatgagggcg   5160
aagacaacat catattctgg aaatcctttc ctcaaaacct ccgcagtttg agaattaaag   5220
actctgacaa aatgacaagt ttgcccatgg ggatgcagta cttaacctcc ctccaaaccc   5280
tctatctaca ccattgttat gaattgaatt cccttccaga atggataagc agcttatcat   5340
ctcttcaatc cctgcacata ggaaaatgtc cagccctaaa atcactacca gaagcaatgc   5400
```

-continued

```
ggaacctcac ctcccttcag agacttacga tatggcagtg tccagaccta attgaaagat   5460
gcaaagaacc taacggggag gactatccca aaattcaaca catccccaaa attgtaagtc   5520
attgcagaaa gtaatttatt catttatatt tattttatgc ttagaatgat atacaccgtc   5580
gtcctttggt ttcaaatctt gaatttggtt tttgttttct ttctttgttt ctttattcaa   5640
caccagccca tttatgattg attcattaaa aaaaggatgg agttttgtgg atttgaagaa   5700
gacaacgaat tgagattcct ggggttttct ttttgttggg gttggatttc atgtatatgt   5760
tgctgattaa atacgagact gatgatgatg atgatgtgtt tatgggtttt aaatcagatt   5820
aaatatatgg gaaatgtaag ttaatttggg atgcacataa ggtgtttgct gaaatgtcta   5880
tgagaaatgt tgtttcttgg acttagaatg atatacactg tcgtccattg gtttccaatc   5940
ttacatttgg tttgtgtttt cttagtttgt ttctttaatc aacaccaacc cattttttta   6000
aaactacctg caactactaa tttacgttga ccctgtatct caggtactaa atgaatattg   6060
gtgattttca gttactcaac actagcttga tcctgaacgc acccaacctt caggttagaa   6120
tccggcttac tcatcctttt gtccagtttt caagtaattg ttttggcagg atcaattctc   6180
taattgttgt acaccgtata ttgcaattta tagtgactac agttaatgaa tgtttacaaa   6240
aaattagtca tgtaaaaact tcttctctgt ccattacata aactcttttt ctctttctaa   6300
cttatcatgt tcatgtctaa aaaattaaac atgctcacat caatgttcat ttaagctaac   6360
ttacttctgt aagagagcga gctagttaaa aactccttta actttctgtt ttatactcag   6420
gacatggatt gatgcaagca tgaagaactt cgggaatttg ctaaaactct accaaagcga   6480
tgagagtttg gactttgttt cacttgaagt cagggactgt caacaaagcc acagtgtgca   6540
tgttggctgt ttcacttgga cgataaaaag gtttatttaa ttgttttcct aagtgtattt   6600
ggcttacaag cttttacttt tcgcttgaaa gggtttttct tgttttaagc tttttgaatt   6660
agagtttcgg ttgaagtaag agtagtcgta ttagtctttt actttgcagg agtctatgcc   6720
tatataaggt aagactcgta tttgtaattt tcagattatg caattcaagt tttcgagtgt   6780
tttcttaaaa aaacatatca tacctgtgtg tagcataaag ataaattctg atgctgtgct   6840
tcttgttatg gctcacattg gttttcattg tttggattgt ttcacaggga agcagagaat   6900
acctggaacc tgtaaaggac gctatatcta tagcagcttt cacaggccaa gtaatataat   6960
gttctttatc aatcactcaa tacctggaga ttgtttgaac acataattca cctctttttt   7020
tccatctcaa attgcagact tttactggga tttgaatgac agcaaacatt tgattgtcac   7080
gaggattgat ctaactggtg aatgttgtga tcaccatatt ggtctttctc attcaaacaa   7140
acttgcatac cgttcttttg aagtttgaag acaagcaggc gataatcaac tcaggtcgaa   7200
gctcatgtgc aggagagaat agaatataga ggagattatt tttaaaagaa acgctcaaag   7260
gtattgtagc acctttccta tttgctactg cagtgatgtt tttatttctt gtttgcagcg   7320
cttgtttctc atatttcaac ctacttttag aaaaaaaaac atctccgaac ataaccaaaa   7380
ataaagttcc cttatcagtg ctttccctgc tttcttctaa acaacatata caattataaa   7440
cccttttttct ctcttacctt tgttattctt ccttgcttca ttgagataac actctcctgt   7500
ttttgttttg ttgttagtca ttacatggat atatcaagga caacagttct gtagtccgtc   7560
aactgtggtt aggaaggcta aactggagca caataacccc atgtcaattg aatagtaaag   7620
gtgtgctata tcagtttcgt ttggcttggc ttacctgaaa aatggctggt tatttatcct   7680
tgtctctttc tatgacgtgc agtggcttgt taatgtgtct cggacaacaa ttcctcactt   7740
tccaagttcc atacacgctg atgtaactat cttctgcagt ctgttctttc atttttgcca   7800
```

```
cgtgctctaa ttataacttt ttgtactcaa taatcaactc cttgtcccgg tatttgcaga   7860

gactacttaa acaggtaaag tgacaatcct ggcgaagttg tctgtttctt agctctgaac   7920

ccatcattca ggtaagatta agtatttaag aagaaatttt gtttttacct aaaatgaatg   7980

atcttgtgta actgcttgct tcttgcatta aataagaact ttctgctgca tatgtgacag   8040

ttacatccac aaaaaagttg gaggtttgtt cagggattgg aaatgaaggt acttcagaat   8100

tcctggaatg tttatgaatg ctccagactt cagagtcttt aatggaaaat tcgagtcact   8160

aaaaaaacat tattcctatc atcagagctt tgaagttcct ctatacaagg tcaactgagt   8220

tcctctttgc ctcttgttta attgtattta cttgtacctt aattataatc tgtatattgt   8280

tttagttaag ttctaaaaca ggttattatt catcatttgt gcagcatatt gctggaatca   8340

agaatctagt gcttcttctt cctgacttca ctgtcaaaat agcagttccc atgctggaaa   8400

taagcgcgct agcaatgtaa ttgatgacat ggatgttgct gcttctgagt tttgatcata   8460

aaaagctgtt atgtgtttct tgaatgtaat gaaggagagg agaaaactga aaactcttgg   8520

caaaaacgtg aaattgcagt gcctcggggt ggtagggatc acccggattc agttcagacg   8580

atactttttt caacccggtt tgttccggtt ttcagcttcg ggttttcctt gtacttttgg   8640

ggcacacata caaggctact tcatgtttga gaaacctaat tgaggctatc ttgtagcaaa   8700

tgcacaccac actctttctc tcttctctcc ttttttcacc ttccatttgt aaaaatcctc   8760

ttttaaaggt taataaaaaa aagcttcaag tctcgtaggg tggatgtagg tcacattgac   8820

cgaaccacgg taaactcttt gtgttctttc ttctctcttt gtttctcatt tttacggcaa   8880

gtgtttatgg ttaaccatgc atcttagaat agcttaaggc attaacataa taacatcaat   8940

gttctccaaa gattcacctt acttgttgta cataatcaca atgttaagcc tatgaaggta   9000

gaatgctctc atgatttggt ttaaccaaaa aataaactct aaaataatac ggagtaataa   9060

aaattggcca taaattattt acaaagtttg atttttgtat agggtatctt g            9111
```

<210> SEQ ID NO 16
<211> LENGTH: 8389
<212> TYPE: DNA
<213> ORGANISM: Spinacia oleracea
<220> FEATURE:
<221> NAME/KEY: misc_feature
<222> LOCATION: 5171..5230
<223> OTHER INFORMATION: /note="n = a or t or c or g"
<220> FEATURE:
<221> NAME/KEY: misc_feature
<222> LOCATION: 5553..5602
<223> OTHER INFORMATION: /note="n = a or t or c or g"

<400> SEQUENCE: 16

```
atggccgaaa tcggatactc ggtttgtgcg aaactcatcg aagtgattgg cagtgagctg     60

atcaaagaga tttgtgacac atggggttac aaatctcttc ttgaggacct caacaaaact    120

gtattgacgg tcaggaacgt tctcattcaa gccggggtga tgcgggagct tactagtgaa    180

caacaaggtt tcattgcaga ccttaaagat gttgtttatg atgctgatga cttgttcgac    240

aagttactca ctcgtgctga gcgaaaacag attgatggaa acgaaatctc tgaaaaggta    300

cgtcgtttct tttcctctag taacaagatc ggtcaagctt actacatgtc tcgtaaggtt    360

aaggaaatta agaagcagtt ggatgaaatt gttgataggc atacaaaatt tgggtttagt    420

gccgagttta tacctgtttg tagggaaagg gggaacgaga gggaaacacg ttcatatata    480

gatgtcaaga atattcttgg gagggataaa gataagaatg atatcataga taggttgctt    540
```

-continued

```
aatcgtaatg gtaatgaagc ttgtagtttc ctgaccatag tgggagcggg aggattggga    600
aaaactgctc ttgcacaact tgtgttcaat gatgaaaggg tcaaaattga gttccatgat    660
ttgaggtatt gggtttgtgt ctctgatcaa gatgggggcc aatttgatgt gaaagaaatc    720
ctttgtaaga ttttagaggt ggttactaag gagaaagttg ataatagttc cacattggaa    780
ttggtacaaa gccaatttca agagaagtta agaggaaaga agtacttcct tgttcttgat    840
gatgtatgga acgaagatcg tgagaagtgg cttcctttgg aagagttgtt aatgttgggt    900
caagggggaa gcaaggttgt agtgaccgca cgttcagaga agacagcaaa tgtcataggg    960
aaaagacatt tttatacact ggaatgtttg tcaccagatt attcatggag cttatttgaa   1020
atgtcggctt ttcagaaagg gcatgagcag gaaaaccatc acgaactagt tgatattggg   1080
aaaaagattg ttgaaaaatg ttataacaat ccacttgcta taacggtggt aggaagtctt   1140
ctttatggag aggagataag taagtggcgg tcatttgaaa tgagtgagtt ggccaaaatt   1200
ggcaatgggg ataataagat tttgccgata ttaaagctca gttaccataa tcttataccc   1260
tcgttgaaga gttgcttcag ttattgtgca gtgtttccca aggatcatga aataaagaag   1320
gagatgttga ttgatctttg gatagcacaa ggatacgttg tggcacttga tggaggtcaa   1380
agtatagaag atgctgccga agaacatttt gtaattttgt tacggagatg tttctttcaa   1440
gatgtaaaga aggatgaata tggtgatgtt gattctgtta aaatccacga cttgatgcac   1500
gatgtcgccc aagaagtggg gagggaggaa atatgtgtag tgaatgataa tacaaagaac   1560
ttgggtgata aaatccgtca tgtacatggt gatgtcaata gatatgcaca aagagtctct   1620
ctgtgtagcc atagccataa gattcgttcg tatattggtg gtgattgtga aaaacgttgt   1680
gtggatacac taatagacaa gtggatgtgt cttaggatgt tggacttgtc atggtcggat   1740
gttaaaaatt tgcctaattc aataggtaaa ttgttgcact tgaggtatct taacctgtca   1800
gataatagaa atctaaagat acttcctgat gcaattacaa gactgcataa tttgcagaca   1860
ctgcttttaa aagattgcag aagtttaaag gagttgccaa aagatttttg caaattggtc   1920
aaactgagac acttggattt atggggttgt gatgatttga ttggtatgcc atttggaatg   1980
gataagctaa ctagtcttag aatactacca aacattgtgg tgggtaggaa ggaacaaagt   2040
gttgatgatg agctgaaagc ccttaaaggc ctcaccgaga taaaaggcga cattgatatc   2100
aaaatctgtg aaaattatag aatagttgaa ggcatgaatg acacaggagg agctgggtat   2160
ttgaagagca tgaaacatct cagggagatt ggtattacat ttgatggtgg atgtgttaac   2220
cctgaagctg tgttggcaac cctagagcca ccttcaaata tcaagagctt atctatacat   2280
cgttttgatg gtaaaacact tccagtatgg ggaagagcag agattaattg ggcaatctcc   2340
ctctcacatc ttgtcgacat ccagctttgg cattgtcgta atttgcagga gatgccagtg   2400
ctgagtaaac tgcctcattt gaaatcactg gaactttata atttgattag tttagagtac   2460
atggagagca caagcagaag cagtagcagt gacacagaag cagcaacacc agaattacca   2520
acattcttcc cttcccttga aaaacttaca ctttggggtc tggaaaagtt gaagggtttg   2580
gggaacagga gatcgagtag ttttccccgc ctctctgaat tgaaaatcat ggaatgccca   2640
gatctaacgt ggtttcctcc ctgtccaagc cttgaaaaac ttacactttg gcgtctggac   2700
aagttgaagg gttttgggaa ccggagatcg agtacttttc cccgcctctc tgaattggaa   2760
atcaagaaat gcccagatct aacgtcattt ccttcttgtc caagccttga gaagttggaa   2820
ttgaaagaaa gcaatgaagc attgcaaata atagtaaaaa taacaacaag aggtaaagaa   2880
aaagaagaga acaataatgc tggtgttaga aattcacaag atgatgacaa agtcaaatta   2940
```

```
cggaagatgg tgatagacaa tctgggttat ctcaaatcac tgcccacaaa ttgtcttact   3000
cacctcgacc ttacaataag tgattccaag gagggggagg gtgaatggga agttggggat   3060
gcatttcaga agtgtgtatc ttctttgaga agcctcacca taatcggaaa tcacggaata   3120
aataaagtga agagactgtc tggaagaaca gggttggagc atttcactct gttggaatca   3180
ctcaaacttt cagatataga agaccaggaa gatgagggcg aagacaacat catattctgg   3240
aaatcctttc ctcaaaacct ccgcagtttg agaattaaag actctgacaa aatgacaagt   3300
ttgcccatgg ggatgcagta cttaacctcc ctccaaaccc tctatctaca ccattgttat   3360
gaattgaatt cccttccaga atggataagc agcttatcat ctcttcaata cctgcgcata   3420
tactactgtc cagccctgaa atcactacca gaagcaatgc ggaacctcac ctcccttcag   3480
acacttggga tatcggattg tccagaccta gttaaaagat gcagaaaacc caacggcaag   3540
gactatccca aaattcaaca catcccctat tggagtatag aacatcaggt tataactagc   3600
ttgtaactaa cttgtaacta cctagtataa atacagtagt ttgtactatt ttacattcaa   3660
ttacacaatt aataaaatgt agactctcac tctctctctc taagccacga gctccaagct   3720
cgtcaatggc ttcccttctc tgttcttgct ttcttctttc ctcttcaatt cacaaattca   3780
acatggtatc agagcgggac gatccttgct cttcacttcc gcacaaaatt ttcgttcaat   3840
tcaacccatc aaattttttt tttcccccaa attttctcga attcggtcaa aattcgacga   3900
attagggatt caatttaccc tgatttcttc tgattccatt caatgattgt tcatttcgaa   3960
tcttgaatca aataattgtt gattctggat tccccaaatt ctagggttct tgaaggattt   4020
acaagaatct ggcattgctg atagattctt gaagcaattt gcgtctccgt gttcctcggt   4080
ggtcttgagt ttgtttccgt attcgctgct ctcatcttta ctggggattg tggtctgatt   4140
tcttggcttc ctctgtcgat gatgtgattg gtaatactta aaacccctct ctctctttcc   4200
gaaattattg atgctggttc gtcatttttt tttttggaat catctcagtt tatcgccgca   4260
atttgagttg ttgttgggta attgttgttg ctgccgatga tgttttgtga atttgagaat   4320
tgttagaatg attcttgttc aatcaatttg gttctcatac tctaatggaa gcctgttttg   4380
gagcgacgaa ttatgcaatt ctgagatttc ttttgatcct tatttctttt cttcacttga   4440
atttctggtg tttgtgagta attcttggtt aatgtttgat ctgggtagtt cttgggttta   4500
ctgaagacgt ttcttgaagg ttttgacaga aaagctgagg tttaattcca aaattcttct   4560
gtccaattac atttttattg ttgatggttc ttatgtgaga actagactga gttttttta    4620
tgaaattgtt tcgaccttca gatggattcg agagatttga gttcattttc tttgatgaat   4680
gtgttagaaa aggttttggt gcagtgacca ttttaaacca aatagagtta cataaatatt   4740
gggattcttt tctgggaatg tagttaggag ttgaaatctt ttggagctgc tttaccataa   4800
aacccagcct cagagtctgt taaccagtta ggaccgtgta aacatgatcc caggctgcat   4860
ttgcgttatc agatttgatt cagttttgga attgtggatt ttgagggttt aaaagcttac   4920
agttgctcct ggagaatggt gtgagcaata taggaattca gcactagtat tgcagaaaat   4980
gaagcttggt tgttgattgt tggcatgttt tgttgccatt gttttgggtt gatgttttcc   5040
ttttcttttg aatgttggca cgattcaaca tttctttcct gcaacagatt tggagttcag   5100
tacctgtata atcaggtcaa ttttgttcat ttttcccagc aacagatctg gagaatcaga   5160
acctgtaaaa nnnnnnnnnn nnnnnnnnnn nnnnnnnnnn nnnnnnnnnn nnnnnnnnnn   5220
nnnnnnnnnn acccaaagag gtcagttttc attgatccat tgtgatcatt cttttgatga   5280
```

-continued

```
gacccattga ggctcatttc ttcaaggcaa tattggaagt tgtagattga tatgagcagt   5340
tggtacaaca gcaacaaaag tggccagcat ctatgcttgt tcatgaggag ttcttggtgc   5400
agagttaatg aagagtctgt tttgaagctt tcaaactgaa gatgtttatc accatctcca   5460
gtttgagggg gggtattgga gtatagaaca tcaggttata actagcttgt aactaacttg   5520
taactaccta gtataaatac agtagtttgt acnnnnnnnn nnnnnnnnnn nnnnnnnnnn   5580
nnnnnnnnnn nnnnnnnnnn nnccacgagc tccaagctcg tcaatggctt cccttctctg   5640
ttcttgcttt cttctttcct cttcaattca caaattcaac atccccaaaa ttgtaagtca   5700
ttgcagaaag taatttattc atttatattt attttatgct tagaatgata tacgcagtcg   5760
tcctttggtt tcaaatcttg aatttggttt ttgttttctt tctttgtttc tttattcaac   5820
accagcccat ttatgattga ttcattaaaa aaaggatgga gttttatgga tttgaagaag   5880
acaacgaatt gagattcctg ggttttcttt tttgttgggg ttggatttca tgtatatgtt   5940
gctgattaaa tacgagactg atgatgatga tgtgtttatg ggttttaaat cagattaaat   6000
atatgggaaa tgcaagttaa tttgggatgc acataaggtg tttgctgaaa tgtctatgag   6060
aaatgttgtt tcttggactt agaatgatat acactgtcgt cctttggttt ccaatcttac   6120
atttggtttg tgttttctta gtttgtttct ttaatcaaca ccaacccgtt tttttaaac   6180
tacctgcaac tactaattta cgtttaccct gtatctcagg tactaaatga atattggtga   6240
ttttcagtta ctcaacacta gcttgatcct gaacgcaccc aaccttcagg ttagaatccg   6300
gcttactcat ccttttgtcc agttttcaag taattgtttt ggcaggatca attctctaat   6360
tgttgtacac cgtatattgc aatttatagt gactacagtt aatgaatgtt tacaaaaaat   6420
tagtcatgta aaaacttctt ctctgtccat tacataaact ctttttctct ttctaactta   6480
tcatgttcat gtctaaacaa ttaaacatgc tcacatcaat gttcatttaa gctaacttac   6540
ttctgtaaga gagcgagcta gttaaaaact cctttaactt tctgttttat actcaggaca   6600
tggattgatg caagcatgaa gaacttcggg aatttgctaa aactctacca aagcgatgag   6660
agtttggact ttatttcact tgaagtcagg gactgtcaac aaagccacag tgtgcatgtt   6720
ggctgtttca cttggacgat aaaaaggttt atttaattgt tttcctaagt gtatttggct   6780
tacaagcttt tacttttcac ttgaaagggt ttttcttgtt ttaagctttt cgaattagag   6840
ttttcggttg aagtaagagt agtcgtatta gtcttttacc taaggaagac tcttttttgt   6900
aattttcaga ctatgcaatt caagttttcg agtgttttct tgcttgtgtg attgtgagtt   6960
ggtgaattcg tctttcatac attttgagat tatcagaagc tttatgctcc accggtagtc   7020
tagtaccttt tctgttactg tgcagggaag taatctggta ccttctatat atatggaaaa   7080
acatacatta tacattatgc aaaattctta caggttagtt acttcctgga acttcattta   7140
cacttagttt tttttgttcc attccctcgg aatcaagtca ttccctctga gaaatatgta   7200
atgaacttct gtatgttgct gtttggttcc tgttttaatc ttcaattttc ttgtatagtt   7260
acagctgcat ttacaatgaa gtttaagcag acactctctt tatatagtgc ctctttctgg   7320
agcaccgtag agctgtctgt ggttgatcac catctgctgc cgagagattc agcaatcgcg   7380
tgtttgatca ggtaaaagtt tttatgtcaa tgtgtttttt tttccgtttg atcaatttat   7440
gtctgtattc agattcttat cttcttacag tagcataaca cattgtttct ttcatttatg   7500
taaactgttt caagattaca gagatgtatg cttcagtcga cattgatgat aacttaagat   7560
ggcattccta caacagttgc aggcgcattc taactccggc aattctagtt aggcaagagg   7620
agcattgcca atacctgcca cctctgggat ttactatacc agggttgaag tttatggaag   7680
```

acaccagcta tgcacaagcc ttcaaggggt catcctacat aacaagttga accaaccaat 7740
tgcttgttgg ttcagtggta attgaagctg aatttggtag ggatggcccg tgttcgatcc 7800
ccacaacaac aattgggagg ggactggaac ctatccacac agaactcgcc ctgaatccgg 7860
attagcccta agggtgaacg gggtgctaac accaaaaaaa aaaacataac aagttgaacc 7920
aaacatactt tgtttgaatt gaagatttag tgatttcatt tgatcgattg agatgtctta 7980
ttataagcgt atatgctctt ggatttggcc acttaggtgt tgtttgacaa ttggacatta 8040
actcgctttt atattttctt ttctcttagg aaaggtgatc ctgagaattt atattggaac 8100
actttttttt tctcactagc tttaaaaaag tgttctgtgt tacctgcaat tcaatttgat 8160
tatttttcac atagttttac ctgaaaaagt gttacctgaa aaagtgttac ctgaaaatca 8220
actgacataa gtttttgttt ggatccaatt aaggacacta gataaatcgg aataaataat 8280
caaccaatta agtacttcat aattaaatat gaagtgtatt attatcttat gcttgtgaca 8340
ttgaaggatg ttatgatatt ttaactcaat accttgcaaa atatactgg 8389

<210> SEQ ID NO 17
<211> LENGTH: 8953
<212> TYPE: DNA
<213> ORGANISM: Spinacia oleracea

<400> SEQUENCE: 17
tttgaagtta ggcttaactt gctcaccaat tcttaaatag actcgactta cactgaattt 60
attgtgtact atgtctagaa agtaaggtca acaactttct tctaaattat tttggcatgt 120
ttattagggt tattatgaaa aacatatcaa attggtgttg ttagttaggc ttgaataata 180
tgattttaag tcacgagact tttataaatt aggtaatttg atttaaaaaa ttgttacata 240
tctaagaaaa tggatgttaa atttatcagt caatgtataa acaataaaag tcaatatgta 300
tgtaaaaggg ttgctagata aaatctttgg ttttttggtc cacaactcca cactaagagg 360
aactccaatg cttagttaca aggtggtgta gttaaaaagt aactccaata gttaactaca 420
cggtattata gttaaatttg ccaactcaaa tttctaacta caatatattt aagctacaaa 480
gtttctcatt ggctgactac aatacgttgt agcgccttat aatattttat tcaatataca 540
attttattta ttttaccttt ttaacaattt ttttttgatc tacctgctgt cctgttcata 600
tgagctacac taatttgata gctgcttacg caattcttat atcaacggtt ggctacttgt 660
tcaaatattt ttattttttt acgagtaagt cattttatga tcattgaagt ggctctatta 720
ttattatcat gcaccgatta acgcaagaat aattaactcg gtacgaatta gtttcaaaat 780
aaaatccctc aaaaaaaaaa gtttcaaaat aaaattaaca gaaaaccaac cttctccggt 840
ttactgttgt tagagcatgg aattttccag taatcgcaga ccccaaatta tcttccagtt 900
gaatcaatcc ttgatttttg gatttgccag aaaactcctt gaattttagg gttcatattt 960
gatccgtaat tgggaaaatt ttcagcaatt gatcttccaa atcagcccta cttgtttcca 1020
gactgcaaat gaaaggtgcg aactttatac tgcattttgg ttttccatta gtgtaattta 1080
ttaagatgaa ctgcattttg caattgtttt attcgactac tcatttttaa atcaaattgc 1140
ttaattgcta gttagttttc ttatcatatt gccaaaaaaa attatttttg tttaattggt 1200
gaaaaagggt aaattatacc tagtgtacaa gattttcttg cacaccaccg ttaatttgtt 1260
gacacatcat caaacgtact gaaaaatgag aatgaaagac aataaatatg tcattttaac 1320
caatagaaaa acatgatgta gtaagatcct taattgatag ataaataatt aaatatcagt 1380

-continued ccattagttg aatattcaat gaaaatgtat ggtccaaaaa tggcgtttaa tagtcaatgt 1440
catgctttat ggggtggtgg agtactatgt gactgtgtgt ggacttggag aagactagag 1500
agtatgatta tcaacctatg gaccctcaaa atgaaaatga aaatgatgtt tacacgtgct 1560
atttgcacgg acttcaatgc aaatagtata aatttacggt caaagttttc attctaaagc 1620
gtaaataact ttcatgaatg gaggacggta gtataagtat aacgttatag cctaccattt 1680
tcttatcata ttcacataaa tttgttgctg aaatttgttt tacttggcta aaatactttt 1740
gttcttattg gcagataaac atcagtacgt ccattattgg ccaacttgct gagtccatta 1800
ttggccaact tgaacatata cctccaaaca ataatcaata atgtcgatta tgaagtttgt 1860
gaatgcaatt tattatcact ttcatttata aaatgactac ttgattaaca catacaatat 1920
tacctttctc caaacaccct ttcaattctg cttaatcttg ttttctcatc atctcttcat 1980
ctttctgaaa acacaaccca atggccgaaa tcggatactc ggtttgtgcg aaactcatcg 2040
aagtgattgg cagtgagctg atcaaagaga tttgtgacac atggggttac aaatctcttc 2100
ttgaggacct caacaaaact gtattgacgg tcaggaacgt tctcattcaa gccggggtga 2160
tgcgggagct tactagtgaa caacaaggtt tcattgcaga ccttaaagat gttgtttatg 2220
atgctgatga cttgttcgac aagttactca ctcgtgctga gcgaaaacag attgatggaa 2280
acgaaatctc tgaaaaggta cgtcgtttct tttcctctag taacaagatc ggtcaagctt 2340
actacatgtc tcgtaaggtt aaggaaatta agaagcagtt ggatgaaatt gttgataggc 2400
atacaaaatt tgggtttagt gccgagttta tacctgtttg tagggaaagg gggaacgaga 2460
gggaaacacg ttcatatata gatgtcaaga atattcttgg gagggataaa gataagaatg 2520
atatcataga taggttgctt aatcgtaatg gtaatgaagc ttgtagtttc ctgaccatag 2580
tgggagcggg aggattggga aaaactgctc ttgcacaact tgtgttcaat gatgaaaggg 2640
tcaaaattga gttccatgat ttgaggtatt gggtttgtgt ctctgatcaa gatgggggcc 2700
aatttgatgt gaaagaaatc ctttgtaaga ttttagaggt ggttactaag gagaaagttg 2760
ataatagttc cacattggaa ttggtacaaa gccaatttca agagaagtta agaggaaaga 2820
agtacttcct tgttcttgat gatgtatgga acgaagatcg tgagaagtgg cttcctttgg 2880
aagagttgtt aatgttgggt caagggggaa gcaaggttgt agtgaccgca cgttcagaga 2940
agacagcaaa tgtcataggg aaaagacatt tttatacact ggaatgtttg tcaccagatt 3000
attcatggag cttatttgaa atgtcggctt ttcagaaagg gcatgagcag gaaaaccatc 3060
acgaactagt tgatattggg aaaaagattg ttgaaaaatg ttataacaat ccacttgcta 3120
taacggtggt aggaagtctt ctttatggag aggagataag taagtggcgg tcatttgaaa 3180
tgagtgagtt ggccaaaatt ggcaatgggg ataataagat tttgccgata ttaaagctca 3240
gttaccataa tcttataccc tcgttgaaga gttgcttcag ttattgtgca gtgtttccca 3300
aggatcatga aataaagaag gagatgttga ttgatctttg gatagcacaa ggatacgttg 3360
tggcacttga tggaggtcaa agtatagaag atgctgccga agaacatttt gtaattttgt 3420
tacggagatg tttctttcaa gatgtaaaga aggatgaata tggtgatgtt gattctgtta 3480
aaatccacga cttgatgcac gatgtcgccc aagaagtggg gagggaggaa atatgtgtag 3540
tgaatgataa tacaaagaac ttgggtgata aaatccgtca tgtacatcgt gatgtcatta 3600
gatatgcaca aagagtctct ctgtgtagcc atagccataa gattcgttcg tatattggtg 3660
gtaattgtga aaaacgttgt gtggatacac taatagacaa gtggatgtgt cttaggatgt 3720
tggacttgtc atggtcggat gttaaaaatt tgcctaattc aataggtaaa ttgttgcact 3780

```
tgaggtgtct taacctgtct tataataaag atctgttgat actccctgat gcaattacaa   3840
gactgcataa tttgcagaca ctgcttttaa aagagtgcag aagtttaaag gagttgccaa   3900
aagatttttg caaattggtc aaactgaggc acttggattt aaggtgttct gatttgaagg   3960
agttgccaaa agatttttgc aaattggtca aactgaggca cttggattta aggtgttctg   4020
atttgaagga gttgccaaaa gatttttgca aattggtcaa actgaggcac ttggatttat   4080
ggggttgtga tgatttgatt ggtgtgccat tgggaatgga taggctaatt agtcttagag   4140
tactgccatt ctttgtggtg ggtaggaagg aacaaagtga tgatgatgag ctgaaagccc   4200
taaaaggcct caccgagata aaaggctcca ttcgtattag aatctattca aagtatagaa   4260
tagttgaagg catgaatgac acaggaggag ctgggtattt aaagagcatg aaacatctca   4320
cgggggttga tattacattt gatggtggat gtgttaaccc tgaagctgtg ttggcaaccc   4380
tagagccacc ttcaaatatc aagaggttag agatgtggca ttacagtggt acaacaattc   4440
cagtatgggg aagagcagag attaattggg caatctccct ctcacatctt gtcgacatcc   4500
agctttggtg ttgtagtaat ttgcaggaga tgccagtgct gagtaaactg cctcatttga   4560
aatcactgta tctttttaag ttttgtaagt tagagtacat ggagagtaga agcagcagca   4620
gtagcagtga cacagaagca gcaacaccag aattaccaac attcttccct tcccttgaaa   4680
aacttagact ttggtatctg gaaaagttga agggtttggg gaacaggaga ccgagtagtt   4740
ttccccgcct ctctgaattg gaaatctggg aatgcccaga tctaacgtgg tttcctccct   4800
gtccaagcct tgaaaaactt acactttggc gtctggacaa gttgaagggt ttggggaaca   4860
ggagatcgag tagttttccc cgcctctcta aattggtaat ctggaaatgc ccagatctaa   4920
cgtggtttcc tccctgtcca agccttgaaa aacttacact ttggcgtctg gacaagttga   4980
agggtttggg gaacaggaga tcgagtagtt ttccccgcct ctctgaattg gaaatcaaga   5040
aatgcccaga tctaacgtgg tttcctcctt gtccaagcct tgaaacgttg aaattggaaa   5100
aaaacaatga agcgttgcaa ataatagtaa aaataacaac aacaagaggt aaagaagaaa   5160
aagaagaaga caagaatgct ggtgttggaa attcacaaga tgatgacaat gtcaaattat   5220
ggacggtgga aatagacaat ctgggttatc tcaaatcact gcccacaaat tgtcttactc   5280
acctcaaaat aactggaata gattacaggg agggggagat tgaatcagat tccgtggagg   5340
aggagattga attggaagtt ggggaggcat ttcagaagtg tgcatcttct ttgagaagcc   5400
tcatcataat cggaaatcac ggaataaata aagtgatgag actgtctgga agaacagggt   5460
tggagcattt cactctgttg gactcactca aactttcaaa tatagaagac caggaagatg   5520
agggcgaaga caacatcata ttctggaaat cctttcctca aaaccttcgc agtttgagaa   5580
ttaaagactc tgacaaaatg acaagtttgc ccatggggat gcagtactta acctccctcc   5640
aaaccctcga actatcatat tgtgatgaat tgaattccct tccagaatgg ataagcagct   5700
tatcatctct tcaatacctg cgcatataca actgtccagc cctgaaatca ctaccagaag   5760
caatgcggaa cctcacctcc cttcagacac ttgggatatc ggattgtcca gacctagtta   5820
aaatatgcag aaaacccaac ggcgaggact atcccaaaat tcaacacatc cccggcattg   5880
taagtgattg cagaaagtat tttattcatt tatatttatt ttatgcttag aatgatatac   5940
gccgtcgtcc ttaggtttcc aatcttgaat ttggttttg ttttctttct ttgtttcttt   6000
attcaacacc agcccattta tgattgattc attaaaaaaa ggaagaagac aacgaattga   6060
gattcctggg gtttttttt cgttggggtt ggttttcatg tatatgttgc tgattaaata   6120
```

```
cgagactgat gatgattatg tgtttatggg ttttaaatca gattaaatat atggaaaatg   6180
taagttagtt ggggatgcac ataaggtgtt tgatgaaatg tcttttagaa atgttgtttc   6240
ttggacttag aatgatatac actgtcgtcc tttggtttcc aatcttacat ttggtttgtg   6300
ttttcttagt ttgtttcttt aatcaacacc aacccatttt ttttaaacta cctgcaacta   6360
ctaatttacg tttacccttt atctcaggta ctaaatgaat attggtgatt ttcagttact   6420
caacactagc ttgatcctga acgcacccaa ccttcaggtt agaatccggc ttactcatcc   6480
ttttgtccag ttttcaagta attgttttgg caggatcaat tctctaattg ttgtacaccg   6540
tatattgcaa tttatagtga ctacagttaa tgaatgttta caaaaaatta gtcatgtaaa   6600
aacttcttct ctgtccatta cataaactct ttttctcttt ctaacttatc atgttcatgt   6660
ctaaaaaatt aaacatgctc acatcaatgt tcatttaagc taacttactt ctgtaagaga   6720
gcgagctagt taaaaactcc tttaactttc tgttttatac tcaggagtca ggaaggatat   6780
ggattgatgc agctttcaca ggccaagtaa tataatgttc tttatcaatc actcaatacc   6840
tggagattgt ttgaacacat aattcacctc tttttttcca tctcaaattg cagcctttta   6900
ctgggatttg aatgacagca aacatttgat tgtcacgagg attgatctaa ctggtgaatg   6960
ttgtgatcac catattggtc tttctcattc aaacaaactt gcataccgtt cttttgaagt   7020
ttgaagacaa gcaggcgata atcaactcag gtcgaagctc atgtgcagga gagaatagaa   7080
tatagaggag attattttta aaagaaacgc tcaaaggtat tgtagcacct ttcctatttg   7140
ctactgcagt gatgttttta tttcttgttt gcagcgcttg tttctcatat ttcaacctac   7200
ttttagaaaa aaaaacatct ccgaacataa ccaaaaataa agttccctta tcagtgcttt   7260
ccctgctttc ttctgaacaa catatacaat tataaaccct ttttctctct tacctttgtt   7320
attcttcctt gcttcattga gataacactc tcctgttttt gttttgttgt tagtcattac   7380
atggatatat caaggacaac agttctgtag tccgtcaact gtggttagga aggctaaact   7440
ggagcacaat aaccccatgt caattgaata gtaaaggtgt gctatatcag tttcgtttgg   7500
cttggcttgt ttacctgaaa aatggctggt tatttatcct tgtctctttc tatgacgtgc   7560
agtggcttgt taatgtgtct cggacaacaa ttcctcactt tccaagttcc atacacgctg   7620
atgtaactat cttctgcagt ctgttctttc atttttgcca cgtgctctaa ttataacttt   7680
ttgtactcaa taatcaactc cttgtcccgg tatttgcaga gactacttaa acaggtaaag   7740
tgacaatcct ggcgaagttg tctgtttctt agctctgatc ccatcattca ggtaagatta   7800
agtagttaag aagaaacatt tatttttacc taatttgaat gaacttgtgt aactgcttgc   7860
ttcctgcatt aaataagaaa tttctgctgc atatgtgaca gttacatcca caaaaaagtt   7920
ggaggtttgt tcagggattg gaaatgaagg tacttcagaa tttgtttatg aatgctccag   7980
acttcagagt ctttaatgga aaattcgagt cactaaaaat acattattcc tatcatcaga   8040
gctttcaagt tcctctatac aaggtcaact gagttcctct ttgcctcttg tttaattgta   8100
tttacttgta ccttaattat aatctgtata ttgttttagt taagttctaa aacaggttac   8160
tattcatcat ttgtgcagca tattgctgga atcaagaatc tagtgcttct tcttcctgac   8220
ttcactgtca aaatagcagt tcccatgctg gaaataagcg cgctagcaat gtaattgatg   8280
acatggatgt tgctgcttct gagttttgat cataaaaagc tgttatgtgt ttcttgaatg   8340
taatgtagaa gaggagaaaa ctgaaaactc ttggcaaaaa cgtgaaattg cagtgcctcg   8400
gggtgggagg gatcacccgg attcagttca gacgatactt ttttcaaccc ggtttgttcc   8460
ggttttcagc ttcaggtttt ccttgtactt ttgggggaca cagacaaggc tacttcatgt   8520
```

```
ttgagaaacc taattgaggc tatcttgtag caaatgcaca ccacactctt tctctcttct   8580

ctccttttttt caccttccat ttgtaaaaat cctcctttaa aggttaataa aaaaaaagct   8640

ccaagtctcg tagggtggat gtaggtcaca ttgaccgaac cacggtaaac tctttgtgtt   8700

ctttcttctc tctttgtttc tcatttttac ggcaagtgtt tatggttaac catgcatctt   8760

agaatagctt aaggcattaa cataataaca tcaatgttct ccaaagattc accttacttg   8820

ttgtacataa tcacaatgtt aagcctatga aggtagaatg ctctcatgat ttggtttaac   8880

caaaaaataa actctaaaat aatacggagt aataaaaatt ggccataaac taattacaaa   8940

gtttgatttt tgt                                                      8953
```

<210> SEQ ID NO 18
<211> LENGTH: 10415
<212> TYPE: DNA
<213> ORGANISM: Spinacia oleracea

<400> SEQUENCE: 18

```
ggcttaactt gctcaccaat tcttaaatag actcgactta cactgaattt attgtgtact     60

atgtctagaa agtaaggtca acaactttct tctaaattat tttggcatgt ttattagggt    120

tattatgaaa aacatatcaa attggtgttg ttagttaggc ttgaataata tgattttaag    180

tcacgagact tttataaatt aggtaatttg atttaaaaaa ttgttacata tctaagaaaa    240

tggatgttaa atttatcagt caatgtataa acaataaaag tcaatatgta tgtaaaaggg    300

ttgctagata aaatctttgg ttttttggtc cacaactcca cactaagagg aactccaatg    360

cttagttaca aggtggtgta gttaaaaagt aactccaata gttaactaca cggtattata    420

gttaaatttg ccaactcaaa tttctaacta caatatattt aagctacaaa gtttctcatt    480

ggctgactac aatacgttgt agcgccttat aatattttat tcaatataca attttattta    540

ttttaccttt ttaacaattt ttttttgatc tacctgctgt cctgttcata tgagctacac    600

taatttgata gctgcttacg caattcttat atcaacggtt ggctacttgt tcaaatattt    660

ttattttttt acgagtaagt cattttatga tcattgaagt ggctctatta ttattatcat    720

gcaccgatta acgcaagaat aattaactcg gtacgaatta gtttcaaaat aaaatccctc    780

aaaaaaaaaa gtttcaaaat aaaattaaca gaaaaccaac cttctccggt ttactgttgt    840

tagagcatgg aattttccag taatcgcaga ccccaaatta tcttccagtt gaatcaatcc    900

ttgatttttg gatttgccag aaaactcctt gaattttagg gttcatattt gatccgtaat    960

tgggaaaatt ttcagcaatt gatcttccaa atcagcccta cttgtttcca gactgcaaat   1020

gaaaggtgcg aactttatac tgcattttgg ttttccatta gtgtaattta gtgtaattta   1080

ttaagataaa ctgcattttg caattgtttt attcgactac tcatttttaa atcaaattgc   1140

ttaattgcta gttagttttc ttatcatatt gccaaaaaaa attatttttg tttaattggt   1200

gaaaaagggt aaattatacc tagtgtacaa gattttcttg cacaccaccg ttaatttgtt   1260

gacacatcat caaacgtact gaaaaatgag aatgaaagac aataaatatg tcattttaac   1320

caatagaaaa acatgatgta gtaagatcct taattgatag ataaataatt aaatatcagt   1380

ccattagttg aatattcaat gaaaatgtat ggtccaaaaa tggcgtttaa tagtcaatgt   1440

catgctttat ggggtggtgg agtactatgt gactgtgtgt ggacttggag aagactagag   1500

agtatgatta tcaacctatg gaccctcaaa atgaaaatga aaatgatgtt tacacgtgct   1560

atttgcacgg acttcaatgc aaatagtata aatttacggt caaagttttc attctaaagc   1620
```

-continued

```
gtaaataact ttcatgaatg gaggacggta gtataagtat aacgttatag cctaccattt   1680
tcttatcata ttcacataaa tttgttgctg aaatttgttt tacttggcta aaatactttt   1740
gttcttattg gcagataaac atcagtacgt ccattattgg ccaacttgct gagtccatta   1800
ttggccaact tgaacatata cctccaaaca ataatcaata atgtcgatta tgaagtttgt   1860
gaatgcaatt tattatcact ttcatttata aaatgactac ttgattaaca catacaatat   1920
tacctttctc caaacaccct ttcaattctg cttaatcttg ttttctcatc atctcttcat   1980
ctttctgaaa acacaaccca atggccgaaa tcggatactc ggtttgtgcg aaactcatcg   2040
aagtgattgg cagtgagctg atcaaagaga tttgtgacac atggggttac aaatctcttc   2100
ttgaggacct caacaaaact gtattgacgg tcaggaacgt tctcattcaa gccggggtga   2160
tgcgggagct tactagtgaa caacaaggtt tcattgcaga ccttaaagat gttgtttatg   2220
atgctgatga cttgttcgac aagttactca ctcgtgctga gcgaaaacag attgatggaa   2280
acgaaatctc tgaaaaggta cgtcgtttct tttcctctag taacaagatc ggtcaagctt   2340
actacatgtc tcgtaaggtt aaggaaatta agaagcagtt ggatgaaatt gttgataggc   2400
atacaaaatt tgggtttagt gccgagttta tacctgtttg tagggaaagg gggaacgaga   2460
gggaaacacg ttcatatata gatgtcaaga atattcttgg gagggataaa gataagaatg   2520
atatcataga taggttgctt aatcgtaatg gtaatgaagc ttgtagtttc ctgaccatag   2580
tgggagcggg aggattggga aaaactgctc ttgcacaact tgtgttcaat gatgaaaggg   2640
tcaaaattga gttccatgat ttgaggtatt gggtttgtgt ctctgatcaa gatgggggcc   2700
aatttgatgt gaaagaaatc ctttgtaaga ttttagaggt ggttactaag gagaaagttg   2760
ataatagttc cacattggaa ttggtacaaa gccaatttca agagaagtta agaggaaaga   2820
agtacttcct tgttcttgat gatgtatgga acgaagatcg tgagaagtgg cttcctttgg   2880
aagagttgtt aatgttgggt caagggggaa gcaaggttgt agtgaccgca cgttcagaga   2940
agacagcaaa tgtcataggg aaaagacatt tttatacact ggaatgtttg tcaccagatt   3000
attcatggag cttatttgaa atgtcggctt ttcagaaagg gcatgagcag gaaaaccatc   3060
acgaactagt tgatattggg aaaaagattg ttgaaaaatg ttataacaat ccacttgcta   3120
taacggtggt aggaagtctt ctttatggag aggagataag taagtggcgg tcatttgaaa   3180
tgagtgagtt ggccaaaatt ggcaatgggg ataataagat tttgccgata ttaaagctca   3240
gttaccataa tcttataccc tcgttgaaga gttgcttcag ttattgtgca gtgtttccca   3300
aggatcatga aataaagaag gagatgttga ttgatctttg gatagcacaa ggatacgttg   3360
tggcacttga tggaggtcaa agtatagaag atgctgccga agaacatttt gtaattttgt   3420
tacggagatg tttctttcaa gatgtaaaga aggatgaata tggtgatgtt gattctgtta   3480
aaatccacga cttgatgcac gatgtcgccc aagaagtggg gagggaggaa atatgtgtag   3540
tgaatgataa tacaaagaac ttgggtgata aaatccgtca tgtacatggt gatgtcaata   3600
gatatgcaca aagagtctct ctgtgtagcc atagccataa gattcgttcg tatattggtg   3660
gtgattgtga aaaacgttgt gtggatacac taatagacaa gtggatgtgt cttaggatgt   3720
tggacttgtc atggtcggat gttaaaaatt tgcctaattc aataggtaaa ttgttgcact   3780
tgaggtatct taacctgtca gataatagaa atctaaagat acttcctgat gcaattacaa   3840
gactgcataa tttgcagaca ctgcttttag aagattgcag aagtttaaag gagttgccaa   3900
aagatttttg caaattggtc aaactgagac acttggattt atggggttgt gatgatttga   3960
ttggtatgcc atttggaatg gataagctaa ctagtcttag aatactacca aacattgtgg   4020
```

tgggtaggaa ggaacaaagt gttgatgatg agctgaaagc ccttaaaggc ctcaccgaga 4080
taaaaggcga cattgatatc aaaatctgtg aaaattatag aatagttgaa ggcatgaatg 4140
acacaggagg agctgggtat ttgaagagca tgaaacatct cagggagatt ggtattacat 4200
ttgatggtgg atgtgttaac cctgaagctg tgttggcaac cctagagcca ccttcaaata 4260
tcaagagctt atctatagat aattacgatg gtacaacaat tccagtatgg ggaagagcag 4320
agattaattg ggcaatctcc ctctcacatc ttgtcgacat cacgcttgaa gattgttaca 4380
atttgcagga gatgccagtg ctgagtaaac tgcctcattt gaaatcactg tatcttttta 4440
agttttgtaa gttagagtac atggagagta gaagcagcag cagtagcagt gacacagaag 4500
cagcaacacc agaattacca acattcttcc cttcccttga aaaacttaga ctttggtatc 4560
tggaaaagtt gaagggtttg gggaacagga gaccgagtag ttttccccgc ctctctgaat 4620
tggaaatctg ggaatgccca gatctaacgt ggtttcctcc ttgtccaagc cttaaaacgt 4680
tgaaattgga aaaaaacaat gaagcgttgc aaataatagt aaaaataaca acaacaagag 4740
gtaaagaaga aaaagaagaa gacaagaatg ctggtgttgg aaattcacaa gatgatgaca 4800
atgtcaaatt acggaaggtg gaaatagaca atgtgagtta tctcaaatca ctgcccacaa 4860
attgtcttac tcacctcaaa ataactggaa tagattacag ggagggggag attgaatcag 4920
attccgtgga ggaggagatt gaattggaag ttggggaggc atttcagaag tgtgcatctt 4980
ctttgagaag cctcatcata atcggaaatc acggaataaa taaagtgatg agactgtctg 5040
gaagaacagg gttggagcat ttcactctgt tggactcact caaattttca aagatagaag 5100
accaggaaga tgagggcgaa gacaacatca tattctggaa atcctttcct caaaacctcc 5160
gcagtttgga aattaaaggc tcttgcaaaa tgacaagttt gcccatgggg atgcagtact 5220
taacctccct ccaaaccctc gaactatcat attgtgatga attgaattcc cttccagaat 5280
ggataagcag cttatcatct cttcaatacc tgcgcatata caactgtcca gccctgaaat 5340
cactaccaga agcaatgcgg aacctcacct cccttcagac acttgggata tcggattgtc 5400
cagacctagt taaaatatgc agaaaaccca acggcgagga ctatcccaaa attcaacaca 5460
tccccggcat tgtaagtgat tgcagaaagt attttattca tttatattta ttttatgctt 5520
agaatgatat acgccgtcgt ccttaggttt ccaatcttga atttggtttt tgttttcttt 5580
ctttgtttct ttattcaaca ccagcccatt tatgattgat tcattaaaaa aaggaagaag 5640
acaacgaatt gagattcctg gggttttttt ttcgttgggg ttggttttca tgtatatgtt 5700
gctgattaaa tacgagactg atgatgatta tgtgtttatg ggttttaaat cagattaaat 5760
atatggaaaa tgtaagttag ttggggatgc acataaggtg tttgatgaaa tgtctattag 5820
aaatgttgtt tcttggactt agaatgatat acactgtcgt cctttggttt ccaatcttac 5880
atttggtttg tgttttctta gtttgtttct ttaatcaaca ccaacccatt ttttttaaac 5940
tacctgcaac tactaattta cgtttaccct ttatctcagg tactaaatga atattggtga 6000
ttttcagtta ctcaacacta gcttgatcct gaacgcaccc aaccttcagg ttagaatccg 6060
gcttactcat ccttttgtcc agttttcaag taattgtttt ggcaggatca attctctaat 6120
tgttgtacac cgtatattgc aatttatagt gactacagtt aatgaatgtt tacaaaaaat 6180
tagtcatgta aaaacttctt ctctgtccat tacataaact cattttctct ttctaactta 6240
tcatgttcat gtttaaaaaa ttaaacatgc tcacatcatt gttcatttga gctaacttac 6300
ttctgtaaga gagcgagcta gttaacaact cctttaactt tctgttttat actcaggaca 6360

-continued

```
tggattgatg caagcatgaa gaacttctgg aatttgctaa aactctacca aagcgatgag   6420
agtttggact ttgtttcact tgaagtcagg gattgtcaac aaagccacag tgtgcatgtt   6480
ggctgtgtca cttggacgat aaaaaggttt atttaattgt tttcctaagt gtatttggct   6540
tacaagcttt tacttttcac ttgaaagggt ttttttgtt ttaagctttt tgaattagag   6600
tttcggttga agtaagagta gtcgtattag tcttttactt tgcaggagtc tatgcctata   6660
taaggtaaga ctcgtatttg taattttcag attatgcaat tcaagttttc gagtgttttc   6720
ttaaaaaaac atatcatacc tgtgtgtagc ataaagataa attctgatgc tgtgcttctt   6780
gttatggctc acattggttt tcattgtttg gattgtttca cagggaagca gagaatacct   6840
ggaacctatg aaggacgcta tatctatagc agctttcaca ggccaagtaa tataatgttc   6900
tttatcaatc actcaatacc tggagattgt ttgaacacat aattcacctc tttttttcca   6960
tctcaaattg cagactttta ctgggatttg aatgacagca aacatttgat tgtcacgagg   7020
attgatctaa ctggtgaatg ttgtgatcac catattggtc tttctcattc aaacaaactt   7080
gcataccgtt cttttgaatt ttgaagacaa gcaggcgata atcaactcag gtcgaagctc   7140
atgtgcagga gagaatcgaa tatagaggag attattttta aaagaaacgc tcaaaggtat   7200
tgtagcacct ttcctatttg ctactgcagt gatgttttta tttcttgttt gcagcgcttg   7260
tttctcatat ttcaacctac ttttagaaaa aaaaacatct ccgaacataa ccaaaaataa   7320
agttccctta tcagtgcttt ccctgctttc ttctaaacaa catatacaat tataaaccct   7380
ttttctctct tacctttgtt attcttcctt gcttcattga gataacactc tcctgttttt   7440
gttttgttgt tagtcattac atggatatat caaggacaac agttctgtag tccgtcaact   7500
gtggttagga aggctaaact ggagcacaat aaccccatgt caattgaata gtaaaggtgt   7560
gctatatcag tttcgtttgg cttggcttgt ttacctgaaa aatggctggt tatttatcct   7620
tgtctctttc tatgacgtgc agtggcttgt taatgtgtct cggacaacaa ttcctcactt   7680
tccaagttcc atacacgctg atgtaactat cttctgcagt ctgttctttc atttttgcca   7740
cgtgctctaa ttataacttt ttgtactcaa taatcaactc cttgtcccgg tatttgcaga   7800
gactacttaa acaggtaaag tgacaatcct ggcgaagttg tctgtttctt agctctgaac   7860
ccatcattca ggtaagatta agtatttaag aagaaatttt gtttttacct aaaatgaatg   7920
atcttgtgta actgcttgct tcttgcatta aataagaact ttctgctgca tatgtgacag   7980
ttacatccac aaaaaagttg gaggtttgtt cagggattgg aaatgaaggt acttcagaat   8040
tcctggaatg tttatgaatg ctccagactt cagagtcttt aatggaaaat tcgagtcact   8100
aaaaatacat tattcctatc atcagagctt tcaagttcct ctatacaagg tcaactgagt   8160
tcctctttgc ctcttgttta attgtattta cttgtacctt aactataatc tgtatattgt   8220
tttagttaag ttctaaaaca ggttactatt catcatttgt gcagcatatt gctggaatca   8280
agaatctagt gcttcttctt cctgacttca ctgtaaacct taatctgttg ctgaattttt   8340
ttaatcgaaa gactttctgt ttaattatat tctaaatcta ttacgatgtc ttaaacagct   8400
tgaaaatgac acaaaatata atagctccac acctagataa gaccctcaaa tggaaatgtc   8460
agtaacttgt tacatagaga caatatgctg atatatagtt ccacatagat cactcttctt   8520
tactaaaaac acattatttt tataacctgg acattagtcg agagggggat gtcacgtcat   8580
gagaaatctt catcagagcc ttcattactc ggaattttat tttctcccaa agctggtgaa   8640
tttgccatag atgttgctgt acttcattct tatgatgttc aggtgacttg tcaggcctca   8700
ctgcctcaga ctaacactct cgtgtttctt ttctgttgtt agtcatgaca tggatacatc   8760
```

```
acgaacaaca gttctgtagt ccagcaactg tggtgtagga agactaaact ggagcacaat   8820
aactccatgt caattgaatg gtaaagatgt gctatctcag tttcttttgg cttgtttaca   8880
tgaaaaacgg ctcgtttttt atctgtgtct ttctatgacg ttcaggtgca gtggcttgtt   8940
aatgtgtctc agacaacaat tttctcactt tccaagttcc atacatgctg atgtaactat   9000
cttctgcact ctgttctttc attttgcctt ttgctctaat tataactttt tgtactcaat   9060
aatcaactcc ttgtcgcgta tttgcaggga ttacttaaat aggtatagtg acaatcctgg   9120
tgaagttgtc tgtttcttag ctctgatccc atcattcagg taagattaag tagttaagaa   9180
gaaacattta tttttaccta atttgaatga acttgtgtta actgcttgct tcctgcatta   9240
aataagaact ttctgctgca tatgtgacag ttacatccac aaaaaagttg gaggtttgtt   9300
cagggattgg aaatgaaggt acttcagaat tcctggaatg tttatgaatg ctccagactt   9360
cagagtcttt aatggaaaat tcgagtcact aaaaatacat tattcctatc atcagagctt   9420
tcaagttcct ctatacaagg tcaactgagt tcctctttgc ctcttgttta attgtattta   9480
ctcgtacctt aattataatc tgtatattgt tttagttaag ttctaaaaca ggttactatt   9540
catcatttgt gcagcatatt gctggaatca agaatctagt gcttcatctt cctgacttca   9600
ctgtcaaaat agtagttccc atgctggaaa taagcgcgct agcaatgtaa ttgatgacat   9660
ggatgttgct gcttctgagt tttgatcata aaaagctgtt atgtgtttct tgaatgtaat   9720
gaaggagagg agaaaactga aaactcttgg caaaaacgtg aaattgcagt gcctcggggt   9780
ggtagggatc acccggattc agttcagacg atactttttt caacccggtt tgttccggtt   9840
ttcagcttcg ggttttcctt gtacttttgg ggcacacata caaggctact tcatgtttga   9900
gaaacctaat tgaggctatc ttgtagcaaa tgcacaccac actctttctc tcttctctcc   9960
ttttttcacc ttccatttgt aaaaatcctc ttttaaaggt taataaaaaa aagcttcaag  10020
tctcgtaggg tggatgtagg tcacattgac cgaaccacgg taaactcttt gtgttctttc  10080
ttctctcttt gtttctcatt tttacggcaa gtgtttatgg ttaaccatgc atcttagaat  10140
agcttaaggc attaacataa taacatcaat gttctccaaa gattcacctt acttgttgta  10200
cataatcaca atgttaagcc tatgaaggta gaatgctctc atgatttggt ttaaccaaaa  10260
aataaactct aaaataatac ggagtaataa aaattggcca taaactaatt acaaagtttg  10320
atttttgtat agggtatctt gtacttgtga taaaaaaaat taaaaaaaaa aaatttactt  10380
atttcttcta tttttacttg ttacactttt ctaca                             10415
```

<210> SEQ ID NO 19
<211> LENGTH: 9116
<212> TYPE: DNA
<213> ORGANISM: Spinacia oleracea

<400> SEQUENCE: 19

```
tttgaagtta ggcttaactt gctcaccaat tcttaaatag actcgactta cactgaattt     60
attgtgtact atgtctagaa agtaaggtca acaactttct tctaaattat tttggcatgt    120
ttattagggt tattatgaaa aacatatcaa attggtgttg ttagttaggc ttgaataata    180
tgattttaag tcacgagact tttataaatt aggtaatttg atttaaaaaa ttgttacata    240
tctaagaaaa tggatgttaa atttatcagt caatgtataa acaataaaag tcaatatgta    300
tgtaaaaggg ttgctagata aaatctttgg ttttttggtc cacaactcca cactaagagg    360
aactccaatg cttagttaca aggtggtgta gttaaaaagt aactccaata gttaactaca    420
```

-continued

```
cggtattata gttaaatttg ccaactcaaa tttctaacta caatatattt aagctacaaa    480
gtttctcatt ggctgactac aatacgttgt agcgccttat aatattttat tcaatataca    540
attttattta ttttaccttt ttaacaattt ttttttgatc tacctgctgt cctgttcata    600
tgagctacac taatttgata gctgcttacg caattcttat atcaacggtt ggctacttgt    660
tcaaatattt ttattttttt acgagtaagt cattttatga tcattgaagt ggctctatta    720
ttattatcat gcaccgatta acgcaagaat aattaactcg gtacgaatta gtttcaaaat    780
aaaatccctc aaaaaaaaaa gtttcaaaat aaaattaaca gaaaaccaac cttctccggt    840
ttactgttgt tagagcatgg aattttccag taatcgcaga ccccaaatta tcttccagtt    900
gaatcaatcc ttgatttttg gatttgccag aaaactcctt gaattttagg gttcatattt    960
gatccgtaat tgggaaaatt ttcagcaatt gatcttccaa atcagcccta cttgtttcca   1020
gactgcaaat gaaaggtgcg aactttatac tgcattttgg ttttccatta gtgtaattta   1080
ttaagatgaa ctgcattttg caattgtttt attcgactac tcatttttaa atcaaattgc   1140
ttaattgcta gttagttttc ttatcatatt gccaaaaaaa attatttttg tttaattggt   1200
gaaaaagggt aaattatacc tagtgtacaa gatttcttg cacaccaccg ttaatttgtt   1260
gacacatcat caaacgtact gaaaaatgag aatgaaagac aataaatatg tcattttaac   1320
caatagaaaa acatgatgta gtaagatcct taattgatag ataaataatt aaatatcagt   1380
ccattagttg aatattcaat gaaaatgtat ggtccaaaaa tggcgtttaa tagtcaatgt   1440
catgctttat ggggtggtgg agtactatgt gactgtgtgt ggacttggag aagactagag   1500
agtatgatta tcaacctatg gaccctcaaa atgaaaatga aaatgatgtt tacacgtgct   1560
atttgcacgg acttcaatgc aaatagtata aatttacggt caaagttttc attctaaagc   1620
gtaaataact ttcatgaatg gaggacggta gtataagtat aacgttatag cctacaattt   1680
tcttatcata ttcatataaa tttgtttcta aaagttgttt tacttggcta aaatactttt   1740
gttcttattg gcagataaac atcagtacgt ccattattgg ccaacttgct gagtccatta   1800
ttggccaact tgaacatata cctccaaaca ataatcaata atgtcgatta tgaagtttgt   1860
gaatgcaatt tattatcact ttcatttata aaatgactac ttgattaaca catacaatat   1920
tacctttctc caaacaccct ttcaattctg cttaatcttg ttttctcatc atctcttcat   1980
ctttctgaaa acacaaccca atggccgaaa tcggatactc ggtttgtgcg aaactcatcg   2040
aagtgattgg cagtgagctg atcaaagaga tttgtgacac atggggttac aaatctcttc   2100
ttgaggacct caacaaaact gtattgacgg tcaggaacgt tctcattcaa gccggggtga   2160
tgcgggagct tactagtgaa caacaaggtt tcattgcaga ccttaaagat gttgtttatg   2220
atgctgatga cttgttcgac aagttactca ctcgtgctga gcgaaaacag attgatggaa   2280
acgaaatctc tgaaaaggta cgtcgtttct tttcctctag taacaagatc ggtcaagctt   2340
actacatgtc tcgtaaggtt aaggaaatta agaagcagtt ggatgaaatt gttgataggc   2400
atacaaaatt tgggtttagt gctgagttta tacctgtttg taggggaagg ggaaacgaga   2460
gggaaacacg ttcatatata gatgtcaaga atattcttgg gagggataaa gataagaatg   2520
atatcataga taggttgctt aatcgtaatg gtaatgaagc ttgtagtttc ctgaccatag   2580
tgggagcggg aggattggga aaaactgctc ttgcacaact tgtgttcaat gatgaaaggg   2640
tcaaaattga gttccatgat ttgaggtatt gggtttgtgt ctctgatcaa gatgggggcc   2700
aatttgatgt gaaagaaatc ctttgtaaga ttttagaggt ggttactaag gagaaagttg   2760
ataatagttc cacattggaa ttggtacaaa gccaatttca agagaagtta agaggaaaga   2820
```

```
agtacttcct tgttcttgat gatgtatgga acgaggatcg tgagaagtgg cttcctttgg   2880
aagagttgtt aatgttgggt caagggggaa gcaaggttgt agtgaccaca cgttcagaga   2940
agacagcaaa tgtcataggg aaaagacatt tttatacact ggaatgtttg tcaccagatt   3000
attcatggag cttatttgaa atgtcggctt ttcagaaagg gcatgagcag gaaaaccatc   3060
acgaactagt tgatattggg aaaaagattg ttgaaaaatg ttataacaat ccacttgcta   3120
taacggtggt aggaagtctt ctttatggag aggagataag taagtggcgg tcatttgaaa   3180
tgagtgagtt ggccaaaatt ggcaatgggg ataataagat tttgccgata ttaaagctca   3240
gttaccataa tcttataccc tcgttgaaga gttgttttag ttattgtgca gtgtttccca   3300
aggatcatga aataaagaag gagatgttga ttgaactttg gatggcacaa ggatatgttg   3360
tgccgttgga tggaggtcaa agtatagaag atgctgccga ggaacatttt gtaattttgt   3420
tacgaaggtg tttctttcaa gatgtaaaga aggataaata tggtgatgtt gattctgtta   3480
aaatccacga cttgatgcac gatgtcgccc aagaagtggg gagggaggaa ttatgtgtag   3540
tgaatgataa tacaaagaac ttgggtgata aaatccgtca tgtacatcgt gatgtcatta   3600
gatatgcaca aagagtctct ctgtgtagcc atagccataa gattcgttcg tatattggtg   3660
gtaattgtga aaaacgttgt gtggatacac taatagacaa gtggatgtgt cttaggatgt   3720
tggacttgtc aaggtcggat gttaaaaatt tgcctaattc aataggtaaa ttgttgcact   3780
tgaggtatct taacctgtca gataatagaa atctaaagat acttcctgat gcaattacaa   3840
gactgcataa tttgcagaca ctacttttag aacgttgcga aagtttaaag gagttgccaa   3900
aagatttttg caaattggtc aaactgagac acttggattt aaggggatgt ttttctttga   3960
ttggtatgcc attgggaatg gataggctaa ttagtcttag aatactacca aacattgtgg   4020
tgggtaggaa ggaacaaagt gatgatgatg agctgaaagc cctaaaaggc ctcaccgaga   4080
taaaaggctc cattcgtatt agaatctatt caaagtatag aatagttgaa ggcatgaatg   4140
acacaggagg agctgggtat ttaaagagca tgaaacatct cacgggggtt gatattacat   4200
ttgatggtgg atgtgttaac cctgaagctg tgttggcaac cctagagcca ccttcaaata   4260
tcaagaggtt agagatgtgg cattacagtg gtacaacaat tccagtatgg ggaagagcag   4320
agattaattg ggcaatctcc ctctcacatc ttgtcgacat ccagctttgg cattgtcgta   4380
atttgcagga gatgccagtg ctgagtaaac tgcctcattt gaaatcactg gaactttata   4440
atttgattag tttagagtac atggagagca caagcagaag cagtagcagt gacacagaag   4500
cagcaacacc agaattacca acattcttcc cttcccttga aaaacttaca ctttggcgtc   4560
tggacaagtt gaagggtttt gggaacagga gatcgagtag ttttccccgc ctctctaaat   4620
tggaaatctg ggaatgccca gatctaacgt ggtttcctcc ttgtccaagc cttaaaacgt   4680
tgaaattgga aaaaaacaat gaagcgttgc aaataatagt aaaaataaca acaacaagag   4740
gtaaagaaga aaaagaagaa gacaagaatg ctggtgttgg aaattcacaa gatgatgaca   4800
atgtcaaatt acggaaggtg gaaatagaca atgtgagtta tctcaaatca ctgcccacaa   4860
attgtcttac tcacctcaaa ataactggaa tagattacag ggagggggag attgaatcag   4920
attccgtgga ggaggagatt gaattggaag ttggggaggc atttcagaag tgtgcatctt   4980
ctttgagaag cctcatcata atcggaaatc acggaataaa taaagtgatg agactgtctg   5040
gaagaacagg gttggagcat ttcactctgt tggactcact cgaactttca aagatagaag   5100
accaggaaga tgagggcgaa gacaacatca tattctggaa atcctttcct caaaacctcc   5160
```

```
gcagtttgga aattaaaggc tcttgcaaaa tgacaagttt gcccatgggg atgcagtact   5220
taacctccct ccaaaccctc aaactagaaa attgtgatga attgaattcc cttccagaat   5280
ggataagcag cttatcatct cttcaatacc tgggcatatt caactgtcca gccctagaat   5340
cactaccaga agcaatgcgg aacctcacct cccttcagag acttgtgata cggctgtgtc   5400
cagacctagt taaaagatgc ggaaaaccca aaggcaagga ctatcccaaa attcaacaca   5460
tccccgaaat tgtaagtgat tgcagaaagt attttattca tttatattta ttttatgctt   5520
agaatgatat acaccgtcgt cctttggttt caaatcttga atttggtttt tgttttcttt   5580
ctttgtttct ttattcaaca ccagcccatt tatgattgat tcattaaaaa aaggatggag   5640
ttttgtgtat ttgaagaaga caacgaattg agattcctgg ggttttcttt ttgttggggt   5700
tggatttcat gtatatgttg ctgattaaat acgagactga tgatgatgat gatgtgttta   5760
tgggttttaa atcagattaa atatatggga aatgtaagtt aatttgggat gcacataagg   5820
tgtttgctga aatgtctatg agaaatgttg tttcttggac ttagaatgat atacactgtc   5880
gtccattggt ttccaatctt acatttggtt tgtgttttct tagtttgttt ctttaatcaa   5940
caccaaccca ttttttttaaa actacctgca actactaatt tacgttgacc ctgtatctca   6000
ggtactaaat gaatattggt gattttcagt tactcaacac tagcttgatc ctgaacgcac   6060
ccaaccttca ggttagaatc cggcttactc atccttttgt ccagttttca agtaattgtt   6120
ttggcaggat caattctcta attgttgtac accgtatatt gcaatttata gtgactacag   6180
ttaatgaatg tttacaaaaa attagtcatg taaaaacttc ttctctgtcc attacataaa   6240
ctcttttttct ctttctaact tatcatgttc atgtctaaaa aattaaacat gctcacatca   6300
atgttcattt aagctaactt acttctgtaa gagagcgagc tagttaaaaa ctcctttaac   6360
tttctgtttt atactcagga catggattga tgcaagcatg aagaacttcg ggaatttgct   6420
aaaactctac caaagcgatg agagtttgga ctttgtttca cttgaagtca gggactgtca   6480
acaaagccac agtgtgcatg ttggctgttt cacttggacg ataaaaaggt ttatttaatt   6540
gttttcctaa gtgtatttgg cttacaagct tttacttttc gcttgaaagg gtttttcttg   6600
ttttaagctt tttgaattag agtttcggtt gaagtaagag tagtcgtatt agtcttttac   6660
tttgcaggag tctatgccta tataaggtaa gactcgtatt tgtaattttc agattatgca   6720
attcaagttt tcgagtgttt tcttaaaaaa acatatcata cctgtgtgta gcataaagat   6780
aaattctgat gctgtgcttc ttgttatggc tcacattggt tttcattgtt tggattgttt   6840
cacagggaag cagagaatac ctggaacctg taaaggacgc tatatctata gcagctttca   6900
caggccaagt aatataatgt tctttatcaa tcactcaata cctggagatt gtttgaacac   6960
ataattcacc tcttttttttc catctcaaat tgcagacttt tactgggatt tgaatgacag   7020
caaacatttg attgtcacga ggattgatct aactggtgaa tgttgtgatc accatattgg   7080
tctttctcat tcaaacaaac ttgcataccg ttcttttgaa gtttgaagac aagcaggcga   7140
taatcaactc aggtcgaagc tcatgtgcag gagagaatag aatatagagg agattatttt   7200
taaaagaaac gctcaaaggt attgtagcac ctttcctatt tgctactgca gtgatgtttt   7260
tatttcttgt ttgcagcgct tgtttctcat atttcaacct acttttagaa aaaaaaacat   7320
ctccgaacat aaccaaaaat aaagttccct tatcagtgct ttccctgctt tcttctaaac   7380
aacatataca attataaacc ctttttctct cttacctttg ttattcttcc ttgcttcatt   7440
gagataacac tctcctgttt ttgttttgtt gttagtcatt acatggatat atcaaggaca   7500
acagttctgt agtccgtcaa ctgtggttag gaaggctaaa ctggagcaca ataaccccat   7560
```

```
gtcaattgaa tagtaaaggt gtgctatatc agtttcgttt ggcttggctt acctgaaaaa   7620
tggctggtta tttatccttg tctctttcta tgacgtgcag tggcttgtta atgtgtctcg   7680
gacaacaatt cctcactttc caagttccat acacgctgat gtaactatct tctgcagtct   7740
gttctttcat ttttgccacg tgctctaatt ataacttttt gtactcaata atcaactcct   7800
tgtcccggta tttgcagaga ctacttaaac aggtaaagtg acaatcctgg cgaagttgtc   7860
tgtttcttag ctctgaaccc atcattcagg taagattaag tatttaagaa gaaattttgt   7920
ttttacctaa aatgaatgat cttgtgtaac tgcttgcttc ttgcattaaa taagaacttt   7980
ctgctgcata tgtgacagtt acatccacaa aaaagttgga ggtttgttca gggattggaa   8040
atgaaggtac ttcagaattc ctggaatgtt tatgaatgct ccagacttca gagtctttaa   8100
tggaaaattc gagtcactaa aaaaacatta ttcctatcat cagagctttg aagttcctct   8160
atacaaggtc aactgagttc ctctttgcct cttgtttaat tgtatttact tgtaccttaa   8220
ttataatctg tatattgttt tagttaagtt ctaaaacagg ttattattca tcatttgtgc   8280
agcatattgc tggaatcaag aatctagtgc ttcttcttcc tgacttcact gtcaaaatag   8340
cagttcccat gctggaaata agcgcgctag caatgtaatt gatgacatgg atgttgctgc   8400
ttctgagttt tgatcataaa aagctgttat gtgtttcttg aatgtaatga aggagaggag   8460
aaaactgaaa actcttggca aaaacgtgaa attgcagtgc ctcggggtgg tagggatcac   8520
ccggattcag ttcagacgat actttttttca acccggtttg ttccggtttt cagcttcggg   8580
ttttccttgt acttttgggg cacacataca aggctacttc atgtttgaga aacctaattg   8640
aggctatctt gtagcaaatg cacaccacac tctttctctc ttctctcctt ttttcacctt   8700
ccatttgtaa aaatcctctt ttaaaggtta ataaaaaaaa gcttcaagtc tcgtagggtg   8760
gatgtaggtc acattgaccg aaccacggta aactctttgt gttctttctt ctctctttgt   8820
ttctcatttt tacggcaagt gtttatggtt aaccatgcat cttagaatag cttaaggcat   8880
taacataata acatcaatgt tctccaaaga ttcaccttac ttgttgtaca taatcacaat   8940
gttaagccta tgaaggtaga atgctctcat gatttggttt aaccaaaaaa taaactctaa   9000
aataatacgg agtaataaaa attggccata aattatttac aaagtttgat ttttgtatag   9060
ggtatcttgt acttgtgata aaaaaaatta aaaaaaaaaa aattacttat ttcttc       9116

<210> SEQ ID NO 20
<211> LENGTH: 6853
<212> TYPE: DNA
<213> ORGANISM: Spinacia oleracea

<400> SEQUENCE: 20

atggccgaaa tcggatactc ggtttgtgcg aaactcatcg aagtgattgg cagtgagctg     60
atcaaagaga tttgtgacac atggggttac aaatctcttc ttgaggacct caacaaaact    120
gtattgacgg tcaggaacgt tctcattcaa gccggggtga tgcgggagct tactagtgaa    180
caacaaggtt tcattgcaga ccttaaagat gttgtttatg atgctgatga cttgttcgac    240
aagttactca ctcgtgctga gcgaaaacag attgatggaa acgaaatctc tgaaaaggta    300
cgtcgtttct tttcctctag taacaagatc ggtcaagctt actacatgtc tcgtaaggtt    360
aaggaaatta agaagcagtt ggatgaaatt gttgataggc atacaaaatt tgggtttagt    420
gccgagttta tacctgtttg tagggaaagg gggaacgaga gggaaacacg ttcatatata    480
gatgtcaaga atattcttgg gagggataaa gataagaatg atatcataga taggttgctt    540
```

-continued

```
aatcgtaatg gtaatgaagc ttgtagtttc ctgaccatag tgggagcggg aggattggga    600
aaaactgctc ttgcacaact tgtgttcaat gatgaaaggg tcaaaattga gttccatgat    660
ttgaggtatt gggtttgtgt ctctgatcaa gatgggggcc aatttgatgt gaaagaaatc    720
ctttgtaaga ttttagaggt ggttactaag gagaaagttg ataatagttc cacattggaa    780
ttggtacaaa gccaatttca agagaagtta agaggaaaga agtacttcct tgttcttgat    840
gatgtatgga acgaagatcg tgagaagtgg cttcctttgg aagagttgtt aatgttgggt    900
caagggggaa gcaaggttgt agtgaccgca cgttcagaga agacagcaaa tgtcataggg    960
aaaagacatt tttatacact ggaatgtttg tcaccagatt attcatggag cttatttgaa   1020
atgtcggctt ttcagaaagg gcatgagcag gaaaaccatc acgaactagt tgatattggg   1080
aaaaagattg ttgaaaaatg ttataacaat ccacttgcta taacggtggt aggaagtctt   1140
ctttatggag aggagataag taagtggcgg tcatttgaaa tgagtgagtt ggccaaaatt   1200
ggcaatgggg ataataagat tttgccgata ttaaagctca gttaccataa tcttataccc   1260
tcgttgaaga gttgcttcag ttattgtgca gtgtttccca aggatcatga aataaagaag   1320
gagatgttga ttgatctttg gatagcacaa ggatacgttg tggcacttga tggaggtcaa   1380
agtatagaag atgctgccga agaacatttt gtaattttgt tacggagatg tttctttcaa   1440
gatgtaaaga aggatgaata tggtgatgtt gattctgtta aaatccacga cttgatgcac   1500
gatgtcgccc aagaagtggg gagggaggaa atatgtgtag tgaatgataa tacaaagaac   1560
ttgggtgata aaatccgtca tgtacatggt gatgtcaata gatatgcaca aagagtctct   1620
ctgtgtagcc atagccataa gattcgttcg tatattggtg gtgattgtga aaaacgttgt   1680
gtggatacac taatagacaa gtggatgtgt cttaggatgt tggacttgtc atggtcggat   1740
gttaaaaatt tgcctaattc aataggtaaa ttgttgcact tgaggtatct taacctgtca   1800
gataatagaa atctaaagat acttcctgat gcaattacaa gactgcataa tttgcagaca   1860
ctgcttttag aagattgcag aagtttaaag gagttgccaa aagatttttg caaattggtc   1920
aaactgaggc acttggaatt acagggttgt catgatttga ttggtatgcc atttggaatg   1980
gataagctaa ctagtcttag aatactacca aacattgtgg tgggtaggaa ggaacaaagt   2040
gatgatgagc tgaaagccct aaaaggcctc accgagataa aaggctccat ttctatcaga   2100
atctattcaa agtatagaat agttgaaggc atgaatgaca caggaggagc tgcttatttg   2160
aagagcatga aacatctcag ggagattgat attacatttt tgggtgaatg tgttggccct   2220
gaagctgtat tggaaacctt agagccacct tcaaatatca agagcttata tatatataat   2280
tacagtggta caacaattcc agtatgggga agagcagaga ttaattgggc aatctccctc   2340
tcacatctcg tcgacatcca gcttagttgt tgtagtaatt tgcaggagat gccagtgctg   2400
agtaaactgc ctcatttgaa atcgctgaaa cttggatggt tggataactt agagtacatg   2460
gagagtagca gtagcagtga cacagaagca gcaacaccag aattaccaac attcttccct   2520
tcccttgaaa aacttacttt acagcatctg gaaaagttga agggttttgg gaacaggaga   2580
tcgagtagtt ttccccgcct ctctgaattg gaaatcaaga aatgcccaga tctaacgtca   2640
tttccttctt gtccaagcct tgagaagttg gaattgaaag aaagcaatga agcattgcaa   2700
ataatagtaa aaataacaac aagaggtaaa gaaaaagaag agaacaataa tgctggtgtt   2760
agaaattcac aagatgatga caaagtcaaa ttacggaaga tggtgataga caatctgggt   2820
tatctcacgg gggttgatat tagatttgat gatagagaag gtggatttgt taaccctgaa   2880
gctgtgttgg caaccctaga gccaccttca aatatcaaga gcttatctat acatcgtttt   2940
```

```
gatggtaaaa cacttccagt atggggaaga gcagagatta attgggcaat ctccctctca   3000
catcttgtcg acatccagct ttggcattgt cgtaatttgc aggagatgcc agtgctgagt   3060
aaactgcctc atttgaaatc actggaactt tataatttga ttagtttaga gtacatggag   3120
agcacaagca gaagcagtag cagtgacaca gaagcagcaa caccagaatt accaacattc   3180
ttcccttccc ttgaaaaact tagactttgg tatctggaaa agttgaaggg tttggggaac   3240
aggagaccga gtagttttcc ccgcctctct gaattggaaa tctgggaatg cccagatcta   3300
acgtggtttc ctccttgtcc aagccttaaa acgttgaaat tggaaaaaaa caatgaagcg   3360
ttgcaaataa tagtaaaaat aacaacaaca agaggtaaag aagaaaaaga agaagacaag   3420
aatgctggtg ttggaaattc acaagatgat gacaatgtca aattacggaa ggtggaaata   3480
gacaatgtga gttatctcaa atcactgccc acaaattgtc ttactcacct caaaataact   3540
ggaatagatt acagggaggg ggagattgaa tcagattccg tggaggagga gattgaattg   3600
gaagttgggg aggcatttca gaagtgtgca tcttctttga gaagcctcat cataatcgga   3660
aatcacggaa taaataaagt gatgagactg tctggaagaa cagggttgga gcatttcact   3720
ctgttggact cactcaaatt ttcaaagata gaagaccagg aagatgaggg cgaagacaac   3780
atcatattct ggaaatcctt tcctcaaaac cttcgcagtt tgagaattaa agactctgac   3840
aaaatgacaa gtttgcccat ggggatgcag tacttaacct ccctccaaac cctcgaacta   3900
tcatattgtg atgaattgaa ttcccttcca gaatggataa gcagcttatc atctcttcaa   3960
tacctgcgca tatactactg tccagccctg aaatcactac cagaagcaat gcggaacctc   4020
acctcccttc agacacttgg gatatcggat tgtccagacc tagttaaaag atgcagaaaa   4080
cccaacggca aggactatcc caaaattcaa cacatcccca aaattgtaag tcattgcaga   4140
aagtaattta ttcatttata tttattttat gcttagaatg atatacgcag tcgtcctttg   4200
gtttcaaatc ttgaatttgg tttttgtttt ctttctttgt ttctttattc aacaccagcc   4260
catttatgat tgattcatta aaaaaaggat ggagttttat ggatttgaag aagacaacga   4320
attgagattc ctggggtttt ctttttgttg gggttggatt tcatgtatat gttgctgatt   4380
aaatacgaga ctgatgatga tgatgtgttt atgggtttta aatcagatta aatatatggg   4440
aaatgcaagt taatttggga tgcacataag gtgtttgctg aaatgtctat gagaaatgtt   4500
gtttcttgga cttagaatga tatacactgt cgtcctttgg tttccaatct tacatttggt   4560
ttgtgttttc ttagtttgtt tctttaatca acaccaaccc gtttttttta aactacctgc   4620
aactactaat ttacgtttac cctgtatctc aggtactaaa tgaatattgg tgattttcag   4680
ttactcaaca ctagcttgat cctgaacgca cccaaccttc aggttagaat ccggcttact   4740
catccttttg tccagttttc aagtaattgt tttggcagga tcaattctct aattgttgta   4800
caccgtatat tgcaatttat agtgactaca gttaatgaat gtttacaaaa aattagtcat   4860
gtaaaaactt cttctctgtc cattacataa actcttttc  tctttctaac ttatcatgtt   4920
catgtctaaa caattaaaca tgctcacatc aatgttcatt taagctaact tacttctgta   4980
agagagcgag ctagttaaaa actcctttaa ctttctgttt tatactcagg acatggattg   5040
atgcaagcat gaagaacttc gggaatttgc taaaactcta ccaaagcgat gagagtttgg   5100
actttatttc acttgaagtc agggactgtc aacaaagcca cagtgtgcat gttggctgtt   5160
tcacttggac gataaaaagg tttatttaat tgttttccta agtgtatttg gcttacaagc   5220
ttttactttt cacttgaaag ggtttttctt gttttaagct tttcgaatta gagttttcgg   5280
```

```
ttgaagtaag agtagtcgta ttagtctttt acctaaggaa gactcttttt tgtaattttc   5340

agactatgca attcaagttt tcgagtgttt tcttgcttgt gtgattgtga gttggtgaat   5400

tcgtctttca tacattttga gattatcaga agctttatgc tccaccggta gtctagtacc   5460

ttttctgtta ctgtgcaggg aagtaatctg gtaccttcta tatatatgga aaaacataca   5520

ttatacatta tgcaaaattc ttacaggtta gttacttcct ggaacttcat ttacacttag   5580

tttttttgt tccattccct cggaatcaag tcattccctc tgagaaatat gtaatgaact   5640

tctgtatgtt gctgtttggt tcctgtttta atcttcaatt ttcttgtata gttacagctg   5700

catttacaat gaagtttaag cagacactct ctttatatag tgcctctttc tggagcaccg   5760

tagagctgtc tgtggttgat caccatctgc tgccgagaga ttcagcaatc gcgtgtttga   5820

tcaggtaaaa gtttttatgt caatgtgttt ttttttccgt ttgatcaatt tatgtctgta   5880

ttcagattct tatcttctta cagtagcata acacattgtt tctttcattt atgtaaactg   5940

tttcaagatt acagagatgt atgcttcagt cgacattgat gataacttaa gatggcattc   6000

ctacaacagt tgcaggcgca ttctaactcc ggcaattcta gttaggcaag aggagcattg   6060

ccaatacctg ccacctctgg gatttactat accagggttg aagtttatgg aagacaccag   6120

ctatgcacaa gccttcaagg ggtcatccta cataacaagt tgaaccaacc aattgcttgt   6180

tggttcagtg gtaattgaag ctgaatttgg tagggatggc ccgtgttcga tccccacaac   6240

aacaattggg aggggactgg aacctatcca cacagaactc gccctgaatc cggattagcc   6300

ctaagggtga acggggtgct aacaccaaaa aaaaaaacat aacaagttga accaaacata   6360

ctttgtttga attgaagatt tagtgatttc atttgatcga ttgagatgtc ttattataag   6420

cgtatatgct cttggatttg gccacttagg tgttgtttga caattggaca ttaactcgct   6480

tttatatttt cttttctctt aggaaaggtg atcctgagaa tttatattgg aacacttttt   6540

ttttctcact agctttaaaa aagtgttctg tgttacctgc aattcaattt gattattttt   6600

cacatagttt tacctgaaaa agtgttacct gaaaaagtgt tacctgaaaa tcaactgaca   6660

taagtttttg tttggatcca attaaggaca ctagataaat cggaataaat aatcaaccaa   6720

ttaagtactt cataattaaa tatgaagtgt attattatct tatgcttgtg acattgaagg   6780

atgttatgat attttaactc aataccttgc aaaatatact ggttaaattt cttaacaagg   6840

taacttggca aca                                                      6853
```

<210> SEQ ID NO 21
<211> LENGTH: 17524
<212> TYPE: DNA
<213> ORGANISM: Spinacia oleracea
<220> FEATURE:
<221> NAME/KEY: misc_feature
<222> LOCATION: 9188..9229
<223> OTHER INFORMATION: /note="n = a or c or t or g"

<400> SEQUENCE: 21

```
tttgaagtta ggcttaactt gctcaccaat tcttaaatag actcgactta cactgaattt     60

attgtgtact atgtctagaa agtaaggtca acaactttct tctaaattat tttggcatgt    120

ttattagggt tattatgaaa aacatatcaa attggtgttg ttagttaggc ttgaataata    180

tgattttaag tcacgagact tttataaatt aggtaatttg atttaaaaaa ttgttacata    240

tctaagaaaa tggatgttaa atttatcagt caatgtataa acaataaaag tcaatatgta    300

tgtaaaaggg ttgctagata aaatctttgg ttttttggtc cacaactcca cactaagagg    360

aactccaatg cttagttaca aggtggtgta gttaaaaagt aactccaata gttaactaca    420
```

```
cggtattata gttaaatttg ccaactcaaa tttctaacta caatatattt aagctacaaa    480
gtttctcatt ggctgactac aatacgttgt agcgccttat aatattttat tcaatataca    540
atttattta ttttaccttt ttaacaattt ttttttgatc tacctgctgt cctgttcata    600
tgagctacac taatttgata gctgcttacg caattcttat atcaacggtt ggctacttgt    660
tcaaatattt ttattttttt acgagtaagt cattttatga tcattgaagt ggctctatta    720
ttattatcat gcaccgatta acgcaagaat aattaactcg gtacgaatta gtttcaaaat    780
aaaatccctc aaaaaaaaaa gtttcaaaat aaaattaaca gaaaaccaac cttctccggt    840
ttactgttgt tagagcatgg aattttccag taatcgcaga ccccaaatta tcttccagtt    900
gaatcaatcc ttgattttg gatttgccag aaaactcctt gaattttagg gttcatattt    960
gatccgtaat tgggaaaatt ttcagcaatt gatcttccaa atcagcccta cttgtttcca   1020
gactgcaaat gaaaggtgcg aactttatac tgcattttgg ttttccatta gtgtaattta   1080
ttaagatgaa ctgcattttg caattgtttt attcgactac tcatttttaa atcaaattgc   1140
ttaattgcta gttagtttc ttatcatatt gccaaaaaaa attatttttg tttaattggt   1200
gaaaaagggt aaattatacc tagtgtacaa gattttcttg cacaccaccg ttaatttgtt   1260
gacacatcat caaacgtact gaaaaatgag aatgaaagac aataaatatg tcattttaac   1320
caatagaaaa acatgatgta gtaagatcct taattgatag ataaataatt aaatatcagt   1380
ccattagttg aatattcaat gaaaatgtat ggtccaaaaa tggcgtttaa tagtcaatgt   1440
catgctttat ggggtggtgg agtactatgt gactgtgtgt ggacttggag aagactagag   1500
agtatgatta tcaacctatg gaccctcaaa atgaaaatga aatgatgtt tacacgtgct   1560
atttgcacgg acttcaatgc aaatagtata aatttacggt caaagttttc attctaaagc   1620
gtaaataact ttcatgaatg gaggacggta gtataagtat aacgttatag cctaccattt   1680
tcttatcata ttcacataaa tttgttgctg aaatttgttt tacttggcta aaatactttt   1740
gttcttattg gcagataaac atcagtacgt ccattattgg ccaacttgct gagtccatta   1800
ttggccaact tgaacatata cctccaaaca ataatcaata atgtcgatta tgaagtttgt   1860
gaatgcaatt tattatcact ttcatttata aaatgactac ttgattaaca catacaatat   1920
tacctttctc caaacaccct ttcaattctg cttaatcttg ttttctcatc atctcttcat   1980
ctttctgaaa acacaaccca atggccgaaa tcggatactc ggtttgtgcg aaactcatcg   2040
aagtgattgg cagtgagctg atcaaagaga tttgtgacac atggggttac aaatctcttc   2100
ttgaggacct caacaaaact gtattgacgg tcaggaacgt tctcattcaa gccggggtga   2160
tgcgggagct tactagtgaa caacaaggtt tcattgcaga ccttaaagat gttgtttatg   2220
atgctgatga cttgttcgac aagttactca ctcgtgctga gcgaaaacag attgatggaa   2280
acgaaatctc tgaaaaggta cgtcgtttct tttcctctag taacaagatc ggtcaagctt   2340
actacatgtc tcgtaaggtt aaggaaatta agaagcagtt ggatgaaatt gttgataggc   2400
atacaaaatt tgggtttagt gctgagttta tacctgtttg taggggaagg ggaaacgaga   2460
gggaaacacg ttcatatata gatgtcaaga atattcttgg gagggataaa gataagaatg   2520
atatcataga taggttgctt aatcgtaatg gtaatgaagc ttgtagtttc ctgaccatag   2580
tgggagcggg aggattggga aaaactgctc ttgcacaact tgtgttcaat gatgaaaggg   2640
tcaaaattga gttccatgat ttgaggtatt gggtttgtgt ctctgatcaa gatgggggcc   2700
aatttgatgt gaaagaaatc ctttgtaaga ttttagaggt ggttactaag gagaaagttg   2760
```

```
ataatagttc cacattggaa ttggtacaaa gccaatttca agagaagtta agaggaaaga   2820
agtacttcct tgttcttgat gatgtatgga acgaagatcg tgagaagtgg cttcctttgg   2880
aagagttgtt aatgttgggt caagggggaa gcaaggttgt agtgaccaca cgttcagaga   2940
agacagcaaa tgtcataggg aaaagacatt tttatacact ggaatgtttg tcaccagatt   3000
attcatggag cttatttgaa atgtcggctt ttcagaaagg gcatgagcag gaaaaccatc   3060
acgaactagt tgatattggg aaaaagattg ttgaaaaatg ttataacaat ccacttgcta   3120
taacggtggt aggaagtctt ctttatggag aggagataag taagtggcgg tcatttgaaa   3180
tgagtgagtt ggccaaaatt ggcaatgggg ataataagat tttgccgata ttaaagctca   3240
gttaccataa tcttataccc tcgttgaaga gttgttttag ttattgtgca gtgtttccca   3300
aggatcatga aataaagaag gagatgttga ttgaactttg gatggcacaa ggatatgttg   3360
tgccgttgga tggaggtcaa agtatagaag atgctgccga ggaacatttt gtaattttgt   3420
tacgaaggtg tttctttcaa gatgtaaaga aggataaata tggtgatgtt gattctgtta   3480
aaatccacga cttgatgcac gatgtcgccc aagaagtggg gagggaggaa ttatgtgtag   3540
tgaatgataa tacaaagaac ttgggtgata aaatccgtca tgtacatcgt gatgtcatta   3600
gatatgcaca aagagtctct ctgtgtagcc atagccataa gattcgttcg tatattggtg   3660
gtaattgtga aaaacgttgt gtggatacac taatagacaa gtggatgtgt cttaggatgt   3720
tggacttgtc atggtcggat gttaaaaatt tgcctaattc aataggtaaa ttgttgcact   3780
tgaggtgtct taacctgtct tataataaag atctgttgat actccctgat gcaattacaa   3840
gactgcataa tttgcagaca ctgcttttaa aagagtgcag aagtttaaag gagttgccaa   3900
aagatttttg caaattggtc aaactgaggc acttggattt aaggtgttct gatttgaagg   3960
agttgccaaa agatttttgc aaattggtca aactgaggca cttggattta tggggttgtg   4020
atgatttgat tggtgtgcca ttgggaatgg ataggctaat tagtcttaga gtactgccat   4080
tctttgtggt gggtaggaag gaacaaagtg atgatgatga gctgaaagcc ctaaaaggcc   4140
tcaccgagat aaaaggctcc attcgtatta gaatctattc aaagtataga atagttgaag   4200
gcatgaatga cacaggagga gctgggtatt taaagagcat gaaacatctc acgggggttg   4260
atattacatt tgatggtgga tgtgttaacc ctgaagctgt gttggcaacc ctagagccac   4320
cttcaaatat caagaggtta gagatgtggc attacagtgg tacaacaatt ccagtatggg   4380
gaagagcaga gattaattgg gcaatctccc tctcacatct tgtcgacatc cagctttggc   4440
attgtcgtaa tttgcaggag atgccagtgc tgagtaaact gcctcatttg aaatcactgg   4500
aactttataa tttgattagt ttagagtaca tggagagcac aagcagaagc agtagcagtg   4560
acacagaagc agcaacacca gaattaccaa cattcttccc ttcccttgaa aaacttacac   4620
tttggcgtct ggacaagttg aagggttttg ggaacaggag atcgagtagt tttccccgcc   4680
tctctaaatt ggaaatctgg aaatgcccag atctaacgtc atttccttct tgtccaagcc   4740
ttgaagagtt ggaattgaaa gaaaacaatg aagcattgca aataatagta aaaataacaa   4800
caacaagagg taaagaagaa aaagaagaag acaagaatgc tggtgttgga aattcacaag   4860
atgatgacaa tgtcaaatta tggacggtgg aaatagacaa tctgggttat ctcaaatcac   4920
tgcccacaaa ttgtcttact ctgttggact cactcgaact ttcaaatata gaagaccagg   4980
aagatgaggg cgaagacaac atcatattct ggaaatcctt tcctcaaaac ctccgcagtt   5040
tggaaattga aaactcttac aaaatgacaa gtttgcccat ggggatgcag tacttaacct   5100
ccctccaaac cctctatcta caccattgtt atgaattgaa ttcccttcca gaatggataa   5160
```

gcagcttatc atctcttcaa tccctgcaca taggaaaatg tccagcccta aaatcactac 5220
cagaagcaat gcggaacctc acctcccttc agacacttgg gatatcgcgg tgtccagacc 5280
taattgaaag atgcgaagaa cccaacggcg aggactatcc caaaattcaa cacatcccca 5340
aaattgtaag tcattgcaga aagtaattta ttcatttata tttattttat gcttagaatg 5400
atatacaccg tcgtcctttg gtttcaaatc ttgaatttgg tttttgtttt ctttctttgt 5460
ttctttattc aacaccagcc catttatgat tgattcatta aaaaaaggat ggagttttgt 5520
ggatttgaag aagacaacga attgagattc ctggggtttt ctttttgttg gggttggatt 5580
tcatgtatat gttgctgatt aaatacgaga ctgatgatga tgatgatgtg tttatgggtt 5640
ttaaatcaga ttaaatatat gggaaatgta agttaatttg ggatgcacat aaggtgtttg 5700
ctgaaatgtc tatgagaaat gttgtttctt ggacttagaa tgatatacac tgtcgtccat 5760
tggtttccaa tcttacattt ggtttgtgtt ttcttagttt gtttctttaa tcaacaccaa 5820
cccatttttt taaaactacc tgcaactact aatttacgtt gaccctgtat ctcaggtact 5880
aaatgaatat tggtgatttt cagttactca acactagctt gatcctgaac gcacccaacc 5940
ttcaggttag aatccggctt actcatcctt ttgtccagtt ttcaagtaat tgttttggca 6000
ggatcaattc tctaattgtt gtacaccgta tattgcaatt tatagtgact acagttaatg 6060
aatgtttaca aaaaattagt catgtaaaaa cttcttctct gtccattaca taaactcttt 6120
ttctctttct aacttatcat gttcatgtct aaaaaattaa acatgctcac atcaatgttc 6180
atttaagcta acttacttct gtaagagagc gagctagtta aaaactcctt taactttctg 6240
ttttatactc aggacatgga ttgatgcaag catgaagaac ttcgggaatt tgctaaaact 6300
ctaccaaagc gatgagagtt tggactttgt ttcacttgaa gtcagggact gtcaacaaag 6360
ccacagtgtg catgttggct gtttcacttg gacgataaaa aggtttattt aattgttttc 6420
ctaagtgtat ttggcttaca agcttttact tttcgcttga aagggttttt cttgttttaa 6480
gctttttgaa ttagagtttc ggttgaagta agagtagtcg tattagtctt ttactttgca 6540
ggagtctatg cctatataag gtaagactcg tatttgtaat tttcagatta tgcaattcaa 6600
gttttcgagt gttttcttaa aaaaacatat catacctgtg tgtagcataa agataaattc 6660
tgatgctgtg cttcttgtta tggctcacat tggttttcat tgtttggatt gtttcacagg 6720
gaagcagaga atacctggaa cctgtaaagg acgctatatc tatagcagct ttcacaggcc 6780
aagtaatata atgttcttta tcaatcactc aatacctgga gattgtttga acacataatt 6840
cacctctttt tttccatctc aaattgcaga cttttactgg gatttgaatg acagcaaaca 6900
tttgattgtc acgaggattg atctaactgg tgaatgttgt gatcaccata ttggtctttc 6960
tcattcaaac aaacttgcat accgttcttt tgaagtttga agacaagcag gcgataatca 7020
actcaggtcg aagctcatgt gcaggagaga atagaatata gaggagatta tttttaaaag 7080
aaacgctcaa aggtattgta gcacctttcc tatttgctac tgcagtgatg tttttatttc 7140
ttgtttgcag cgcttgtttc tcatatttca acctactttt agaaaaaaaa acatctccga 7200
acataaccaa aaataaagtt ccccttatcag tgctttccct gctttcttct aaacaacata 7260
tacaattata aacccttttt ctctcttacc tttgttattc ttccttgctt cattgagata 7320
acactctcct gtttttgttt tgttgttagt cattacatgg atatatcaag gacaacagtt 7380
ctgtagtccg tcaactgtgg ttaggaaggc taaactggag cacaataacc ccatgtcaat 7440
tgaatagtaa aggtgtgcta tatcagtttc gtttggcttg gcttacctga aaaatggctg 7500

```
gttatttatc cttgtctctt tctatgacgt gcagtggctt gttaatgtgt ctcggacaac   7560
aattcctcac tttccaagtt ccatacacgc tgatgtaact atcttctgca gtctgttctt   7620
tcatttttgc cacgtgctct aattataact ttttgtactc aataatcaac tccttgtccc   7680
ggtatttgca gagactactt aaacaggtaa agtgacaatc ctggcgaagt tgtctgtttc   7740
ttagctctga acccatcatt caggtaagat taagtattta agaagaaatt ttgtttttac   7800
ctaaaatgaa tgatcttgtg taactgcttg cttcttgcat taaataagaa ctttctgctg   7860
catatgtgac agttacatcc acaaaaaagt tggaggtttg ttcagggatt ggaaatgaag   7920
gtacttcaga attcctggaa tgtttatgaa tgctccagac ttcagagtct ttaatggaaa   7980
attcgagtca ctaaaaaaac attattccta tcatcagagc tttgaagttc ctctatacaa   8040
ggtcaactga gttcctcttt gcctcttgtt taattgtatt tacttgtacc ttaattataa   8100
tctgtatatt gttttagtta agttctaaaa caggttatta ttcatcattt gtgcagcata   8160
ttgctggaat caagaatcta gtgcttcttc ttcctgactt cactgtcaaa atagcagttc   8220
ccatgctgga aataagcgcg ctagcaatgt aattgatgac atggatgttg ctgcttctga   8280
gttttgatca taaaaagctg ttatgtgttt cttgaatgta atgaaggaga ggagaaaact   8340
gaaaactctt ggcaaaaacg tgaaattgca gtgcctcggg gtggtaggga tcacccggat   8400
tcagttcaga cgatactttt ttcaacccgg tttgttccgg ttttcagctt cgggttttcc   8460
ttgtactttt ggggcacaca tacaaggcta cttcatgttt gagaaaccta attgaggcta   8520
tcttgtagca aatgcacacc acactctttc tctcttctct cctttttca ccttccattt    8580
gtaaaaatcc tcttttaaag gttaataaaa aaaagcttca agtctcgtag ggtggatgta   8640
ggtcacattg accgaaccac ggtaaactct ttgtgttctt tcttctctct ttgtttctca   8700
tttttacggc aagtgtttat ggttaaccat gcatcttaga atagcttaag gcattaacat   8760
aataacatca atgttctcca aagattcacc ttacttgttg tacataatca caatgttaag   8820
cctatgaagg tagaatgctc tcatgatttg gtttaaccaa aaaataaact ctaaaataat   8880
acggagtaat aaaaattggc cataaattat ttacaaagtt tgatttttgt atagggtatc   8940
ttgtacttgt gataaaaaaa attaaaaaaa aaaaaattac ttatttcttc tatttttact   9000
tgttacactt ttctacaaca gaaacatcaa aacgcccgca acacactata aatgaaaaac   9060
cattttgtat gcaatgatat ttacgttctc actttattct ctttaataac tcctactacg   9120
taattctcac caatcaaata aaattataga aattttcatt tataccctct taaaatgatg   9180
ttgatttnnn nnnnnnnnnn nnnnnnnnnn nnnnnnnnnn nnnnnnnnna ggtgtgaaaa   9240
agtttgtgtt ataagttaca acaatttaaa aacggagaac atacttataa tactagtgta   9300
atctttggcc ggattatggt cgttgacaaa aaaactccgg ccttgaccct ccacgtgccg   9360
gtcaagtgac ttaataaacc ttttattcca ccctttttc attcttcttt ttattcttct    9420
ttttctctcc attaatacaa atcaagtgat tatgtcgatc cgatccttct gttctctact   9480
gtaattgatt acaccaacaa caaccaagcg aaacagtcaa tgttaccgaa ttgaattgcg   9540
gaaaatagtt tatgattgat tcattaaaaa aggatggagt tttgtggatt tgaataagac   9600
aacgaattga gattcctggg gttttctttc tgttggggtt ggatttcatg tacttgttgc   9660
tgatcaaata tgtgattgaa gattgaagat gatgatgtgt ttatgggttt gaaatcggat   9720
taaatttatg ggaaatgtaa gtgaattggg gatgcacata aggtgtttga tgaaatgtct   9780
atgagaaata ttgtttcttg cacttgtatg ataatttgtg gggatttgat tagttcatgg   9840
tgcgagtttg atgcaacgcc gaagagaaat caggtcttta gagaaactca aatggttgaa   9900
```

-continued

```
taggcttcca acaatgttgt ttcgtagtac actgccatga ttgatagaga aggaagcaga   9960
tgaaggagaa ggctcatgtg accggcacat gggtagtaag tcaacgccgg aaatcgtggt  10020
caacgtccaa aaccgagcta aggtaacata ttggagtaca agtaattaca acaaaaagtg  10080
ttacttcctt gtacattatt attttacttg aaatgctagt tgtgtttgtg catctgtgga  10140
actctaaatt aattaattaa caatcaacca aacaacttta gtgtaaattg gccaaccttt  10200
tgccatcagc cacagaaaag tgaaatatca ccccattatt gcccattctg tatttgcact  10260
ttttttaag gcatagcaca gccggttttc cggatcttag ctccgtctac attcggatcc  10320
gatccatttc gcacacctta tttgtggtgg atgagtctcc caacaagaat ttctcgctcg  10380
aaactgagaa ccccccttaag cggcatcaag ttgcttacca cttgagccaa ctctatgttg  10440
gtttctgcat ttgcagttag ttaggtcgtc tgagtgcgaa atgggaatgc tttatcacac  10500
actccacagt ttagtcaggc tgatggaaac gtaataattg agttatttga gtgttcaaac  10560
ttaaagtcac tcactcactc aaacactcaa tactttctcc atcttgtttt ctcattacat  10620
atgaaaaccc aaacaccttt catttctgct taatcttctt tctctcatct ttcagttatt  10680
cacctgttca tctttctgaa aacaacccaa acacccttca tttctgttta atcttctttc  10740
ctcatcttca tccacctgtt tatctttctg taaacacaac ccaaacacct ttcatttctg  10800
atttatcttg ttatctcatc ttcattcacc tgttcatctt tctgaaaatc taaacaccct  10860
tcatttctgc taatcttctt ttctcatctc cccctaaatc atctttctga aaacccaaac  10920
acctttcttt tctgctttta tcttgttttc tcatcttaat tcatctcttc atctttctga  10980
aaaacccaac ccaatggctg aaatcggata ctcggtttgt tcaaaactta ttgaagtgat  11040
gggcagtaat atcattaaag agattcgcga catgtggggt tacaattctc atcttgaaga  11100
cctcaacaaa tctgtcttga cgatcaagga tgtgctcttg gatgctgagg cgaagcggga  11160
tctttcccgt gaacaacaga gttacattgc agaacttaag gatgttgttt acgatgctga  11220
tgatttgttc gatgagttcc tcactcttgc tgagctcaaa cagattgatg gaaacaaggg  11280
tggtggtaaa ttctccaaaa aggtacgtcg tttcttttct tctaataagg agaagatggg  11340
tcaagcttac aagatgtctc atatggttaa agaaattaag aagcagttgg gtgaaattgt  11400
tgataggtat accaaatttg ggtttattgt tgattataaa cctattatta ggagaaggga  11460
ggaaacatgt tcttattttg taggtgccaa ggagattgtt gggagggata aggataaaga  11520
tgttatcata ggcatgttgc tagatcatga taacgattgt agtttcttgg ctgttgtggg  11580
ggttggaggg gtgggaaaaa ctactcttgc ccaacttgtg tataatgatg aaagagtcaa  11640
aagtgagttc caagatttga ggtattgggt ttgtgtctct gatcaagatg ggggacaatt  11700
tgatgacaaa agaattcttt gtaagattat agagttagtt acgggccaga ttcctccgag  11760
taacgagagc atggaatcgg tgcgtaagaa atttcaagag gaattaggag gaaagaagta  11820
cttccttgtt cttgatgatg tatggaacga ggatcgccag aagtggcttc atctagaaaa  11880
tttcttgaaa ttgggtcaag ggggaagcaa ggttgtggta accacacgtt cagagaagac  11940
ggcaaatgtt atagggaaaa gacaagacta taaactagaa tgtttgtcag cagaggattc  12000
atggcgctta tttgaaatgt cagcttttga cgaagggcat ggccaggaaa actatgacga  12060
attagtgacg attggcaaga agattgttga aaaatgttat aacaatccac ttgctataac  12120
agtggtagga agccttcttt ttggacaaga gataaataag tggcggtcgt ttgaaaacag  12180
tggattagcc caaattgcca atggtgataa tcagattttc ccgatattaa agctcagtta  12240
```

```
ccacaatctt ccacactcct tgaagagctg ctttagctat tgtgcagtgt ttcccaaaga  12300
taatgaaata aagaaggaga tgttgattga tctttggata gcacaaggat acattatacc  12360
gttggatgga ggtcaaagta tagaagatgc tgccgaggaa cattttgtaa ttttgttaag  12420
aagatgtttc tttcaagatg taaagaagga ttctcttggt aatgttgatt atgttaaaat  12480
ccacgactta atgcacgatg tcgctcaaga agtggggaag gaggaaattt gtgtagtgac  12540
ttcaggtaca aagaagttgg ctgataaaat ccgtcacgtg ggttgtgttg tcgatagaga  12600
tccagaaata gtctttttat gtagcaataa gattcgttcg tatattagcg gtcgttgtat  12660
aaagaatccg gtggattcac aaatagacaa ctggatgcgc cttagggtgt tggacttgtc  12720
agattcatgt gttaaagatt tgtctgattc aataggtaag ctgctgcact taaggtatct  12780
taacctctct tctaatataa agttggagat aatccctgat gcaattacaa gactgcataa  12840
cttgcagaca ctacttttag aagattgcag aagtttaaag gagttgccaa aagatttttg  12900
caaattggtc aaactgaggc acttggaatt acagggttgt catgatttga ttggtatgcc  12960
atttggaatg gataagctaa ctagtcttag aatactacca aacattgtgg tgggtaggaa  13020
ggaacaaagt gatgatgagc tgaaagccct aaaaggcctc atcgagataa aaggctccat  13080
ttctatcaga atctattcaa agtatagaat agttgaaggc atgaatgaca caggaggagc  13140
tgcttatttg aagagcatga aacatctcag ggagattgat attacatttt tgggtgaatg  13200
tgttagccct gaagctgtat tggaaacctt agagccacct tcaaatatca agagcttata  13260
tatatataat tacagtggta caacaattcc agtatgggga agagcagaga ttaattgggc  13320
aatctccctc tcacatctcg tcgacatcca gcttagttgt tgtagtaatt tgcaggagat  13380
gccagtgctg agtaaactgc ctcatttgaa atcgctgaaa cttggatggt tggataactt  13440
agagtacatg gagagtagca gtagcagtga cacagaagca gcaacaccag aattaccaac  13500
attcttccct tcccttgaaa aacttacttt acagcatctg gaaaagttga agggttttgg  13560
gaacaggaga tcgagtagtt ttccccgcct ctctgaattg gaaatcaaga aatgcccaga  13620
tctaacgtca tttccttctt gtccaagcct tgagaagttg gaattgaaag aaagcaatga  13680
agcgttgcaa ataatagtaa aaataacaac aagaggtaaa gaaaaagaag agaacaataa  13740
tgctggtgtt ggaaattcac aagatgatga caaagtcaaa ttacggaaga tggtgataga  13800
caatctgggt tatctcaaat cactgcccac aaattgtctt actcaccttg aaattgagga  13860
gtttattgaa tcagattccg aggaagagat tgaatcagaa gtcggggagg aggaggttga  13920
attggaagtt gtggaggcat ttcagaagtc tgcatcttct ctgcaaagcc tcgaaatata  13980
cagaataaat aaactgaata gactaactgg aacaacagga ttagtgcatt tcagtgcctt  14040
ggacgaactc acattgaatt ttgtcgacga ttttgaagta tcctttcctc aaagcctccg  14100
cagtttgaaa attgaatact cttataaaat gacaagtctg cccatgggga tgcagtactt  14160
aacctccctc caaaccctcg aactaaaatg ttgtgatgaa ttgaattccc ttccagaatg  14220
gataagcaac ttatcatctc ttcaatccct gtccatatcc tactgtgaag ccctgaaatc  14280
actaccagaa gcaatgcaga acctcacctc ccttcagaga cttgtgataa gagaatgtcg  14340
agacctagct gaaagatgcg aagaacccaa tggggaagac tatcacaaaa ttcaacacat  14400
ccccaaaatt gtaagtgatt gcggaaagtg tttcttttat ttatttttaa ttttatgctt  14460
agaatgatat acatcagcat tcagcgtcca ttggtttcca atcttacatt tggtttttgt  14520
ttcttagttt gtttctttaa tcaacaccag cccatttttt ttaaactacc tgcaactact  14580
aattttcatt taccctgtat ctcaggaaat atggtagtat tctcatttac tcaacactag  14640
```

```
cttgatcctg aacgcagcca accttcaggt tagaatccgc cttactcatc cttttgtcat  14700
gcattgtttt aagttgtttt gcttgcttgt gtaatcataa ttcatagtat acgattcatc  14760
attcactatg tctacaggca agatattgga attgttcacg attccctgaa gtttctttgt  14820
ttttgttgat accaccatat tgcagcttat agtgactaag ttaatgaatg tttccaaaaa  14880
attagtcata taaattcttc ttctctctct attacataaa ctctttttct ctttctaact  14940
atcatgttca tgtctaaaac ttatacatgc tcacatcatt gttcgtttca gctgacttac  15000
ttctgtaaga gagctatcta gttaacaact cttgtaacat tttatttgct agtcagaaca  15060
tggattggtg caagcatggg aatttgccaa cactctacca aatcgattgg agtttggact  15120
tagtttcacc agaagccata cccggacact tactggggac tgtcaacaaa gccgcattat  15180
gatgtacttg gatgtttcac gtgcctgagg tgtgagttac ttggaaggga agcggtttat  15240
ttaattgttt tcctaagtag attttgctta gaagctttta cttttcactt gaaagggttt  15300
ttcttgtttt aagcttttcg aattagagtt tcggttgcat taagagtagt cgtattagtc  15360
ttttttacc taaggaagac ttttttgtaa ttttcagacg atgcaattca acttttcgag  15420
tgttttgttg cttgtgtgat tgtgagtttg tgaatttgtc tttcataaat attgagttca  15480
tcagaagctt tatgctccac cggtagtcta gtacctttg ttattgttca gggaagtaat  15540
ctggtacctt ctatatatat gagaaaacat acattatgca aaattcttac aggttagtta  15600
cttcctagaa cttcagttat acttttttt tgttccatgt ccttggaatc aagtcattcc  15660
ctctgaaaaa tgtgtactga acttttgaaa gttgctgttt gattcctgtt tgaatcttca  15720
cttttcttgc atcgtgacag ctgtgtttac aatgaagttt aagcagacac tctctttata  15780
tagtgcctcc ttttggagca tcggagagtt gtggctgatc actatgtgcg accaagagat  15840
tcattaatcg cgtgtttgat caggtaaaag tttttatgtc aatgtgtttt atttttcttt  15900
ctgtttgatc agtttatgtc tgtattcaga ttcttatctt cttctagtag cataacaaat  15960
ttgtttgttt cattatataa accgtttcag gattacaaat gatcggacag agatgtatgc  16020
ttcagtcgat attgatgata acttaaggta gtattgctag aacagttaca gagctgtggc  16080
tgatcactat gtgctgcaaa cagattcatc aatcacgtgt ttgataaggt agagttttca  16140
tgtcaacgcg tttttctgt ttgatcaatt tatgtctgta ttcagattct tatctacttc  16200
tagtagcata acatatctgt ttctatcatt atataattgt ttcagggtta caaatgaccg  16260
gacagagatg tatgcttcag tcgatattga tgctaactta agatagcatt gctagaacag  16320
tttcaggttg ccattgaaat ttgaaaacag aaagacacca tcaggtagag ttttcatgtc  16380
aatgcttttt tttttgat caatttatgt ttgtataaaa atttgtatct tcttctatac  16440
tataaattct atataacgta tctgtttatt tcattataat aaaccgtttc aggattacaa  16500
atgatcgaac agtgatgtat gcttcagtcg ataacttcag gtagcattgc cagaagaatt  16560
gcagacacat cctaacttaa gagggttatg gttgattgac taactctcga aattctagtt  16620
aggcaagagg agcattgcag tacctgcctt aaaaggggtc gtcttatata gatatctcta  16680
tcagtagtca tttacgtctt aagtcctgaa ataagttgaa ctaaacatac tttgtttgaa  16740
tcgaagattt agtgaatttt actttgtatt tgattgtgtt gagatgaccg tagggaaaag  16800
ttaactaatt ataagcgtaa attatgttct tggattcggc ttttatattt tcttttcgtt  16860
taataaaagt ggtcatagag atattctaca atgtattttg gtaagttacc taaaatttaa  16920
tttgattatt tttcacataa ttaatcaact gataaaattt tatttggatc aaccgatcaa  16980
```

-continued

```
gaagtgaaaa cgtaaagaac aaaaagaaac agagggagta tattattatc ttttactttt  17040

gatagtgaag gatgttatga tattttaact caatccctta caaaatatac tggttaaatt  17100

tcttaacaat gtagtacttt ggcaacaagt tcaggttgaa agctttgaga aatagagtta  17160

ggaaacataa gaatcacaaa atttatgctt ctctcatctg tgaatcaaaa cacaaattct  17220

tatttacaaa ggttgtacaa taattattgt acaccgaagt aaaagttaac tcaaaatgct  17280

taaaagttag gcttatatat gtaaaagtta tctattgttt agtgataaaa aatttcattt  17340

taataaaact tattttttca aaatcactaa taatgtataa aattaatcat ttaattattt  17400

aaaatattta tctatcaaat ttttttacta atataaaagt tactcaaaac taggttaaaa  17460

ttacaaaaaa atggattaaa gttattttgg tgtacaataa atttattgta tactttgtgc  17520

gcgc                                                               17524


<210> SEQ ID NO 22
<211> LENGTH: 9
<212> TYPE: PRT
<213> ORGANISM: Spinacia oleracea
<220> FEATURE:
<223> OTHER INFORMATION: N-terminal motif

<400> SEQUENCE: 22

Met Ala Glu Ile Gly Tyr Ser Val Cys
1               5


<210> SEQ ID NO 23
<211> LENGTH: 6
<212> TYPE: PRT
<213> ORGANISM: Spinacia oleracea
<220> FEATURE:
<223> OTHER INFORMATION: alpha-WOLF motif

<400> SEQUENCE: 23

Lys Trp Met Cys Leu Arg
1               5


<210> SEQ ID NO 24
<211> LENGTH: 8
<212> TYPE: PRT
<213> ORGANISM: Spinacia oleracea
<220> FEATURE:
<223> OTHER INFORMATION: Beta-WOLF motif

<400> SEQUENCE: 24

His Val Gly Cys Val Val Asp Arg
1               5


<210> SEQ ID NO 25
<211> LENGTH: 9
<212> TYPE: PRT
<213> ORGANISM: Spinacia oleracea
<220> FEATURE:
<223> OTHER INFORMATION: Optional motif

<400> SEQUENCE: 25

Asp Gln Glu Asp Glu Gly Glu Asp Asn
1               5
```